United States Patent
Oren et al.

(10) Patent No.: US 11,028,127 B2
(45) Date of Patent: *Jun. 8, 2021

(54) PEPTIDES CAPABLE OF REACTIVATING P53 MUTANTS

(71) Applicant: Yeda Research and Development Co. Ltd., Rehovot (IL)

(72) Inventors: Moshe Oren, Rehovot (IL); Varda Rotter, Rehovot (IL); Perry Tal, Rehovot (IL)

(73) Assignee: Yeda Research and Development Co. Ltd., Rehovot (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/704,010

(22) Filed: Dec. 5, 2019

(65) Prior Publication Data

US 2020/0095282 A1    Mar. 26, 2020

Related U.S. Application Data

(60) Division of application No. 16/451,081, filed on Jun. 25, 2019, now Pat. No. 10,550,152, which is a division of application No. 15/796,811, filed on Oct. 29, 2017, now Pat. No. 10,336,789, which is a division of application No. 15/015,208, filed on Feb. 4, 2016, now Pat. No. 9,856,289, which is a continuation-in-part of application No. PCT/IB2014/063777, filed on Aug. 7, 2014.

(60) Provisional application No. 61/862,977, filed on Aug. 7, 2013.

(51) Int. Cl.
| | |
|---|---|
| C07K 14/00 | (2006.01) |
| C07K 14/47 | (2006.01) |
| C07K 7/06 | (2006.01) |
| A61K 38/16 | (2006.01) |
| A61K 38/08 | (2019.01) |
| C07K 7/08 | (2006.01) |
| A61K 38/00 | (2006.01) |

(52) U.S. Cl.
CPC .............. C07K 7/06 (2013.01); A61K 38/08 (2013.01); A61K 38/16 (2013.01); C07K 7/08 (2013.01); C07K 14/00 (2013.01); C07K 14/4746 (2013.01); A61K 38/00 (2013.01)

(58) Field of Classification Search
None
See application file for complete search history.

(56) References Cited

U.S. PATENT DOCUMENTS

| | | | |
|---|---|---|---|
| 5,294,605 A | 3/1994 | Houghten et al. | |
| 5,614,393 A | 3/1997 | Thomas et al. | |
| 9,657,064 B2* | 5/2017 | Derouazi ............. | C07K 14/05 |
| 9,856,289 B2 | 1/2018 | Oren et al. | |
| 10,550,152 B2* | 2/2020 | Oren ...................... | A61K 38/16 |
| 2003/0224379 A1 | 12/2003 | Tang et al. | |
| 2004/0214184 A1* | 10/2004 | Skubitz ................. | A61P 35/00 435/6.12 |
| 2006/0251726 A1 | 11/2006 | Lin et al. | |
| 2008/0069839 A1* | 3/2008 | Guan .................... | A61K 39/215 424/221.1 |
| 2013/0011356 A1 | 1/2013 | Fahnestock et al. | |
| 2016/0215019 A1 | 7/2016 | Oren et al. | |
| 2018/0057533 A1 | 3/2018 | Oren et al. | |
| 2019/0048053 A1 | 2/2019 | Rotter et al. | |
| 2019/0315804 A1 | 10/2019 | Oren et al. | |

FOREIGN PATENT DOCUMENTS

| | | | |
|---|---|---|---|
| EP | 0989136 | 3/2000 | |
| JP | 11-500311 | 1/1999 | |
| RU | 2181772 | 4/2002 | |
| RU | 2192431 | 11/2002 | |
| WO | WO 96/21022 | 7/1996 | |
| WO | WO 96/25434 | 8/1996 | |
| WO | WO 97/30074 | 8/1997 | |
| WO | WO 98/11907 | 3/1998 | |
| WO | WO 98/51707 | 11/1998 | |
| WO | WO 03/072600 | 9/2003 | |
| WO | WO-2009094006 A2 * | 7/2009 | ............. A61P 37/04 |
| WO | WO 2009/112075 | 9/2009 | |
| WO | WO 2013/036208 | 3/2013 | |
| WO | WO 2013/040142 | 3/2013 | |
| WO | WO 2015/019318 | 2/2015 | |
| WO | WO 2017/134671 | 8/2017 | |

OTHER PUBLICATIONS

NADH dehydrogenase subunit 6, partial (mitochondrion) [Capra hircus], GenBank: AFJ15095.1; 1 page (Year: 2012).*
UniProtKB/Swiss-Prot: Q6END9.1, "Translation initiation factor IF-1, chloroplastic", 2019 (Year: 2019).*
UniProtKB/Swiss-Prot: O19884.1, "50S ribosomal protein L21, chloroplastic", 2019 (Year: 2019).*
E3 ubiquitin-protein ligase HUWE1 [Collichthys lucidus], GenBank: TKS77569.1, 4 pages, 2019 (Year: 2019).*
Communication Pursuant to Rule 164(1) EPC [Supplementary Partial European Search Report] dated Feb. 9, 2017 From the European Patent Office Re. Application No. 14834903.8. (9 Pages).
International Preliminary Report on Patentability dated Aug. 16, 2018 From the International Bureau of WIPO Re. Application No. PCT/IL2017/050132. (12 Pages).

(Continued)

*Primary Examiner* — Lianko G Garyu
(74) *Attorney, Agent, or Firm* — J.A. Lindeman & Co., PLLC

(57) ABSTRACT

The invention provides peptides that can reactivate p53 mutants efficiently and specifically, as well as methods that allow the identification, selection and isolation of such peptides, in a precise, cost and time effective manner. In particular, there are provided mutant p53 reactivating peptides that can restore the native wild type p53 folding, and hence the tumor suppressor activity, to the mutant p53 protein. Such peptides are useful for treating various conditions and diseases in which p53 is mutated.

23 Claims, 26 Drawing Sheets

Specification includes a Sequence Listing.

(56) References Cited

OTHER PUBLICATIONS

International Preliminary Report on Patentability dated Feb. 18, 2016 From the International Bureau of WIPO Re. Application No. PCT/IB2014/063777.
International Search Report and the Written Opinion dated Dec. 1, 2014 From the International Searching Authority Re. Application No. PCT/IB2014/063777.
International Search Report and the Written Opinion dated Apr. 19, 2017 From the International Searching Authority Re. Application No. PCT/IL2017/050132. (20 Pages).
International Search Report and the Written Opinion dated Jun. 19, 2017 From the International Searching Authority Re. Application No. PCT/IL2017/050132. (20 Pages).
Notice Of Allowance dated Sep. 18, 2017 From the US Patent and Trademark Office Re. U.S. Appl. No. 15/015,208. (25 pages).
Notice Of Allowance dated Jan. 31, 2019 From the US Patent and Trademark Office Re. U.S. Appl. No. 15/796,811. (12 pages).
Notice of Reasons for Refusal dated May 16, 2018 From the Japan Patent Office Re. Application No. 2016-532782 and Its Translation Into English. (10 Pages).
Notification of Office Action and Search Report dated May 29, 2019 From the National Intellectual Property Administration of the People's Republic of China Re. Application No. 201480053550.8 and Its Translation Into English. (17 Pages).
Notification Regarding Patentability dated Nov. 20, 2018 From the ROSPATENT, Federal Government Institution, Federal Institute of Industrial Property of the Federal Service for Intellectual Property, Patents and Trademarks of the Russian Federation Re. Application No. 2016106583. (4 Pages).
Office Action dated Dec. 27, 2017 From the Israel Patent Office Re. Application No. 243944 and Its Translation Into English. (6 Pages).
Official Action dated May 4, 2017 From the US Patent and Trademark Office Re. U.S. Appl. No. 15/015,208. (26 pages).
Official Action dated Sep. 18, 2018 From the US Patent and Trademark Office Re. U.S. Appl. No. 15/796,811. (19 Pages).
Request for Examination dated Mar. 29, 2018 From the ROSPATENT, Federal Government Institution, Federal Institute of Industrial Property of the Federal Service for Intellectual Property, Patents and Trademarks of the Russian Federation Re. Application No. 2016106583. (4 Pages).
Restriction Official Action dated Jun. 27, 2019 From the US Patent and Trademark Office Re. U.S. Appl. No. 16/074,086. (8 pages).
Supplementary European Search Report and the European Search Opinion dated Apr. 11, 2017 From the European Patent Office Re. Application No. 14834903.8. (15 Pages).
Translation Dated Jan. 11, 2018 of Notification Regarding Patentability dated Nov. 20, 2018 From the ROSPATENT, Federal Government Institution, Federal Institute of Industrial Property of the Federal Service for Intellectual Property, Patents and Trademarks of the Russian Federation Re. Application No. 2016106583. (2 Pages).
Translation Dated Apr. 24, 2018 of Request for Examination dated Mar. 29, 2018 From the ROSPATENT, Federal Government Institution, Federal Institute of Industrial Property of the Federal Service for Intellectual Property, Patents and Trademarks of the Russian Federation Re. Application No. 2016106583. (2 Pages).
Friedler et al. "A Peptide That Binds and Stabilizes P53 Core Domain: Chaperone Strategy for Rescue of Oncogenic Mutants", Proc. Natl. Acad. Sci. USA, PNAS, XP002257716, 99(2): 937-942, Jan. 22, 2002.
Friedler et al. "Binding of Rad51 and Other Peptide Sequences to A Promiscuous, Highly Electrostatic Binding Site in P53", The Journal of Biological Chemistry, XP055339957, 280(9): 8051-8059, Mar. 4, 2005.
Hupp et al. "Small Peptides Activate the Latent Sequence-Specific DNA Binding Function of P53", Cell, XP002003077, 83(2): 237-245, Oct. 20, 1995. Fig.7.
Issaeva et al. "Rescue of Mutants of the Tumor Suppressor P53 in Cancer Cells by A Designed Peptide", Proc. Natl. Acad. Sci. USA, PNAS, 100(23): 13303-13307, Nov. 11, 2003.
Madhumalar et al. "Dimerization of the Core Domain of the P53 Family: A Computational Study", Cell Cycle, XP002768956, 8(1): 137-148, Published Online Jan. 1, 2009. Abstract, Fig.1.
NCBI "Cell Cycle Checkpoint Control Protein RAD9A", UniProtKB/Swiss-Prot: Database [Online], GenBank Accession No. Q99638.1, Database Accession No. Q99638, 12 P., Mar. 7, 2006.
NCBI "Hypothetical Protein MLP_53520 [Microlunatus Phosphovorus NM-1]", UNIPROT Database [Online], GenBank Accession No. BAK38366.1, Database Accession No. BAK38366, 2 P., May 20, 2011.
Petty et al. "An Induced Fit Mechanism Regulates P53 DNA Binding Kinetics to Confer Sequence Specificity", The EMBO Journal, XP055361536, 30(11): 2167-2189, Published Online Apr. 26, 2011. Abstract, Fig.4.
Qiu et al. "A Small Peptide Derived From P53 Linker Region Can Resume the Apoptotic Activity of P53 by Sequestering iASPP With P53", Cancer Letters, XP029105208, 356(2): 910-917, 2014. Abstract, Fig.1.
Selivanova et al. "Reactivation of Mutant p53 Through Interaction of A C-Terminal Peptide with the Core Domain", Molecular and Cellular Biology,19(5): 3395-3402, May 1, 1999.
Suad et al. "Structural Basis of Restoring Sequence-Specific DNA Binding and Transactivation to Mutant P53 by Suppressor Mutations", Journal of Molecular Biology, XP025846137, 385(1): 249-265, Available Online Oct. 30, 2008. Abstract.
Wright et al. "Factors Governing Loss and Rescue of DNA Binding Upon Single and Double Mutations in the P53 Core Domain", Nucleic Acids Research, XP055361548, 30(7): 1563-1574, Apr. 2002. Abstract, Tables 1-4.
Translation Dated Jan. 26, 2020 of Request for Examination and Search Report dated Dec. 30, 2019 From the Federal Service for Intellectual Property, Federal Government Budgetary Institution, Federal Institute of Industrial Property of the Russian Federation Re. Application No. 2019119609. (2 Pages).
Official Action dated Feb. 26, 2020 From the US Patent and Trademark Office Re. U.S. Appl. No. 16/074,086. (39 pages).
Colloc'h et al. "β-Breakers: An Aperiodic Secondary Structure", Journal of Molecular Biology, 221(2): 603-613, Sep. 20, 1991.
Kim et al. "p53 Requires an Intact C-Terminal Domain for DNA Binding and Transactivation", Journal of Molecular Biology 415(5): 843-854, Feb. 3, 2012.
Li et al. "An All-D Amino Acid Peptide Model of al(IV)531-543 from Type IV Collagen Binds the α3β1 Integrin and Mediates Tumor Cell Adhesion, Spreading, and Motility", Biochemistry, 36, 15404-15410, 1997.
Office Action dated Jan. 14, 2020 From the Israel Patent Office Re. Application No. 268355 and Its Translation Into English. (7 Pages).
Request for Examination and Search Report dated Dec. 30, 2019 From the Federal Service for Intellectual Property, Federal Government Budgetary Institution, Federal Institute of Industrial Property of the Russian Federation Re. Application No. 2019119609. (7 Pages).
Communication Pursuant to Article 94(3) EPC dated May 19, 2020 From the European Patent Office Re. Application No. 17706901.0. (11 Pages).
Bykov et al., (2005) Reactivation of mutant p53 and induction of apoptosis in human tumor cells by maleimide analogs J Biol Chem 280(34): 30384-30391 with erratum.
Cook and Milner (1990) Evidence for allosteric variants of wild-type p53, a tumour suppressor protein. Br J Cancer 61(4): 548-552.
Foster et al., (1999) Pharmacological rescue of mutant p53 conformation and function. Science 286(5449): 2507-2510.
Hainaut et al., (1995) Temperature sensitivity for conformation is an intrinsic property of wild-type p53. Br J Cancer 71(2): 227-231.
Joerger et al., (2004) Crystal structure of a superstable mutant of human p53 core domain. Insights into the mechanism of rescuing oncogenic mutations. J Biol Chem 279(2): 1291-1296.
Kern et al., (1991) Identification of p53 as a sequence-specific DNA-binding protein. Science 252(5013): 1708-1711.
Legros et al., (1994) Mutations in p53 produce a common conformational effect that can be detected with a panel of monoclonal antibodies directed toward the central part of the p53 protein. Oncogene 9(12): 3689-3694. Abstract.

(56) References Cited

OTHER PUBLICATIONS

Levine (1997) p53, the cellular gatekeeper for growth and division. Cell 88(3): 323-331.
McLure and Lee (1999) p53 DNA binding can be modulated by factors that alter the conformational equilibrium. EMBO J 18(3): 763-770.
Michalovitz et al., (1990) Conditional inhibition of transformation and of cell proliferation by a temperature-sensitive mutant of p53. Cell 62(4): 671-680.
Olive et al., (2004) Mutant p53 gain of function in two mouse models of Li-Fraumeni syndrome. Cell 119(6): 847-860.
Peng et al., (2003) Rescue of mutant p53 transcription function by ellipticine. Oncogene 22(29): 4478-4487.
Ravera et al., (1998) Identification of an allosteric binding site on the transcription factor p53 using a phage-displayed peptide library. Oncogene 16(15): 1993-1999.
Rippin et al., (2002) Characterization of the p53-rescue drug CP-31398 in vitro and in living cells. Oncogene 21(14): 2119-2129.
Rivlin et al., (2014) Rescue of embryonic stem cells from cellular transformation by proteomic stabilization of mutant p53 and conversion into WT conformation. Proc Natl Acad Sci U S A 111(19): 7006-7011.
Samuels-Lev et al., (2001) ASPP proteins specifically stimulate the apoptotic function of p53. Mol Cell 8(4): 781-794.
Stephen and Lane (1992) Mutant conformation of p53. Precise epitope mapping using a filamentous phage epitope library. J Mol Biol 225(3): 577-583.
Ventura et al., (2007) Restoration of p53 function leads to tumour regression in vivo. Nature 445(7128): 661-665.
Vojtesek et al., (1995) Conformational changes in p53 analysed using new antibodies to the core DNA binding domain of the protein. Oncogene 10(2): 389-393. Abstract.
Wang et al., (2001) The 'wildtype' conformation of p53: epitope mapping using hybrid proteins Oncogene 20(18): 2318-2324.
Zhang et al., (1994) A temperature-sensitive mutant of human p53. EMBO J 13(11): 2535-2544.
Notice of Reasons for Refusal dated Jun. 23, 2020 From the Japan Patent Office Re. Application No. 2019-125644 and Its Translation Into English. (7 Pages).
Request for Examination and Search Report dated Jun. 25, 2020 From the Federal Government Institution, Federal Institute of Industrial Property of the Federal Service of Intellectual Property, Patents and Trademarks of the Russian Federation, FIPS Re. Application No. 2018131120 and Its Translation of Request for Examination Into English. (9 Pages).
Chumakov "Protein P53 and Its Universal Functions in A Multicellular Organism", Advances in Biological Chemistry, 47(1): 3-52, 2007. English Abstract.
Vilgelm et al. "The Coordinated Interaction of Multifunctional Members of P53 Family Determines Many Key Processes in Multicellular Organisms", Molecular Biology, 45(1): 180-197, 2011. English Abstract.

\* cited by examiner

HindIII    EcoRI    p53RE-Consensus
Biotin-5'-CTGCTG<u>AAGCTT</u>C<u>GAATTC</u>CT<u>*AGACATGCCCAGACATGTCC*</u>TACTGCTGCTGCTGCTGCTGC<u>*GAACATGTCCCAACATGTT*</u>GCTGCTGCTGCTG-3'
p53RE- p21 promoter
FIGURE 4
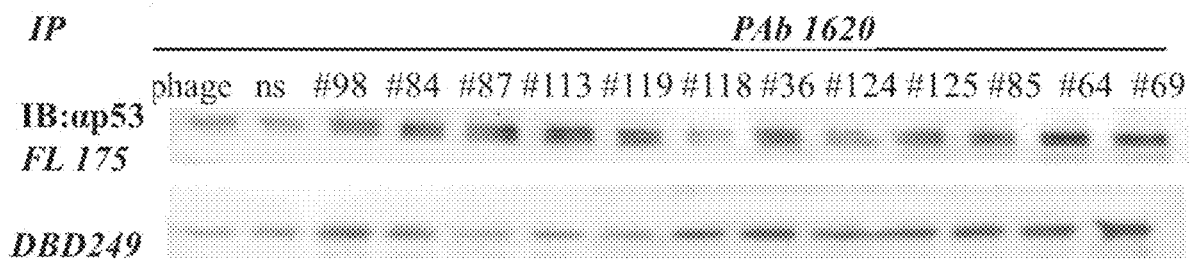
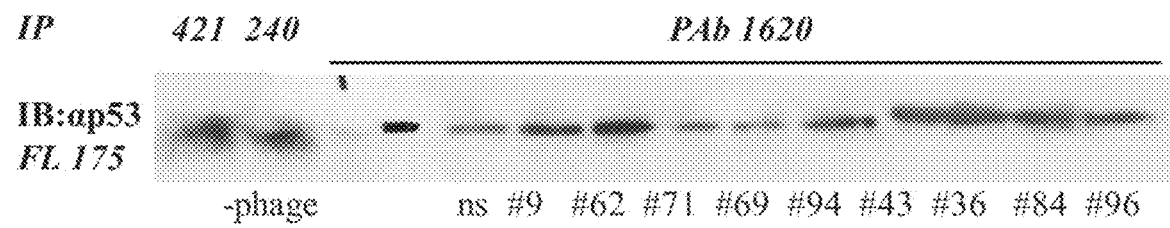
FIGURE 5

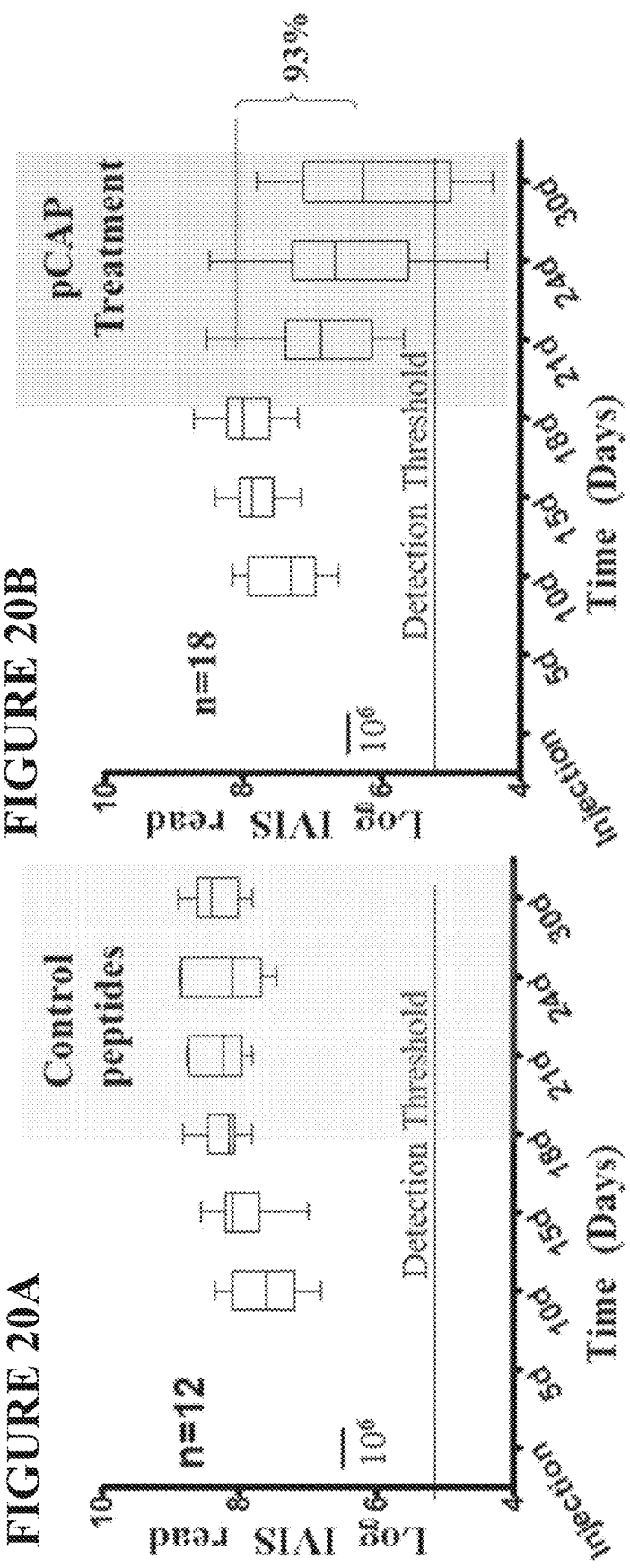
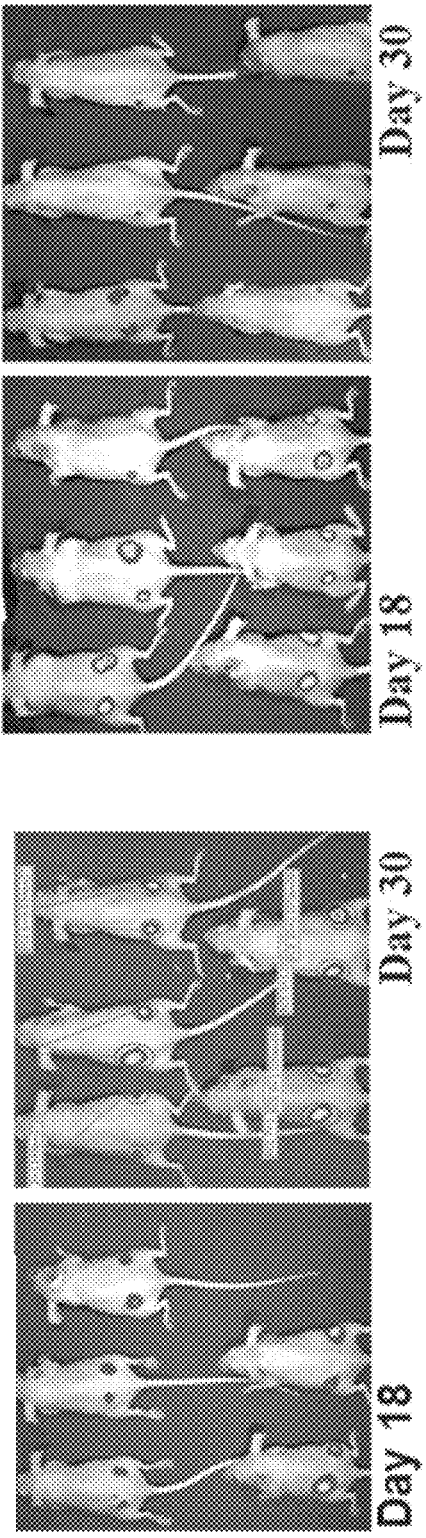
FIGURE 20A
FIGURE 20B
FIGURE 20C
FIGURE 20D

PEPTIDES CAPABLE OF REACTIVATING P53 MUTANTS

RELATED APPLICATIONS

This application is a division of U.S. patent application Ser. No. 16/451,081 filed on Jun. 25, 2019, which is a division of U.S. patent application Ser. No. 15/796,811 filed on Oct. 29, 2017, now U.S. Pat. No. 10,336,789, which is a division of U.S. patent application Ser. No. 15/015,208 filed on Feb. 4, 2016, now U.S. Pat. No. 9,856,289, which is a Continuation In Part of PCT Patent Application No. PCT/IB2014/063777 having International Filing Date of Aug. 7, 2014, which claims the benefit of priority under 35 USC § 119(e) of U.S. Provisional Patent Application No. 61/862,977 filed on Aug. 7, 2013. The contents of the above applications are all incorporated by reference as if fully set forth herein in their entirety.

SEQUENCE LISTING STATEMENT

The ASCII file, entitled 79778SequenceListing.txt, created on Nov. 28, 2019, comprising 91,930 bytes, submitted concurrently with the filing of this application is incorporated herein by reference.

FIELD OF THE INVENTION

The invention relates to peptides capable of reactivating mutant p53 proteins, and use thereof in therapy.

BACKGROUND OF THE INVENTION

Cancer is a leading cause of death in developed countries, and as the average age of the population continues to rise, so do the numbers of diagnosed cases and economic implications. Cancer is not a single disease, but rather a group of more than 200 diseases characterized by uncontrolled growth and spread of abnormal cells. Cancer is a highly heterogeneous disease with major molecular differences in the expression and distribution of tumor cell surface markers even among patients with the same type and grade of cancer. Moreover, cellular mutations tend to accumulate as cancer progresses, further increasing tumor heterogeneity. Most tumor cells exhibit genomic instability with an increased expression of oncogenes and inactivation of tumor suppressor genes.

The p53 gene is considered to be the most important tumor suppressor gene, which acts as a major barrier against cancer progression. The p53 protein responds to various types of cellular stress, and triggers cell cycle arrest, apoptosis, or senescence (Levine, J. A., p53, the cellular gatekeeper for growth and division. Cell, 1997. 88: p. 323-331). This is achieved by transcriptional transactivation of specific target genes carrying p53 DNA binding motifs. It is widely agreed that the p53 pathway is impaired in almost all human cancers. Mutation of p53 is viewed as a critical step in malignant transformation process and over 50% of cancer cases carry mutations in their p53 genes. Most of these mutations are missense point mutations that target the DNA-binding core domain (DBD) of p53, thereby abolishing specific DNA binding of p53 to its target site. These mutations prevent p53-dependent transcription and consequently p53-mediated tumor suppression. The exceptionally high frequency of p53 mutations in human tumors of diverse types makes p53 unique among genes involved in tumor development, rendering mutated p53 (Mut-p53) an attractive target for novel cancer therapies.

Structural studies have revealed that the tumor-derived missense mutations in the DBD of p53 produce a common effect: destabilization of DBD folding at physiological temperature (Joerger, A. C., M. D. Allen, and A. R. Fersht, *Crystal structure of a superstable mutant of human p53 core domain. Insights into the mechanism of rescuing oncogenic mutations.* J Biol Chem, 2004. 279(2): p. 1291-6). This destabilization may be reversible, since some mutants can revert to wild-type conformation and bind DNA at reduced temperatures. Thus, most mutations of p53 destabilize p53 protein folding, causing partial denaturation at physiological temperature.

Mutant p53 proteins accumulate at high levels in tumor cells, mainly due to their inability to upregulate the expression of p53's own destructor Mdm2. Moreover, many p53 activating stress signals (like hypoxia, genomic instability and oncogene expression) are constitutively induced in cancer cells. Therefore, reactivation of Mut-p53 is expected to exert major anti-tumor effects. Furthermore, it has been shown in a mouse model that restoration of p53 functions is well tolerated in normal tissues and produces no visible toxic effects (Ventura, A., et al., Restoration of p53 function leads to tumour regression in vivo. Nature, 2007. 445(7128): p. 661-5).

p53 has evolved to be dynamic and conformationally unstable. The lack of a rigid structure of the p53 protein may result in a number of p53 conformers displaying different activity, depending on the type of stress and cellular context. In a simplified model, p53 can assume either a wild type, active conformation or a mutant, misfolded, inactive conformation. The two conformational states of p53 can be distinguished by two specific monoclonal antibodies, PAb240 and PAb1620 (Wang, P. L., F. Salt, and G. Winter, *The 'wild type' conformation of p53: epitope mapping using hybrid proteins.* Oncogene, 2001. 20(18): p. 2318-24). PAb240 binds to residues 212-217 in the DBD of p53. This region is inaccessible to the antibody (Ab) in the wild type (WT) conformation. However, in denatured or mutant p53, it is exposed (Vojtesek, B., et al., *Conformational changes in p53 analyzed using new antibodies to the core DNA binding domain of the protein.* Oncogene, 1995. 10(2): p. 389-93). PAb1620 recognizes a conformational, nonlinear epitope in the DBD, composed of two distinct regions of p53 and including residues R156, L206, R209 and N210 (Cook, A. and J. Milner, *Evidence for allosteric variants of wild-type p53, a tumor suppressor protein.* Br J Cancer, 1990. 61(4): p. 548-52). In the WT conformation the protein is folded in a way that holds the loops in close proximity to each other (Ravera, M. W., et al., *Identification of an allosteric binding site on the transcription factor p53 using a phage-displayed peptide library.* Oncogene, 1998. 16(15): p. 1993-9), forming the complete epitope recognized by PAb1620. When p53 protein is misfolded (as a result of mutation, temperature, denaturation or the like), these two loops move farther away, the epitope is destroyed and therefore the mutant conformation is PAb1620 negative. It has been shown that p53 is a conformationally flexible protein. However, the defect in folding in such mutants is not irreversible: some p53 mutants maintain residual DNA-binding ability, mutants that fail to bind DNA at 37° C. can bind at sub-physiological temperatures (32° C. or 25° C.), and activate transcription from a p53-responsive promoter at 26° C. In addition, the isolated DBD's of mutant proteins R245S, R282W, V143A and others were shown to have residual (30-60%) DNA-binding activity at 20° C.

Structural studies show that the extent of misfolding differs among mutants; however, there is no defined alternative fold but rather a partial denaturation. This suggests that a "small molecule" approach to reverse the effect of p53 mutation on folding could be applicable to a wide range of mutant forms. Another important prediction from structural studies is that a ligand that binds to the properly folded fraction of the protein is expected to shift the equilibrium towards the native fold according to the law of mass action.

p53 was first identified as a cellular protein interacting with the SV40 large T antigen (LT). The interface area between LT and p53 is large: a total of 23 LT residues and 19 p53 residues are either buried in this interface or are found to directly participate in the interactions between these two molecules. p53/DNA interaction residues are adjacent and overlapping with the p53/LT interface. The binding of LT to these p53 residues can effectively shield the entire DNA-binding surface of p53, including the three most commonly mutated p53 residues in cancer: R273, R248, and G245. This inhibits transactivation of p53-dependent promoters. Since the p53/LT interface involves several different p53 regions and loops, the p53 protein has to be folded correctly to align amino acids in the correct location and orientation to form the binding context to LT. Therefore, p53 binding to LT can serve as a marker to the p53 conformational state.

Several correctional approaches were attempted in the p53 conformation field. Proof of principle for conformation stabilizing peptides was provided by Friedler and colleagues (Friedler, A., et al., *A peptide that binds and stabilizes p53 core domain: chaperone strategy for rescue of oncogenic mutants*. Proc. Natl. Acad. Sci. USA, 2002. 99(2): p. 937-42). A nine-residue peptide, CDB3, was designed based on the crystal structure of the complex between the p53 DBD and ASPP (Samuels-Lev, Y., et al., *ASPP proteins specifically stimulate the apoptotic function of p53*. Mol. Cell, 2001. 8(4): p. 781-94). This peptide was shown to bind Mut-p53 and act as a chaperone, shifting equilibrium towards the WT conformation, as indicated by increased reactivity to PAb1620. However, the biological effects of CDB3 (Issaeva, N., et al., *Rescue of mutants of the tumor suppressor p53 in cancer cells by a designed peptide*. Proc. Natl. Acad. Sci. USA, 2003. 100(23): p. 13303-7) are only partial since the conformation of the Mut-p53/CDB3 complex is in an intermediate state between WT and mutant.

Small molecule compounds targeting Mut-p53 have been identified using either protein-based or cell-based assays (Peng, Y., et al., *Rescue of mutant p53 transcription function by ellipticine*. Oncogene, 2003. 22(29): p. 4478-87). CP-31398 was identified by screening for molecules that protect the isolated p53 DBD from thermal denaturation, as assessed by maintenance of PAb1620 reactivity upon protein heating (Foster, B. A., et al., *Pharmacological rescue of mutant p53 conformation and function*. Science, 1999. 286 (5449): p. 2507-10). The mechanism of action of CP-31398 remains unclear. NMR studies failed to detect any binding of CP-31398 to the p53 DBD (Rippin, T. M., et al., *Characterization of the p53-rescue drug CP-31398 in vitro and in living cells*. Oncogene, 2002. 21(14): p. 2119-29). CP-31398 affects gene expression and induces cell death both in a p53-dependent and independent manner. Thus, it appears that CP-3138 has other cellular targets than p53 that may account for its cellular toxicity.

Two other small molecules that rescue p53 function in living cancer cells, PRIMA-1 and MIRA-1, were discovered by using cell-based screening assays. PRIMA-1 and MIRA-1 have similar activity profiles (Bykov, V. J., et al., *Reactivation of mutant p53 and induction of apoptosis in human tumor cells by maleimide analogs*. J Biol Chem, 2005. 280(34): p. 30384-91), but are structurally unrelated. So far, direct binding to Mut-p53 has not been demonstrated. It seems that the mechanism may involve the JNK pathway.

In the field of anti-cancer drug discovery and design, two different and at times complementary, strategies may be employed. Rational design, which uses biological, mathematical or computational tools to design molecules for a certain purpose, has been used in the case of CDB3. However, since the interactions between different proteins and their environment are complex, this is extremely difficult and often yields molecules with a modest biological impact. The second strategy is high throughput screening of molecule libraries, to isolate compounds with the best traits. Such screening can employ either chemical, small molecule libraries or peptide libraries. Most drugs available to date are small molecules because of their ability to cross cell membranes. Chemical libraries usually consistent of $10^4$-$10^5$ different compounds; screening such a library requires functional assessment of individual molecules, making it impractical for a small laboratory since it calls for large investments in robotics and/or manpower. Peptide display libraries are much larger. Selection of peptides is based on binding of peptides (and hence the phage), to an immobilized target, elution and amplification and then identification by sequencing.

In the phage display procedure, enrichment of phages that present a peptide is achieved by affinity selection of a phage library on immobilized target. In this "panning" process, binding phages are captured whereas nonbinding ones are washed off. In the next step, the bound phages are eluted and amplified by reinfection of *E. coli* cells. The amplified phage population can, in turn, be subjected to the next round of panning. The selection from phage display libraries is a cyclic process of selective enrichment and amplification. After several rounds of selection, phages are diluted in a way that allows isolation of individual phage clones. Individual clones are then picked, cultivated in *E-coli*, phage DNA is extracted and then sent to sequencing. Recently developed next-generation sequencing technologies are greatly increasing the effectiveness of phage display, allowing analysis of the entire selected peptide repertoire, with fewer selection rounds performed.

Phage display offers several important advantages over other screening methods; the major advantage of phage display is the diversity of sequences that can be represented, enabling finding molecules with very high affinity and biological effect. Once a consensus peptide sequence is found, it can be further improved by either directed evolution techniques or rational design.

Nevertheless, there remains an unmet need in the art for agents that can reactivate p53 mutant proteins efficiently and specifically. Such specific and efficient agents can further be used as an effective mean for treating various conditions in which p53 is mutated, in particular, by restoring the native folding and activity of the mutant p53 proteins.

SUMMARY OF THE INVENTION

The present invention provides highly potent peptides and modified peptide agents that can efficiently reactivate p53 conformational mutants, ideally by changing the mutant p53 proteins conformation and/or activity to resemble that of a wild type, functional p53 protein. The present invention thus provides peptides and their use in treating mutant p53 related conditions, where activation of present yet conformationally defective p53 proteins may be beneficial.

The present invention is based on the suprising identification of highly potent peptide and peptide-based agents that can efficiently reactivate p53 conformational mutants, more efficiently than previously known peptides identified for this use. The present invention thus provides, in an aspect, a recombinant or synthetic peptide consisting of the amino-acid sequence set forth in any one of SEQ ID NOs:321-286.

The present invention further provides, in another aspect, a recombinant or synthetic peptide comprising the amino-acid sequence set forth in any one of SEQ ID NOs:321-286, wherein said peptide at least partially reactivates a mutant p53 protein.

The present invention further provides, in yet another aspect, a recombinant or synthetic peptide comprising the amino-acid sequence set forth in any one of SEQ ID NOs: 302-321, 312-321 and 316-321, wherein said peptide at least partially reactivates a mutant p53 protein. Each possibility represents a separate embodiment of the invention.

The present invention further provides, in yet another aspect, a recombinant or synthetic peptide comprising the amino-acid sequence set forth in any one of SEQ ID NOs: 316-321, wherein said peptide at least partially reactivates a mutant p53 protein. Each possibility represents a separate embodiment of the invention.

The present invention further provides, in yet another aspect, a recombinant or synthetic peptide comprising a consensus motif of the amino-acid sequence set forth in any one of SEQ ID NOs: 314, 268, 282, 328, 376, 298, 377, 378, 253, 20, 379, 302, 275, 380, 273, 381, 280 or 382, wherein said peptide at least partially reactivates a mutant p53 protein. According to a specific embodiment the consensus motif is as set forth in SEQ ID NO: 314.

In certain embodiments, the peptide consists of the amino-acid sequence set forth in any one of SEQ ID NO:321, SEQ ID NO:314, SEQ ID NO:313, SEQ ID NO:310 or SEQ ID NO:307. Each possibility represents a separate embodiment of the invention. In certain embodiments, the peptide described above consists the amino-acid sequence set forth in any one of SEQ ID NOs:321-302. Each possibility represents a separate embodiment of the invention. In certain embodiments, the peptide described above consists the amino-acid sequence set forth in any one of SEQ ID NOs:321-312. Each possibility represents a separate embodiment of the invention. In certain embodiments, the peptide described above consists the amino-acid sequence set forth in any one of SEQ ID NOs:321-316. Each possibility represents a separate embodiment of the invention. In certain embodiments, the peptide described above consists the amino-acid sequence set forth in any one of SEQ ID NOs: 302-321, 312-321 and 316-321, wherein said peptide at least partially reactivates a mutant p53 protein. Each possibility represents a separate embodiment of the invention.

In certain embodiments, the peptide described above consists the amino-acid sequence set forth in any one of SEQ ID NOs: 302-321, 312-321 and 316-321, wherein said peptide at least partially reactivates a mutant p53 protein. Each possibility represents a separate embodiment of the invention.

In certain embodiments, the peptide comprises of the amino-acid sequence set forth in any one of SEQ ID NO:321, SEQ ID NO:314, SEQ ID NO:313, SEQ ID NO:310 or SEQ ID NO:307. Each possibility represents a separate embodiment of the invention. In certain embodiments, the peptide described above comprises the amino-acid sequence set forth in any one of SEQ ID NOs:321-302. In certain embodiments, the peptide described above comprises the amino-acid sequence set forth in any one of SEQ ID NOs:321-312. Each possibility represents a separate embodiment of the invention. In certain embodiments, the peptide described above comprises the amino-acid sequence set forth in any one of SEQ ID NOs:321-316. Each possibility represents a separate embodiment of the invention. In certain embodiments, the peptide described above comprises the amino-acid sequence set forth in any one of SEQ ID NOs: 307, 310, 313, 314 and 321. Each possibility represents a separate embodiment of the invention.

In certain embodiments, the peptide described above comprises the amino-acid sequence set forth in any one of SEQ ID NOs: 302-321, 312-321 and 316-321. Each possibility represents a separate embodiment of the invention.

In certain embodiments, the peptide is conjugated to at least one cell penetrating moiety (lipid and/or proteinaceous). The cell penetrating moiety may be conjugated N-terminally to the peptide, C terminally to the peptide, anywhere in the backbone of the peptide or to a combination of same. Each possibility represents a separate embodiment of the invention.

In certain embodiments, the cell penetrating moiety is selected from the group consisting of a fatty acid moiety, a protennacious moiety and a combination of same.

In certain embodiments, the peptide is conjugated to at least one fatty acid moiety. In certain embodiments, the fatty acid is selected from the group consisting of myristic acid, lauric acid, palmitic acid and stearic acid. Each possibility represents a separate embodiment of the invention. In certain embodiments, the fatty acid is a myristoyl fatty acid.

In certain embodiments, the peptide is conjugated to at least one proteinacious moiety. In certain embodiments, the proteinaceous moiety is a poly-cationic amino acid e.g., poly-Lysine and/or poly-Arginine e.g., having 2-15 arginine residues e.g., conjugated to at least one end of the peptide (N and/or C). Each possibility represents a separate embodiment of the invention. According to a specific embodiment, the protenaceious moiety comprises at least one positively charged amino acid at either of the peptide's termini i.e., N and/or C terminus. Each possibility represents a separate embodiment of the invention. For instance, at least one positively charged (e.g., R, RR, RRR) can be conjugated to the N-terminus or C-terminus of SEQ ID NO: 314. Each possibility represents a separate embodiment of the invention.

In certain embodiments, the peptide at least partially changes the conformation of said mutant p53 protein to a conformation of a wild-type (WT) p53 protein.

In certain embodiments, the peptide at least partially changes the conformation of said mutant p53 protein such that said mutant p53 protein is recognized by a monoclonal antibody directed against a WT p53 protein. In certain embodiments, the monoclonal antibody is Ab1620.

In certain embodiments, the peptide at least partially restores the activity of said mutant p53 protein to the activity of a WT p53 protein.

In certain embodiments, the activity is reducing viability of cells expressing said mutant p53 protein. In certain embodiments, the activity is promoting apoptosis of cells expressing said mutant p53 protein. In certain embodiments, the activity is activating pro-apoptotic genes of cells expressing said mutant p53 protein. In certain embodiments, the pro-apoptotic genes are selected from the group consisting of CD95, Bax, DR4, DR5, PUMA, NOXA, Bid, 53AIP1 and PERP. Each possibility represents a separate embodiment of the invention.

In certain embodiments, the activity is binding to a p53 consensus DNA binding element in cells expressing said mutant p53 protein. In certain embodiments, the consensus DNA binding element comprises the amino acid sequence set forth in SEQ ID NO:339.

In certain embodiments, the binding results in at least partial activation of an endogenous p53 target gene. In certain embodiments, the endogenous target gene is selected from the group consisting of p21, MDM2 and PUMA. Each possibility represents a separate embodiment of the invention.

In certain embodiments, the mutant p53 protein is of a different conformation than a WT p53 protein. In certain embodiments, the mutant p53 protein is at least partly inactive compared to a WT p53 protein.

In certain embodiments, the mutant p53 protein is not recognized by a monoclonal antibody directed against a WT p53 protein. In certain embodiments, the mutant p53 protein, upon binding to said peptide, is recognized by a monoclonal antibody directed against a WT p53 protein. In certain embodiments, the monoclonal antibody is Ab1620.

In certain embodiments, the mutant p53 protein comprises a mutation selected from the group consisting of R175H, V143A, R249S, R273H, R280K, P309S, P151S, P151H, C176S, C176F, H179L, Q192R, R213Q, Y220C, Y220D, R245S, R282W, D281G, S241F, C242R, R248Q, R248W, D281G, R273C and V274F. Each possibility represents a separate embodiment of the invention.

In certain embodiments, the peptide comprises the consensus motif set forth in SEQ ID NO:314. In certain embodiments, the peptide comprises the amino-acid sequence set forth in any one of SEQ ID NO:321, SEQ ID NO:314, SEQ ID NO:313, SEQ ID NO:310 or SEQ ID NO:307. Each possibility represents a separate embodiment of the invention. In certain embodiments, the peptide consists of the amino-acid sequence set forth in any one of SEQ ID NO:321, SEQ ID NO:314, SEQ ID NO:313, SEQ ID NO:310 or SEQ ID NO:307. Each possibility represents a separate embodiment of the invention. In certain embodiments, the peptide comprises the amino-acid sequence set forth in any one of SEQ ID NOs:268, 282, 328, 376, 298, 377, 378, 253, 20, 379, 302, 275, 380, 273, 381, 280 or 382. Each possibility represents a separate embodiment of the invention. In certain embodiments, the peptide comprises the amino-acid sequence set forth in any one of SEQ ID NOs:379, 302, 275, 380, 273, 381, 280 or 382. Each possibility represents a separate embodiment of the invention. In certain embodiments, the peptide comprises the amino-acid sequence set forth in any one of SEQ ID NOs: SEQ ID NOs:302, 275, 380, 273, 381, 280 or 382. Each possibility represents a separate embodiment of the invention. In certain embodiments, the peptide described above comprises the amino-acid sequence set forth in any one of SEQ ID NOs: 307, 310, 313, 314 and 321. Each possibility represents a separate embodiment of the invention. In certain embodiments, the peptide described above comprises the amino-acid sequence set forth in any one of SEQ ID NOs: 302-321, 312-321 and 316-321. Each possibility represents a separate embodiment of the invention.

The present invention further provides, in another aspect, an expression vector, capable of expressing the peptides described above.

The present invention further provides, in yet another aspect, a pharmaceutical composition, comprising the peptides described above.

The present invention further provides, in yet another aspect, a pharmaceutical composition, comprising the expression vector described above.

In an aspect, the pharmaceutical compositions described above are for use in treating a disease, disorder or condition associated with a mutant p53 protein.

In some embodiments, the disease is cancer. In some embodiments, the cancer is selected from the group consisting of breast cancer, colon cancer and lung cancer. Each possibility represents a separate embodiment of the invention.

In some embodiments, the cells of the cancer express the mutant p53 protein.

The present invention further provides, in another aspect, a method of treating a disease, disorder or condition associated with a mutant p53 protein, comprising the step of administering a therapeutically effective amount of the pharmaceutical compositions described above to a subject in need thereof, thereby treating said disease, disorder or condition.

The present invention further provides, in yet another aspect, a kit comprising the pharmaceutical compositions described above.

In an aspect, the kit described above is for use in treating a disease, disorder or condition associated with a mutant p53 protein.

Other objects, features and advantages of the present invention will become clear from the following description and drawings.

BRIEF DESCRIPTION OF THE SEVERAL VIEWS OF THE DRAWINGS

FIG. 4 is the sequence of the oligonucleotide used as the binding element for p53 proteins. The oligonucleotide (SEQ ID NO:61) comprises a 5' biotin label, followed by a HindIII recognition site (underlined), followed by EcoRI recognition site (underlined), followed by a p53 consensus binding element (underlined, p53 binding site is composed of two half sites, each half site binds a dimmer of p53 and together this site forms a complex of DNA and p53 tetramer), followed by two copies of the p53 recognition element of the p21 promoter (underlined). For binding experiments, this oligonucleotide was annealed to a complementary oligonucleotide to form a double stranded (ds) oligonucleotide.

FIG. 5 is a pictograms of western blot analysis of IP experiments, in which beads that were covalently cross-linked to a PAb1620 antibody were incubated with purified mutant p53 R175H in the presence of phage obtained by phage display selection with either full length Mut-p53 R175H (175) or recombinant Mut-p53 R249S (249 DBD), with prior pre-clearing step performed by incubation of the phage pool with PAb1620 beads. Non selected phage (NS) were used as control. Incubation was done for 3 hours at 4° C. Bound p53 in the immunoprecipitate was analyzed by western blot analysis using antibody against p53 (αp53). Non selected phage (NS) were used as control. "In" stands for 10% of the IP input material that was loaded directly on the gel. Immunoprecipitation with the PAb-421 was used as a positive control and as standard for immunoprecipitated p53, since this antibody binds p53 epitope at the C-terminus regardless of p53 protein conformation.

FIG. 15A: MDA-MB-231 cells expressing Mut-p53 with a mutation at position 280 of the DBD. FIG. 15B: SKBR3 cells expressing Mut-p53 with a mutation at position 175 within the DBD. The bar graphs in FIGS. 15A and 15B show for each tested peptide the optical density reads at 595 nm, reflecting the number of cells in the plate after treatment, normalized to the non-treated (NT) samples.

FIG. 16 illustrates the relative fold induction of transcription of the tested genes in the various samples relative to their transcription level in non-treated cells. GAPDH mRNA was measured in parallel as a control.

FIG. 18A shows a logarithmic scale graph demonstrating the luciferase readings in each tumor as a function of time after initiation of treatment (peptide injection). FIG. 18B shows live imaging images of mice (7-10), at the beginning of treatment. FIG. 18C shows live imaging images of treated mice (7-9) at day 35, when the experiment was terminated. Mouse 10 had to be sacrificed after 28 days due to large tumor size.

FIG. 19A shows a logarithmic scale graph demonstrating the luciferase readings in each tumor as a function of time after initiation of treatment (peptide injection). FIG. 19B shows live imaging images of mice 1-6 at the beginning of treatment. FIG. 19C shows live imaging images of treated mice 1-6 at day 35, when the experiment was terminated. Two of the tumors (mouse 1 and mouse 4) showed a partial response to the treatment, as measured by a decrease of 50% and 65%, respectively, in the luciferase signal after 35 days. Mice 2 and 5 showed a complete response, reaching bioluminescence readings that are as low as or close to the background threshold detection levels of the IVIS system ($5 \times 10^6$ photons) even after 21 days of treatment. Following cessation of the treatment after 35 days, mice numbers 2 and 5 were kept alive and monitored for an additional 21 days; no reappearance of tumors was detected either visually or by live imaging.

FIGS. 20A, 20B, 20C and 20D illustrate the in vivo effect of the indicated peptides in a mouse xenograft model. MDA-MB-231 cells expressing endogenous mutant p53 and stably expressing luciferase were injected into the left hip of CD1 nude/nude mice. When tumors reached visible size, bioluminescence (indicative of the number of cancer cells) was measured with the IVIS200 system. The mice were then treated by intra-tumoral injection, three times a week, with either a mixture of 3 control peptides that showed no phenotype in vitro (pCAPs 76, 77 and 12; 2 ug of each peptide) or a mixture of 3 test peptides that exhibited mutant p53-reactivating ability (pCAPs 159, 155 and 174; 2 ug of each peptide). FIGS. 20A and 20B show a logarithmic scale graph demonstrating the average luciferase readings in tumors as a function of time, before (until day 18) and after initiation of treatment (peptide injection). FIGS. 20C and 20D show live imaging images of mice, at the beginning of treatment (day 18, left) and 12 days into treatment (day 30, right). 40% of mice showed a complete response, reaching bioluminescence readings that are as low as or close to the background threshold detection levels of the IVIS system ($5 \times 10^6$ photons).

FIGS. 21A, 21B and 21C show a logarithmic scale graph demonstrating the average luciferase readings in tumors as a function of time, before (until day 0) and after initiation of treatment (peptide injection). FIGS. 21D and 21E shows box plot of tumors volume and tumor weight, respectively. As seen in FIGS. 21D and 21E tumors extracted from mice treated with either peptide mix or the pCAP-325 single peptide, are significantly smaller in size and weight compared to tumors extracted from mice treated with the control peptides (p-value <0.05).

DETAILED DESCRIPTION OF THE INVENTION

Figure 1A:
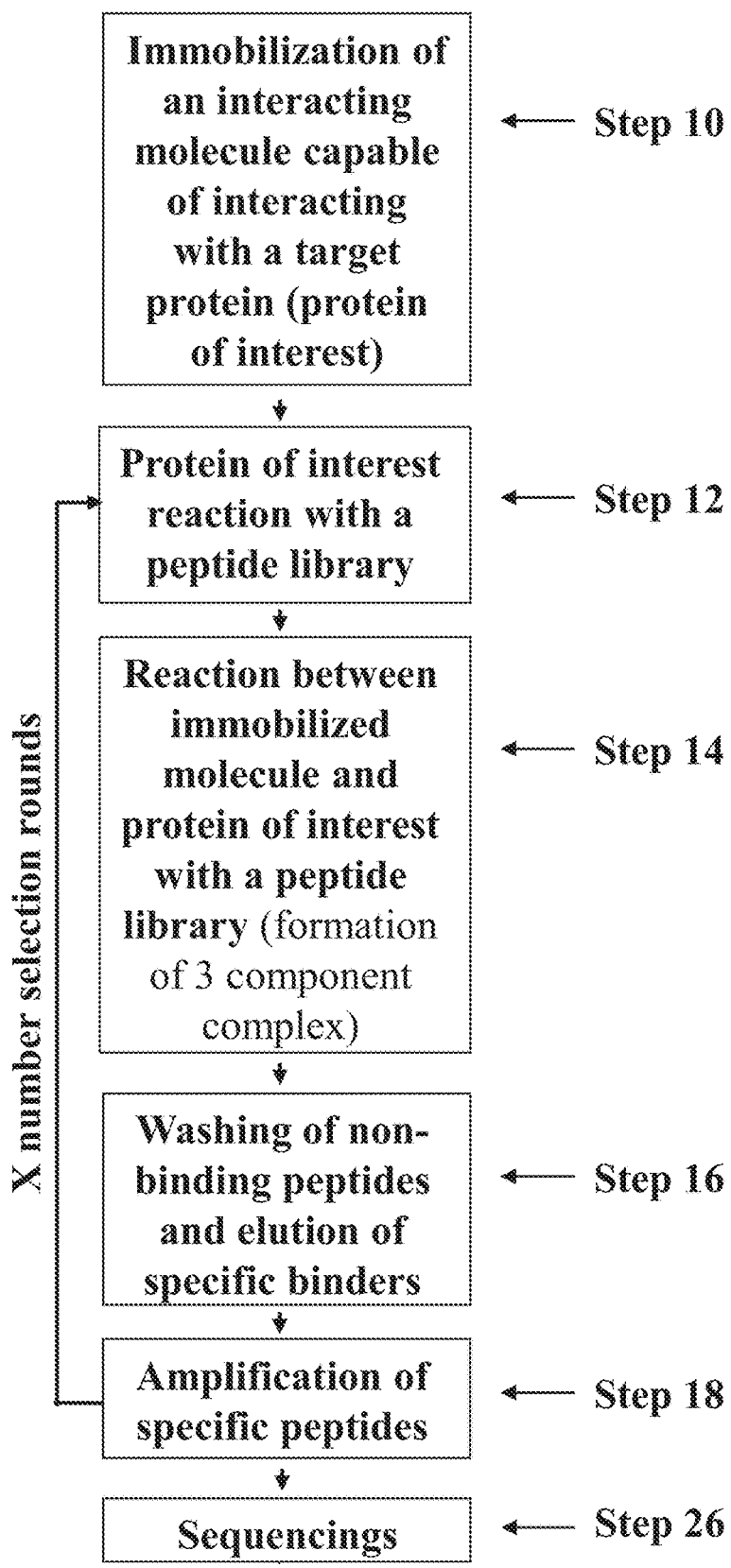
FIG. 1A is a block diagram of steps in a screening method, which provides for selection of binding partners (such as peptides), in a non-direct way, through their effect on conformation or structure of a target molecule.

The present invention provides highly potent peptides and modified peptide agents that can efficiently reactivate p53 conformational mutants, ideally by changing the mutant p53 proteins conformation and/or activity to resemble that of a wild type, functional p53 protein. The present invention thus provides peptides and their use in treating mutant p53 related conditions, where activation of present yet conformationally defective p53 proteins may be beneficial.

The present invention is based on the suprising identification of highly potent peptide and peptide-based agents that can efficiently reactivate p53 conformational mutants, more efficiently than previously known peptides identified for this use.

The present invention provides agents capable of at least partly elevating the anti-cancer and/or pro-apoptotic effect of mutant p53 proteins, and their use in treatment of any disease or condition caused by, or correlated with, a conformationally-aberrant p53 protein. Without being bound to any mechanism or theory, it is speculated that the conformational change in mutant p53 proteins upon binding to the agents provided by the present invention brings them closer to a 3D conformation of a wild type p53 protein, and thus at least partly restores at least part of the functions of a wild type p53 protein to the mutant p53 proteins.

More specifically, the present invention provides, in an aspect, a recombinant or synthetic peptide consisting of the amino-acid sequence set forth in any one of SEQ ID NOs:321-286.

The present invention further provides, in another aspect, a recombinant or synthetic peptide comprising the amino-acid sequence set forth in any one of SEQ ID NOs:321-286, wherein the peptide at least partially reactivates a mutant p53 protein.

The present invention further provides, in yet another aspect, a recombinant or synthetic peptide comprising a consensus motif of the amino-acid sequence set forth in any one of SEQ ID NOs:314, 268, 282, 328, 376, 298, 377, 378, 253, 20, 379, 302, 275, 380, 273, 381, 280 or 382, wherein the peptide at least partially reactivates a mutant p53 protein.

In certain embodiments, the peptide consists of the amino-acid sequence set forth in any one of SEQ ID NO:321, SEQ ID NO:314, SEQ ID NO:313, SEQ ID NO:310 or SEQ ID NO:307. Each possibility represents a separate embodiment of the invention. In certain embodiments, the peptide described above consists the amino-acid sequence set forth in any one of SEQ ID NOs:321-302. Each possibility represents a separate embodiment of the invention. In certain embodiments, the peptide described above consists the amino-acid sequence set forth in any one of SEQ ID NOs:321-312. Each possibility represents a separate embodiment of the invention. In certain embodiments, the peptide described above consists the amino-acid sequence set forth in any one of SEQ ID NOs:321-316. Each possibility represents a separate embodiment of the invention.

In certain embodiments, the peptide comprises of the amino-acid sequence set forth in any one of SEQ ID NO:321, SEQ ID NO:314, SEQ ID NO:313, SEQ ID NO:310 or SEQ ID NO:307. Each possibility represents a separate embodiment of the invention. In certain embodiments, the peptide described above comprises the amino-acid sequence set forth in any one of SEQ ID NOs:321-302. In certain embodiments, the peptide described above comprises the amino-acid sequence set forth in any one of SEQ ID NOs:321-312. Each possibility represents a separate embodiment of the invention. In certain embodiments, the peptide described above comprises the amino-acid sequence set forth in any one of SEQ ID NOs:321-316. Each possibility represents a separate embodiment of the invention.

The present invention further provides, in yet another aspect, a recombinant or synthetic peptide comprising the amino-acid sequence set forth in any one of SEQ ID NOs: 307, 310, 313, 314 and 321, wherein said peptide at least partially reactivates a mutant p53 protein.

The present invention further provides, in yet another aspect, a recombinant or synthetic peptide comprising the amino-acid sequence set forth in any one of SEQ ID NOs: 312, 314, 315, 316, 318 and 321, wherein said peptide at least partially reactivates a mutant p53 protein. Each possibility represents a separate embodiment of the invention.

According to a specific embodiment the consensus motif is as set forth in SEQ ID NO: 314.

In certain embodiments, the peptide consists of the amino-acid sequence set forth in any one of SEQ ID NOs: 307, 310, 313, 314 and 321, wherein said peptide at least partially reactivates a mutant p53 protein. Each possibility represents a separate embodiment of the invention.

In certain embodiments, the peptide consists of the amino-acid sequence set forth in any one of SEQ ID NOs: 312, 314, 315, 316, 318 and 321, wherein said peptide at least partially reactivates a mutant p53 protein. Each possibility represents a separate embodiment of the invention.

In certain embodiments, the peptide the peptide comprises SEQ ID NOs: 307, 310, 313, 314 and 321. Each possibility represents a separate embodiment of the invention.

In certain embodiments, the peptide comprises the amino-acid sequence set forth in SEQ ID NOs:321-316. Each possibility represents a separate embodiment of the invention.

In certain embodiments, the peptide is conjugated to at least one fatty acid moiety. In certain embodiments, the fatty acid is selected from the group consisting of myristic acid, lauric acid, palmitic acid and stearic acid. Each possibility represents a separate embodiment of the invention. In certain embodiments, the fatty acid is a myristoyl fatty acid.

In certain embodiments, the peptide at least partially changes the conformation of the mutant p53 protein to a conformation of a wild-type (WT) p53 protein.

Known in the art are antibodies that specifically recognize only wild type p53 proteins. Such antibodies are highly useful in determining whether a certain p53 protein, either wild type or mutant, holds the conformation of a wild type, functional p53 protein. Thus, in certain embodiments, the peptide at least partially changes the conformation of the mutant p53 protein such that the mutant p53 protein is recognized by a monoclonal antibody exclusively directed against a WT p53 protein or against a p53 protein holding a WT p53 protein conformation. In certain embodiments, the monoclonal antibody is Ab1620.

It should be understood that since p53 is expressed from both alleles, the overall content of intra-cellular p53 can be either wild-type (wt/wt), mixture of wt and mutant p53 (wt/mut) or mutant p53 only (when both alleles are mutated (mut/mut), or one allele is deleted (mut/−)). In cancer, the situation is often wt/mut, mut/mut or mut/−. Since p53 acts as a tetramer, mutant p53 proteins may abrogate the activity of wild type p53 proteins, which may exist in the cancer's cells. Therefore, the peptides provided by the present invention are particularly useful in treating cancers in which increasing the level of wild type p53 proteins is not fruitful.

In certain embodiments, the peptide at least partially restores the activity of the mutant p53 protein to at least one of the activities of a WT p53 protein.

As used herein the term "reducing" refers to statistically significantly decreasing a certain phenotype by at least about 10%, 20%, 30%, 40%, 50%, 60%, 70%75%, 80%, 95% or even 100% as compared to a control (e.g., same cell/animal system treated with a control vehicle or non-treated at all) under the same assay conditions.

As used herein the term "increasing" or "improving" refers to statistically significantly increasing a certain phenotype by at least about 10%, 20%, 30%, 40%, 50%, 60%, 70%75%, 80%, 95% or even 100% as compared to a control (e.g., same cell/animal system treated with a control vehicle or non-treated at all) under the same assay conditions.

In certain embodiments, the activity is reducing viability of cells expressing the mutant p53 protein. In certain embodiments, the activity is promoting apoptosis of cells expressing the mutant p53 protein. In certain embodiments, the activity is activating pro-apoptotic genes of cells expressing said mutant p53 protein. In certain embodiments, the pro-apoptotic genes are selected from the group consisting of CD95, Bax, DR4, DR5, PUMA, NOXA, Bid, 53AIP1 and PERP. Each possibility represents a separate embodiment of the invention.

In certain embodiments, the activity is binding to a p53 consensus DNA binding element in cells expressing the mutant p53 protein. In certain embodiments, the consensus DNA binding element comprises or consists the amino-acid sequence set forth in SEQ ID NO:339.

Methods of monitoring cellular changes induced by the any of the peptides of the present invention are known in the art and include for example, the MTT test which is based on the selective ability of living cells to reduce the yellow salt MTT (3-(4, 5-dimethylthiazolyl-2)-2, 5-diphenyltetrazolium bromide) (Sigma, Aldrich St Louis, Mo., USA) to a purple-blue insoluble formazan precipitate; the BrDu assay [Cell Proliferation ELISA BrdU colorimetric kit (Roche, Mannheim, Germany]; the TUNEL assay [Roche, Mannheim, Germany]; the Annexin V assay [ApoAlert® Annexin V Apoptosis Kit (Clontech Laboratories, Inc., CA, USA)]; the Senescence associated-β-galactosidase assay (Dimri G P, Lee X, et al. 1995. A biomarker that identifies senescent human cells in culture and in aging skin in vivo. Proc Natl Acad Sci USA 92:9363-9367); as well as various RNA and protein detection methods (which detect level of expression and/or activity) which are further described hereinbelow.

In certain embodiments, the binding results in at least partial activation of an endogenous p53 target gene. In certain embodiments, the endogenous target gene is selected from the group consisting of p21, MDM2 and PUMA. Each possibility represents a separate embodiment of the invention.

In certain embodiments, the mutant p53 protein is of a different conformation than a WT p53 protein. In certain embodiments, the mutant p53 protein is at least partly inactive compared to a WT p53 protein.

In certain embodiments, the mutant p53 protein is not recognized by a monoclonal antibody directed against a WT p53 protein. In certain embodiments, the mutant p53 protein, upon binding to the peptide, is recognized by a monoclonal antibody directed against a WT p53 protein. In certain embodiments, the monoclonal antibody is Ab1620.

In certain embodiments, the mutant p53 protein comprises a mutation selected from the group consisting of R175H, V143A, R249S, R273H, R280K, P309S, P151S, P151H, C176S, C176F, H179L, Q192R, R213Q, Y220C, Y220D, R245S, R282W, D281G, S241F, C242R, R248Q, R248W, D281G, R273C and V274F. Each possibility represents a separate embodiment of the invention.

In certain embodiments, the peptide comprises the consensus motif set forth in SEQ ID NO:314. In certain embodiments, the peptide comprises the amino-acid sequence set forth in any one of SEQ ID NO:321, SEQ ID NO:314, SEQ ID NO:313, SEQ ID NO:310 or SEQ ID NO:307. Each possibility represents a separate embodiment of the invention. In certain embodiments, the peptide consists of the amino-acid sequence set forth in any one of SEQ ID NO:321, SEQ ID NO:314, SEQ ID NO:313, SEQ ID NO:310 or SEQ ID NO:307. Each possibility represents a separate embodiment of the invention. In certain embodiments, the peptide comprises the amino-acid sequence set forth in any one of SEQ ID NOs:268, 282, 328, 376, 298, 377, 378, 253, 20, 379, 302, 275, 380, 273, 381, 280 or 382. Each possibility represents a separate embodiment of the invention. In certain embodiments, the peptide comprises the amino-acid sequence set forth in any one of SEQ ID NOs:379, 302, 275, 380, 273, 381, 280 or 382. Each possibility represents a separate embodiment of the invention. In certain embodiments, the peptide comprises the amino-acid sequence set forth in any one of SEQ ID NOs:302, 275, 380, 273, 381, 280 or 382. Each possibility represents a separate embodiment of the invention. According to a specific embodiment the consensus motif is as set forth in SEQ ID NO: 314. In certain embodiments, the peptide consists of the amino-acid sequence set forth in any one of SEQ ID NOs: 307, 310, 313, 314 and 321, wherein said peptide at least partially reactivates a mutant p53 protein. Each possibility represents a separate embodiment of the invention. In certain embodiments, the peptide consists of the amino-acid sequence set forth in any one of SEQ ID NOs: 312, 314, 315, 316, 318 and 321, wherein said peptide at least partially reactivates a mutant p53 protein. Each possibility represents a separate embodiment of the invention. In certain embodiments, the peptide the peptide comprises SEQ ID NOs: 307, 310, 313, 314 and 321. Each possibility represents a separate embodiment of the invention. In certain embodiments, the peptide comprises the amino-acid sequence set forth in SEQ ID NOs:321-316. Each possibility represents a separate embodiment of the invention.

The present invention further provides, in another aspect, an expression vector, capable of expressing the peptides described above.

The present invention further provides, in another aspect, a pharmaceutical composition, comprising the peptides described above.

The present invention further provides, in yet another aspect, a pharmaceutical composition, comprising the expression vector described above.

In an aspect, the pharmaceutical compositions described above are for use in treating a disease, disorder or condition associated with a mutant p53 protein.

In some embodiments, the disease is cancer. In some embodiments, the cancer is selected from the group consisting of breast cancer, colon cancer and lung cancer. Each possibility represents a separate embodiment of the invention. In some embodiments, the cancer cells express the mutant p53 protein.

The present invention further provides, in another aspect, a method of treating a disease, disorder or condition associated with a mutant p53 protein, comprising the step of administering a therapeutically effective amount of the pharmaceutical compositions described above to a subject in need thereof, thereby treating the disease, disorder or condition.

The present invention further provides, in yet another aspect, a kit comprising the pharmaceutical compositions described above.

In an aspect, the kit described above is for use in treating a disease, disorder or condition associated with a mutant p53 protein.

Definitions

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

The term "recombinant or synthetic peptide" as used herein refers to a peptide produced by standard biotechnological methods known in the art, such as expression in bacteria or Solid-phase peptide synthesis (SPPS).

The term "capable of at least partially reactivating a mutant p53 protein" or "at least partially reactivates a mutant p53 protein" as interchangeably used herein refers to peptide, wherein upon binding of the peptide to a mutant p53 protein, the mutant p53 protein gains or increases an activity similar to a corresponding activity of a wild type p53 protein.

The term "consensus motif" as used herein refers to an amino acid sequence of at least three amino acids, which was found in more than one peptide provided by the present invention.

As used herein the phrase "permeability-enhancing moiety" refers to an agent which enhances translocation of any of the attached peptide across a cell membrane.

Any moiety known in the art to facilitate actively or passively or enhance permeability of compositions into cells may be used for conjugation with the peptide core according to the present invention. Non-limiting examples include: hydrophobic moieties such as fatty acids, steroids and bulky aromatic or aliphatic compounds; moieties which may have cell-membrane receptors or carriers, such as steroids, vitamins and sugars, natural and non-natural amino acids and proteinaceous moiety e.g., transporter peptides, also referred to as "cell penetrating peptides" or a CPP, poly-Arginine or poly-Lysine, a combination of same or an antibody. According to some embodiments, the proteinaceous moiety is a CPP.

According to some embodiments, the proteinaceous moiety is poly-Arginine.

According to some embodiments, the hydrophobic moiety is a lipid moiety or an amino acid moiety.

Cell-Penetrating Peptides (CPPs) are short peptides (≤40 amino acids), with the ability to gain access to the interior of almost any cell. They are highly cationic and usually rich in arginine and lysine amino acids. Indeed the present inventors have used positively charged amino acids (on either peptide termini) or poly-cationic amino acids (at least 2 e.g., 2-12) poly-Arg to impart the peptides with cell permeation. They have the exceptional property of carrying into the cells a wide variety of covalently and noncovalently conjugated cargoes such as proteins, oligonucleotides, and even 200 nm liposomes. Therefore, according to additional exemplary embodiment CPPs can be used to transport the peptides to the interior of cells.

TAT (transcription activator from HIV-1), pAntp (also named penetratin, *Drosophila* antennapedia homeodomain transcription factor) and VP22 (from Herpes Simplex virus) are examples of CPPs that can enter cells in a non-toxic and efficient manner and may be suitable for use with some embodiments of the invention. Protocols for producing CPPs-cargos conjugates and for infecting cells with such conjugates can be found, for example L Theodore et al. [The Journal of Neuroscience, (1995) 15(11): 7158-7167], Fawell S, et al. [Proc Natl Acad Sci USA, (1994) 91:664-668], and Jing Bian et al. [Circulation Research (2007) 100: 1626-1633].

However, the disclosure is not so limited, and any suitable penetrating agent may be used, as known by those of skill in the art.

When the peptides of the present invention are attached to cell penetrating peptides, it is contemplated that the full length peptide is no greater than 30 amino acids, no greater than 25 amino acids, no greater than 22 amino acids, no greater than 20 amino acids, no greater than 15 amino acids, no greater than 12 amino acids, no greater than 10 amino acids, no greater than 9 amino acids, no greater than 8 amino acids, or no greater than 7 amino acids.

The term "fatty acid moiety" as used herein refers to a part of a fatty acid that exhibits a particular set of chemical and pharmacologic characteristics similar to the corresponding complete fatty acid origin molecule. The term further refers to any molecular species and/or molecular fragment comprising the acyl component of a fatty (carboxylic) acid.

A permeability-enhancing moiety according to the present invention is preferably connected covalently to the peptide sequence via a direct bond or via a linker, to form a peptide conjugate. The permeability-enhancing moiety may be connected to any position in the peptide moiety, directly or through a spacer, preferably to the amino terminus of the peptide. According to certain embodiments, the permeability enhancing moiety is a fatty acid.

The term "Permeability" as used herein refers to the ability of an agent or substance to penetrate, pervade, or diffuse through a barrier, membrane, or a skin layer. A "cell permeability" or a "cell-penetration" moiety refers to any molecule known in the art which is able to facilitate or enhance penetration of molecules through membranes. Non-limitative examples include: hydrophobic moieties such as lipids, fatty acids, steroids and bulky aromatic or aliphatic compounds; moieties which may have cell-membrane receptors or carriers, such as steroids, vitamins and sugars, natural and non-natural amino acids, transporter peptides, nanoparticles and liposomes.

The hydrophobic moiety according to the invention may preferably comprise a lipid moiety or an amino acid moiety. According to a specific embodiment the hydrophobic moiety is selected from the group consisting of: phospholipids, steroids, sphingosines, ceramides, octyl-glycine, 2-cyclohexylalanine, benzolylphenylalanine, propionoyl ($C_3$); butanoyl ($C_4$); pentanoyl ($C_5$); caproyl ($C_6$); heptanoyl ($C_7$); capryloyl ($C_8$); nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phtanoyl (($CH_3)_4$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); and lignoceroyl ($C_{24}$); wherein said hydrophobic moiety is attached to said chimeric polypeptide with amide bonds, sulfhydryls, amines, alcohols, phenolic groups, or carbon-carbon bonds.

Other examples for lipidic moieties which may be used according to the present invention: Lipofectamine, Transfectace, Transfectam, Cytofectin, DMRIE, DLRIE, GAP-DLRIE, DOTAP, DOPE, DMEAP, DODMP, DOPC, DDAB, DOSPA, EDLPC, EDMPC, DPH, TMADPH, CTAB, lysyl-PE, DC-Cho, -alanyl cholesterol; DCGS, DPPES, DCPE, DMAP, DMPE, DOGS, DOHME, DPEPC, Pluronic, Tween, BRIJ, plasmalogen, phosphatidylethanolamine, phosphatidylcholine, glycerol-3-ethylphosphatidylcholine, dimethyl ammonium propane, trimethyl ammonium propane, diethylammonium propane, triethylammonium propane, dimethyldioctadecylammonium bromide, a sphingolipid, sphingomyelin, a lysolipid, a glycolipid, a sulfatide, a glycosphingolipid, cholesterol, cholesterol ester, cholesterol salt, oil, N-succinyldioleoylphosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine, palmitoylhomocystiene, N,N'-Bis (dodecyaminocarbonylmethylene)-N,N'-bis((—N,N,N-trimethylammoniumethyl-aminocarbonylmethylene)ethylenediamine tetraiodide; N,N"-Bis(hexadecylaminocarbonylmethylene)-N,N',N"-tris ((—N,N,N-trimethylammonium-ethylaminocarbonylmethylenediethylenetri amine hexaiodide; N,N'-Bis(dodecylaminocarbonylmethylene)-N,N"-bis((—N,N,N-trimethylammonium ethylaminocarbonylmethylene) cyclohexylene-1,4-diamine tetraiodide; 1,7,7-tetra-((—N,N, N,N-tetramethylammoniumethylamino-carbonylmethylene)-3-hexadecylaminocarbonyl-methylene-1,3,7-triaazaheptane heptaiodide; N,N,N',N'-tetra((—N,N,N-trimethylammonium-ethylaminocarbonylmethylene)-N'-(1,2-dioleoylglycero-3-phosphoethanolamino carbonylmethylene) diethylenetriamine tetraiodide; dioleoylphosphatidylethanolamine, a fatty acid, a lysolipid, phosphatidylcholine, phosphatidylethanolamine, phosphatidylserine, phosphatidylglycerol, phosphatidylinositol, a sphingolipid, a glycolipid, a glucolipid, a sulfatide, a glycosphingolipid, phosphatidic acid, palmitic acid, stearic acid, arachidonic acid, oleic acid, a lipid bearing a polymer, a lipid bearing a sulfonated saccharide, cholesterol, tocopherol hemisuccinate, a lipid with an ether-linked fatty acid, a lipid with an ester-linked fatty acid, a polymerized lipid, diacetyl phosphate, stearylamine, cardiolipin, a phospholipid with a fatty acid of 6-8 carbons in length, a phospholipid with asymmetric acyl chains, 6-(5-cholesten-3b-yloxy)-1-thio-b-D-galactopyranoside, digalactosyldiglyceride, 6-(5-cholesten-3b-yloxy)hexyl-6-amino-6-deoxy-1-thio-b-D-galactopyranoside, 6-(5-cholesten-3b-yloxy)hexyl-6-amino-6-deoxyl-1-thio-a-D-mannopyranoside, 12-(((7'-diethylamino-coumarin-3-yl)carbonyl) methylamino)-octadecanoic acid; N-[12-(((7'-diethylaminocoumarin-3-yl)carbonyl)methyl-amino) octadecanoyl]-2-aminopalmitic acid; cholesteryl)4'-trimethyl-ammonio)butanoate; N-succinyldioleoyl-phosphatidylethanolamine; 1,2-dioleoyl-sn-glycerol; 1,2-dipalmitoyl-sn-3-succinyl-glycerol; 1,3-dipalmitoyl-2-succinylglycerol, 1-hexadecyl-2-palmitoylglycero-phosphoethanolamine, and palmitoylhomocysteine.

According to a specific embodiment, the p53 protein is human p53. According to a specific embodiment, the subject, the biological sample derived therefrom or the cell (as described below) are of a human being.

The term "cells expressing the mutant p53 protein" as used herein refers to cells which express from at least one allele a mutant p53 protein. In certain embodiments, the term "cells expressing the mutant p53 protein" is interchangeable with "cancer cells".

The term "pro-apoptotic genes" refers to a gene, or a multitude of genes, involved in apoptosis, either directly (such as certain caspases) or indirectly (for example, as part of a signal transduction cascade).

The term "pharmaceutical composition" as used herein refers to any composition comprising at least one pharmaceutically active ingredient.

The term "associated with a mutant p53 protein" as used herein refers to any disease, disorder or condition which is caused by a mutant p53 protein or related to the presence of a mutant p53 protein in a cell or an organ.

It should be understood that since p53 is expressed from both alleles, the overall content of intra-cellular p53 can be either wild-type (wt/wt), mixture of wt and mutant p53 (wt/mut) or mutant p53 only (when both alleles are mutated (mut/mut), or one allele is deleted (mut/−)). In cancer, the situation is often wt/mut, mut/mut or mut/−. Since p53 acts as a tetramer, mutant p53 proteins may abrogate the activity of wild type p53 proteins, which do exist in the cancer's cells. Therefore, the peptides provided by the present invention are particularly useful in treating cancers in which increasing the level of wild type p53 proteins is not fruitful.

The term "therapeutically effective amount" as used herein refers to an amount of a composition containing a peptide according to the present invention that is sufficient to reduce, decrease, and/or inhibit a disease, disorder or condition in an individual.

As used herein, the term p53 is directed to a p53 protein that can have a conformation of a WT p53, a mutated p53, or an intermediate conformation between WT and mutated p53.

As used herein, the terms "wild type p53", "wt p53" and "WT p53" may interchangeably be used and are directed to a wild type p53 protein, having the conformation of a wild type p53 protein and hence, activity of a wild type p53 protein. In some embodiments, wild type p53 can be identified by a specific monoclonal antibody.

As used herein, the terms "mutant p53", "Mut-p53", "mutated p53", and "p53 mutant" may interchangeably be used and are directed to a mutated p53 protein, incapable of efficiently functioning in a target cell. In some embodiments, a Mut-p53 cannot bind its target site. In some embodiments, a Mut-p53 is mutated at the DNA binding domain (DBD) region. In some embodiments, a Mut-p53 is misfolded in an inactive conformation. In some exemplary embodiments, the Mut-p53 is a temperature sensitive (ts) mut p53 R249S (R249S p53), a hot spot full length mutant p53 Mut-p53 R175H (R175H p53), or any other Mut-p53 protein. In some embodiments, a Mut-p53 is identified by a specific monoclonal antibody, capable of recognizing a misfolded conformation of p53 (induced by the mutation of the p53). In some embodiments, a Mut-p53 is identified by a specific monoclonal antibody.

The phrase "peptide reactivates a mutant p53 protein" as used herein refers to a peptide which upon its interaction with a mutant p53 protein, the mutant p53 protein increases at least one of his activities, wherein the activities are the activities of a wild type p53 protein. For example, upon its interaction with a peptide provided by the present invention, a mutant p53 protein may increase, directly or indirectly, the expression of pro-apoptotic proteins such as caspases in a cancer cell, in a similar way to what would a wild type p53 protein do in a similar situation.

As referred to herein, the terms "reactivating peptide", "Mut-p53 reactivating peptide" or "the peptide" may interchangeably be used and are directed to a peptidic agent capable of at least partially restoring activity to Mut-p53. In some embodiments, the reactivating agent can reactivate a Mut-p53 by affecting the conformation of the Mut-p53, to assume a conformation which is more similar to or identical to a native, WT p53. In some embodiments, the reactivating agent can reactivate a Mut-p53 to restore binding of the Mut-p53 to a WT p53 binding site in a target DNA. In some embodiments, the reactivating agent can restore biochemical properties of the Mut-p53. In some embodiments, the reactivating agent can induce the Mut-p53 protein to exhibit p53-selective inhibition of cancer cells. In some embodiments, the reactivating agent can reactivate a Mut-p53 to have structural properties, biochemical properties, physiological properties and/or functional properties similar to or identical to a WT p53 protein. In some embodiments, the reactivating agent is a peptide. In some embodiments, the reactivating agent is a peptide having 3-30 amino acids in length. In some embodiments, the reactivating agent is a peptide having 7-30 amino acids in length. In some embodiments, the reactivating agent is a peptide having 12-30 amino acids in length. In some embodiments, the reactivating agent is a peptide having 3-25 amino acids in length. In some embodiments, the reactivating agent is a peptide having 7-25 amino acids in length. In some embodiments, the reactivating agent is a peptide having 12-25 amino acids in length. In some embodiments, the reactivating agent is a peptide having 3-22 amino acids in length. In some embodiments, the reactivating agent is a peptide having 7-22 amino acids in length. In some embodiments, the reactivating agent is a peptide having 12-22 amino acids in length. In some embodiments, the reactivating agent is a peptide having 7-9 amino acids in length. In some embodiments, the reactivating agent is a peptide having 6-9 amino acids in length. In some embodiments, the reactivating agent is a peptide having 7-10 amino acids in length. In some embodiments, the reactivating agent is a peptide having 6-10 amino acids in length. In some embodiments, the reactivating agent is a peptide having 5-20 amino acids in length. In some embodiments, the reactivating agent is a peptide having 6-15 amino acids in length. In some embodiments, the reactivating agent is a peptide having 7 or 12 amino acids in length.

The term "conformation" with respect to a protein is directed to the structural arrangement (folding) of a protein in space.

The terms "deep sequencing" and "next generation sequencing" may interchangeably be used and are directed to an enhanced sequencing method enabling the rapid parallel sequencing of multiple nucleic acid sequences.

The "phage display" method includes the screening of a library of phages, each expressing and presenting a specific, exogenous molecule, such as a peptide. The enrichment of phages that express and present a specific peptide is achieved by affinity selection of a phage library on immobilized target. In this "panning" process, binding phages (i.e. phages which express and present a peptide that can bind the immobilized target) are captured, whereas nonbinding phages (i.e., phages which do not express and present a peptide that can bind the immobilized target) are washed off. A next step in the method can include the elution and amplification of the bound phages by reinfection of E. coli cells with the identified phages. In some embodiments, a phage library can be an original library, or a commercially available phage display library.

The terms "polypeptide" and "peptide" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated amide bonds (—N(CH3)-CO—), ester bonds (—C(=O)—O—), ketomethylene bonds (—CO—CH2-), sulfinylmethylene bonds (—S(=O)—CH2-), α-aza bonds (—NH—N(R)—CO—), wherein R is any alkyl (e.g., methyl), amine bonds (—CH2-NH—), sulfide bonds (—CH2-S—), ethylene bonds (—CH2-CH2-), hydroxyethylene bonds (—CH(OH)—CH2-), thioamide bonds (—CS—NH—), olefinic double bonds (—CH=CH—), fluorinated olefinic double bonds (—CF=CH—), retro amide bonds (—NH—CO—), peptide derivatives (—N(R)—CH2-CO—), wherein R is the "normal" side chain, naturally present on the carbon atom.

These modifications can occur at any of the bonds along the peptide chain and even at several (2-3) bonds at the same time.

"Conservative substitution" refers to the substitution of an amino acid in one class by an amino acid of the same class, where a class is defined by common physico-chemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gin, Glu); Class IV (His, Arg, Lys); Class V (He, Leu, Val, Met); and Class VI (Phe, Tyr, Trp). For example, substitution of an Asp for another Class III residue such as Asn, Gin, or Glu, is a conservative substitution.

Other classifications include positive amino acids (Arg, His, Lys), negative amino acids (Asp, Glu), polar uncharged (Ser, Thr, Asn, Gln), hydrophobic side chains (Ala, Val, Ile, Leu, Met, Phe, Tyr, Trp).

pCap 250 (SEQ ID NO: 321) comprising the core sequence of HSTPHP (SEQ ID NO: 314), may be conservatively modified to include any of the above amino acid conservative substitutions, wherein each option is considered as a separate embodiment.

"Non-conservative substitution" refers to the substitution of an amino acid in one class with an amino acid from another class; for example, substitution of an Ala, a Class II residue, with a Class III residue such as Asp, Asn, Glu, or Gin.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr. Other synthetic options are listed hereinbelow in Table B.

The peptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables A and B below list naturally occurring amino acids (Table A), and non-conventional or modified amino acids (e.g., synthetic, Table B) which can be used with some embodiments of the invention.

TABLE A

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE B

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |

TABLE B-continued

| Non-conventional amino acid | Code | Non-conventional amino acid | Code |
| --- | --- | --- | --- |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl)carbamylmethyl-glycine | Nnbhm |

TABLE B-continued

| Non-conventional amino acid | Code | Non-conventional amino acid | Code |
| --- | --- | --- | --- |
| N-(3,3-diphenylpropyl)glycine | Nbhe | N-(N-(3,3-diphenylpropyl)carbamylmethyl-glycine | Nnbhe |
| 1-carboxy-1-(2,2-diphenyl ethylamino)cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The peptides of some embodiments of the invention are preferably utilized in a linear form, although it will be appreciated that in cases where cyclicization does not severely interfere with peptide characteristics, cyclic forms of the peptide can also be utilized.

In order to improve bioavailability, the peptide may comprise at least one D amino acid.

Alternatively or additionally, the peptide may comprise C-terminal amidation.

Yet alternatively or additionally the peptide may be conjugated to non-proteinaceous non-toxic moiety such as, but are not limited to, polyethylene glycol (PEG), Polyvinyl pyrrolidone (PVP), poly(styrene comaleic anhydride) (SMA), and divinyl ether and maleic anhydride copolymer (DIVEMA).

It will be appreciated that the peptides of the invention can also utilize peptide homologues which exhibit the desired activity (e.g., reactivation of p53 mutants)), also referred to herein as functional equivalents, whereby the activity of the peptide homologue is determined according to methods known in the art such as described herein. Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO: 286-321 (e.g., 302-321, 312-321, 316-321 e.g., 321 or 314, e.g., 321), as determined using the BestFit software.

The terms "nucleic acid", "polynucleotide", "oligonucleotide" or "oligo" relates to a single-stranded or double-stranded polymer composed of DNA (Deoxyribonucleic acid) nucleotides, RNA (Ribonucleic acid) nucleotides or a combination of both types, and may include natural nucleotides, chemically modified nucleotides and synthetic nucleotides.

"Chemically modified" refers to an amino acid that is modified either by natural processes, or by chemical modification techniques which are well known in the art. Among the numerous known modifications, typical, but not exclusive examples include: acetylation, acylation, amidation, ADP-ribosylation, glycosylation, glycosaminoglycanation, GPI anchor formation, covalent attachment of a lipid or lipid derivative, methylation, myristlyation, pegylation, prenylation, phos-phorylation, ubiqutination, or any similar process.

As referred to herein, the term "treating a disease" or "treating a condition" is directed to administering a composition, which includes at least one agent, effective to ameliorate symptoms associated with a disease, to lessen the severity or cure the disease, or to prevent the disease from occurring in a subject. Administration may include any administration route. In some embodiments, the disease is a disease that is caused by or related to the presence of a mutated p53 in a cell, tissue, organ, body, and the like. In some embodiments, the disease is cancer. In some embodiments, the cancer is selected from the group consisting of breast cancer, colon cancer and lung cancer. Each possibility represents a separate embodiment of the invention. In some embodiments, the subject is a mammal, such as a human. In some embodiments, the subject is a mammal animal. In some embodiments, the subject is a non-mammal animal.

The term "expression", as used herein, refers to the production of a desired end-product molecule in a target cell. The end-product molecule may include, for example an RNA molecule; a peptide or a protein; and the like; or combinations thereof.

The term "construct", as used herein refers to an artificially assembled or isolated nucleic acid molecule which may be one or more nucleic acid sequences, wherein the nucleic acid sequences may comprise coding sequences (that is, sequence which encodes an end product), regulatory sequences, non-coding sequences, or any combination thereof. The term construct encompasses, for example, vector but should not be seen as being limited thereto.

"Expression vector" refers to vectors that have the ability to incorporate and express heterologous nucleic acid fragments (such as, for example, DNA), in a foreign cell. In other words, an expression vector comprises nucleic acid sequences/fragments (such as DNA, mRNA, tRNA, rRNA), capable of being transcribed. Many prokaryotic and eukaryotic expression vectors are known and/or commercially available. Selection of appropriate expression vectors is within the knowledge of those having skill in the art.

The terms "Upstream" and "Downstream", as used herein refers to a relative position in a nucleotide sequence, such as, for example, a DNA sequence or an RNA sequence. As well known, a nucleotide sequence has a 5' end and a 3' end, so called for the carbons on the sugar (deoxyribose or ribose) ring of the nucleotide backbone. Hence, relative to the position on the nucleotide sequence, the term downstream relates to the region towards the 3' end of the sequence. The term upstream relates to the region towards the 5' end of the strand.

As used herein, the terms "introducing", "transfection" or "transfecting" and "infection" or "infecting" may interchangeably be used and refer to the transfer of molecules, such as, for example, nucleic acids, polynucleotide molecules, vectors, and the like into a target cell(s), and more specifically into the interior of a membrane-enclosed space of a target cell(s). The molecules can be "introduced" into the target cell(s) by any means known to those of skill in the art, for example as taught by Sambrook et al. Molecular Cloning: A Laboratory Manual, Cold Spring Harbor Laboratory Press, New York (2001), the contents of which are incorporated by reference herein. Means of "introducing" molecules into a cell include, for example, but are not limited to: heat shock, calcium phosphate transfection, PEI transfection, electroporation, lipofection, transfection agent(s), viral-mediated transfer, and the like, or combinations thereof. The transfection of the cell may be performed on any type of cell, of any origin.

As referred to herein, the term "exogenous gene" is directed to a gene (or any part thereof) which is introduced from the exterior into a cell. In some embodiments, the exogenous gene is inserted in the form of a polynucleotide (for example, DNA, RNA, and the like). In some embodiments, the exogenous gene is capable of being expressed in the cell.

In some embodiments, the exogenous gene is overexpressed within the cell.

As used herein the term "about" in reference to a numerical value stated herein is to be understood as the stated value +/−10%.

In some embodiments, the reactivating peptide can reactivate a Mut-p53 to have structural properties, biochemical properties, physiological properties and/or functional properties similar to or identical to a WT p53 protein.

According to some embodiments, there are provided Mut-p53 reactivating peptides, wherein the peptides are in the length of about 3-25 amino acids. In some embodiments, the Mut-p53 reactivating peptides are in the length of about 4-15 amino acids. In some embodiments, the Mut-p53 reactivating peptides are in the length of about 7-12 amino acids.

In some embodiments, the Mut-p53 reactivating peptides are in the length of 7 amino acids. In some embodiments, the Mut-p53 reactivating peptides are in the length of 12 amino acids. Each possibility represents a separate embodiment of the invention.

Other peptide lengths are recited throughout the application. Each possibility represents a separate embodiment of the invention.

In some embodiments, there is provided a Mut-p53 reactivating peptide having an amino acid sequence as denoted by any one of the peptide sequences in Tables 6, 7 or 8, herein below.

According to some embodiments, a Mut-p53 reactivating peptide can affect Mut-p53 such that it can trans-activates a reporter gene (such as Luciferase) having WT p53 binding element in its promoter. In some embodiments the transactivation of the reporter gene may be performed in vitro (for example, in a test tube or well), or in-vivo in a cell, harboring the reporter gene construct.

According to some embodiments, a Mut-p53 reactivating peptide can bind to the DNA binding Domain (DBD) of a mutated p53. In some embodiments, the mutated p53 harbors a mutation in its DNA binding domain (DBD).

In some embodiments, cancer is adrenocortical carcinoma, anal cancer, bladder cancer, brain tumor, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors (pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, small cell, lymphoma, AIDS-related, lymphoma, central nervous system (primary), lymphoma, cutaneous T-cell, lymphoma, hodgkin's disease, non-hodgkin's disease, malignant mesothelioma, melanoma, merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, sezary syndrome, skin cancer, cutaneous T-cell lymphoma, skin cancer, kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, or wilms' tumor.

In some embodiments, the cancer is a lung cancer.

In some embodiments, the cancer is an ovarian cancer.

In some embodiments, the cancer is a triple negative breast cancer.

In some embodiments, cancer is a non-solid tumor such as a blood cancer. In another embodiment, a non-solid tumor or blood cancer is leukemia or lymphoma. In another embodiment, a non-solid tumor or blood cancer is acute lymphoblastic leukemia (ALL). In another embodiment, a non-solid tumor or blood cancer is acute myelogenous leukemia (AML). In another embodiment, a non-solid tumor or blood cancer is chronic lymphocytic leukemia (CLL). In another embodiment, a non-solid tumor or blood cancer is small lymphocytic lymphoma (SLL). In another embodiment, a non-solid tumor or blood cancer is chronic myelogenous leukemia (CML). In another embodiment, a non-solid tumor or blood cancer is acute monocytic leukemia (AMOL). In another embodiment, a non-solid tumor or blood cancer is Hodgkin's lymphomas (any of the four subtypes). In another embodiment, a non-solid tumor or blood cancer is Non-Hodgkin's lymphomas (any of the subtypes). In another embodiment, a non-solid tumor or blood cancer is myeloid leukemia.

For use in the methods of the invention, the reactivating peptides may be formulated in a conventional manner using one or more pharmaceutically acceptable carriers, stabilizers or excipients (vehicles) to form a pharmaceutical composition as is known in the art, in particular with respect to protein active agents. Carrier(s) are "acceptable" in the sense of being compatible with the other ingredients of the composition and not deleterious to the recipient thereof. Suitable carriers typically include physiological saline or ethanol polyols such as glycerol or propylene glycol.

The reactivating peptides may be formulated as neutral or salt forms. Pharmaceutically acceptable salts include the acid addition salts (formed with free amino groups) and which are formed with inorganic acids such as hydrochloric or phosphoric acids, or such organic acids such as acetic, oxalic, tartaric and maleic. Salts formed with the free carboxyl groups may also be derived from inorganic bases such as sodium, potassium, ammonium, calcium, or ferric hydroxides, and organic bases as isopropylamine, trimethylamine, 2-ethylamino ethanol, histidine and procaine.

The compositions may be suitably formulated for intravenous, intramuscular, subcutaneous, or intraperitoneal administration and conveniently comprise sterile aqueous solutions of the reactivating peptides, which are preferably isotonic with the blood of the recipient. Such formulations are typically prepared by dissolving solid active ingredient in water containing physiologically compatible substances such as sodium chloride, glycine, and the like, and having a buffered pH compatible with physiological conditions to produce an aqueous solution, and rendering said solution sterile. These may be prepared in unit or multi-dose containers, for example, sealed ampoules or vials.

The compositions may incorporate a stabilizer, such as for example polyethylene glycol, proteins, saccharides (for example trehalose), amino acids, inorganic acids and admixtures thereof. Stabilizers are used in aqueous solutions at the appropriate concentration and pH. The pH of the aqueous solution is adjusted to be within the range of 5.0-9.0, preferably within the range of 6-8. In formulating the reactivating peptides, anti-adsorption agent may be used. Other suitable excipients may typically include an antioxidant such as ascorbic acid.

The compositions may be formulated as controlled release preparations which may be achieved through the use of polymer to complex or absorb the proteins. Appropriate polymers for controlled release formulations include for example polyester, polyamino acids, polyvinyl, pyrrolidone, ethylenevinylacetate, and methylcellulose. Another possible method for controlled release is to incorporate the reactivating peptides into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

In some embodiments, the reactivating peptides of the invention may be formulated in peroral or oral compositions and in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.001% to about 0.9% of reactivating peptides, or in another embodiment, from about 0.01% to about 10%.

In some embodiments, compositions for use in the methods of this invention comprise solutions or emulsions, which in some embodiments are aqueous solutions or emulsions comprising a safe and effective amount of a reactivating peptide and optionally, other compounds, intended for topical intranasal administration.

In some embodiments, injectable solutions of the invention are formulated in aqueous solutions. In one embodiment, injectable solutions of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The reactivating peptides of the invention may be administered by any suitable administration route, selected from oral, topical, transdermal or parenteral administration.

According to some embodiments the route of administration is via topical application selected from dermal, vaginal, rectal, inhalation, intranasal, ocular, auricular and buccal.

According to some embodiments the route of administration is via parenteral injection. In various embodiments, the step of administering is carried out by a parenteral route selected from the group consisting of intravenous, intramuscular, subcutaneous, intradermal, intraperitoneal, intraarterial, intracerebral, intracerebroventricular, intraosseus and intrathecal. For example, the reactivating peptides may be administered systemically, for example, by parenteral routes, such as, intraperitoneal (i.p.), intravenous (i.v.), subcutaneous, or intramuscular routes. The reactivating peptides of the invention and/or any optional additional agent may be administered systemically, for example, by intranasal administration. The reactivating peptides of the invention and/or any optional additional agent may be administered systemically, for example, by oral administration, by using specific compositions or formulations capable of providing oral bioavailability to proteins. The reactivating peptides of the invention and/or any optional additional agent may be administered locally.

The reactivating peptides may be administered in the range of about 0.1 to about 20 mg/kg of subject weight, commonly about 0.5 to about 10 mg/kg, and often about 1 to about 5 mg/kg. In some cases it may be advantageous to administer a large loading dose followed by periodic (e.g., weekly) maintenance doses over the treatment period. The reactivating peptides can also be delivered by slow-release delivery systems, pumps, and other known delivery systems for continuous infusion. Dosing regimens may be varied to provide the desired circulating levels of particular reactivating peptides based on its pharmacokinetics. Thus, doses are calculated so that the desired circulating level of therapeutic agent is maintained.

Typically, the effective dose is determined by the activity of the reactivating peptides and the condition of the subject, as well as the body weight or surface area of the subject to be treated. The size of the dose and the dosing regime is also determined by the existence, nature, and extent of any adverse side effects that accompany the administration of the reactivating peptides in the particular subject.

In some embodiments, there is provided a kit for treating or preventing a p53 related condition. In some embodiments, the kit comprises a container (such as a vial) comprising a Mut-p53 reactivating peptide in a suitable buffer and instructions for use for administration of the reactivating peptide.

It is suggested that the efficacy of treatment with the peptides of the invention may be augmented when combined with gold standard treatments (e.g., anti-cancer therapy). Thus, the peptide can be used to treat diseases or conditions associated with p53 (as described hereinabove) alone or in combination with other established or experimental therapeutic regimen for such disorders. It will be appreciated that treatment with additional therapeutic methods or compositions has the potential to significantly reduce the effective clinical doses of such treatments, thereby reducing the often devastating negative side effects and high cost of the treatment.

Therapeutic regimen for treatment of cancer suitable for combination with the peptides of some embodiments of the invention or polynucleotide encoding same include, but are not limited to chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy and photon beam radiosurgical therapy. According to a specific embodiment, the chometherapy is platinum-based.

Anti-Cancer Drugs

Anti-cancer drugs that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spiro germanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Materials and Methods

Purification of Recombinant Full Length (FL) Proteins from Sf9 Cells: Mutant p53 R249S, Mutant p53 R175H and WT p53:

$2\times10^7$ sf9 cells in the log-phase were grown in nine 175 cm$^2$ flasks containing 25 ml of media and incubated overnight at 27° C. Baculoviruses containing a recombinant p53 were added into each flask, and incubated for 72 hrs. Cells were scraped from the flasks, and centrifuged at 4° C. (3200 g for 5 min), the media was removed and the cell pellet was washed twice with ice-cold isotonic buffer (10 mM Na$_2$HPO$_4$, pH 7.2, 130 mM NaCl, 1 mM DTPA—diethylenetriaminepentaacetic acid). To lyse cells, the cells were resuspended in 50 ml of Buffer A (20 mM Tris-HCl, pH 8.0, 12% sucrose, 2 mM EGTA, 2 mM PMSF, 5 mM DTT) with 0.2% Triton X-100 by gentle inversion. Nuclei centrifuged at 5600G for 8 min and the supernatant was removed. Nuclei was lysed by adding 20 ml of Buffer B (20 mM Tris-HCl, pH 8.0, 12% sucrose, 2 mM EGTA, 2 mM PMSF, 10 mM DTT+protease inhibitors) with 0.5M NaCl and were vortexed vigorously and incubated for 20 min on ice. The nuclear lysate was transferred to ultracentrifuge tubes and centrifuged at 100,000 g for 60 min at 4° C. The supernatant was removed and diluted with Buffer B to a final concentration 0.04 M of NaCl, then centrifuged at 20,000 g for 5 min at 4° C. The nuclear lysate was loaded onto a 5 ml Hitrap Q FF (fast flow) (Amersham Pharmacia) ion-exchange column, pre-washed with 50 ml of buffer A. Then, the column was washed with buffers containing higher salt concentrations to elute the protein. For example, in the case of the mutant p53 R249S, the protein eluted from the Ion exchange column at ~150 mM NaCl. The protein was further purified by gel-filtration chromatography using a preparative Superdex 75 column (Amersham Pharmacia Biotech), pre-equilibrated with 20 mM sodium citrate pH 6.1, 150 mM NaCl, 10 μM ZnCl$_2$, and 10 mM DTT. Fractions containing purified protein were pooled together and concentrated to 6-7 mg/ml, aliquoted and stored at −80° C. The fractions obtained after each purification step were analyzed on dot-blot for presence of mutant p53 and subsequently on SDS-PAGE with Coomassie blue staining to check purity of the fractions.

Sandwich ELISA 96-well plates were coated using 3 different antibodies (1 type of antibody (Ab) in each well): PAb421 recognizes both conformations of p53 and binds to a C-terminus epitope; PAb240 recognizes mutant conformation of p53, binds to epitope within the core domain (amino acids 212-217) (Stephen, C. W. and D. P. Lane, *Mutant conformation of p53. Precise epitope mapping using a filamentous phage epitope library*. J. Mol. Biol., 1992. 225(3): p. 577-83) which is accessible to the Ab when the protein is partially denatured (for example, when the DBD is mutated); and PAb1620, which recognizes WT conformation of p53, binds to epitope with in the core domain (aa 156, 206-210), formed when folding is in WT conformation (Wang, P. L., F. Salt, and G. Winter, *The 'wild type' conformation of p53: epitope mapping using hybrid proteins*. Oncogene, 2001. 20(18): p. 2318-24).

Wells were incubated overnight (ON) with 100 µl Ab (5 µg/ml) in room temp (RT). The liquid was discarded, and the wells were washed 3 times with Phosphate buffered saline (PBS), 200 µl per each wash. Next, blocking with 200 µl of 5% bovine serum albumin (BSA) diluted in PBS in each well for 1.5 hours at room temperature (RT) was performed. Blocking buffer was discarded, followed by 3 washes in PBS as described above. Samples of mutant and WT p53 proteins (100 µl, 10 µg/ml), together with control peptides pCAP-710 (LPNPPER, SEQ ID NO:328) and pCAP-1220 (FRS-FAIPLVVPF, SEQ ID NO:368) (5 µg/ml, Sigma Aldrich, or with test peptides 1-153 (5 µg/ml), were incubated for 1.5 hours together, and then added to the wells. Samples were rotated and incubated for 1 hour at RT. Samples were discarded, following 4 washes as described above, using Trisphosphate buffered saline (TPBS). Next, horseradish peroxidase (HRP) conjugated streptavidin p53 antibody (10 µg/ml HAF1355 (R&D)) was added to the wells and incubated at RT for 1 hour. After the plate was washed 3 times in TPBS, TMB substrate solution (50 µl each well, Thermo, (Cat. No. ES001-1L-K)) was added and incubated at 37° c. for 20 min. The reaction was stopped with 2M sulfuric acid (50 µl). The absorbance was measured at 450 nm with a spectrophotometer. Protein concentration was determined by dividing the absorbencies of each sample to the absorbance of Ab 421 samples.

DNA Binding Assay

For these experiments, a commercial p53/DNA binding kit of "R&D" (Cat-DYC1355-5 Lot-1273366FA) was used, in accordance with manufacturer guide lines. Briefly, 96 well plates are coated with anti-p53 antibody overnight. Cell extracts containing p53 are reacted with an oligonucleotide that contains a p53 consensus binding site (provided in the kit), labeled with biotin, in the presence or absenc.

e (NT) of test peptides. WT p53 is expected to bind this DNA binding site as well as to the antibody coating the test wells of the plate. Excess p53 and oligos were washed away and streptavidin-HRP was used to quantify the amount of oligos in the well, which is proportional to the DNA bound by p53. TMB assay was performed to determine HRP (ES001-1L-K) levels (450 nm).

Crystal Violet Assay

Cells were cultured in 96 wells plates with 2500-4000 cells/well in 0.1 ml and incubated overnight at 37° C. in order to adhere to the plate. Serial dilutions of different peptides (0.5 µg/ml) were added in 0.1 ml aliquots and the plates incubated for additional 48 h at 37° C. Then medium was removed and cell lysis was determined by staining the cells with crystal violet (0.5%) in methanol/water (1:4, v/v), 50 µl each well, for 10 min, followed by 3 washes with PBS. Afterwards, 10% acetic acid (50 µl) was added to each well and shaken for 10 min. Then, automatic plate reading was performed at 595 nm.

Immunofluorescence

Cells were cultured on cover slips overnight and then were treated with peptides using X-fect transfection. After 2 hour recovery, cells were fixed with 4% paraformaldehyde for 30 min at room temperature followed by 3 washes (PBS). Samples were permeabilized with 0.1% Triton (1% BSA in PBS) for 10 min RT followed by blocking (3 washes of 0.5% BSA in PBS), 5 min each wash. Cells were then probed with a mouse anti-p53 (DO-1) antibody diluted 1:500 for 1.5 hours, followed by blocking (3 washes of 0.5% BSA in PBS), 5 min each wash. Then cells were probed with goat anti-mouse Cy3 diluted 1:600 and DAPI diluted 1:1000 for 45 min. Samples were mounted with Elvanol.

Luciferase Assay

Construction of Luciferase Constructs

The oligonucleotide (RGC-W) that has the sequence 5'-TCGAGTTGCCTGGACTTGCCTGGCCTTGCCTTTTC-3' (SEQ ID NO:362), and the oligonucleotide mutant RGC oligonucleotide (RGC-M) that has the sequence 5'-TCGAGTTTAATGGACTTTAATGGCCTTTAATTTTC-3' (SEQ ID NO:363), are both derived from Kern et al. (Kern, S. E., et al., *Identification of p53 as a sequence-specific DNA-binding protein*. Science, 1991. 252(5013): p. 1708-11), and serve as a consensus binding sites for WT p53.

These motifs were cloned into the KPN and Eco53IK sites in pCLuc Mini-TK 2 Vector (NEB, Cat No. N0324S ). The Luciferase construct was used to assess transcriptional activation of p53 in test cells.

ChIP Analysis

Briefly, clones were cross-linked with formaldehyde (1% final concentration) at room temperature for 10 min. The formaldehyde was neutralized with 2.5M glycine (final concentration 0.25M) for 5 min. Cells were washed sequentially with 1 ml of ice-cold PBS, buffer I (0.25% Triton X-100, 10 mM EDTA, 0.5 mM EGTA, 10 mM HEPES, pH 6.5), and buffer II (200 mM NaCl, 1 mM EDTA, 0.5 mM EGTA, 10 mM HEPES, pH 6.5) and harvested by scraping. Cells were then resuspended in 0.3 ml of lysis buffer (1% SDS, 10 mM EDTA, 50 mM Tris-HCl, pH 8.1, 1× protease inhibitor cocktail (Roche Molecular Biochemicals, Indianapolis, Ind.) and sonicated 10 times (20 sec 'on' followed by 40 sec 'off') at the maximum setting (Biorupter, Diagenode, N.Y.) followed by centrifugation for 10 min on ice to produce 200-500 bp fragments. Supernatants were collected and diluted 10 times in the ChIP dilution buffer (1% Triton X-100, 2 mM EDTA, 150 mM NaCl, 20 mM Tris-HCl, pH 8.1) followed by immuno-clearing with 40 µl of pre-blocked protein A-sepharose (Santa Cruz Biotech) with 2 µg sheared salmon sperm DNA and pre-immune serum (1 µg of rabbit serum with 10 µl of 100 mg/mL BSA for 2 hour at 4° C. A sample was retained for the preparation of the input sample.

Immuno-precipitation was performed overnight at 4° C. with specific antibodies obtained from. After immuno-precipitation, 40 µl protein A-Sepharose (pre-blocked with salmon sperm DNA) were added and further incubated for another 1 hr. Precipitates were washed sequentially for 10 min each in TSE I (0.1% SDS, 1% Triton X-100, 2 mM EDTA, 20 mM Tris-HCl, pH 8.1, 150 mM NaCl), TSE II (0.1% SDS, 1% Triton X-100, 2 mM EDTA, 20 mM Tris-HCl, pH 8.1, 500 mM NaCl), and buffer III (0.25 M LiCl, 1% NP-40, 1% deoxycholate, 1 mM EDTA, 10 mM Tris-HCl, pH 8.1). Precipitates were then washed three times with TE buffer and extracted twice with 1% SDS, 0.1 M NaHCO$_3$. Eluates were pooled and heated at 65° C. for a minimum of 6 hour to overnight to reverse the formaldehyde cross-linking. DNA fragments were purified with a QIAquick Spin Kit (Qiagen, CA). Immuno-precipitation reactions were performed in triplicate using beads only as a non-specific control. Quantitative analysis of the active and repressive histone marks in the ChIP products from clones were assessed by quantitative real-time PCR. In order to normalize the efficiency of immunoprecipitation (IP), the normalization of chromatin IP was done using specific primers for necdin promoter region and 5' region (which corresponds to a repressive chromatin region).

Cell Culture and Luciferase Reporter Assays

H1299 p53-null cells were cultured overnight and then transfected with the luciferase constructs using MaxFect Transfection Agent (Mediatech) according to the manufacturer's protocol. Prior to the transfection, cell medium was exchanged to OPTI-MEM.

The cells were treated with different peptides 24 hours after transfection. After additional 24 hours, growth medium was collected to 96 black plates: 40 μl for Cluc assay, and 20 μl for Gluc assay. Assay was performed using Turner BioSystems Modulus Microplate. Value was calculated by Cluc/gluc/NT (non-treated cells).

RT-PCR

RNA was obtained using Macherey-Nagel NucleoSpin RNA II Kit on cells pellet according to the manufacturer's protocol. Aliquots of 0.4-1 μg were reverse transcribed using Bio-RT 2000 (Bio-Lab) and random hexamer primers. Quantitative real-time polymerase chain reaction (QRT-PCR) was performed on an ABI 7300 instrument (Applied Biosystems) using PerfeCTa SYBR Green FastMix ROX (Quanta). RT-PCR primers used are presented in Table 1 (primers sequences are presented 5' to 3').

Phage Display Library

Phage display library used were commercially available phage libraries, generated by New England Biolabs (NEB). One library is of linear hepta-peptides (PhD-7), the other library is of linear dodeca-peptides (PhD-12) (CAT NOs.: PhD-7, E8100S; PhD-12, E8110S). The randomized peptide sequences in both libraries are expressed at the N-terminus of the minor coat protein pIII, resulting in a valency of 5 copies of the displayed peptide per virion. All of the libraries contain a short linker sequence between the displayed peptide and pIII.

Deep Sequencing

Prior to sequencing, a PCR reaction was performed with primers flanking the inserted libraries Forward-5'-NNNNNNNNCATGGAAAGATAGTG (SEQ ID NO:364) and Reverse-5'-NNNNNNNNCCTAAAACGATTTGTG (SEQ ID NO:365), first 8 bases of each primer are randomized and were incorporated as a mixture of all four bases. Randomization of first bases was introduced since the Solexa sequence equipment is incapable of sequencing repetitive sequences for the first few cycles. The PCR reaction yielded DNA in the required quantity 5 ug and length (about 120 bp) which includes the flanking primers and the cloned peptide library for Solexa deep sequencing.

Example 1: Calibration of Experimental Conditions

Choosing a p53 Protein Source

When choosing the protein source for phage display selection, several considerations are taken into account; the use of purified proteins is recommended since interaction of phage clones with different proteins in solution can give rise to nonspecific false positive peptides. The human full length p53 protein purified from SF9 cells (see above), was used in the following experiments (Accession No. CG3336). Therefore, an expression system of p53 in SF9 insect cell line infected by baculovirus (as detailed above) was used. A major advantage of p53 expressed in this system is that it already contains post translational modifications.

Conformation of Baculovirus-Expressed WT p53 and Mut-p53 Proteins

Figure 2:
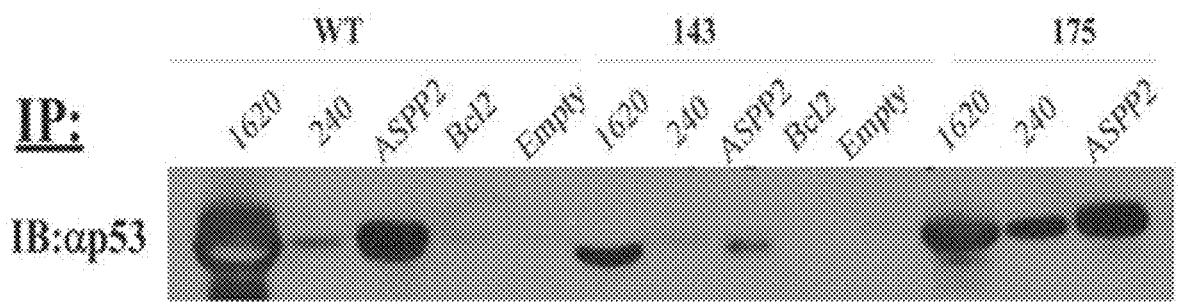
FIG. 2 is a pictogram of a western blot analysis of immunoprecipitation (IP) experiments, in which agarose beads covalently cross-linked to antibodies (PAb1620 or PAb240) or proteins (ASPP2 or Bcl2) were incubate with a WT p53 protein, mutant p53 R175H protein or mutant p53 V143A (each produced from sf9 cells transfected with baculovirus expressing the respective protein) for 3 hours at 4° C. The resultant immunoprecipitate, as well as the supernatant (sup) were subjected to western blot experiments, using an anti p53 (αp53) antibody conjugated to horseradish peroxidase (HRP), to determine the p53 protein level in each sample.

Initial experiments with the Baculo-p53 were made by using the nuclear extracts lysates of Sf9 cells expressing either WT p53, a hot spot full length mutant p53 (R175H), or temperature sensitive (ts) mutant p53 (V143A). SF9 cells were infected with viruses caring either one of the three expressing vectors. 48 hours after infection cells were harvested, nuclei extracted and the extracts were subjected to immunoprecipitation with: PAb1620, PAb240, ASPP2 (also named (P53-BP2)) and/or Bcl2 for 3 hours at 4° C. The immunoprecipitated p53 was detected by western blotting using the αp53-HRP Ab (Cat No. HAF1355 (R&D)). The results of this IP-Western experiment are shown in FIG. 2. As can be seen, the temperature sensitive (ts)-mutant p53 V143A (4° C.) and the WT p53 both bind well to the PAb1620 antibody, but not to PAb240. On the other hand, the mutant p53 R175H exhibits stronger binding to PAb240 than to PAb1620. This suggests that Baculo-expressed mutant p53 R175H assumes a conformation that is an intermediate between mutant and wild type p53. Bcl2 does not exhibit binding to either one of the p53 forms, whereas ASPP2 (P53-BP2) binds to all forms of p53 with approximately the same affinity. Therefore, it is concluded that ASPP2 and Bcl2 cannot be used as markers of p53 conformation under these experimental conditions.

Calibration of Solution Conditions

Figure 3:
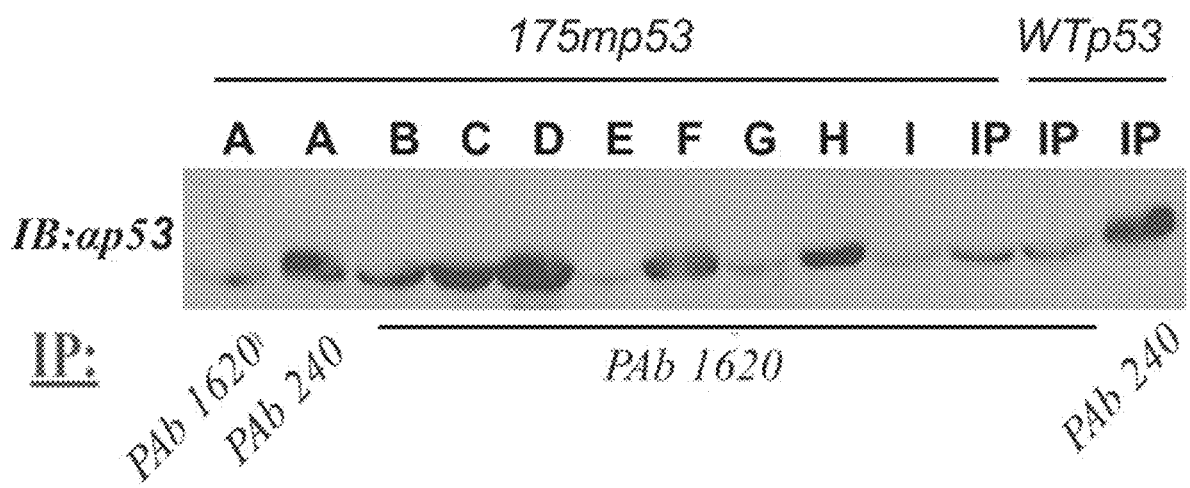
FIG. 3 is a pictograms of western blot analysis of IP experiments, in which beads that were covalently cross linked to PAb1620 or PAb240 antibodies were incubated with WT p53 or mutant p53 R175H for 3 hours at 4° C. with various solutions (A-I and IP buffer). The resultant immunoprecipitate, as well as the supernatant (sup) were subjected to western blot experiments, using an anti p53 (αp53) antibody conjugated to HRP, to determine the p53 protein level in each sample. Solution A—50 mM Tris; solution B—Tris, 150 mM NaCl; solution C—Tris, NaCl, 0.5% Triton; solution D—Tris, 0.5% Glycine; solution E—40 mM $Na_4O_7P_2$; solution F—400 mM Guanidine-HCl; solution G—800 mM Guanidine-HCl; solution H—1M Urea; solution I—3M Urea; IP—IP Buffer.

In order to reduce the relatively high residual binding of the mutant p53 R175H to the PAb1620 and to enhance the binding of WT p53 to that antibody, fine tuning of assay conditions was performed. The results are shown in FIG. 3 which shows a blot of the purified mutant p53 (R175H) and WT p53, extracted from nuclei of Sf9 cells infected with the corresponding baculovirus (as described above). The purified p53 was dissolved in the specified buffers (A-Tris-50 mM; B-Tris, NaCl 150 mM; C-Tris, NaCl, Triton 0.5%; D-Tris, Glicyn 0.5%; E-Na4O7P2 40-mM; F-GndCl 400 mM; G-GndCl 800 mM; H-Urea 1M; I-Urea 3M; IP-IP Buffer) and then immunoprecipitated with PAb1620 and PAb240 for 3 hours at 4° C. and subjected to western blotting using the αp53-HRP-Ab. As can be seen, solution (A) contains only 50 mM Tris. In this solution the binding of mutant p53 R175H to PAb1620 is only about 5% compared to that bound to PAb240. Addition of either 150 mM NaCl (B), 150 mM NaCl+0.5% Triton (C) or 0.5% glycine (D) enhanced the binding of mutant R175H to PAb1620. 3M Urea (I) reduced the binding of p53 mutant R175H to PAb1620, probably by causing denaturation of the protein. A lower concentration of urea, 1M (H), increased the binding of mutant p53 R175H (R175H p53) to PAb1620. 40 mM $Na_4O_7P_2$ (E) reduced the binding of R175H p53 to PAb1620 to the lowest level. Finally, in IP buffer the, R175H p53 remained PAb1620 negative; however in this buffer WT p53 showed strong PAb 240 binding and reduced binding to PAb1620, suggesting that IP buffer causes mild misfolding of the WT form. Hence, buffer containing Tris only is used for further experiments.

Example 2: Initial Screening of Phage Display Library and Selecting for Mut-p53 Reactivating Peptides A phage display screen, using the R175H p53 protein, a single phd-12 phage library (NEB, Cat. No. E8110S) and selection with PAb1620 antibody was initially performed. 200 ng of R175H p53 were reacted with $10^{11}$ phage for 1 hour to allow binding of presented peptides of the phage to the Mut-p53 (R175H). Next, beads cross linked to PAb1620 were added for an additional 1 hour to immunoprecipitate the entire complex. This panning procedure was repeated for three rounds, increasing the stringency of the selection after each round by reducing the amount of incubated Mut-p53: 1$^{st}$ round 200 ng, 2$^{nd}$ round 100 ng and 3$^{rd}$ round 50 ng. Phages were eluted using purified WT p53 DBD, at a concentration of 2 µg/ml (p53 DBD (residues 94-293) was sub-cloned into pET-27b (Novagen)). The plasmid was transformed into *E. coli* BL21 (DE3) strain. Protein production was conducted following a procedure described for the mouse p53 DBD (Suad, O., et al., *Structural basis of restoring sequence-specific DNA binding and transactivation to mutant p53 by suppressor mutations*. J Mol. Biol., 2009. 385(1): p. 249-65). After each round of selection, tittering of the eluted phage was performed, to get an estimate of the number of phages that were selected (Table 2). The eluted phages were amplified by infecting *E-coli*, to yield about 10$^{13}$ phage for selection in the next round. From the second round of panning, a control panning experiment was performed with PAb1620 only (without incubation with Mut-p53); this titer is indicative of the specificity of the panning.

As seen in Table 2, 100 infectious phage particles/µl were obtained in the first selection round and typical enrichment values between selection rounds, giving rise to higher enrichment in the first couple of rounds and then reaching a plateau in the third and fourth round panning. However, the number of phage eluted in both the specific selection panning reactions as well as in the nonspecific PAb1620 control panning reactions was similar. Such enrichment suggests that the phage may bind directly to the PAb1620 and not through interaction with the p53 R175H target.

In order to reduce background (nonspecific binding), additional pre-clearing steps and increasing pre-clearing time were introduced; however, the proportion of background binding remained high. Therefore, alternating selection steps during the phage display process were implemented, in order to reduce background binding. To this aim, different selection strategies at each selection round, while trying to minimize common nonspecific elements in the experimental system (and hence reducing binding to those nonspecific elements) were performed.

Since it is assumed that a prerequisite of conformational change of p53 is the binding of a peptide to p53, an additional selection step for WT p53 binding in between the PAb1620 selections was introduced. It was hypothesized that since PAb1620 would not be present in the second panning round, the phage binding directly to it would be eliminated. Moreover, since a prerequisite of any functional peptide is binding to p53, peptides preferentially binding to the WT form are expected to stabilize this conformation. The first and third rounds of panning were similar to the previous experiment. In the second selection round, however, a selection for phage binding for WT-p53 (His tagged) was performed, and the p53/phage complex was immunoprecipitated using nickel beads (which bind to the His tag). The titer of the eluted phage was evaluated after each selection round. As shown in Table 3, 10-fold enrichment was achieved in the elution of phage when the second cycle was compared to the first. Although this may be considered a bit low by phage display standards, the reason for this relatively low enrichment is probably the use of different selection strategies in each round of panning, increasing the specificity but on the other hand reducing the overall yield of selected phage. The enrichment from the second selection round to the third was in the order of 100 fold, indicating a marked increase in phage enrichment, compared to the previous factor of 10. This marked increase is due to the repeated PAb1620 selection. Importantly, the number of phages after the third round was in the order of 10$^5$, whereas with the control PAb1620 it was 4×10$^3$. Therefore, the nonspecific control (i.e., background), constitutes only about 5% of the total selected phage.

Example 3: Method for Screening, and Identifying Mut-p53 Reactivating Peptides

In order to screen, identify and isolate specific p53 reactivating peptides, a method which uses a combination of different and complementary selection strategies was devised and performed.

In this example, three selection strategies were combined. The first selection strategy relies on the reactivity with PAb1620, as described above. The second selection strategy is based on the binding of WT p53 to its consensus DNA sequence motif: p53 responsive element (p53-RE). The binding of p53 to its consensus DNA in-vitro has been extensively demonstrated [Joerger, A. C., M. D. Allen, and A. R. Fersht, *Crystal structure of a superstable mutant of human p53 core domain. Insights into the mechanism of rescuing oncogenic mutations*. J Biol Chem, 2004. 279(2): p. 1291-6). Accordingly, two complementary oligonucleotides were designed to produce dsDNA (after annealing). These oligonucleotides contain two tandem copies of a p53-RE consensus sequences: one consensus sequence is the perfect consensus binding site, deduced from binding experiments (AGACATGCCCAGACATGTCC (SEQ ID NO:339)) and the other sequence is a p53 DNA binding site, derived from the p21 promoter (GAACATGTCCCAACATGTTG (SEQ ID NO:328)), which is located downstream to the first consensus sequence (FIG. 4). In addition, two restriction enzyme sites (HindIII (AAGCTT (SEQ ID NO:341)) and EcoRI (GAATTC (SEQ ID NO:342)), which enable a more specific elution step after selection were further introduced. One oligonucleotide strand was also labeled with biotin, to allow immunoprecipitation of DNA/p53/phage complex with streptavidin coated beads. FIG. 4 shows a schematic sequence of the p53-RE oligonucleotide and the sequence elements thereof. The sequence of the upper strand oligonucleotide is:

(SEQ ID NO: 361)
Biotin-5'-

CTGCTG<u>AAGCTT</u>C<u>GAATTC</u>CTAG*ACATG*CCCAG*ACATG*TCCTACTGCT

GCTGCTGCTGCTGCTGC<u>GA*ACATG*TCCCA*ACATG*TTG</u>CTGCTGCTGCT

GCTG-3'.

In a selection procedure performed using the DNA binding strategy (as detailed below), 0.5-3 pmol of the biotin-p53-RE oligonucleotide was reacted with 200 ng of purified WT p53 for 1 hour to allow binding. 10$^{10}$ phage from either PhD-7 or PhD-12 phage libraries were then introduced for an additional hour. Next, streptavidin coated agarose beads were added for 30 minutes. 5-12 washing steps were then performed, followed by elution performed by adding either the restriction enzymes or an excess of non-biotinylated DNA for 30 minutes. These precautions would reduce selection of phage binding to DNA, biotin and streptavidin.

The third selection strategy is based on the SV40 large T (LT) antigen. The binding between p53 and SV40 LT is considered to be very strong. Therefore, p53 has to be folded properly to form the binding epitope platform to SV40 LT. To this aim, Sf9 cells were infected with baculovirus encoding for SV40 LT. Cells were lysed and the SV40 LT was isolated using protein-A beads cross-linked to PAb 419

(antibody specific for SV40 LT, (Abcam-ab1684)). Beads were washed several times, and then used for phage display selections. The panning procedure for SV40 LT binding was similar to the conformation based strategy, except that instead of using PAb1620 beads, PAb 419-SV40 LT beads were used for the selection.

Figure 1B:
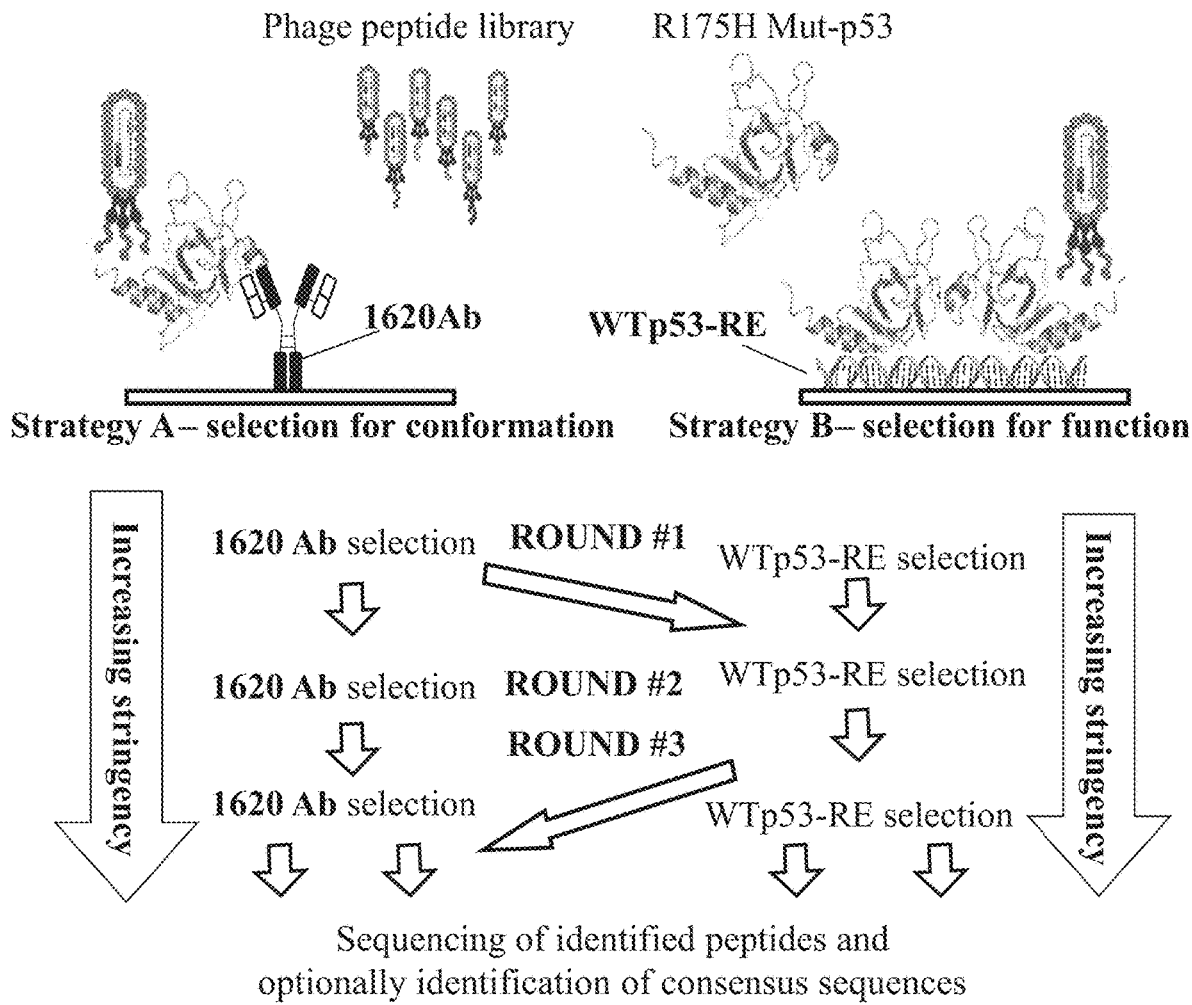
FIG. 1B is a schematic drawing of a method of identification, screening and selection of mutant p53 reactivating peptides. The method comprises alternating various selection strategies, at increasing stringencies, to screen and identify mutant p53 reactivating peptides, by utilizing a phage display method. Strategy A (left): selection according to conformation: selection of peptides expressed and presented by a phage, which can bind a mutant p53 protein (for example, R175H Mut-p53). The Mut-p53 protein is bound to a specific p53 antibody (for example, PAb1620) that is immobilized to a substrate, thereby enabling selection of a bound phage. Strategy B (right): selection according to function: selection of peptides expressed and presented by a phage, which can reactivate a Mut-p53 (for example, R175H Mut-p53), whereby the activation is determined by the ability of the Mut-p53 protein to bind its DNA consensus binding element. The DNA binding element (for example, WT p53-RE) is immobilized to a substrate. A Mut-p53 cannot bind the WT p53-RE, unless it is at least partially reactivated by the reactivating peptide bound thereto. The method may further comprise sequencing (for example, deep sequencing) of the identified peptides to determine their sequences, and optionally identify a consensus sequence for reactivating peptides.

A combination of all three selection strategies in alternating rounds yields the best results, since each cycle gradually increases the percentage of phage that harbor the desired specific peptides, while reducing non-specific background. A schematic illustration of the method of identification and selection is illustrated in FIGS. 1A and 1B.

Phage display screening was performed in parallel with PhD-7 and PhD-12 phage peptide libraries. Alternating cycles of phage selection, using a different immobilized platform (PAb1620, p53-RE DNA or SV40 LT) at each step were performed. Table 4 shows the different selection routes taken to produce enriched phage libraries, and specifies the titer values after each round of selection. By using such different combinations of selection platforms (e.g. PAb1620 followed by p53 consensus DNA followed again by PAb1620, or SV40 LT followed by PAb1620 followed by SV40 LT), as well as the 2 different phage libraries, a panel of sub-libraries was obtained, that could then be compared after sequencing. After 3 cycles of selection, over 60 different pools (sub-libraries) containing a high proportion of Mut-p53-reactivating phage (Table 4) were obtained.

Example 5: Selected Phage Pools Induce Binding of Mut-p53 to PAb1620

To determine whether the phage display selection method as performed above can enrich for phage that reactivate Mut-p53, the ability of the phage pools obtained after 3 cycles of selection to induce the binding of either full length R175H Mut-p53 (BD Pharmingen, Cat. No. 556439), or the recombinant R249S p53 DBD (249 DBD) proteins to PAb1620 was tested. To reduce the undesirable effect of contaminating phage that exhibit direct binding to PAb1620, a pre-clearing step was included whereby the phage pool was first incubated with PAb1620 only, before being added to the test reaction. Beads covalently cross-linked to PAb1620 were incubated with purified mutant p53 R175H in the presence of phage obtained by phage display selection with either Mut-p53 R175H (175) or Mut-p53 R249S (249), either without or with prior pre-clearing step performed by incubation of the phage pool with PAb1620 beads. Non selected phage (ns) were used as control. Incubation was performed for 3 hours at 4° C. Bound p53 was visualized by western blot analysis using antibody against p53. As can be seen in the results presented in FIG. 5, some of the selected phage pools indeed induced binding of Mut-p53 to PAb1620, as compared to no phage or non-selected input phage (ns).

Example 6: Selected Phage Pools Induce Binding of Mut-p53 to p53 Consensus DNA

Figure 6:
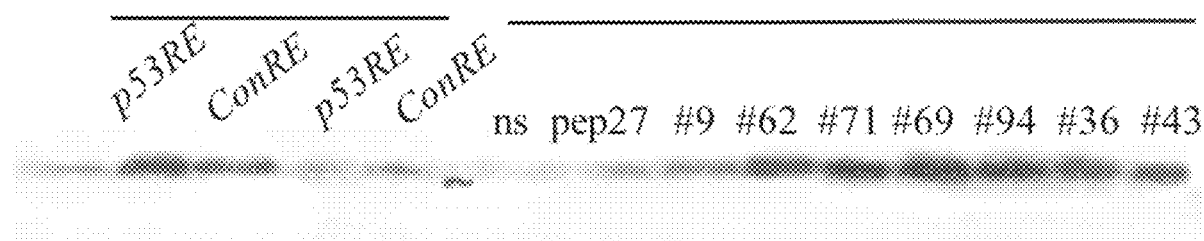
FIG. 6 is a pictograms of western blot analysis of IP experiments, in which streptavidin-coated beads bound either to p53-RE-DNA or control-RE-DNA oligonucleotides labeled with biotin were incubated with purified WT-p53-DBD or mutant p53-R249S-DBD in the presence of phage obtained by phage display selection with Mut-p53 R175H (175), clone 27 (a single clone isolated from the 175 selection, SEQ ID NO:328); pools #69 and #94 selected with WT and Mut-p53 R175H using combinations of SV-40 large T antigen (T-ag) and PAb1620 at alternating selection rounds. Non selected phage (NS) were used as control. Incubation was performed for 3 hours at 4° C. Bound p53 was visualized by western blot analysis using antibody against p53 (αp53).
Figure 6:
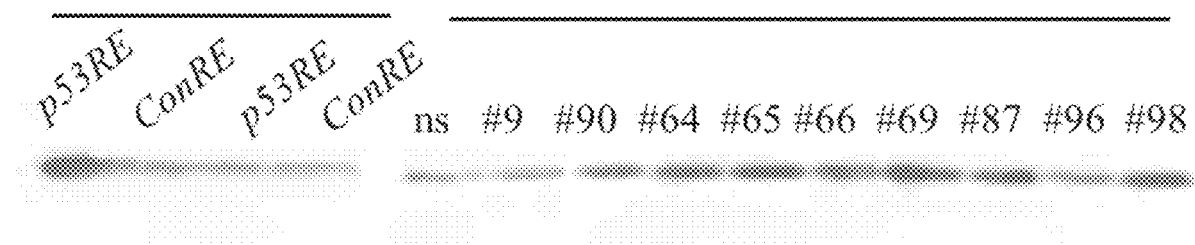

To further test whether the selected phage pools can facilitate the binding of Mut-p53 to p53 consensus DNA binding element, biotin-labelled oligonucleotides corresponding to the p53 responsive element consensus (p53-RE) biotin-AGACATGCCCAGACATGTC CTTATAGA-CATGCCCAGACATGTCC (SEQ ID NO:366) or control oligonucleotides mutated in key residues crucial for p53 binding (Con-RE biotin-AGAaATGCCCAGA aATGTCCT-TATAGAaATGCCCAGAaATGTCC (SEQ ID NO:367), were immobilized by reacting these oligos with streptavidin coated beads. The p53-RE or Con-RE beads were incubated with either WT p53 DBD or mutant 249 DBD, together with the phage pools obtained after 3 cycles of selection. Streptavidin coated beads bound either to p53-RE-DNA or Con-RE-DNA oligonucleotides, labelled with biotin, were incubated with purified WT p53-DBD or mutant p53 R249S-DBD in the presence of phage obtained by phage display selection with Mut-p53 R175H (175), clone 27 (LPNPPER, SEQ ID NO:328) (a single clone isolated from the R175H selection), pools #69 and #94, selected with WT and Mut-p53 R175H using combinations of T-AG and PAb1620 at alternating selection rounds. Non selected phage (NS) were used as control. Incubation was for 3 hours at 4° C. Bound p53 was visualized by western blot analysis. As can be seen in the results presented in FIG. 6, the WT p53 DBD bound to p53-RE better than to the Con-RE, as expected. The 249DBD did not bind to the p53-RE, consistent with its known loss of sequence-specific DNA binding ability. Importantly, the selected phage pools were capable of inducing the binding of Mut-p53 to the p53-RE, demonstrating that they are indeed capable of reactivating and restoring the lost function of Mut-p53.

Example 7: Deep Sequencing of Selected Phage Pools

Next generation sequencing, which greatly increases the effectiveness of phage display, allowing extraction and analysis of the entire selected peptide repertoire, with fewer selection cycles was performed. Eight phage pools were selected for deep sequencing using criteria of increased enrichment between selection rounds and functional activity. Prior to sequencing, a PCR reaction was performed with primers flanking the inserted libraries: Forward-5'-NNNNNNNNCATGGAAAGATAGTG (SEQ ID NO:364), and Reverse-5'-NNNNNNNNCCTAAAACGATTTGTG (SEQ ID NO:365), the first 8 bases of each primer are randomized and were incorporated as a mixture of all four bases. Randomization of first bases was introduced to improve sequencing efficiency and accuracy. The PCR reaction yielded DNA in the required quantity 5 µg and length (about 120 bp), which includes the flanking primers and the cloned peptide library for Solexa deep sequencing.

The deep sequencing yielded a database of 36 million reads. 95% of the sequences contained the primer sequences used in the PCR when extracting the libraries. Next, a preliminary bioinformatics analysis of the data was performed. This analysis included the removal of sequences that do not contain the original primers, removal of sequences that are not in the correct reading frame, segregation of the database into the original 12 amino-acid and 7 amino-acid libraries according to insert length, and finally counting of unique sequences and sorting them according to number of appearances in the database. It was found that most sequences appeared only once or twice in the database, presumably corresponding to background phage. 12 reads were defined as a cutoff, beneath which the enrichment of sequences was considered to be insignificant. The DNA sequences in the database were then translated into amino acid sequences.

As an internal quality control, the sequences and their abundance as the percent from the total library between the two strands that were sequenced from opposite directions and therefore contained a different primer at their 5' were compared. The comparison showed that the sequences and their abundance was similar between the two strands, indicating that the obtained sequence database is valid.

Table 5 shows a list of peptide sequences obtained from the deep sequencing database of 5' strands. This database contains $10^7$ sequences in total, after filtering irrelevant sequences. A cut-off counting and translation was then performed. The column (#Reads) shows the number of times the sequence repeats in the described database and therefore corresponds to the enrichment of that specific sequence. Since the bioinformatics analysis was performed on DNA sequences, and individual peptides can be encoded by several different DNA sequences because of the genetic code degeneracy, there are quite a few peptides that appear in the table more than once. If a certain peptide is encoded by different DNA sequences, it means that it was selected independently within different phage clones.

Alternatively, a number of DNA sequences coding for the same peptide could be a result of sequencing errors: however, in this case it would be expected that the result of such a mistake would be in a random base and therefore not enriched in a high number of reads. Therefore, DNA sequences that were under 30 reads in the #Repeats count were excluded. The column (#Repeats) shows the number of DNA sequences coding for the same peptide sequence, and is therefore a further indication of the specificity and strength of the selection.

As seen in Table 5, the sequences could be segregated into their two libraries of origin. The peptide sequence is depicted in the middle column and the sequences are sorted in descending order according to the number of reads that corresponds to the enrichment in each library. The 12aa library was found to be dominated by a single sequence—KPPDRLWHYTQP (SEQ ID NO:322), that makes up almost 20% of the total number of sequences. The 7aa library is more diverse and contains many more sequences, but with lower enrichment values.

Table 5 presents the analysis of deep sequencing database—sequences are divided into to their two libraries of origin, the peptide sequence is depicted in the middle column and the sequences are sorted in descending order according to the number of reads that corresponds to the enrichment in each library. The column (#Repeats) shows the number of DNA sequences coding for the same peptide sequence.

Example 8: Bioinformatics Motif Analysis of the Deep Sequencing Database

Next, a more comprehensive bioinformatics analysis was performed in order to identify consensus motifs. Such motifs could be elucidated in several ways. First, comparison between peptide sequences identified in the 12aa and the 7aa libraries. The appearance of common motifs in both libraries would support the strength of such a motif since it was clearly selected in two completely independent experiments. Secondly, the abundance of a certain amino acid in a particular position and its similarity to other amino acids in the same position of the motif can serve as an indication for the significance of such amino acid in this particular position. Thirdly, the position of a motif may be of critical importance to its function: a short motif can shift along a longer peptide sequence with variability in other amino-acid sequences and the distance from the free N-terminus of the peptide may inform on significance to its activity. An algorithm was developed to check the amino acid sequence in a growing window of peptide length as follows:

1. scoring each peptide, integrating the number of different nucleotide sequences that translate into the same peptide with the occurrences of each such type of nucleotide sequence;
2. clustering the different peptides, scoring the sequence similarity between different peptides; and
3. identifying groups of related peptide sequences and extracting a consensus therefrom.

Candidate peptides were those with the top occurrences ≥0.2%: 40 from the 7aa library, and 32 from the 12aa library. These could be clustered into 40 groups by their Blastp similarities and occurrence of a short amino acid (aa motif). Most groups included a single peptide, but 9 groups included 2-13 peptides, and 6 of these groups included both 7aa and 12aa peptides.

The groups were transformed into block multiple alignments, with the % occurrences being the sequence weights. The blocks were used to query the 7aa and 12aa peptide-clustered sequence files, and the top results were again transformed into blocks in the same way. In some blocks, but not in all, results from the two libraries were similar to each other.

Figure 7:
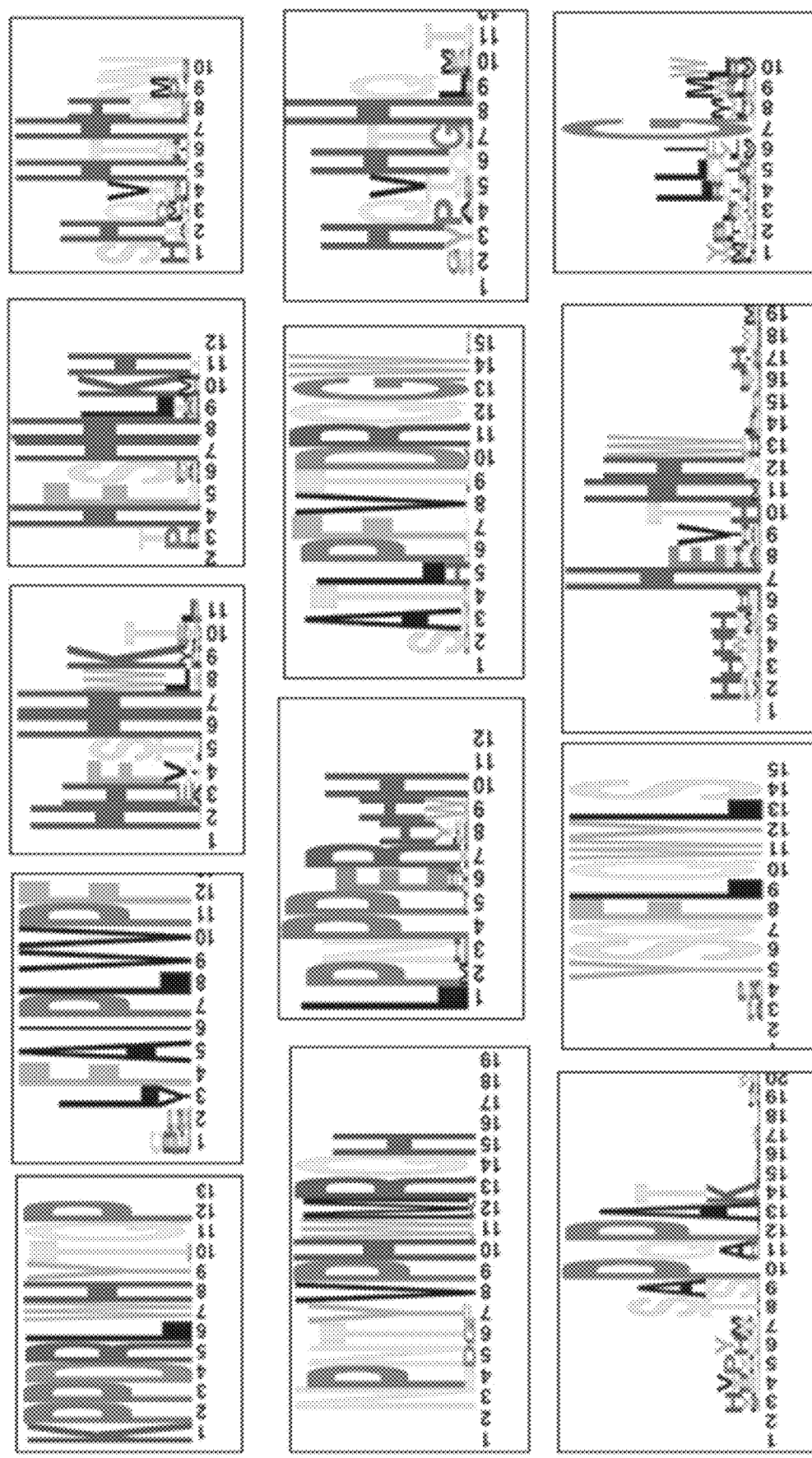
FIG. 7 is a schematic illustration of several consensus peptide motifs identified as described herein.

The deep sequencing output (i.e. creation of database of millions of peptide sequences as compared to hundreds of sequences by conventional sequencing) enabled a much more detailed and comprehensive analysis of consensus motifs. Overall, about 130 motifs of significantly enriched sequences were identified; most of these peptide motifs are represented by several DNA sequences and 16 of these motifs are shared between both the 7aa and 12aa libraries. FIG. 7 shows several such motifs. Some of the motifs resulted from combining overlapping sequences and therefore are longer than the original peptide libraries.

Example 9: Synthesis of Peptides

From the obtained list of peptide motifs identified as described above, 128 peptides were chemically synthesized by PEPTIDE 2.0 at crude purity taking advantage of a 96 well format. This semi high throughput synthesis enabled a relatively low cost of each peptide. Table 6 below lists the peptides synthesized. This list also includes some peptides derived from proteins that are known from the literature to interact with p53. The list also includes 10 peptides synthesized in two versions, both without and with a poly arginine C-terminal addition. This poly-Arg addition was reported to enable the crossing of peptides across cell membranes. This allows the evaluation of both the ability of the poly Arg C-terminal addition to enable peptide delivery into the cells and whether it interferes with the activity of these particular peptides in-vivo. The poly Arg may include 0-10 Arg residues and is designated as $R_{0-10}$.

Differences between the chemically synthesized peptides and the peptides that were selected from phage display libraries may occur. In particular, the selected peptides were presented in the context of the phage as fusion proteins with the pIII phage coat protein. Therefore, this transition to synthetic peptide is not trivial, and it is known that in some instances peptides shown to be active when presented on phage lose their activity when the same sequence is synthesized as a free peptide.

Example 10: Functional Screening of Lead Test Peptides

Several alternative and complementary methods to screen the lead peptide candidates for conformational and functional effects on Mut-p53 were used. Since no information regarding the penetration of each test peptide across cell membranes was known, in-vitro based assays for evaluation were first performed: ELISA for assessment of p53 conformation and sequence-specific DNA binding of p53. Subsequently, the peptides' activity was examined in live cells by viability assays, p53 transcriptional activity on a luciferase reporter gene, and examination of p53 target genes in-vivo. Combination of these assays (all performed in a 96 well format) allowed the identification and validation of the peptide's effects on different p53 activities and their ability to confer such ability to Mut-p53 proteins.

Screening Peptides for Effect on p53 Conformation

Figure 8A:
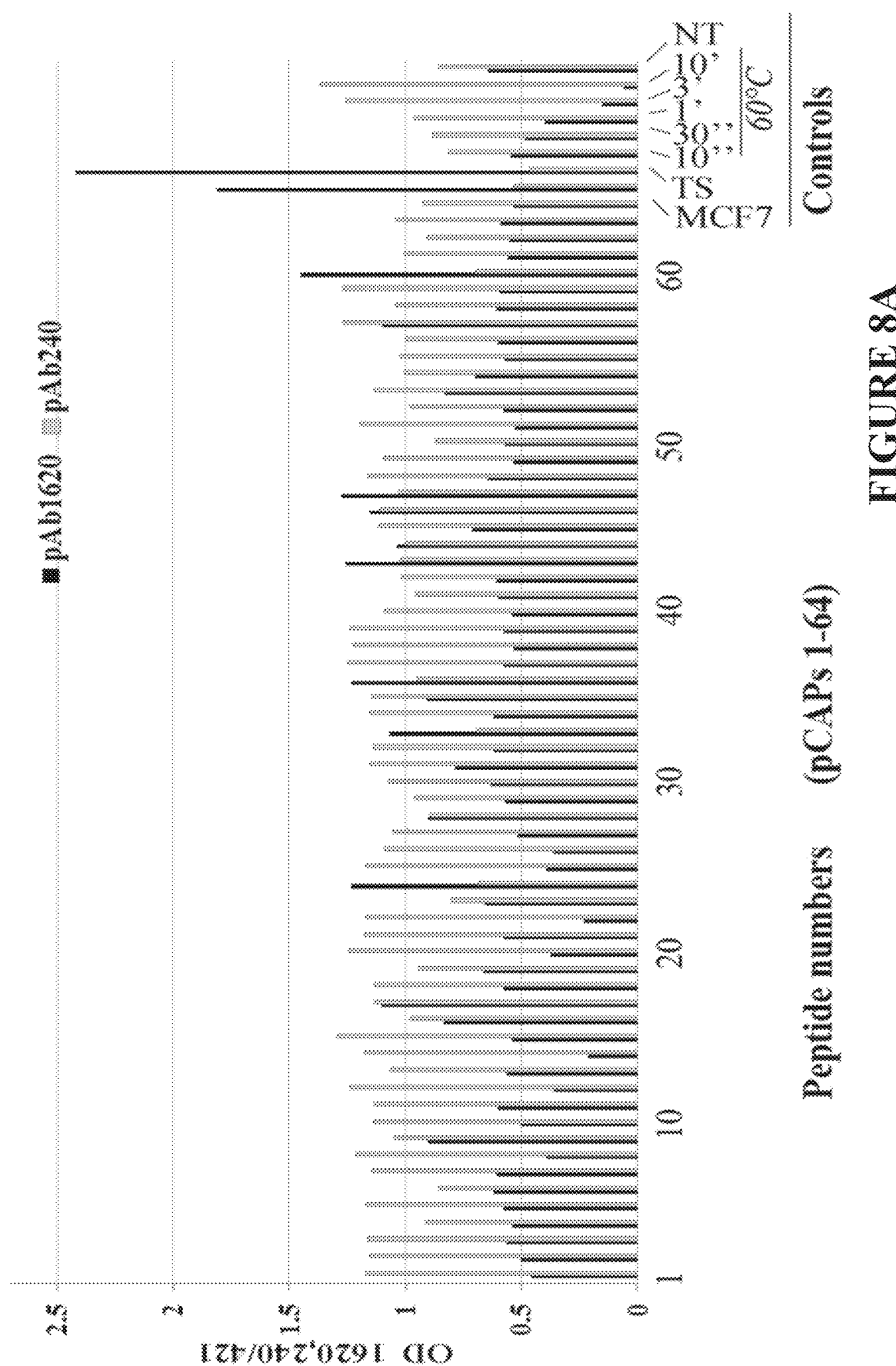
FIGS. 8A and 8B are bar graphs, demonstrating representative ELISA experiments of determining the effect of tested peptides on the conformation changes of Mut-p53 in H1299 cells stably overexpressing Mut-p53 (R175H p53), as determined by immunoassay. To measure the conformational effect of the peptides on Mut-p53, a micro-titer plate was coated with either PAb240, PAb1620 or pAb421 (as a positive control and standard for total p53 protein, since the antibody used recognizes both WT and mutant conformations), overnight incubated, washed, blocked, and cell extracts (with or without peptides) were added for an additional 2 hours. After removal of extracts, plates were washed and incubated with the αp53-HRP conjugated Ab for the detection of p53 levels. A TMB (substrate of HRP) assay was performed and optical density was determined at 450 nm. WT p53 served as a positive control for reactivity with PAb1620, and Mut-p53 served as a negative control. The results are presented as the ratio of absorbance between the PAb1620 or PAb240 samples and the control pAb241 sample. MCF7 and H1299-Mut-p53 (ts) A135V (TS) cells were used as positive controls for the WT p53 conformation (1620/240 ratio equals or exceeds 5:1).
Figure 8B:
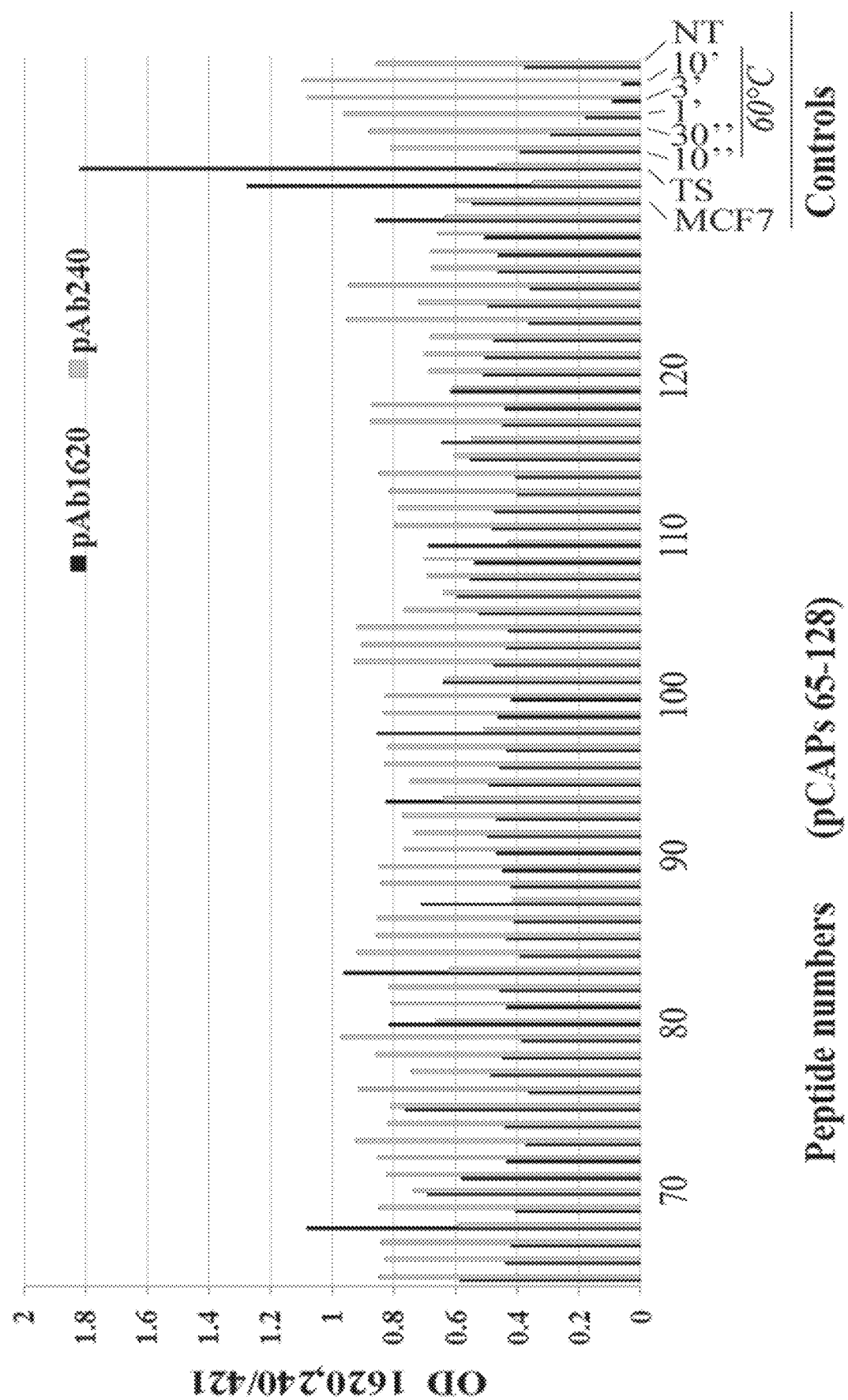

The first screening strategy was based on ELISA. A version of sandwich ELISA was used to examine the effect of the lead test peptides on p53 conformation. To measure the conformational effect of the peptides on Mut-p53, a micro-titer plate was coated with PAb240, PAb1620 or pAb421 (as a positive control), and then the reactivity of p53 to these antibodies was examined. WT p53 served as a positive control for reactivity with PAb1620, and Mut-p53 served as a negative control. To examine the effect of a tested peptide it was added to a solution containing Mut-p53 and change in reactivity to either Ab was tested. If after addition of a peptide an increased reactivity of Mut-p53 towards PAb1620 and a decreased reactivity to PAb240 were observed, it indicated that the tested peptide has reactivated WT conformation of Mut-p53. Several ELISA experiments using different cell extracts were performed. The results are presented in FIGS. 8A-B, which show a representative experiment performed on an extract of H1299 cells stably overexpressing Mut-p53, (R175H p53). Extracts were prepared at 750 ng/µl concentration in standard immunoprecipitation buffer at a physiological pH and salt concentrations and supplemented with 3% BSA for blocking, and then reacted with different peptides at a concentration of 50 ng/ml for 2 hours. Plates were coated with the various antibodies (Abs) overnight, washed, blocked, and cell extracts (with or without peptides) were added for an additional 2 hours. After removal of extracts, plates were washed and incubated with the αp53-HRP conjugated Ab for the detection of p53 levels. Finally, a TMB (substrate of HRP) assay was performed and optical density was determined at 450 nm (as described above). MCF7 and H1299-Mut-p53 (ts) A135V (Zhang, W., et al., *A temperature-sensitive mutant of human p53*. Embo J, 1994. 13(11): p. 2535-44) cells were used as positive controls for the WT p53 conformation (1620/240 ratio equals or exceeds 5:1). The H1299-R175H p53 extracts, while exhibiting more mutant p53 conformation, still maintained reactivity to PAb1620 (1620/240 ratio is 1:2) of PAb1620 or PAb240 over PAb421. However, when discussing the outcome of the analysis, the PAb1620/PAb240 calculated ratio, which better captures the extent of conformational change is referred to. To examine whether this is background binding to the antibody or actual WT folding conformation, increasing levels of denaturation were induced by heating the extracts for different time lengths, monitoring their reactivity to PAb1620 and PAb240. As seen in FIGS. 8A and 8B, increased heat treatment induced an increase in reactivity with PAb240 and a decrease in reactivity with PAb1620, indicating that the R175H p53 in these extracts remained partly in WT conformation under these experimental conditions. Notably, after incubation with some of the tested peptides, increased reactivity of R175H Mut-p53 towards PAb1620 and decreased reactivity towards PAb240 was detected. This was the case, for example, with peptides 24, 36, 47, 60, 68 (Table 6), indicating that these peptides elicit a conformational change in mutant p53 protein.

Screening of Peptides for Effect on Mut-p53 Binding to p53-RE DNA.

Figure 9:
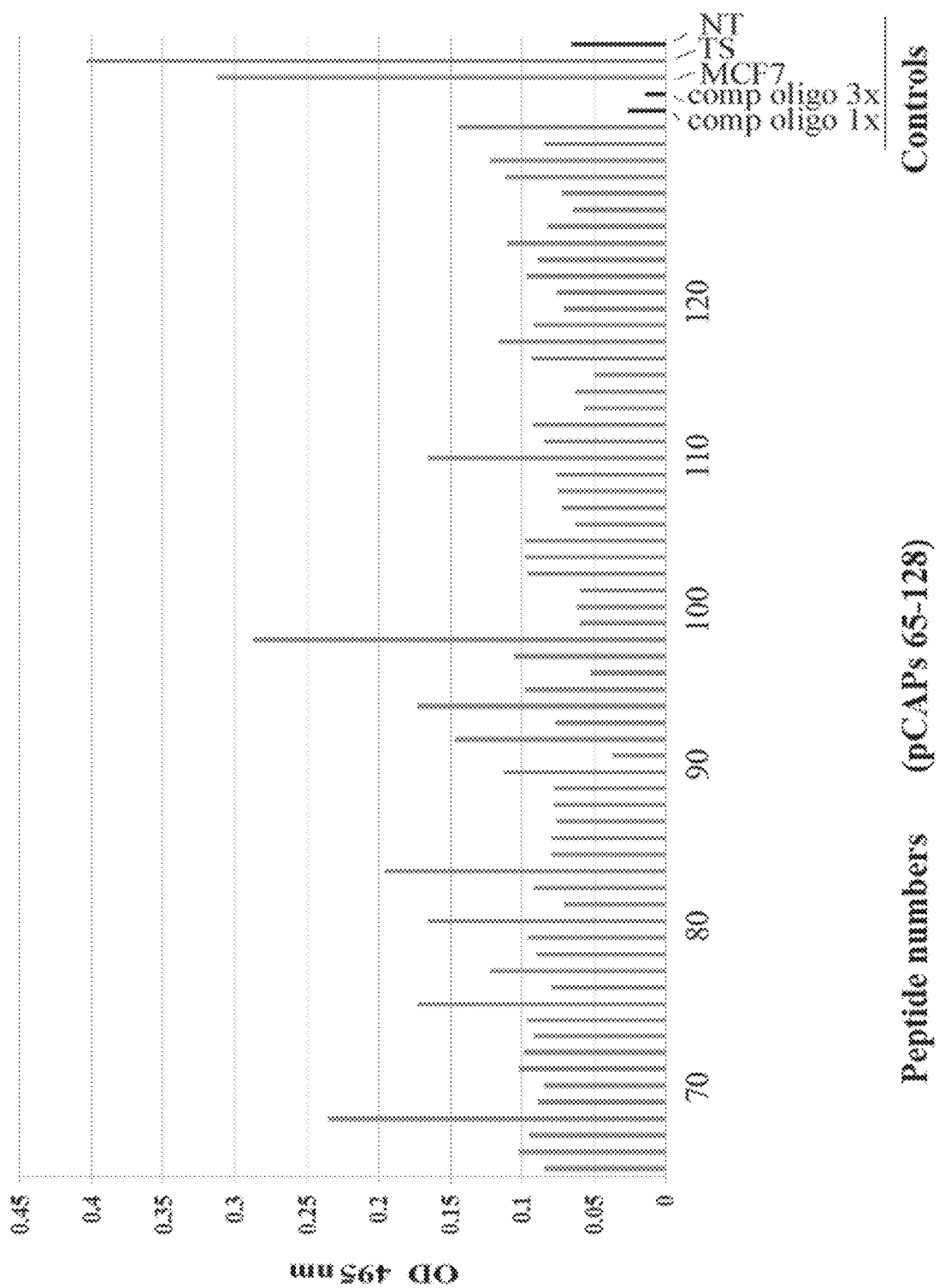
FIG. 9 is a bar graph, demonstrating representative ELISA experiments of determining the effect of tested peptides on the DNA binding activity of Mut-p53 in H1299 cells stably overexpressing Mut-p53 (R175H p53). A commercial p53/DNA binding kit (R&D) was used, according to manufacturer instructions. Briefly, 96 well plates were coated with anti-p53 antibody overnight. Cell extracts containing p53 were reacted with an oligonucleotide that contains a p53 consensus binding site, labeled with biotin, in the presence or absence (NT) of test peptides. WT p53 is expected to bind this DNA binding site as well as to the antibody coating the test wells of the plate. Excess p53 and oligos are washed away and streptavidin-HRP is used to quantify the amount of oligos in the well, which is proportional to the DNA bound by p53. TMB assay was performed to determine HRP levels (450 nm). The results are presented as relative absorbance (at 450 nm) (Y-Axis) of each tested sample. MCF7 and the H1299-Mut-p53 (ts) A135V cells serve as positive controls for WT p53.

To measure the effect of the tested peptides on DNA binding of Mut-p53, a commercial ELISA kit, (R&D Systems DYC1355-5, Lot-1273366FA), was used as a high-throughput assay to quantify p53 activation. This kit uses a 96-well plate format. The kit was used according to manufacturer's instructions. Wells were coated with anti-p53 antibody overnight. Cell extracts containing p53 were reacted with a biotin labeled oligonucleotide containing a p53 consensus binding site (included in the kit). WT p53 is expected to bind this oligo as well as the antibody coating the wells. Excess p53 and oligo were washed away in wash buffer (0.05% Tween 20 in PBS, pH 7.2-7.4; R&D Systems, Catalog #WA126). Then, streptavidin-HRP (R&D Systems, Part 890803, provided in the kit) was added for 15-45 min to quantify the amount of oligo in the well, which is proportional to the DNA bound by p53. If the addition of a peptide to Mut-p53 extracts increases ELISA reading compared to background, this peptide is considered as functionally effective and may be selected for further analysis. FIG. 9 shows a representative experiment: similarly to conformation ELISA, cell extracts were incubated with biotin-p53-RE either in presence or absence (NT) of test peptides. As with the conformational screening, MCF7 and the H1299-Mut-p53 (ts) A135V cells served as positive controls for WT p53. Extracts were added to the wells coated with αp53-Ab, and after several washing steps, streptavidin-HRP was added for 1 hour, and then plates were washed again and TMB (substrate to HRP) assay was performed. As can be seen in FIG. 9, H1299-R175H p53 extracts exhibited some background binding to the p53-RE oligo, which was further reduced by non-labeled competing oligo. Positive controls showed a 3-4 fold higher signal compared to the background. Several peptides appear to elevate the binding of H1299-R175H p53 extracts to p53-RE DNA, for example: 68, 75, 83, 93, 97.

Binding of Peptides to WT p53 and Mutant p53.

To measure the binding of peptides to Mut-p53 and WT p53, a commercial ELISA kit from "TAKARA" (MK100 Lot AK401), was used as a high-throughput assay to quantify the binding of different peptides to proteins or antibodies. The kit was used according to the manufacturer's instructions. The wells were plated with the peptides by performing a chemical reaction attaching the C-terminus of the peptide to the plate.

Figure 10:
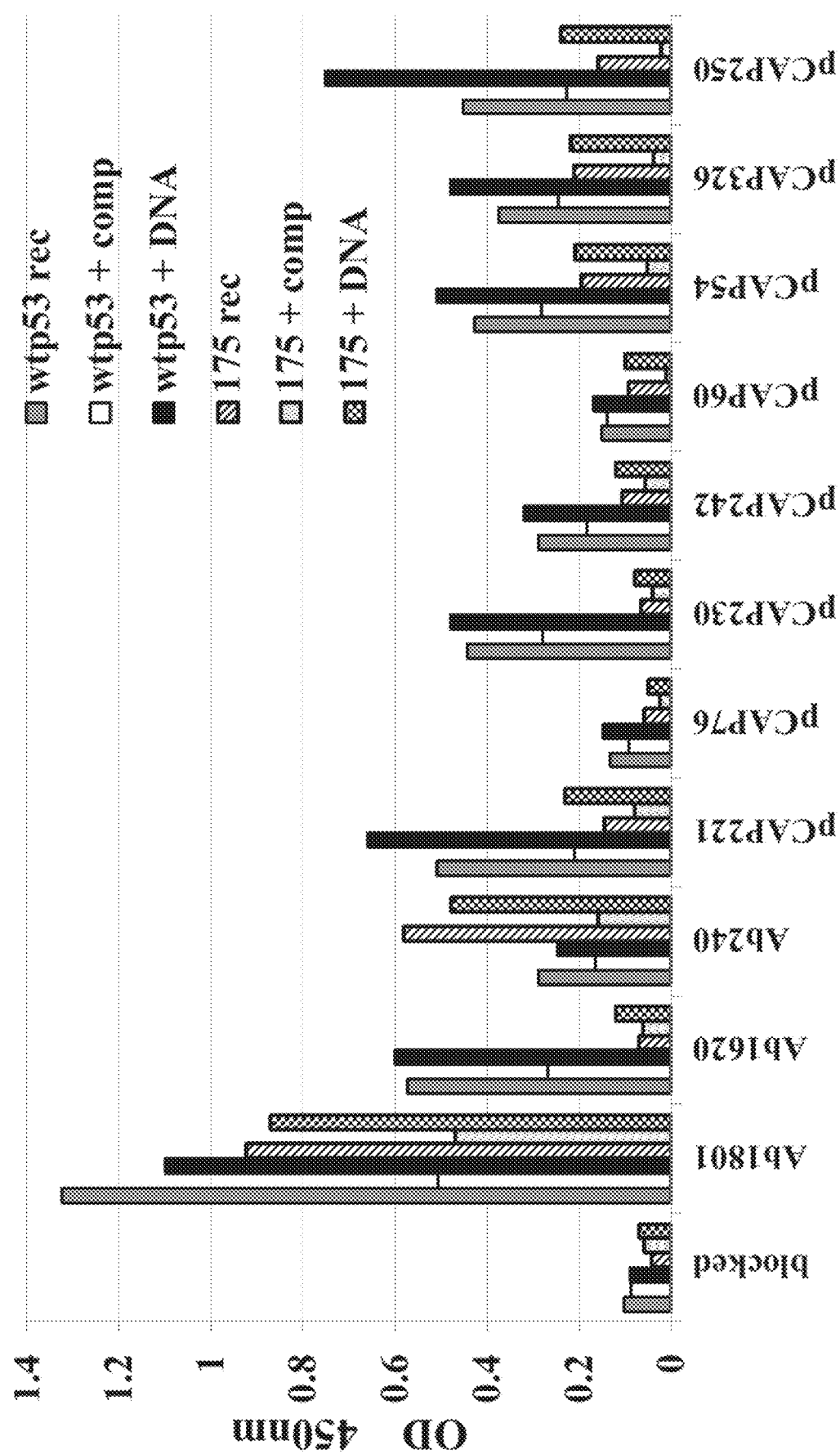
FIG. 10 is a bar graph depicting representative ELISA experiments to determine the binding of tested peptides to recombinant WT p53 and Mut-p53. A commercial peptide-protein binding kit (TAKARA) was used according to the manufacturer's instructions. Briefly, 96 well plates were coated with peptides for 2 hours. Soluble peptides were added to the corresponding wells to serve as a competition control to confirm the specificity of peptide binding to p53 (+comp). p53-RE DNA oligo was added to other wells (+DNA) to examine whether it affects the binding of peptides to p53. After removal of recombinant protein, plates were washed and incubated with αp53-HRP conjugated Ab for quantification of p53. Finally a TMB (substrate of HRP) assay was performed and optical density was determined at 450 nm. The results are presented as relative absorbance at 450 nm (Y-Axis) of each tested sample. The following αp53 monoclonal antibodies served as internal controls: PAb1801; PAb1620 and PAb240.

Recombinant WT p53 or Mut-p53 R175H at a concentration of 10 ng/ml was dissolved in PBS and blocking buffer and then added to the peptide coated plates for 2 hours. Soluble peptides were added to the corresponding wells to serve as a competition control indicating the specificity of peptide binding to p53 (+comp) and p53-RE DNA oligo was added to other wells (+DNA) to examine whether it affects the binding of peptides to p53. After removal of recombinant protein, plates were washed and incubated with the αp53-HRP conjugated Ab to quantify p53 levels. Finally a TMB (substrate of HRP) assay was performed and optical density was determined at 450 nm. FIG. 10 shows a representative experiment performed with the corresponding peptides and antibodies. As seen, wells were attached with αp53 monoclonal antibodies to serve as internal controls of the assay; PAb1801 binds both p53 forms as expected; PAb1620 is specific to WT p53 and PAb240 is more reactive with the mutant form. The (blocked) wells were not coated with peptides and pep76 is control peptide sequence. As can be seen, most peptides shown in the figure bind with higher affinity to the recombinant WT p53 as compared to the mutant p53.

The Effect of pCAP on Mut-p53 Binding to its Responsive Elements in Live Cells.

Figure 11:
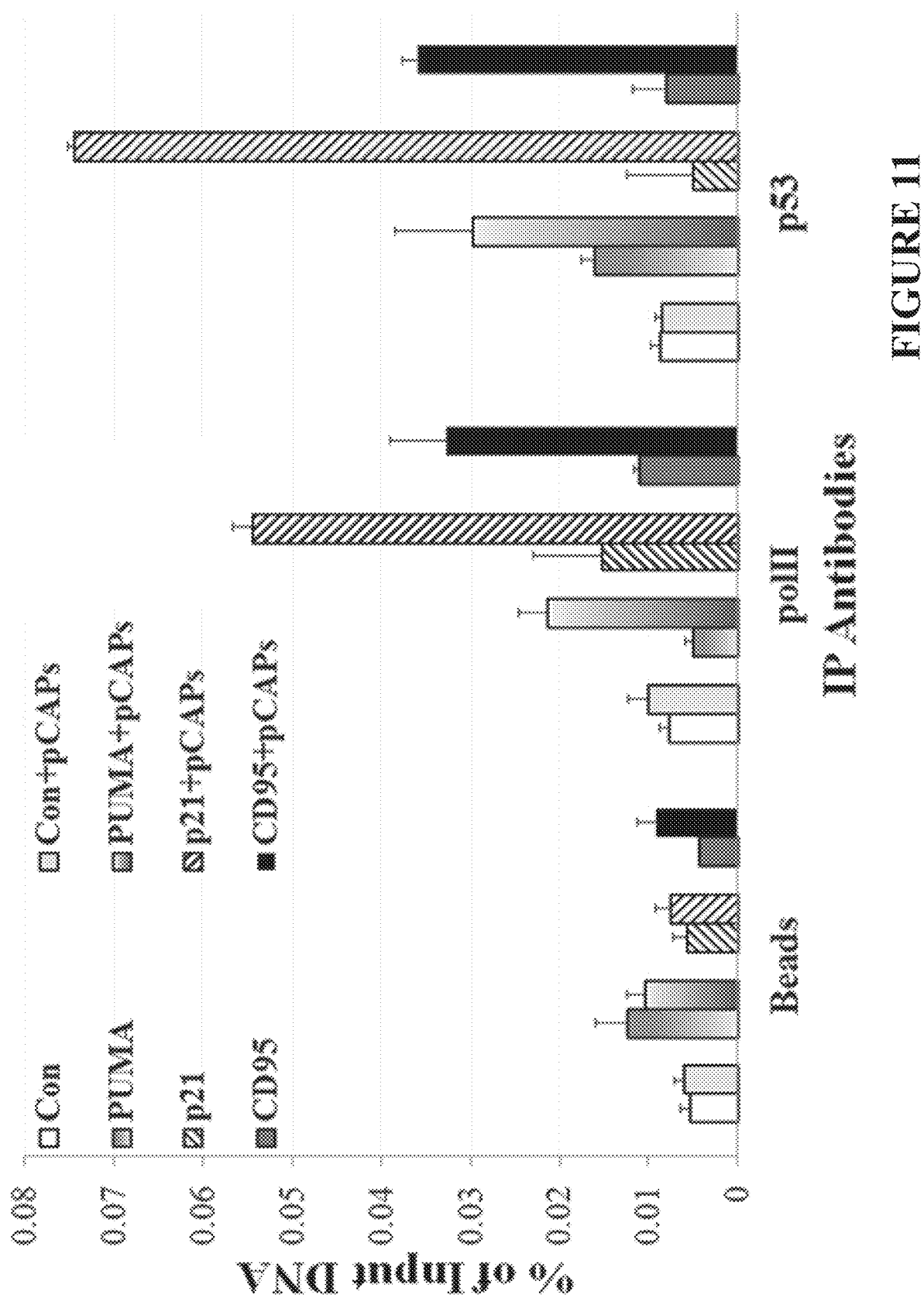
FIG. 11 is a bar graph, demonstrating binding of Mut-p53 to promoters of representative p53 target genes in live cells. BT-549 breast cancer cells endogenously expressing mutant $p53^{R249S}$ were treated for 5 hour with a mix of 3 pCAPs—250, 308 and 325. Cells treated with a mix of control peptides (inert peptides) served as a negative control. Cells were fixed with 1% formaldehyde, harvested and DNA was sheared by sonication. DNA cross-linked to p53 was immunoprecipitated using a polyclonal anti-p53 antibody (H47). DNA was purified and binding to the p53 responsive elements of the PUMA, p21, CD95 and MDM2 gene promoters was quantified by qPCR. Results were normalized to input samples that represent total DNA levels. As a negative control, extracts were immunoprecipitated with beads without antibody (beads). A genomic site not containing any p53 binding element served as a negative control (black).

Next, it was examined whether p53 can also bind to chromatin of its target genes. Using chromatin immunoprecipitation (ChIP) assay, it was examined whether pCAPs can restore the Mut-p53 DNA binding ability to p53 response elements (p53-RE). Breast carcinoma BT-549, endogenously expressing mutant $p53^{R249S}$, were treated for 5 hour with a mix of 3 pCAPs; 250, 308 and 325. Cells treated with a mix of control peptides served as a negative control. Then cells were fixed and DNA was sheared by sonication. The DNA cross-linked to p53 was immunoprecipitated using polyclonal anti p53 antibody. DNA was purified and then p53 responsive elements of different p53 target genes were quantified using different primers in the qPCR reaction. Results were normalized to total DNA input. As a negative control, extracts were immunoprecipitated with beads without antibody (Beads). As seen in FIG. 11, the binding of chromatin to the control beads was at a basal level of 0.005% of the input DNA. pCAP mix did not increase the binding of p53 to a non-specific genomic DNA control sequence, but p53 binding to responsive elements in PUMA, p21 and CD95 genes was increased 2.34, 9.78 and 4.54 fold, respectively, by pCAPs compared to control peptides.

Screening Peptides for Effect on p53 Transcriptional Activity

As additional screening strategy used to identify reactivating peptides was performed in vivo and is based on a reporter gene assay. It measures p53 transcriptional activity by quantifying the activity of a reporter gene, placed under the control of a promoter containing 17 repeats of a p53 consensus binding site (RGC). The luciferase assay is performed on living cells and therefore provides an indication on the effect of test peptides on Mut-p53 function in the context of intact cells. An RGC-based promoter cloned upstream of a secreted luciferase reporter (TK-RGC-luc) (New England Biolabs (CAT. NO. N0324S)) was used, since it does not require lysis of the cells and allows the use of a 96 well format.

Figure 12:
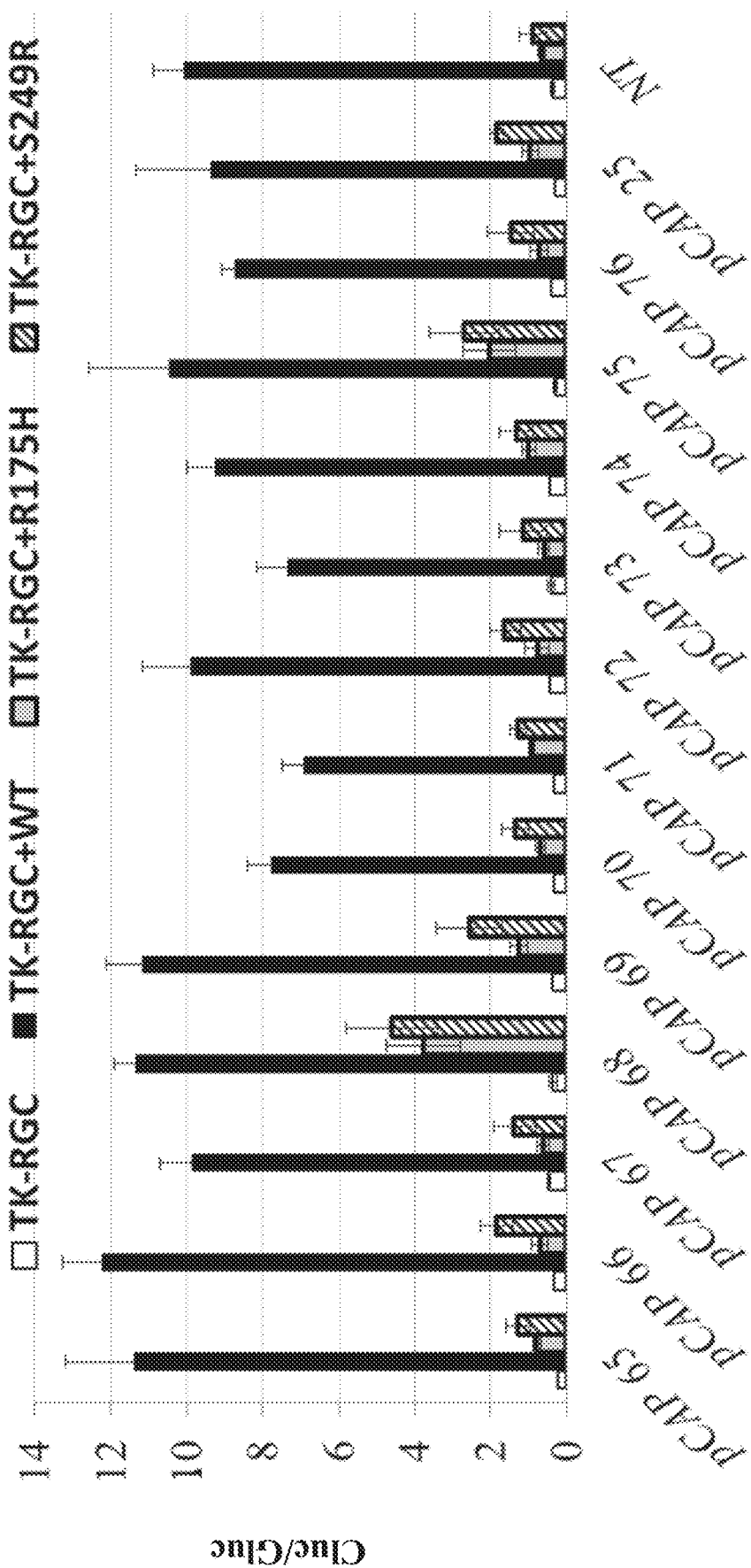
FIG. 12 is a bar graph illustrating the relative luciferase activity (cLuc/gLuc) as measured in the various tested samples. Transient transfection of H1299 p53$^{-/-}$ cells was performed with plasmids expressing WT p53, R175H p53, R249S p53 or empty vector as control, together with TK-RGC-luc, where luciferase expression is under control of a tandem array of multiple p53-responsive elements. 24 hours after transfection, cells were treated with the test peptides. 48 hours after transfection, a sample of the culture medium was taken for bioluminescence measurements.

FIG. 12 shows a representative luciferase assay experiments that were performed to assess the ability of peptides to restore transcriptional activity to mutant p53. For the in vivo luciferase based screening, H1299 cells were used. Transient transfection of these $p53^{-/-}$ cells was performed with vectors expressing WT p53, R175H p53, R249S p53 or empty vector as control (Suad, O., et al., *Structural basis of restoring sequence-specific DNA binding and transactivation to mutant p53 by suppressor mutations*. J. Mol. Biol., 2009. 385(1): p. 249-65). Cells were also co-transfected with TK-RGC-luc (CAT. No. NEB, N0324S). 24 hours after transfection, cells were treated with the test peptides. 48 hours after transfection, a sample of the culture medium was taken for bioluminescence measurements. As can be seen in FIG. 12, in the non-treated samples, transfection of WT p53, (positive control), induced transcription from TK-RGC-luc by 20-30 fold as compared to TK-RGC-luc alone. When examining the peptide treated samples, it is seen that the peptides had no significant effect on WT p53 activity; this is an encouraging result, since peptides greatly increasing WT p53 activity are expected to have toxic effects on normal cells. Two of the tested peptides, namely pCAP-68 and pCAP-75, induce transcription from TK-RGC-luc in the presence of R175H p53 and the R249S p53.

Screening Peptides for Effect on Viability of Mutant p53 Expressing Cells

An important indication for the reactivating peptides activity is their effect in-vivo on cancer cells that express Mut-p53. In particular, reactivating peptides that can cause specifically Mut-p53-dependent death of cancer cells, with minimal toxic effects on normal cells are desired. A crystal-violet based viability assay, in which crystal-violet is employed to stain cells that adhere to the plate and therefore the amount of dye is proportional to cell number was used to determine the effect of the various test peptides on Mut-p53-dependent death. The crystal-violet assay is straightforward, fast, reliable, inexpensive and does not require a complicated preparation of samples.

Cells were plated in 96-well plates, at calibrated density that allows them to grow for 48 hours without reaching confluence. Peptides are added 6 hours later. Different concentrations of etoposide (cytotoxic drug) were used as positive control for cell death and as a standard reference curve to assess the effect of tested peptides. 48 hours after treatment, cells were washed with PBS to exclude dead cells and debris, and cells that remained attached to the plate were stained with crystal-violet for 30 minutes. Crystal-violet was removed and cells were washed with PBS 4 times to eliminate remains of crystal-violet. Then, the stained cells were dissolved in 10% acetic acid and plates were taken for optical density measurement at 595 nM (specific to crystal-violet).

Figure 13A:
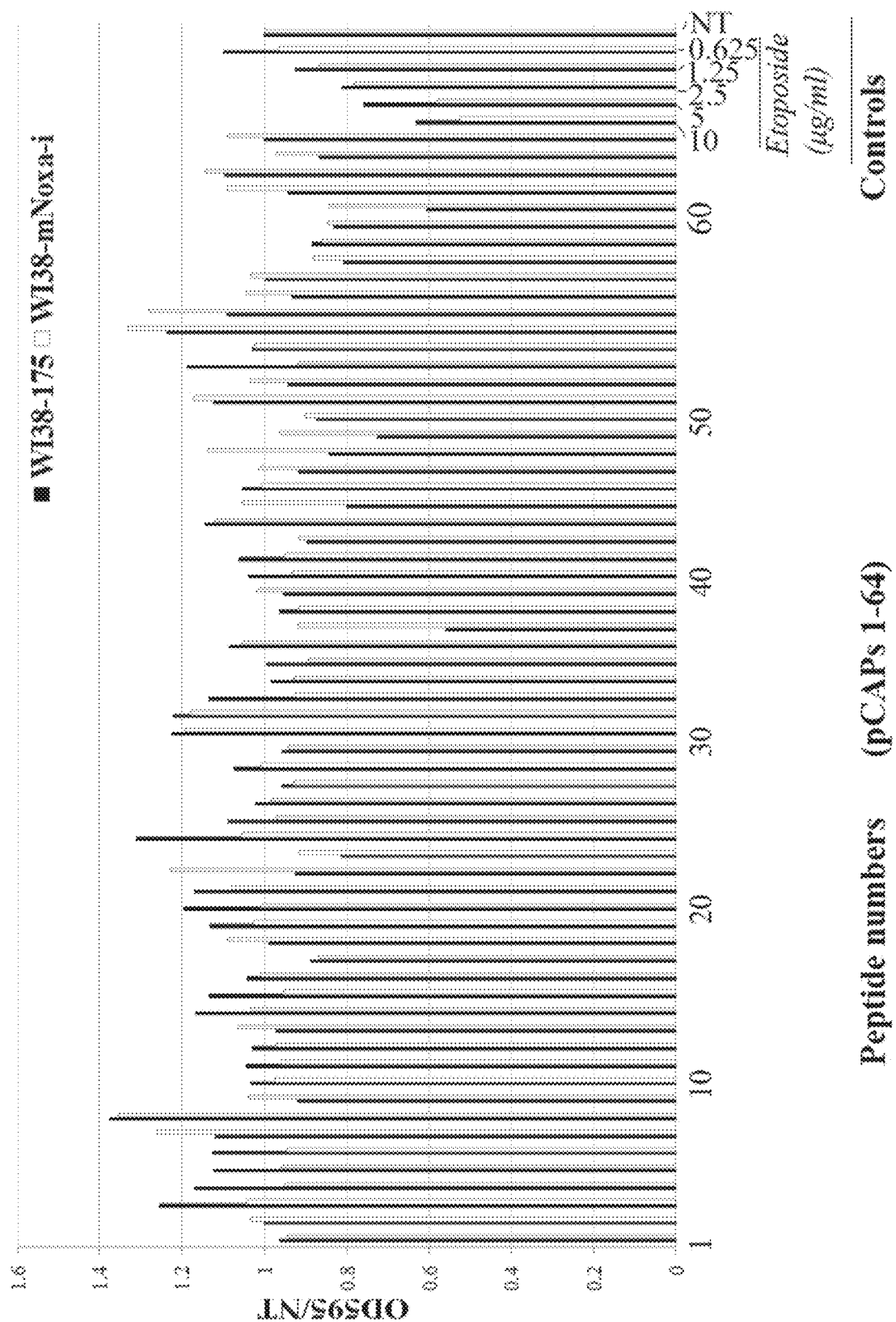
FIGS. 13A and 13B are bar graphs illustrating the effect of various tested peptides on the viability of cells expressing Mut-p53, as determine by crystal violet assay. WI-38 fibroblasts expressing endogenous WT p53 were infected with retroviruses expressing either mouse Noxa shRNA (WI38-m-Noxa-i) as a nonspecific control or the R175H p53 mutant for stable overexpression of mutant p53 (WI38-175). The cells (WI38-m-Noxa-i or WI38-175) were seeded at 3000 cells per well in 96-well plates. Tested peptides were added to the cells. Different concentrations of etoposide (cytotoxic drug, 4'-Demethyl-epipodophyllotoxin 9-[4,6-O—(R)-ethylidene-beta-D-glucopyranoside], 4'-(dihydrogen phosphate) were used as positive control for cell death and as a standard reference curve to assess the effect of tested peptides. 48 hours after treatment, cells were washed with PBS to exclude dead cells and debris, and cells that remained attached to the plate were stained with crystal-violet for 30 minutes. Crystal violet was removed and cells were washed 4 times with PBS to remove residual crystal violet. Then, the stained cells were dissolved in 10% acetic acid and plates were taken for optical density measurement at 595 nM (optimal for crystal violet). The bar graphs of FIGS. 13A and 13B show the optical density reads at 595 nm, which reflect the number of cells in the plate after treatment, normalized to the non-treated (NT) samples.
Figure 13B:
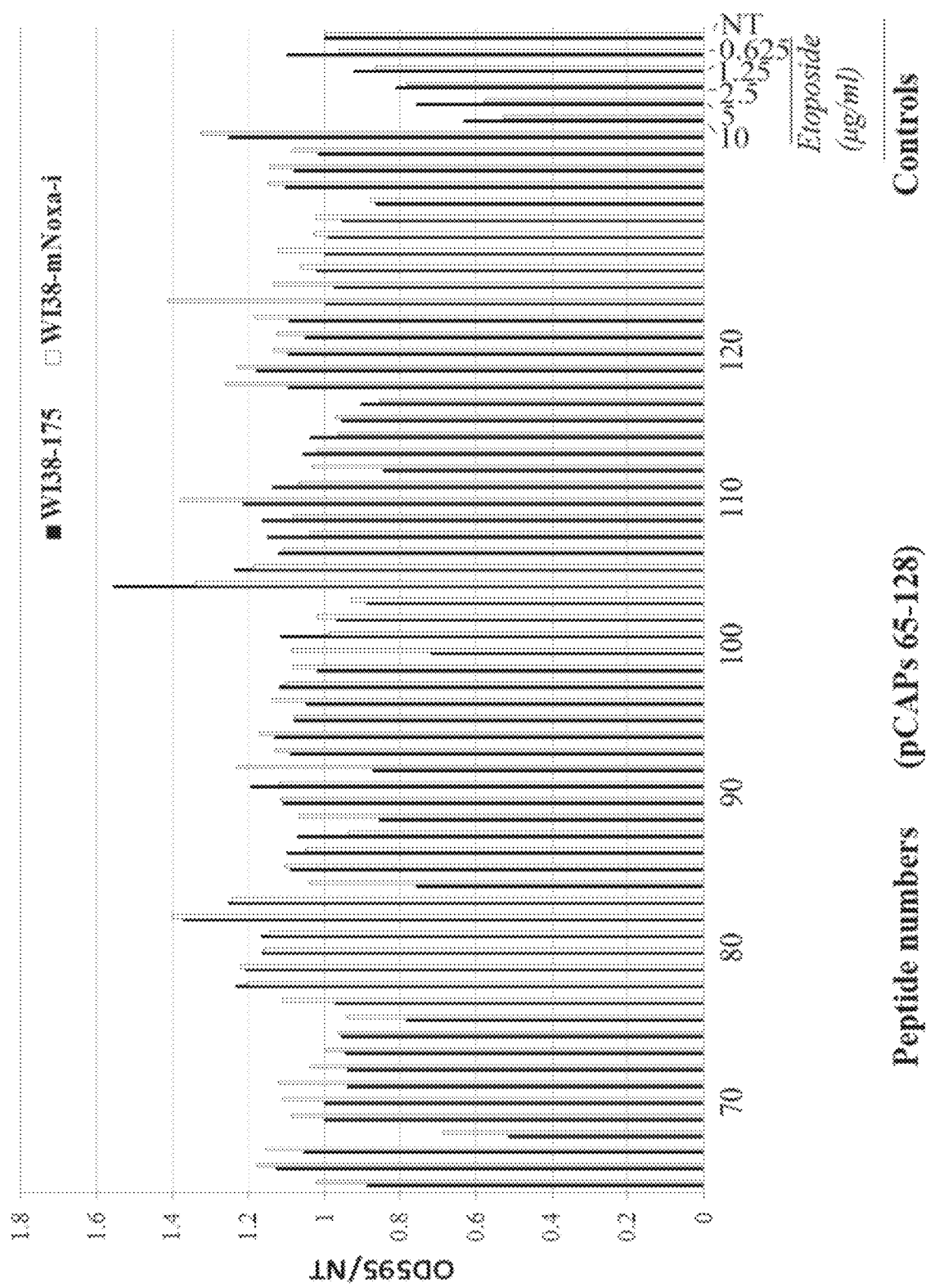

FIGS. 13A and 13B illustrate a representative experiment of screening performed on 128 synthesized peptides. In this experiment, WI-38 fibroblasts were used. These cells express endogenous WT p53 and were further infected with a virus expressing either mouse Noxa shRNA, as a nonspecific control or the R175H p53 mutant for stable overexpression of mutant p53. Both of these sub-lines (mNoxa or R175H p53) were seeded at 3000 cells per well and treated as described above. The optical density reads (595 nm) reflect the number of cells in the plate after treatment, normalized to the non-treated samples that are considered as 100% viable. As seen, although WI-38 cells are relatively resistant to killing, the increasing concentrations of etoposide serve as a good positive control for cell death and growth arrest with the highest concentration reducing cell number by 50% after 48 hours.

Several of the tested peptides indeed caused a significant reduction in cell numbers; this reduction was mutant p53 dependent, since it was much more prominent in the R175H p53 expressing cells as compared to mNoxa-i control cells. These peptides include, for example, pCAP-36, pCAP-46, pCAP-47, pCAP-60, pCAP-97. On the other hand, some peptides were found to have a toxic effect on both cell sub-lines; one example is pCAP-68. Similar assay was performed on several different Mut-p53-expressing human cancer cell lines, the results for the different peptides are summarized in Table 7.

Example 11: Homology of Lead Peptides to Sequences of Known p53 Binding Proteins After performing the functional screen of peptide motifs predicted by phage display, 20 peptides were identified that exerted functional effects on mutant p53 in a variety of assays and cell lines. Next, the similarity of these peptides to sequences of human proteins in general and to proteins known to interact with p53 in particular was examined, since high similarity to proteins interacting with p53 can serve as an indication to the biological significance of a particular motif and can provide validation of the assumption that the peptides selected under artificial in-vitro conditions can indeed interact with p53. Moreover, the protein structure and surrounding sequence might be helpful in designing improved peptides that are based both on selection and rational design. To find similarities between peptide sequences and known human proteins, the BLAST (Basic Local Alignment Search Tool) algorithm was used. The peptide motifs were introduced as query sequences against a sequence database containing human protein sequences. BLAST finds sub-sequences in the database that are similar to subsequences in the query. The main idea of BLAST is that there are often high-scoring segment pairs (HSP) contained in a statistically significant alignment. BLAST searches for high scoring sequence alignments between the query sequence and sequences in the database using a heuristic approach that approximates the Smith-Waterman algorithm. Based on the similarities between the peptide motifs and known human proteins and structural data of these proteins, a list of new peptide sequences was designed (shown in Table 8 below), in which amino acids similar to peptide motifs are flanked by other amino acids derived from the protein sequence either flanking the motif or from structural elements in physical proximity to the homologous motif according to 3-dimensional crystallographic data.

Over 70 different proteins with varying degree of similarity to selected peptide motifs were identified. Many of these proteins had been shown previously to physically interact with p53, while others were reported to be involved in the p53 signaling pathway, either upstream or downstream of p53. Several motifs were found to have a very high degree of homology to known p53 interacting proteins; pCAP-97 (WNHHHSTPHPAH, SEQ ID NO:10) for example has 100% homology to RAD9A (with a p-value of $10^{-8}$) which was shown to interact and activate p53; pCAP-60 (SFIL-FIRRGRLG, SEQ ID NO:302) and pCAP-63 (HNHHHSQHTPQH, SEQ ID NO:226) have 90% homology to GAS2 protein sequence (KILFIRLMHNKH, SEQ ID NO:369) in which these motifs are separated by two amino acids (amino acids similar to peptide motifs are highlighted in bold letters).

Several alternative and complementary methods to screen lead peptide candidates for conformational and functional effects on Mut-p53 were employed. For increased penetration of peptide across cell membranes each peptide contains 3-6 Arginine residues either as part of its sequence or added either at its N-terminus or its C-terminus. 40 peptides were also conjugated to myristoil fatty acid (myr) for enhanced fusion with cell membranes that would potentially lead to better delivery into cells. In-vitro based assays for evaluation were first performed, such as ELISA for assessment of p53 conformation and sequence-specific DNA binding of p53. Subsequently, the peptides' activity was examined in live cells by viability assays, p53 transcriptional activity on a luciferase reporter gene, and examination of p53 target genes in-vivo. Combination of these assays (all performed in a 96 well format) allowed the identification and validation of the peptides' effects on different p53 activities and their ability to confer such ability to Mut-p53 proteins. As seen from Table 8, 12 peptides were found to have a total activity score above 30; all of these 12 peptides were shown to be effective in a variety of different assays including p53 conformation and sequence-specific DNA binding, reduction in viability of Mut-p53 expressing cells and activation of p53 target genes. Some of these lead peptides, which have a core motif derived from phage display with added sequences of known proteins (pCAPs 201-326) showed a significantly increased effect compared to peptides derived from phage display alone (pCAPs 1-180), while others were comparable to pCAPs 1-180.

After careful examination of peptide sequences that have shown the most significant effect in a combination of the assays, it was found that the lead peptides can be classified into several major groups, according to their consensus motifs. The consensus motifs consist of at least 3 consecutive amino-acids, which hypothetically form a sequential or conformational binding site for p53 mutants. These consensus motifs were found to be HSTPHP, FPGHTIH, IRGRIIR, LPNPPER, SFILFIR, HANLHHT, YPTQGHL, WNHHH-STPHP, TLYLPHWHRH, YRRLLIGMMW, IRILMFLIGCG, SFILFIRRGRLG, LRCLLLLIGRVG, SWQALALYAAGW, IRILMFLIGCGR, glrgrriflifs, HSSHHHPVHSWN, LRCLLLLIGRVGRKKRRQ (SEQ ID NOs:314, 268, 282, 328, 376, 298, 377, 378, 253, 20, 379, 302, 275, 380, 273, 381, 280 and 382, respectively).

Effect of Test Peptides on p53 Target Genes

The WT p53 protein works primarily as a transcription factor. Upon activation by different forms of stress it is accumulated, binds to its responsive elements in many target genes and trans-activates their transcription. Proteins that are the products of these target genes execute their functions; transactivation of p21, for example, leads to growth arrest, whereas transactivation of PUMA would lead to apoptosis. Therefore one of the most important indications to p53 functional activation is the induction of its different target genes. The effect of various test peptides on p53 target genes was therefore tested in-vivo.

Figure 14:
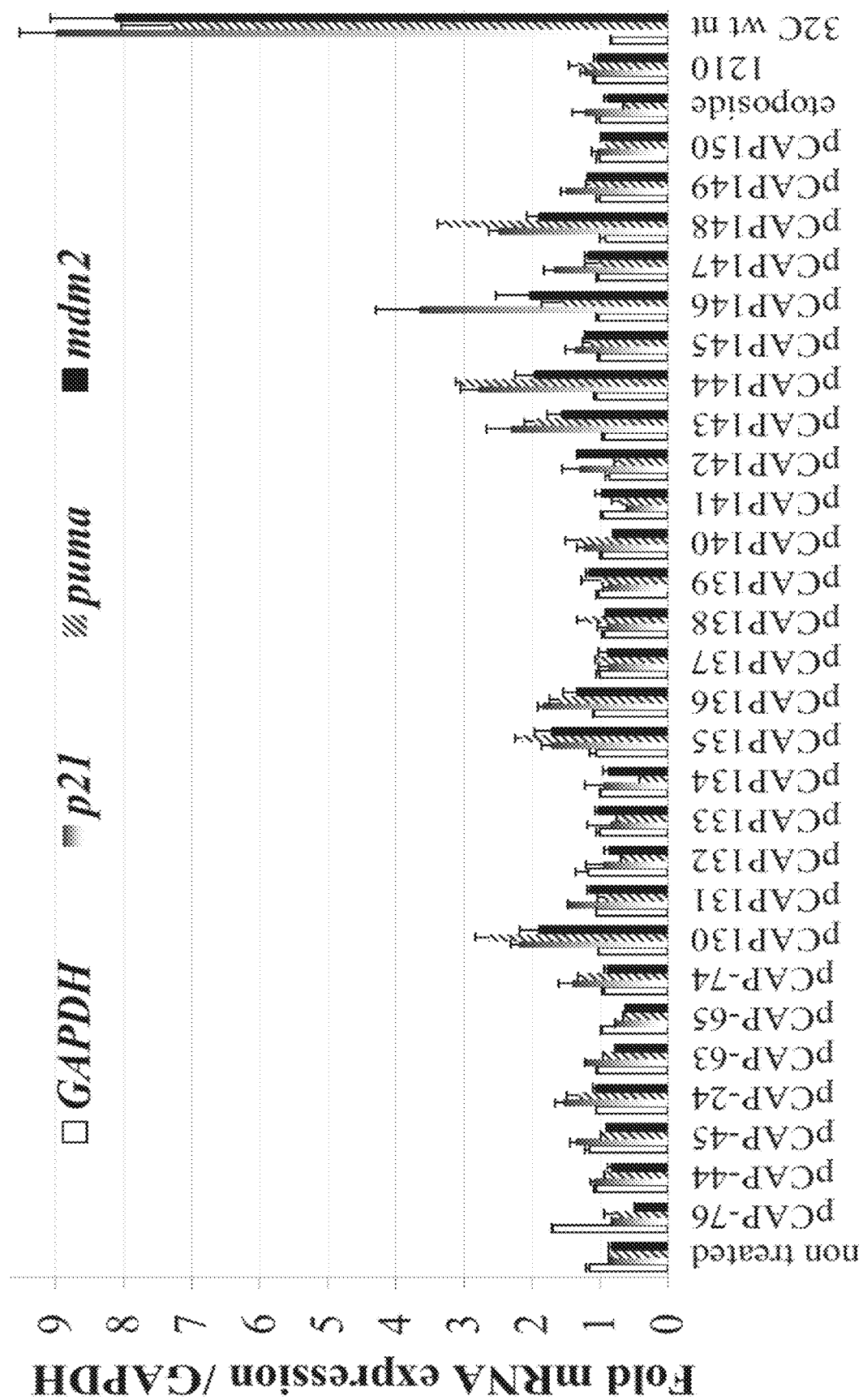
FIG. 14 is a bar graph illustrating the effect of tested peptides on activation of Mut-p53 by measuring transactivation of p53 target genes as determined by qRT-PCR. H1299 cells are p53 null and are widely used for p53 research. H1299 cells stably transfected with Mut-p53 (ts) A135V were used. The cells were plated in 12-well dishes, the indicated peptides were added directly to the medium at a concentration of 5 ug/ml, and cells were then either moved to 32° C. or returned to 37° C. 18 hours later cells were harvested, followed by extraction of RNA, cDNA synthesis and real time PCR analysis. The expression level of 3 representative p53 target genes, p21, PUMA and Mdm2, was examined. The bar graphs shown in FIG. 14 illustrate the relative fold induction of transcription of the tested genes in the various samples relative to their transcription level in non-treated cells.

For the in vivo functional screening, several experimental systems were used. One system is based on H1299 cells, which are p53 null and are widely used for p53 research. H1299 cells stably transfected with Mut-p53 (ts) A135V were used. This form of p53 is a temperature sensitive mutant, which has a mutant conformation at 37° C. and a WT conformation at 32° C. FIG. 14 shows a representative experiment. In essence, the cells were plated in 12-well dishes, the indicated peptides were added directly to the medium at a concentration of 5 ug/ml, and cells were then either moved to 32° C. or returned to 37° C. 18 hours later cells were harvested, followed by extraction of RNA, cDNA synthesis and real time PCR analysis. The expression level of 3 representative p53 target genes was examined; p21, PUMA and Mdm2. Expression of genes in H1299-ts at 37° C. is considered as background level and all results are normalized to it, and also to the GAPDH housekeeping gene. Expression of genes in H1299-ts at 32° C. represents WT p53 conformation and therefore serves as a positive control. As can be seen, temperature shift to 32° C. greatly increased expression of all 3 target genes.

As seen in FIG. 14, the negative control peptide pCAP-76 did not cause induction of p53 targets. Several tested peptides indeed caused a significant increase in the expression of p21, PUMA and Mdm2. This was the case for pCAP-130, pCAP-135, pCAP-142, pCAP-144 and pCAP-148. These peptides induced transcription of target genes by 2-4 fold, compared to 9-11 fold of the positive control, authentic wild type p53. The fact that treatment with peptides induced all three genes but had no effect on expression of these genes in control H1299 (p53$^{-/-}$) cells implies that this induction is p53 dependent.

Since delivery of peptides is a major obstacle in their use as therapeutic agents, different approaches were taken overcome this obstacle. First, based on the tested lead sequences, short peptide sequence motifs (up to 6 amino acids) were elucidated and synthesized, since these small peptides could cross cell membranes by diffusion. A second approach was to synthesize tested peptides with a polyarginine C-terminal tail to facilitate their active uptake by endocytosis-based mechanisms.

Addition of a poly arginine tail to peptides dramatically increases the solubility of peptides with a high content of hydrophobic amino acids. In some cases it also significantly increased the activity of the peptides both in-vitro and in-vivo; pCAP-25 for example was insoluble in DMSO at a concentration of 10 mg/ml and showed no effect on p53 activity when tested either for conformational change or viability. Whereas pCAP-68 which has the same amino acid sequence with the addition of the 9R tail caused a significant shift in Mut-p53 conformation towards PAb1620, as well as massive cell death. Lead peptides were further subjected to rigorous examination of effects on cell viability in a Mut-p53 specific manner.

Figure 15A:
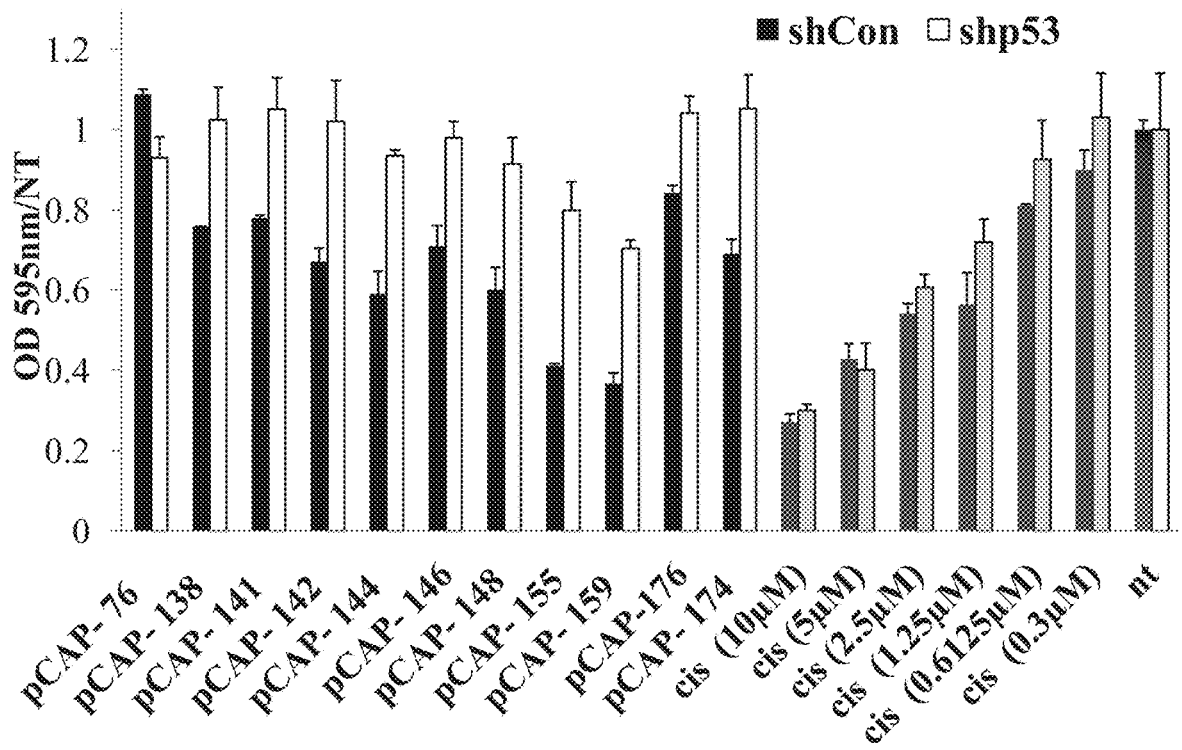
FIGS. 15A and 15B are bar graphs illustrating the effect of the various indicated peptides on the viability of breast cancer cells expressing different Mut-p53 isoforms, as determined by crystal violet assay.
Figure 15B:
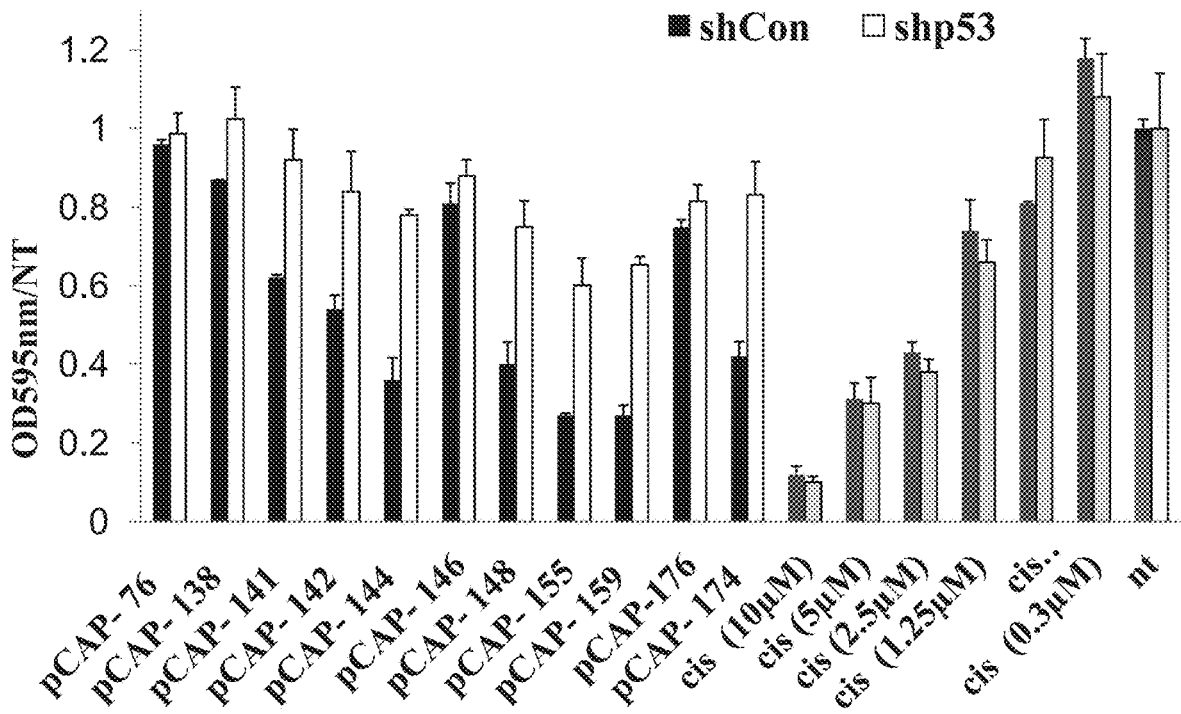

Experiments using different cancer cell lines expressing endogenously different p53 mutant isoforms were performed. FIGS. 15A and 15B illustrate two representative experiments performed on MDA-MB-231 (FIG. 15A) and SKBR3 (FIG. 15B) breast cancer cells expressing Mut-p53 with mutations at positions 280 or 175, respectively, within the DNA Binding Domain (DBD). To examine the peptides' specificity for Mut-p53, the control used was such cells with a knockdown of Mut-p53 (shp53). As seen in FIGS. 15A and 15B, many of the tested peptides showed a reduction in cell viability in a Mut-p53 specific manner, with significant readings of 30%-80% relative to the 100% viability represented by non-treated Mut-p53-expressing cells. Some peptides show some degree of a toxic effect on cell viability in general, as seen in the shp53 cells. For example pCAP-155 exhibited a 30% to 40% reduction in viability in the two shp53 infected cell sublines. Furthermore, it is also seen that some peptides show specific reduction in cell numbers in particular cell types compared to minimal activity in others. pCAP-146 for example caused a significant decrease in MDA-MB-231 shCon cells but almost no specific effect on SKBR3 shCon cells.

Figure 16:
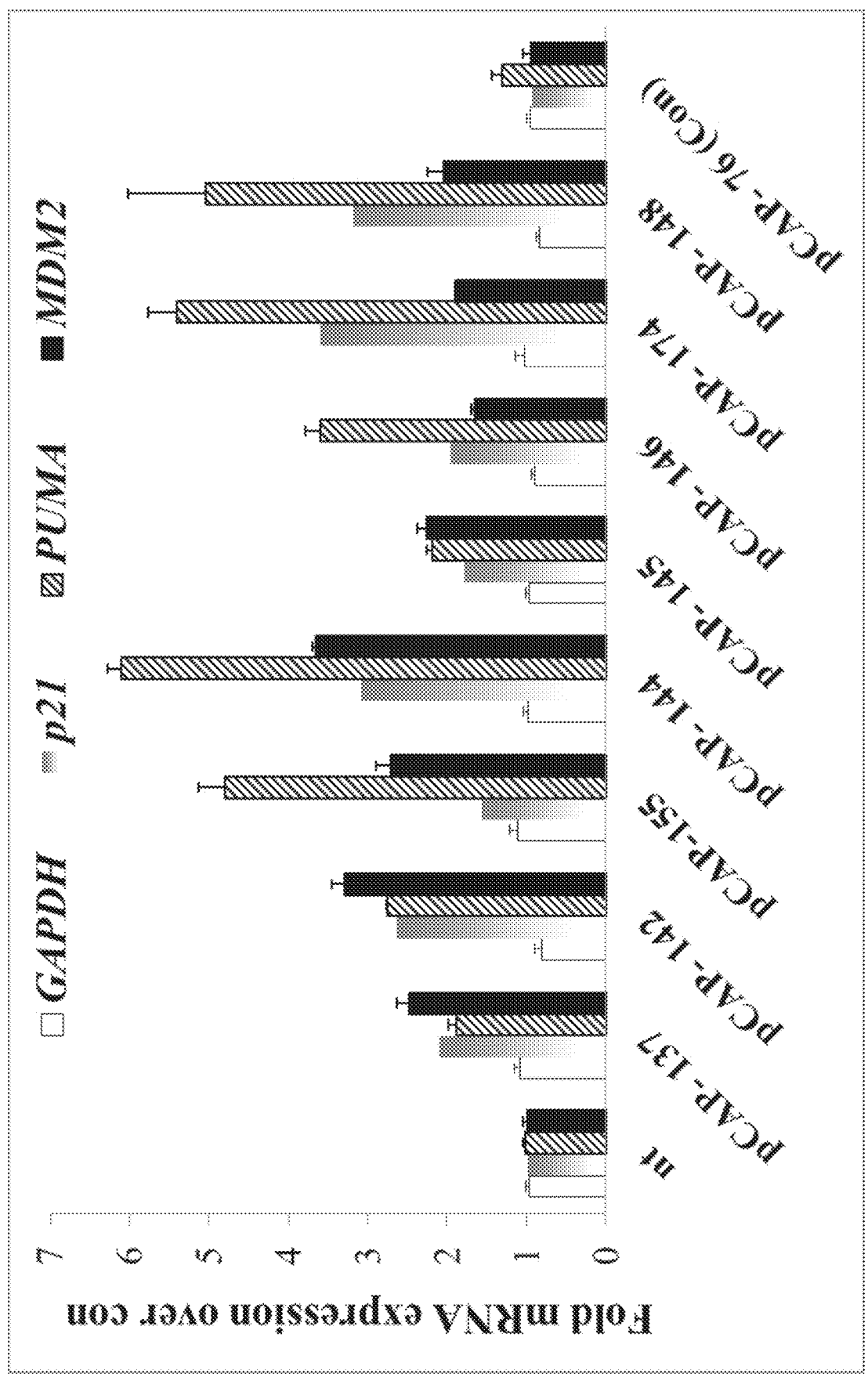
FIG. 16 is a bar graph illustrating the effect of the indicated peptides on activation of Mut-p53 by measuring transactivation of p53 target genes as determined by qRT-PCR. SKBR3 ShCon cells and SKBR3 Shp53 cells knocked down for p53 expression were used. The cells were plated in 12-well dishes and the indicated peptides were added directly to the medium at a concentration of 5 ug/ml. 18 hours later cells were harvested, followed by qRT-PCR analysis. Expression level of p21, PUMA and Mdm2 was evaluated.
Figure 17A:
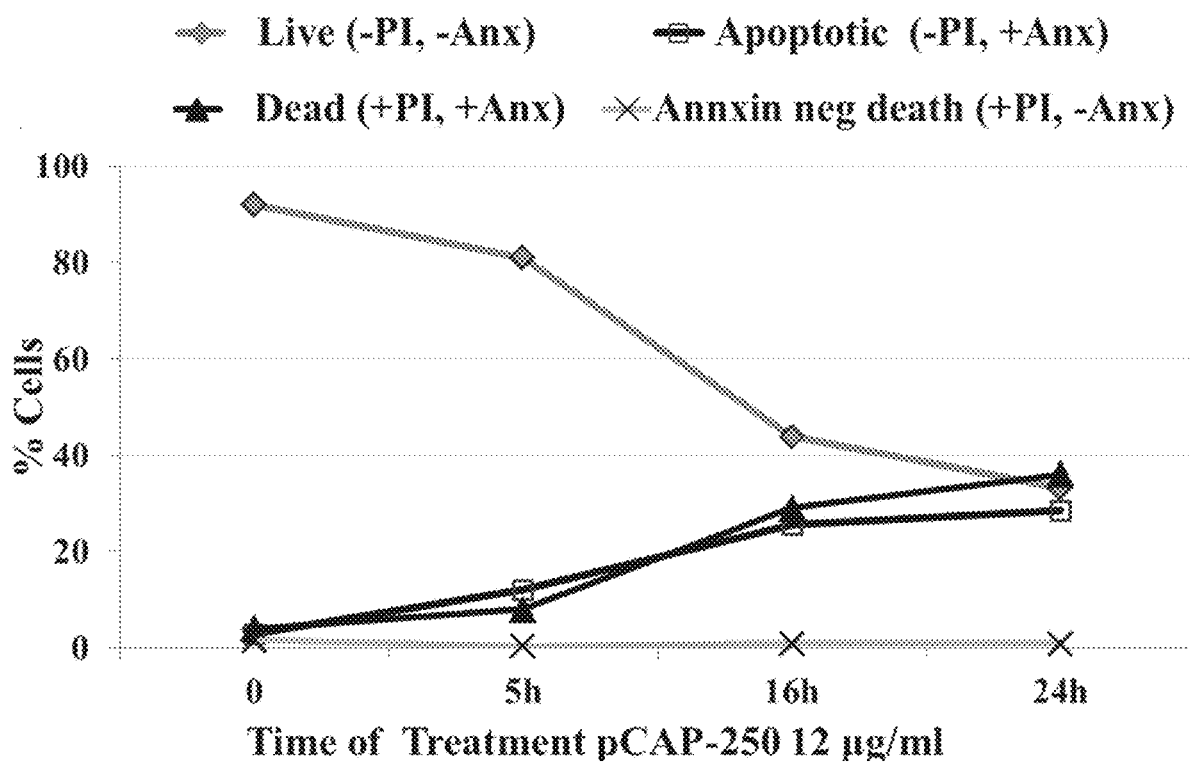
FIGS. 17A, 17B, 17C and 17D illustrate representative experiments performed on ES2 ovarian carcinoma cells expressing Mut-p53 mutated at position 241 within the DBD. In essence, the cells were plated in 6 cm dishes, and the indicated peptides were added directly to the medium at a concentration of 12 ug/ml at the indicated time points. Cells were harvested and an apoptosis assay (FIGS. 17A and 17B) was performed using the Annexin-V staining kit (Roche, REF 11 988 549 001). Non-fixed cells were stained with both anti Annexin FITC conjugated antibody to detect apoptotic cells, and PI (propidium iodide) to stain dead cells, according to the manufacturer's instructions. Stained cells were then analyzed by flow cytometry. A total of 10,000 cells was counted for each sample and divided into four sub populations according to staining intensity; cells negative for both PI and Annexin (−PI, −Annexin) are termed live; cells negative for PI and positive for Annexin (−PI, +Annexin) are going through early stages of apoptosis; cells positive for PI and Annexin (+PI, +Annexin) are dead cells that underwent an apoptotic process; and cells positive for PI and negative for Annexin (+PI, −Annexin) are assumed as dead cells that died by a non-apoptotic process such as necrosis.
Figure 17B:
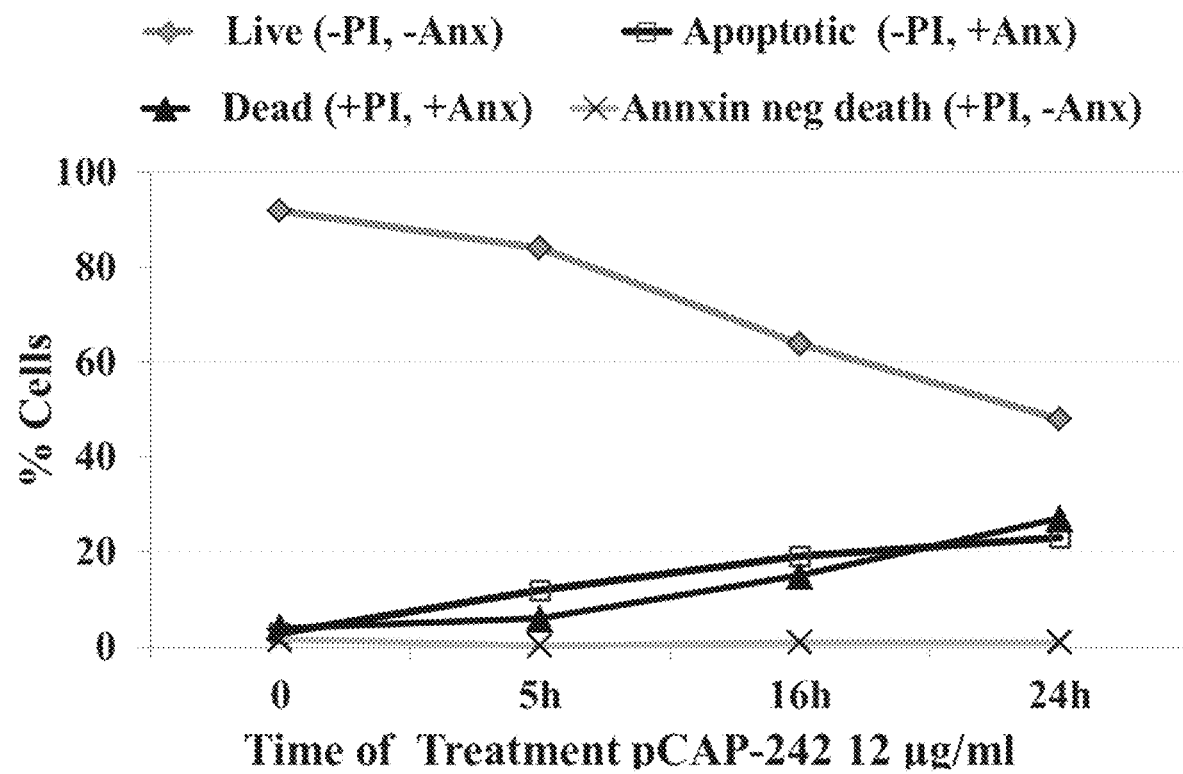
Figure 17C:
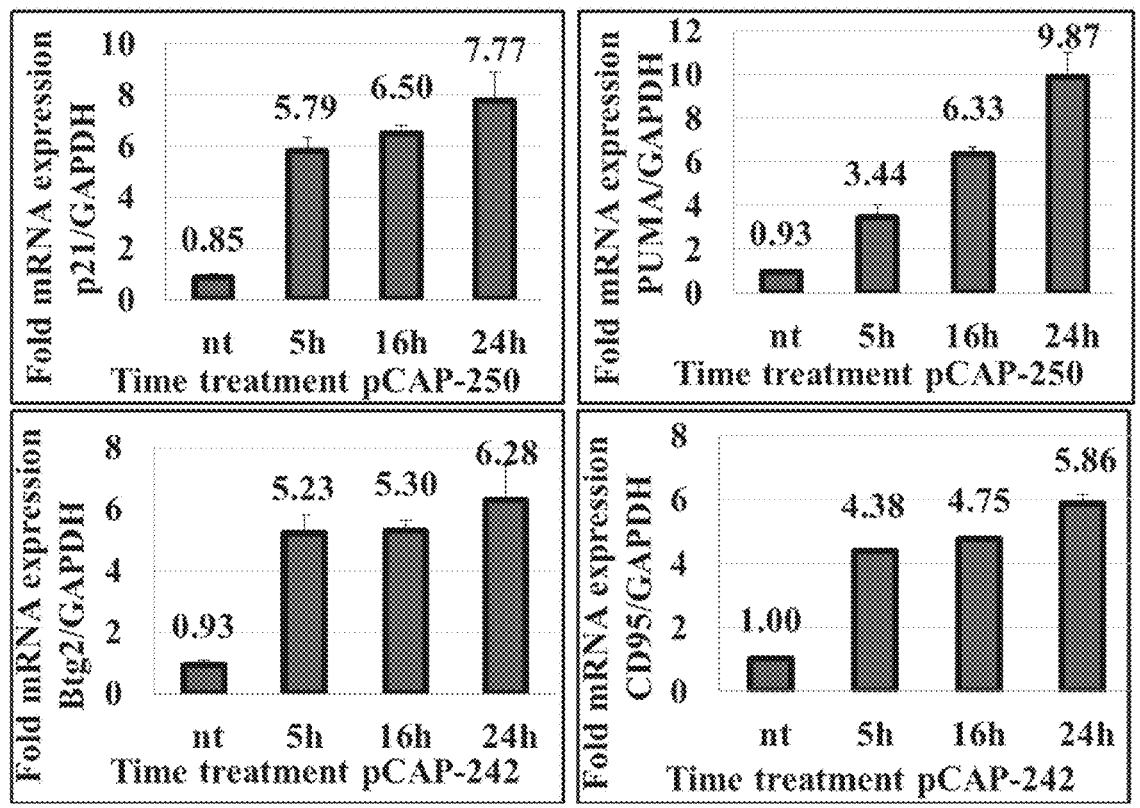
Figure 17D:
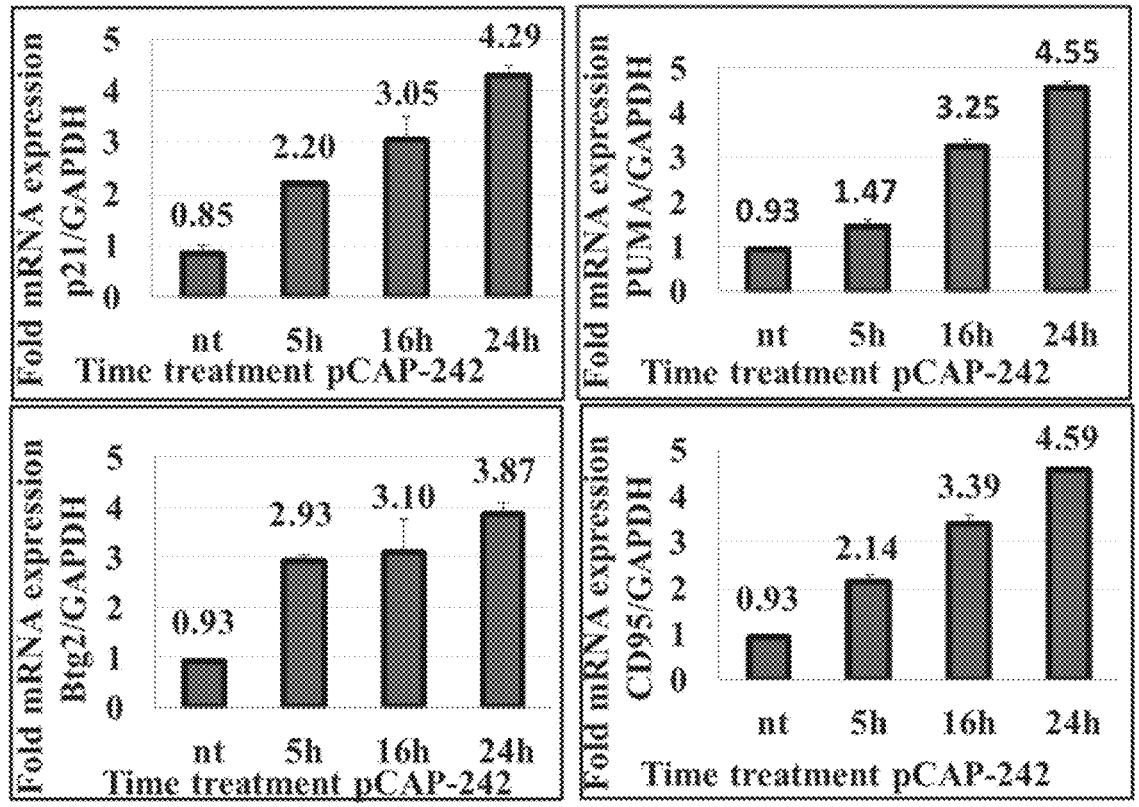

The tested peptides were further tested for their effect on p53 target gene expression in SKBR3 cells expressing endogenous R175H p53. The results are shown in FIG. 16, which shows a bar graph of a representative experiment performed on SKBR3 ShCon cells and SKBR3 Shp53 cells, knocked down for p53 expression. In essence, these cells were plated in 12-well dishes; the indicated peptides were added directly to the medium at a concentration of 5 ug/ml. 18 hours later cells were harvested, followed by qRT-PCR analysis. Expression level of p21, PUMA and Mdm2 was evaluated. Expression of those genes in non-treated cells is considered background and all results were normalized to it, as well as to GAPDH. As seen, some of the lead peptides exhibited a significant transactivation of p53 target genes. This effect was mediated through Mut-p53 since it was not observed in SKBR3 shp53 cells. pCAP-155, pCAP-144 and pCAP-148 showed among the highest transactivation levels. Effect of Test Peptides on Apoptosis and Correlation to Activation of p53 Target Genes FIGS. 17A and 17B illustrate a representative experiments performed on ES2 ovarian carcinoma cells (FIGS. 17A-D) expressing Mut-p53 with a mutation at positions 241 within the DBD. Briefly, the cells were plated in 6 cm dishes, and the indicated peptides were added directly to the medium at a concentration of 12 ug/ml at the indicated time points. Cells were harvested, and 60% of the cells were taken for Annexin-PI apoptosis assay and 40% for extraction of RNA, cDNA synthesis and real time PCR analysis. Apoptosis was assayed using the Annexin-V staining kit (Roche, REF 11 988 549 001). Non-fixed cells were stained with both anti Annexin FITC conjugated antibody to detect apoptotic cells, and PI (propidium-iodide) to stain dead cells permeable to the compound, according to the manufacturer's instructions. Stained cells were then analyzed by flow cytometry. A total of 10,000 cells was counted for each sample and divided into four subpopulations according to staining intensity: cells negative for both PI and Annexin (−PI, −Annexin) are termed live; cells negative for PI and positive for Annexin (−PI, +Annexin) are going through early stages of apoptosis; cells positive for PI and Annexin (+PI, +Annexin) are dead cells that underwent an apoptotic process; and cells positive for PI and negative for Annexin (+PI, −Annexin) are assumed to be dead cells that died a non-apoptotic death such as necrosis. As seen in the FIGS. 17A, 17B non-treated cells (time 0 h) are mostly (94%) negative for both PI and Annexin, meaning that the cells are viable and well. Treatment with pCAPs 242 and 250 causes a rapid increase in apoptotic cells followed by cell death and after 5 hours of treatment 12% of cells are Annexin positive and about 7% are dead. After 16 and 24 hours of treatment with pCAP 250 the apoptotic population increases to about 27% and dead cells accumulate to 29% at 16h and 36% after 24h. This trend is true for pCAP 242 as well, although its effects are attenuated and slower. The effect of peptides on cell viability is accompanied by significant transactivation of p53 target genes as seen in FIGS. 17C and 17D, which show the expression of 4 representative targets. As seen all the genes are activated following peptide treatment, and p21 and PUMA mRNA expression increase over time up to 10 fold and 6 fold following treatment with pCAP 250 and pCAP 242, respectively. CD95 and Btg-2 expression is elevated up to 6 fold over non-treated cells.

Example 12: In-Vivo (Preclinical) Testing of Mut-p53 Reactivating Peptides

The in-vivo (preclinical) experiments were performed in two types of models: human xenograft models in nude mice and Mut-p53 "knock-in" mice. In each model, the effects of intratumoral injection of the tested peptides on tumor growth and animal survival are determined.

In the xenograft preclinical model, tumor cells are transfected with a luciferase expression vector, allowing tumor monitoring by live imaging.

In the Mut-p53 "knock-in" mice model a lung specific conditional Mut-p53 knock-in mouse is used (Kim, C. F., et al., *Mouse models of human non-small-cell lung cancer: raising the bar*. Cold Spring Harb. Symp. Quant. Biol., 2005. 70: p. 241-50. Olive, K. P., et al., *Mutant p53 gain of function in two mouse models of Li-Fraumeni syndrome*. Cell, 2004. 119(6): p. 847-60). This model offers a compound conditional knock-in mice with mutations in K-ras combined with one of three p53 alleles: R273H, R175H, or a p53-null allele. Infection with AdenoCre induces recombination of the conditional alleles and was shown to produce K-ras-induced lung adenocarcinomas as early as 6 weeks after tumor initiation. This model closely recapitulates several aspects of advanced human pulmonary adenocarcinoma and it allows for two different mutants (175 and 273) to be expressed from the endogenous p53 promoter, at physiological levels, with the correct spatial and temporal profile. This model allows to demonstrate the features of the tested reactivating peptides, in vivo, with respect to several crucial; safety-negligible effect on normal mouse tissue or non-infected mice; efficacy-reduction in tumor size and number in treated mice compared to the control; and specificity to tumor reduction in Mut-p53 expressing mice compared to p53 knock out mice. In addition, dose escalation experiments are performed with positive control peptides, to evaluate the minimal active concentrations and the maximal tolerated dose.

Preclinical Trials in a Xenograft Model

Figure 18A:
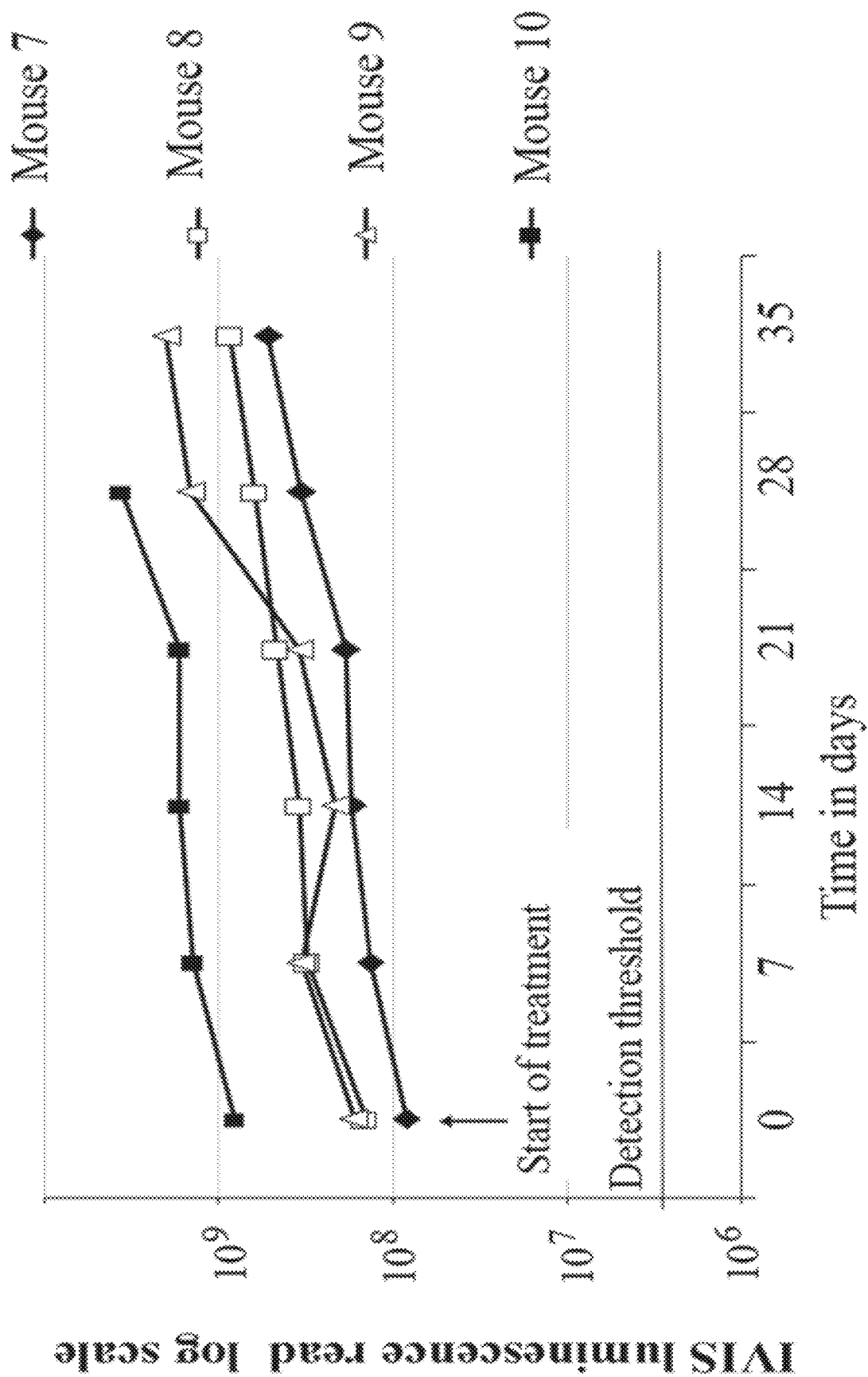
FIGS. 18A, 18B and 18C illustrate the in vivo effect of the indicated peptides in a mouse xenograft model. MDA-MB-231 cells expressing endogenous mutant p53 and stably expressing luciferase were injected into the left hip of CD1 nude/nude mice. When tumors reached visible size, bioluminescence (indicative of the number of cancer cells) was measured with the IVIS200 system. The mice were then treated by intra-tumoral injection, three times a week, with a mixture of 3 control peptides that showed no phenotype in vitro (pCAPs 76, 77 and 12; 2 mg of each peptide). 35 days after initiation of treatment, the experiment was terminated.
Figure 18B:
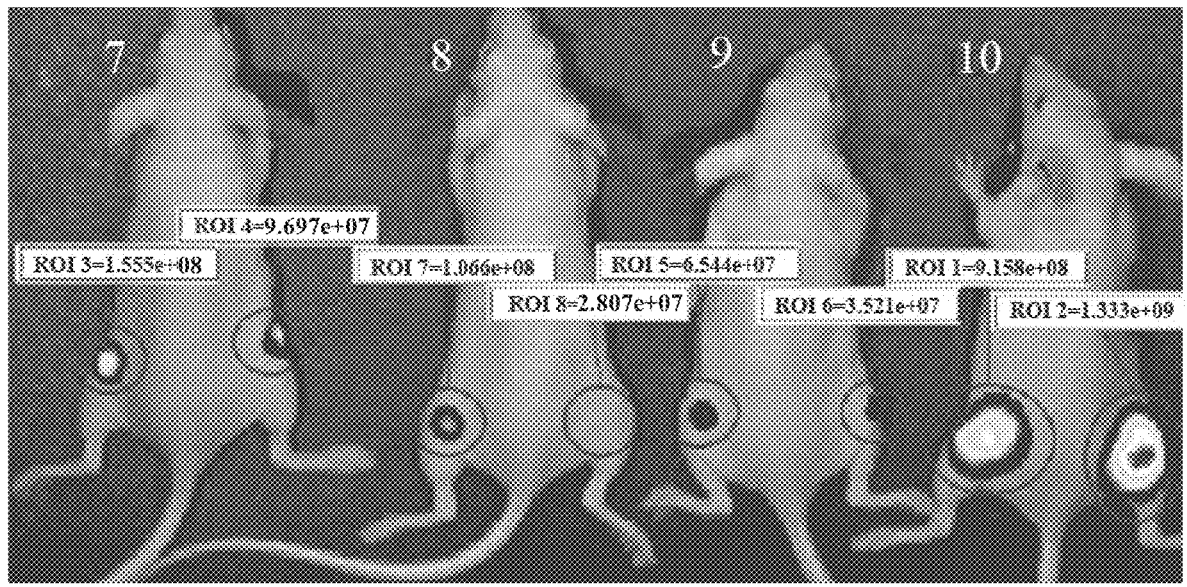
Figure 18C:
Figure 19A:
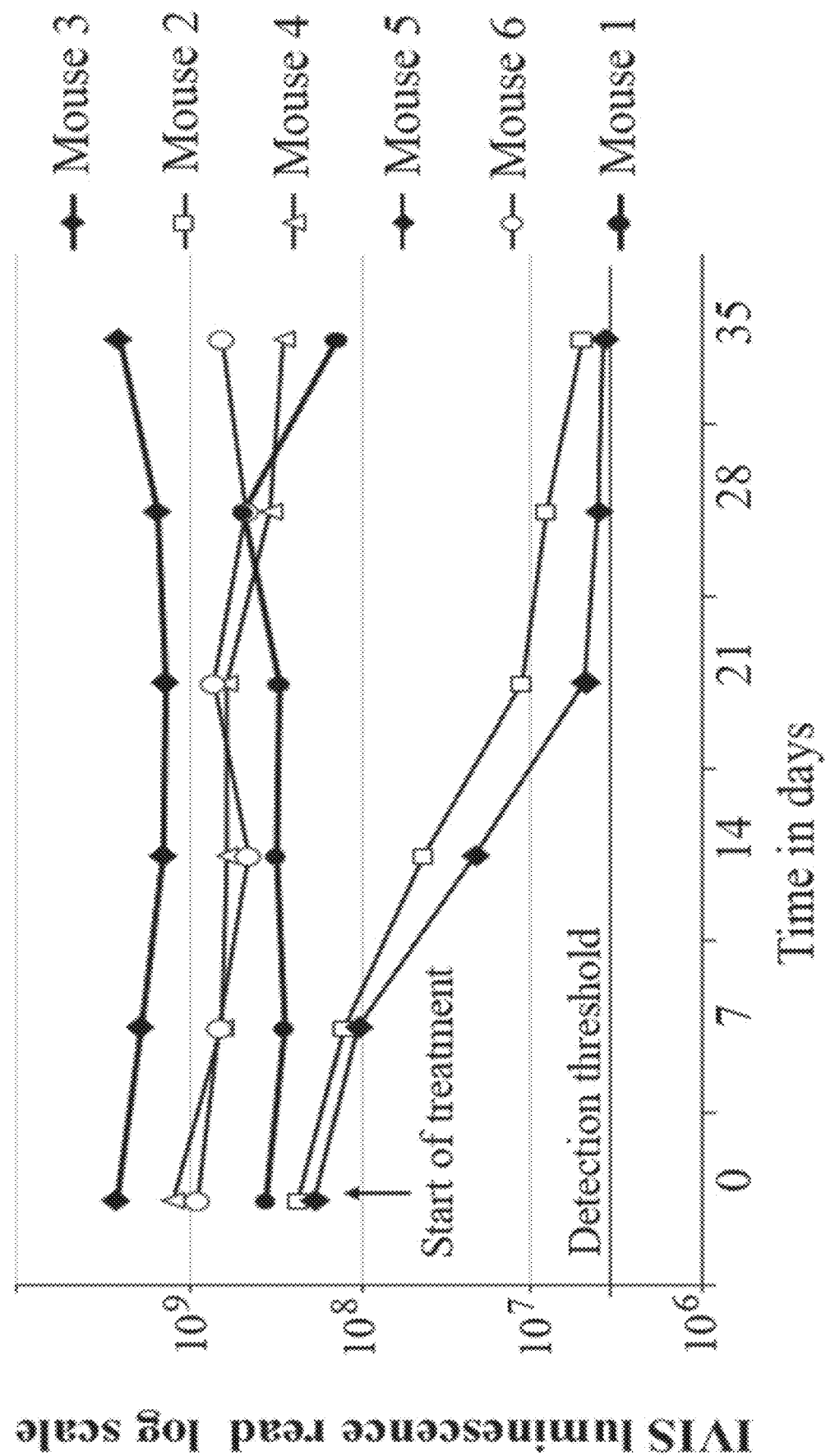
FIGS. 19A, 19B and 19C illustrate the in vivo effect of the indicated peptides in a mouse xenograft model. MDA-MB-231 cells expressing endogenous mutant p53 and stably expressing luciferase were injected into the left hip of CD1 nude/nude mice. When tumors reached visible size, bioluminescence (indicative of the number of cancer cells) was measured with the IVIS200 system. The mice were then treated by intra-tumoral injection, three times a week, with a mixture of 3 test peptides that exhibited mutant p53-reactivating ability (pCAPs 159, 155 and 174; 2 mg of each peptide). 35 days after initiation of treatment, the experiment was terminated.
Figure 19B:
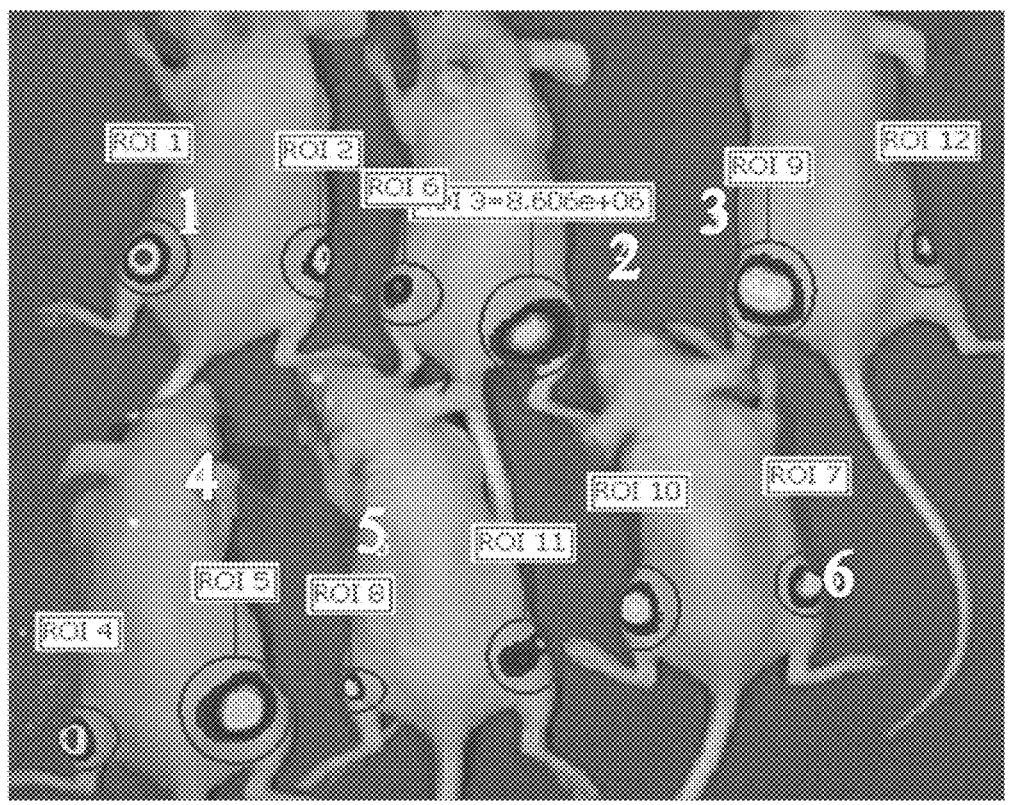
Figure 19C:
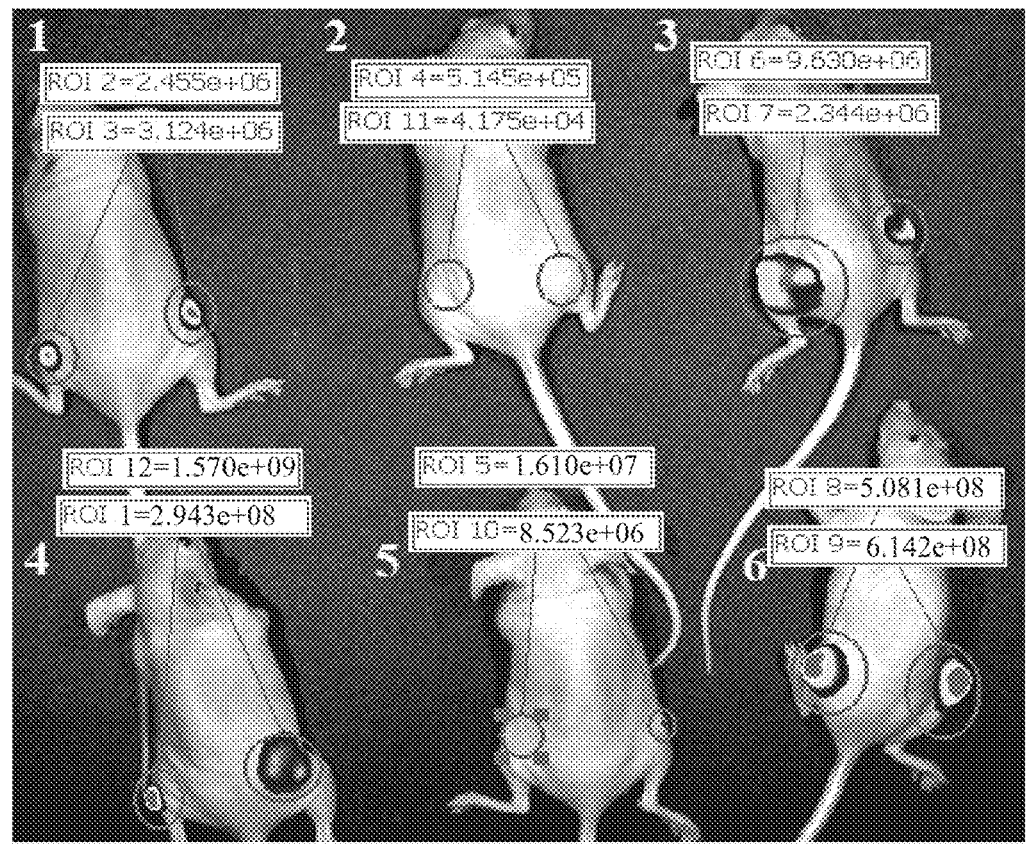
Figure 21A:
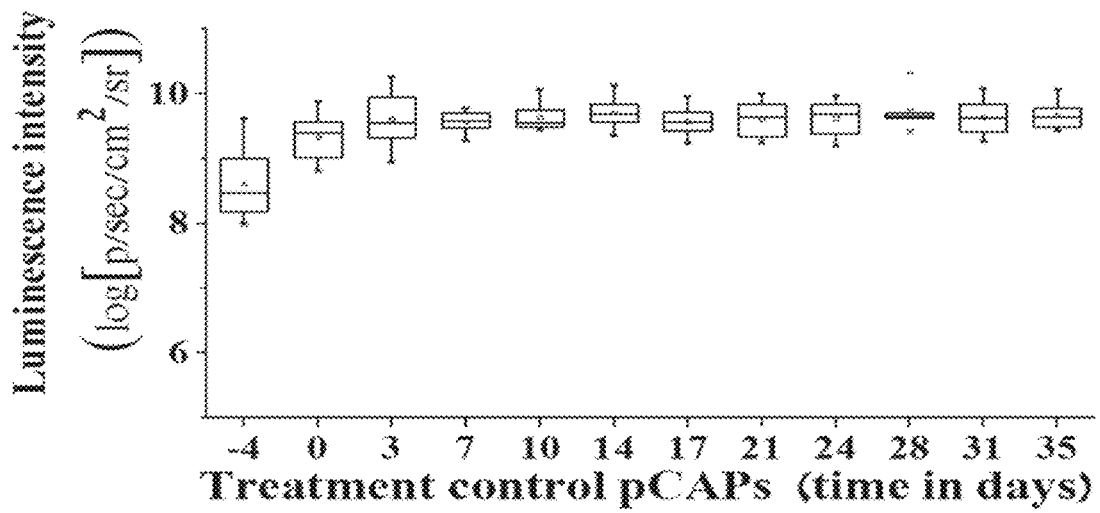
FIGS. 21A, 21B, 21C, 21D and 21E illustrate the in vivo effect of the indicated peptides in a mouse xenograft model. SW-480 colon cancer cells expressing endogenous mutant p53 and stably expressing luciferase were injected into the left hip of CD1 nude/nude mice. When tumors reached visible size, bioluminescence (indicative of the number of cancer cells) was measured with the IVIS200 system. The mice were then treated by intra-tumoral injection, three times a week, with either a mixture of 3 control peptides that showed no phenotype in vitro (pCAPs 76, 77 and 12; 2 ug of each peptide) or a mixture of 3 test peptides that exhibited mutant p53-reactivating ability (pCAPs 250, 308 and 325; 2 ug of each peptide).
Figure 21B:
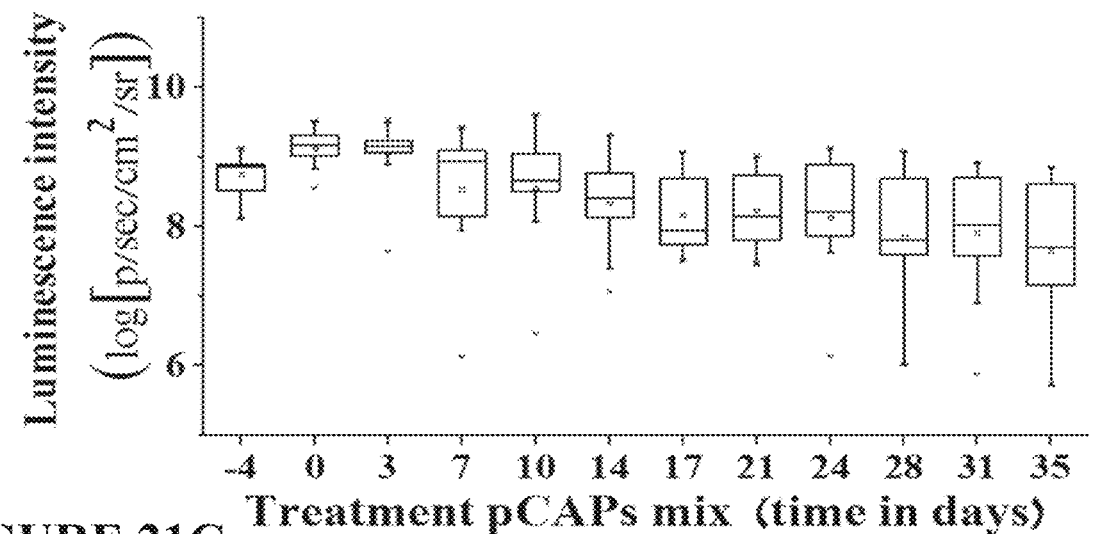
Figure 21C:
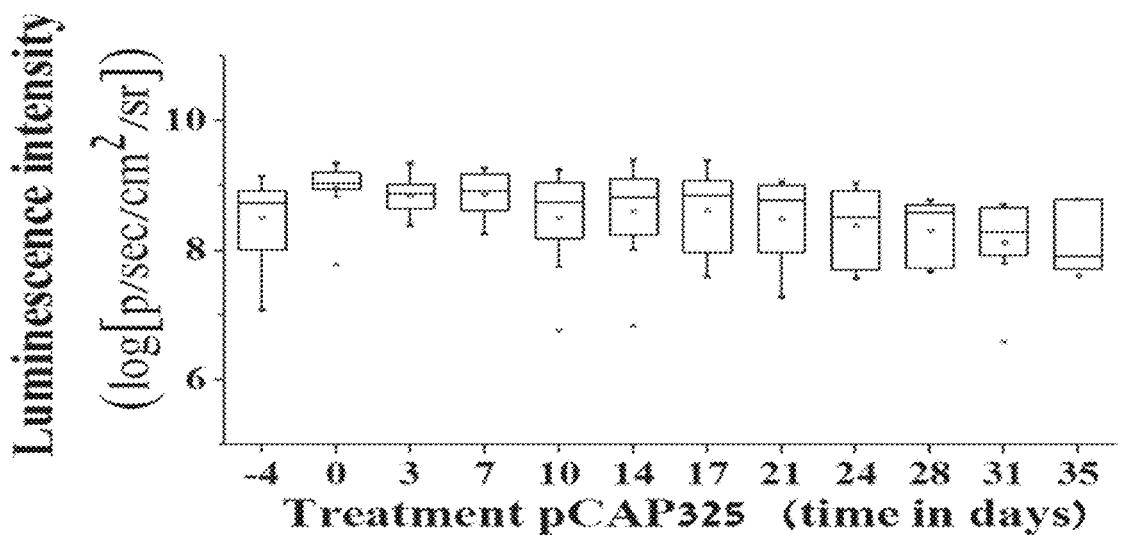
Figure 21D:
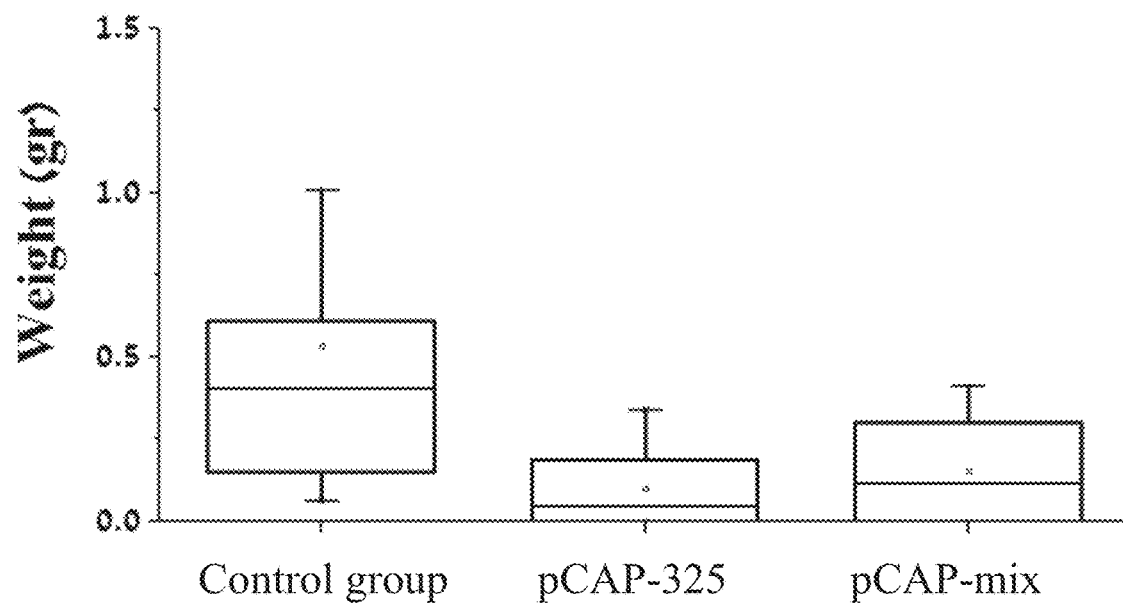
Figure 21E:
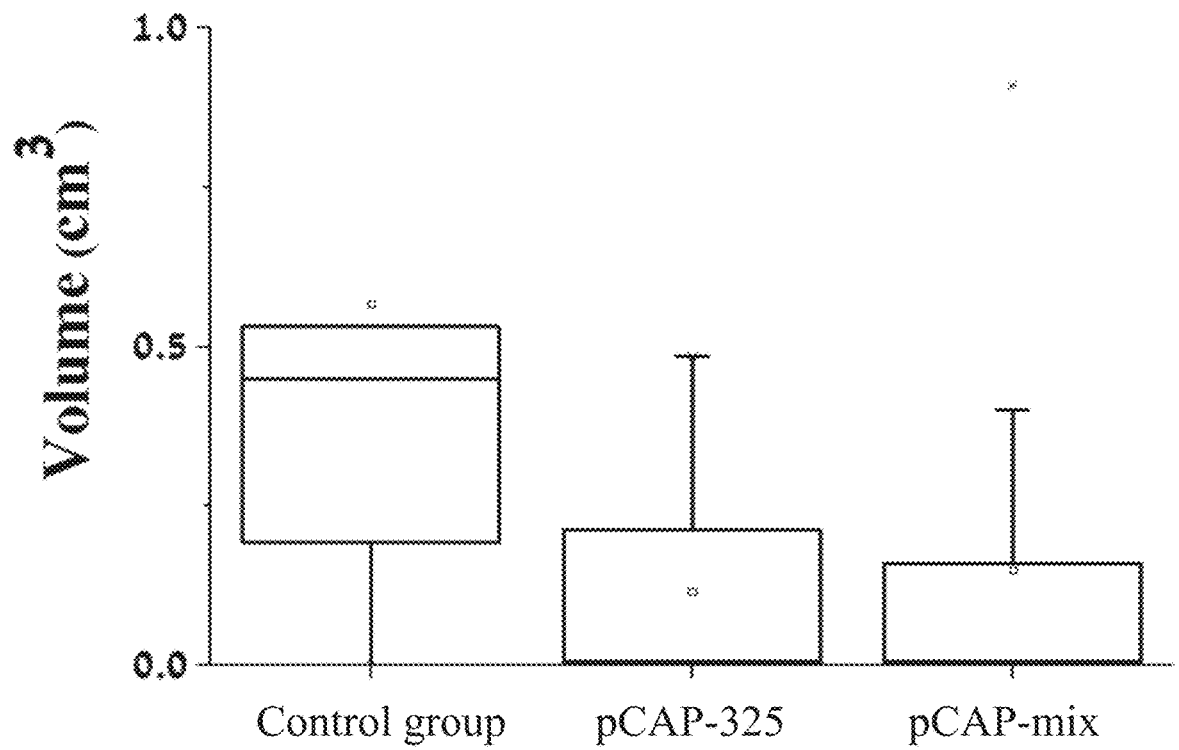

MDA-MB-231 cells endogenously expressing p53 R280K were infected with a luciferase expression vector and either shp53 for p53 knockdown or mouse NOXA shRNA (shmNOXA) as a nonspecific control. MDA-MB-231 cells are highly tumorigenic, forming aggressive, fast growing tumors, as well as being metastatic in humans. In total 10 mice were injected. Each mouse was injected subcutaneously with $2*10^6$ MDA-MB-231 cells expressing shp53 in the right flank, and with $2*10^6$ MDA-MB-231 cells expressing shmNOXA on the left side. Tumors were allowed to grow for 14 days in order to reach visible size. Growth was monitored by live imaging, using the IVIS200 system. In this system, luciferase bioluminescence is proportional to cancer cell number. The results are presented in FIGS. 18A to 18C and FIGS. 19A to 19C. 14 days post injection of the cells, 4 mice (mice 7-10) were assigned to the control group (FIGS. 18A to 18C) and 6 mice (mice 1-6) were assigned to the treatment group (FIGS. 19A to 19C). Control treatment was composed of a mixture of 3 control peptides (pCAPs 76, 77 and 12), which showed no effect (phenotype) on p53 in vitro. The treatment group mice were injected with a mixture of 3 peptides (pCAPs 174, 155 and 159) that showed the best phenotypic effects in vitro on p53. pCAP-159 (SEQ ID NO:312) has a similar sequence to pCAP-60 (SEQ ID NO:302) with the addition of arginine residues, the peptide is composed of D-amino acids and is synthesized in the reverse order (pCAP-159: rrrrrrrrglrgrriflifs (SEQ ID NO:312)) compared to pCAP-60: SFILFIRRGRLG, (SEQ ID NO:302) (lowercase letters stand for D-amino acids), in a "retro-inverso" strategy. Peptides were injected directly into the tumor (intra-tumoral injection) three times a week in a volume of 40p1 per tumor and a concentration of 50 µg/ml for each peptide in the mix. Therefore a total of 6 µg mix of either the control peptides or the treatment peptides was administered each time to each mouse. The mice were monitored for a total of 5 weeks from the start of the peptide treatment. Bioluminescence was measured every 7 days. As shown in FIG. 18A, shmNOXA tumors, expressing endogenous Mut-p53, showed a 6-15 fold (logarithmic scale) increase in luciferase intensity over the time-course of the experiment when treated with the control peptide mix. Mouse 10 had to be sacrificed after 28 days of treatment since the tumors reached a limiting large size. FIG. 19A shows the analysis of mice treated in parallel with a mixture of 3 Mut-p53-activating peptides. As seen in FIG. 19A, none of the tumors showed a significant increase in number of cancer cells over the 35 day period of the experiment. Two of the tumors (mouse-1 and mouse-4) showed a partial response to treatment, evident as a reduction of 50% to 65%, respectively, in bioluminescence. Mice number 2 and 5 showed a complete response, with luciferase readings that were as low or close to background threshold detection levels of the IVIS system ($5*10^6$ photons) even after 21 days of treatment. Administration of peptides was discontinued after 35 days, and mice number 2 and 5 were left without any further treatment and monitored for another 21 days. No tumor reappearance was detected in those mice either visually or by live imaging.

Preclinical Trial #2

MDA-MB-231 cells endogenously expressing p53 R280K were infected with a luciferase expression vector 15 mice were injected subcutaneously with $1\times10^6$ MDA-MB-231-luc cells on both hips. Tumors were allowed to grow for 10 days in order to reach visible size and from that time point onwards tumor growth was monitored by live imaging. The results are presented in FIGS. 20A to 20C. 18 days post injection of the cells, 6 mice were assigned to the control group and 9 mice were assigned to the treatment group. As before, control treatment involved a mixture of 3 control peptides (pCAPs 76, 77 and 12). The treatment group mice were injected with a mixture of 3 peptides (pCAPs 174, 155 and 159). Peptides were injected directly into the tumor (intra-tumoral injection) three times a week in a volume of 40p1 per tumor and a concentration of 50 µg/ml for each peptide in the mix. As shown in FIGS. 20A-D, both the control and the treatment group showed a similar behavior before treatment; about 2-3 fold (logarithmic scale) increase in luciferase intensity (day 10-18). FIG. 20A shows the analysis of mice treated in parallel with a mixture of 3 control peptides: as seen, the control treatment has only a very mild effect on tumor growth, reducing the rate of growth when compared to the period before treatment. However, as seen in FIG. 20B, treatment with the mixture of three p53 reactivating pCAPs caused a significant decrease in the luminescence of the MDA-MB-231 tumors. After a single injection of pCAP mix, the average luminescence was reduced by 70% and 7 out of the 18 tumors showed total regression with live imaging readings close to the background detection threshold (data not shown). As shown in FIG. 20B, 12 days after beginning of treatment (4 injections) the average tumor luminescence was decreased by 93%, and 11 out of 18 tumors showed a complete response. Only one of the 18 tumors showed either no or a week response. This tumor was relatively big before beginning of treatment, therefore it is possible that the pCAP dose was not sufficient to cause a significant response.

Preclinical Trial #3—SW-480 Colon Carcinoma Cells

After observing the highly significant result in the MDA-MB-231 experiment, additional studies were aimed to extend the observation and examine cells from a different origin, harboring a different p53 point mutation. The SW-480 colon carcinoma cell line harbors two endogenous p53 mutations: the R273H and P309S. SW-480 cells were stably infected with the luciferase reporter gene, and $10^6$ cells were subcutaneously injected into nude mice. The experiment contained 15 mice that were randomly divided during the experiment into 3 groups: a control group treated with a cocktail of 3 pCAPs previously proven ineffective, a group treated with a cocktail of 3 effective pCAP (250, 308, 325) and finally a group treated with a single peptide, the pCAP-325. The duration of the SW-480 experiment was 42 days from the point of cell implantation. The time line is relative to the first day of treatment which is marked as day 0. FIGS. 21A-E show tumor growth over time in all three groups as measured by live imaging in the IVIS. As seen, over time the control tumors show an average increase of 2.75 fold in tumor size (as inferred from the change in the log of luminescence intensity mean from 9.24 at day 0 to 9.68 at day 35, presented in FIG. 21A). The tumors in the mix treatment group show a decrease equivalent to a 96.7% tumor size decrease (as inferred from the change in log of luminescence intensity mean from 9.13 at day 0 to 7.65 at day 35, presented in FIG. 21B). Similarly, the tumors in the pCAP 325 group showed an average fold change of 0.043 which is equivalent to a 95.6% tumor size decrease (as inferred from the changed in log of luminescence intensity mean from 8.97 at day 0 to 7.61 at day 35, presented in FIG. 21C).

Summary of Preclinical Experiments 4 pre-clinical experiments have already been performed thus far, using the xenograft model of Mut-p53 expressing cells transfected with a luciferase expression vector, allowing tumor monitoring by live imaging. Two experiments were performed with MDA-MB-231 triple negative breast cancer cells (p53 R280K), one experiment used SW-480 colon cancer carcinoma cells (p53 R273H) and another experiment used SKBR3 breast cancer cells (p53 R175H). In each experiment, cells from the corresponding cell line were injected subcutaneously and allowed the formation of well-established tumors visible both by eye and by live imaging (typically 2-3 weeks). A treatment regimen was then administered, composed of intra-tumor injection of either effective lead peptides or control peptides (showing no activity in-vitro) every three days for a period of up to 42 days.

In all pre-clinical experiments performed, mice treated with lead peptides have shown a very significant decrease in all of their tumor parameters (percentages vary among different experiments); mean luminescence signal (81%-99% as measured by IVIS), tumor weight and volume (72%-93% measured after tumor extraction). The tumors of mice treated with control peptides on the other hand, continued to grow, although at a reduced rate compared to growth rate before treatment. Almost all of the tumors treated with lead peptides responded to treatment, and 35%-70% of treated tumors showed a complete response with tumors regressing to below threshold detection levels. Six of the mice showing complete response were kept alive for two months after completion of the experiment (without treatment) and no recurrence of tumors was detected.

In-Vivo Testing of Toxicity of Peptides

In total, 6 mice were used to test toxicity of the peptide mix: two mice for each peptide concentration. The peptide mix used in this experiment was the same as that described above (FIGS. 19A to 19C) (pCAPs 174, 155 and 159). Mice were injected intraperitoneally, three times a week for three weeks, with a peptide mix prepared at a concentration of 100 ug/ml. Two mice were injected with a volume of 40p1 resembling the total amount received by mice in the pre-clinical testing. Two mice were injected with 120p1, and the remaining two mice were injected with 400p1. Given that the average weight of a mouse is 20 g, these amounts represent concentrations of 0.6, 1.8 and 6 mg/Kg, respectively. The mice were inspected daily after injection. No visible change was detected in any of the mice. Furthermore, the tissue surrounding the tumors of mice used in the preclinical experiment (FIGS. 18A to 18C and FIGS. 19A to 19C) was examined after the mice were sacrificed, for signs of necrosis or inflammation. However, the tissue surrounding the tumor appeared normal in all cases, indicating no major toxic effect of the treatment with the pCAP peptides.

Table 10 summarizes the activity of peptides tested in the present invention.

TABLE 1

| Gene | Forward primer | Reverse primer |
|---|---|---|
| p53 | CCCAAGCAATGGATGATTTGA (SEQ ID NO: 343) | GGCATTCTGGGAGCTTCATCT (SEQ ID NO: 344) |
| p21 | GGCAGACCAGCATGACAGATT (SEQ ID NO: 345) | GCGGATTAGGGCTTCCTCTT (SEQ ID NO: 346) |
| PUMA | GACCTCAACGCACAGTACGAG (SEQ ID NO: 347) | AGGAGTCCCATGATGAGATTGT (SEQ ID NO: 348) |
| MDM2 | AGGCAAATGTGCAATACCAACA (SEQ ID NO: 349) | GGTTACAGCACCATCAGTAGGT ACAG (SEQ ID NO: 350) |
| Wig1 | CGGCAGAGAATTCCACGTGAT (SEQ ID NO: 351) | ATCTCTTCGCCAGCTCCAACA (SEQ ID NO: 352) |
| Noxa | GCAGAGCTGGAAGTCGAGTGT (SEQ ID NO: 353) | AAGTTTCTGCCGGAAGTTCAG (SEQ ID NO: 354) |
| Fas receptor | ACTGTGACCCTTGCACCAAAT (SEQ ID NO: 355) | GCCACCCCAAGTTAGATCTGG (SEQ ID NO: 356) |
| BTG2 | AGGCACTCACAGAGCACTACA AAC (SEQ ID NO: 357) | GCCCTTGGACGGCTTTTC (SEQ ID NO: 358) |
| GAPDH | ACCCACTCCTCCACCTTTGA (SEQ ID NO: 359) | CTGTTGCTGTAGCCAAATTCGT (SEQ ID NO: 360) |

TABLE 2

Selection for R175H p53.

| Selection round | selection marker | Titer of phage |
|---|---|---|
| 1 | 1620Ab + R175Hp53 | 100 |
| 2 | 1620Ab + R175Hp53 | $10^5$ |
| 2 | 1620Ab | $5 * 10^4$ |
| 3 | 1620Ab + R175Hp53 | $10^6$ |
| 3 | 1620Ab | $2 * 10^6$ |

TABLE 3

Alternating selection for Mut-p53 and WT p53.

| Selection round | The selection marker | Titer of phage |
|---|---|---|
| 1 | PAb1620 + p53 R175H | $2 * 10^2$ |
| 2 | His-WT p53 + Ni | $2 * 10^3$ |
| 3 | PAb1620 + p53 R175H | $10^5$ |
| 3 | PAb1620 | $4 * 10^3$ |

TABLE 4

| Selection # | Library | round | Selection type | Titer |
|---|---|---|---|---|
| 1 | phd-7 | 1° | 1620 + 175 | 2 * 10² |
| 31 | phd-12 | 1° | 1620 + 175 | 2 * 10³ |
| 32 | phd-7 | 1° | Tag--wt | 1 * 10³ |
| 81 | phd-12 | 1° | Tag--wt | 5 * 10³ |
| 4 | phd-7 | 1° | RE--wt | 1 * 10³ |
| 33 | phd-7 | 2° | 1620 + 175, 1620-wt | 2 * 10⁵ |
| 39 | phd-7 | 2° | 1620 + 175, 1620 + 175 | 1.5 * 10⁴ |
| 47 | phd-7 | 2° | 1620 + 175, 1620 + 175 | 2 * 10⁴ |
| 45 | phd-7 | 2° | 1620 + 175, 1620-175 | 2 * 10⁴ |
| 52 | phd-12 | 2° | Tag-wt, 1620 + 175 | 1.5 * 10⁶ |
| 41 | phd-7 | 2° | 1620 + 175, 1620 | 8 * 10³ |
| 90 | phd-12 | 2° | Tag-wt, 1620 + 175 | 1.5 * 10⁵ |
| 34 | phd-7 | 2° | 1620 + 175, Tag-wt | 5 * 10⁴ |
| 40 | phd-7 | 2° | 1620 + 175, Tag + 175 | 3 * 10⁴ |
| 48 | phd-12 | 2° | 1620 + 175, Tag + 175 | 4 * 10⁴ |
| 40 | phd-7 | 2° | 1620-wt, Tag + 175 | 4 * 10⁴ |
| 44 | phd-12 | 2° | 1620 + 175, Tag | 1 * 10³ |
| 51 | phd-7 | 2° | 1620-wt, Tag + 175 | 2 * 10⁶ |
| 83 | phd-7 | 2° | Tag-wt, Tag + 175 | 2 * 10⁶ |
| 55 | phd-12 | 2° | 1620 + 175, Tag-wt | 2 * 10⁴ |
| 5 | phd-7 | 2° | 1620 + 175, Ni-wt | 3 * 10⁴ |
| 82 | phd-7 | 2° | Tag-wt, Ni-wt | 3 * 10³ |
| 10 | phd-12 | 2° | 1620 + 175, Ni-wt | 1 * 10⁵ |
| 38 | phd-7 | 2° | 1620 + 175, RE-wt | 5 * 10⁵ |
| 53 | phd-12 | 2° | 1620 + 175, RE-wt | 5 * 10⁴ |
| 86 | phd-7 | 2° | Tag-wt, RE-wt | 2 * 10⁵ |
| 91 | phd-12 | 2° | Tag-wt, RE-wtDBD | 1 * 10⁵ |
| 35 | phd-7 | 3° | 1620 + 175, Ni-wt, 1620-wt | 3 * 10⁵ |
| 42 | phd-12 | 3° | 1620 + 175, Ni-wt, 1620 + 175 | 5 * 10⁴ |
| 64 | phd-7 | 3° | 1620 + 175, RE-wt, 1620 + 175 | 1 * 10⁶ |
| 36 | phd-7 | 3° | 1620 + 175, Ni-wt, Tag-wt | 1 * 10⁶ |
| 43 | phd-7 | 3° | 1620 + 175, Ni-wt, Tag + 175 | 2 * 10⁶ |
| 56 | phd-12 | 3° | 1620 + 175, Ni-wt, Tag + 175 | 2 * 10⁵ |
| 65 | phd-7 | 3° | 1620 + 175, RE-wt , Tag + 175 | 2 * 10⁶ |
| 69 | phd-7 | 3° | Tag-wt, 1620 + 175, Tag + 175 | 5 * 10⁶ |
| 85 | phd-12 | 3° | 1620 + 175, RE-wt, Tag + 175 | 2 * 10⁵ |
| 92 | phd-7 | 3° | 1620 + 175, Ni-wt, Tag-wtDBD | 3 * 10⁵ |
| 93 | phd-7 | 3° | 1620 + 175, Ni-wt, Tag + 175 | 4 * 10⁵ |
| 94 | phd-12 | 3° | 1620 + 175, Ni-wt, Tag + 249DBD | 4 * 10⁶ |
| 95 | phd-7 | 3° | Tag-wt, 1620 + 175, Tag + 175 | 5 * 10⁶ |
| 98 | phd-7 | 3° | 1620-wt, Tag + 175, Tag + 249DBE | 5 * 10⁶ |
| 37 | phd-7 | 3° | 1620 + 175, Ni-wt, RE-wt | 5 * 10⁵ |
| 24 | phd-7 | 3° | 1620 + 175, Ni-wt, RE | 5 * 10² |
| 57 | phd-12 | 3° | 1620 + 175, Ni-wt, RE-wt | 8 * 10⁴ |
| 75 | phd-7 | 3° | Tag-wt, 1620 + 175, RE-wt | 5 * 10⁴ |
| 96 | phd-7 | 3° | Tag-wt, 1620 + 175, RE + wtDBD | 1.5 * 10⁶ |
| 101 | phd-7 | 3° | Tag-wt, 1620 + 175, RE | 1.5 * 10⁶ |
| 97 | phd-12 | 3° | 1620 + 175, Tag-wt, RE + wtDBD | 5 * 10⁴ |
| 118 | phd-12 | 3° | RE + 249DBD | 5 * 10⁴ |

TABLE 5

| 12 aa Library | | | 7 aa Library | | |
|---|---|---|---|---|---|
| #Reads | Sequence | #Repeats | #Reads | Sequence | #Repeats |
| 553571 | KPPDRLWHYTQP (SEQ ID NO: 322) | 177 | 194006 | HFSHHLK (SEQ ID NO: 152) | 150 |
| 71970 | NPNTYVPHWMRQ (SEQ ID NO: 19) | 66 | 149576 | LPNPPER (SEQ ID NO: 328) | 111 |
| 68333 | ATLPFVTDRQGW (SEQ ID NO: 323) | 85 | 119076 | LHSKTLV (SEQ ID NO: 329) | 81 |
| 60270 | FYSHSTSPAPAK (SEQ ID NO: 324) | 72 | 96985 | H*VHTHQ (SEQ ID NO: 330) | 54 |
| 40419 | CYSHSYPTQGHL (SEQ ID NO: 325) | 43 | 94834 | KLQVPIK (SEQ ID NO: 182) | 51 |

TABLE 5-continued

| 12 aa Library | | | 7 aa Library | | |
|---|---|---|---|---|---|
| #Reads | Sequence | #Repeats | #Reads | Sequence | #Repeats |
| 20256 | SLLIGFGIIRSR (SEQ ID NO: 165) | 49 | 93473 | KPDSPRV (SEQ ID NO: 22) | 60 |
| 18938 | KPPDRLWHYTQP (SEQ ID NO: 322) | | 88385 | SSSLGTH (SEQ ID NO: 331) | 90 |
| 13261 | SLLIGFGIIRSR (SEQ ID NO: 165) | | 85894 | HEVTHHW (SEQ ID NO: 332) | 66 |
| 13048 | EFHSFYTARQTG (SEQ ID NO: 326) | 11 | 79729 | SAPQPAT (SEQ ID NO: 333) | 81 |
| 10943 | NHPWQFPNRWTV (SEQ ID NO: 287) | 7 | 76099 | TPPLTLI (SEQ ID NO: 334) | 69 |
| 10914 | SLLIGFGIIRSR (SEQ ID NO: 165) | | 73014 | TIHPSIS (SEQ ID NO: 258) | 42 |
| 8643 | GAMHLPWHMGTL (SEQ ID NO: 285) | 8 | 68925 | HPWTHH (SEQ ID NO: 335) | 48 |
| 8622 | IPMNFTSHSLRQ (SEQ ID NO: 248) | 6 | 51964 | SAASDLR (SEQ ID NO: 336) | 40 |
| 7072 | KPPDRLWHYTQP (SEQ ID NO: 322) | | 43941 | SPLQSLK (SEQ ID NO: 337) | 33 |
| 6657 | SDGFVPHFKRQH (SEQ ID NO: 327) | 4 | 39254 | RPTQVLH (SEQ ID NO: 338) | 27 |
| 6427 | SLLIGFGIIRSR (SEQ ID NO: 165) | | 39167 | DSLHSTY (SEQ ID NO: 101) | 24 |
| 5311 | SEFPRSWDMETN (SEQ ID NO: 24) | 4 | 36985 | WTLSNYL (SEQ ID NO: 100) | 30 |

TABLE 6

| SEQ ID NO: | pCAP NO: | Sequence |
|---|---|---|
| 17 | 8 | LTFEHYWAQLTS |
| 18 | 12 | GGGGGGGGGGGG |
| 19 | 19 | NPNTYVPHWMRQ |
| 20 | 25 | YRRLLIGMMW |
| 21 | 26 | DEFHSFYTARQTG |
| 22 | 29 | KPDSPRV |
| 23 | 31 | PPYSQFLQWYLS |
| 24 | 40 | SEFPRSWDMETN |
| 25 | 45 | HDTHNAHVG |
| 26 | 50 | WSEYDIPTPQIPP |
| 27 | 69 | SILTLSRRRRRRRRR |
| 28 | 73 | SCRCRLRGDRGDR |
| 29 | 76 | GGGGGGGGGRRRRRRR |
| 30 | 77 | SEYLCSSLDAAG |
| 31 | 78 | GESFVQHVFRQN |
| 32 | 79 | SVHHHHRMHLVA |
| 33 | 84 | GRRRFCM |
| 34 | 85 | KLTIHHH |

TABLE 6-continued

| SEQ ID NO: | pCAP NO: | Sequence |
|---|---|---|
| 35 | 86 | FGSHHEL |
| 36 | 96 | GTVDHHA |
| 37 | 107 | DRLSVFLFIM |
| 38 | 114 | AISHHTR |
| 39 | 116 | KHHPFDHRLGNQ |
| 40 | 119 | HSAHHTM |
| 41 | 125 | ELGLHRH |
| 42 | 126 | RRLRICV |
| 43 | 156 | VPHIHEFTRRRRRRR |
| 44 | 164 | PLTLI |
| 45 | 165 | SLLIG |
| 46 | 166 | KPPER |
| 47 | 168 | CRIIR |
| 48 | 169 | SFILI |
| 49 | 171 | PHHHS |
| 50 | 172 | EFHS |
| 51 | 173 | RLRRL |
| 52 | 175 | DSPR |
| 53 | 176 | HPWTH |
| 54 | 177 | HFSHH |
| 55 | 178 | RRVI |
| 56 | 179 | ILVI |
| 57 | 207 | RRSRSNEDVEDKTEDE |
| 58 | 208 | RRIRSGGKDHAWTPLHENH |
| 59 | 209 | HTPHPPVARTSPLQTPRR |
| 60 | 211 | PDSEPPRMELRRR |
| 61 | 215 | RRDTFDIRILMAF |
| 62 | 218 | RREVTELHHTHEDRR |
| 63 | 223 | SPWTHERRCRQR |
| 64 | 232 | RSRSSHLRDHERTHT |
| 65 | 236 | RRRSTNTFLGEDFDQ |
| 66 | 241 | LIGLSTSPRPRIIR |
| 67 | 248 | EIYGESGKTDEHALDTEYRR |
| 68 | 252 | RRVILRSYDGGHSTPHPD |
| 69 | 253 | TGKTFVKRHLTEFEKKYR |
| 70 | 254 | NHFDYDTIELDTAGEYSRR |
| 71 | 255 | DPEPPRYLPPPPERR |
| 72 | 260 | RRTFIRHRIDSTEVIYQDED |
| 73 | 262 | ESKTGHKSEEQRLRRYR |
| 74 | 263 | YDDEHNHHPHHSTHRRR |
| 75 | 264 | RRRREVHTIHQHGIVHSD |
| 76 | 269 | DEPLPPPERRR |
| 77 | 270 | SPHPPY |
| 78 | 271 | SPHPPYSPHPPYSPHPPYP |
| 79 | 272 | RRPHNLHHD |
| 80 | 274 | LRDPHPPERRIR |
| 81 | 283 | RRPADQISYLHPPER |
| 82 | 291 | DLQYDFPRIRR |
| 83 | 292 | YDELYQKEDPHRRR |
| 84 | 294 | FKPERFPQNDRRR |
| 85 | 296 | RPADRIRR |
| 86 | 297 | HDFDPRYRDRR |
| 87 | 300 | RIRRDPDSPLPHPE |
| 88 | 304 | myr-RRIRILMFLIGCGRV |
| 89 | 309 | HPHVILPRIRIRIR |
| 90 | 311 | EIHTIHLLPERR |
| 91 | 320 | EPSHPRSRYPRTF |
| 92 | 321 | RNIIIRDFIHFSHIDR |
| 93 | 322 | RRIRDPQIK-myrLEIHFSHID |
| 94 | 323 | myr-DLHTIHIPRDRR |
| 95 | 324 | SHDFPHREPRPERR |
| 96 | 219 | SYRHYSDHWEDRRR |
| 97 | 2 | VWVHDSCHANLQNYRNYLLP |
| 98 | 4 | EHDFEVRGDVVNGRNHQGPK |
| 99 | 5 | LEVIYMI |
| 100 | 38 | WTLSNYL |
| 101 | 39 | DSLHSTY |
| 102 | 41 | WHHRQQIPRPLE |
| 103 | 64 | APSIFTPHAWRQ |
| 104 | 66 | THFSHHLKGGGRRQRRRP |
| 105 | 67 | LHSKTLVLGGGRRRRGDR |

TABLE 6-continued

| SEQ ID NO: | pCAP NO: | Sequence |
|---|---|---|
| 106 | 71 | WTLSNYLGGRKKRRQRRRR |
| 107 | 81 | VRCIFRGIWVRL |
| 108 | 98 | HSSGHNFVLVRQ |
| 109 | 110 | LFILVFR |
| 110 | 112 | TTSHHPK |
| 111 | 124 | VMVLFRILRGSM |
| 112 | 162 | SILT |
| 113 | 214 | RRRESEQRSISLHHHST |
| 114 | 216 | myr-HFNHYTFESTCRRRRC |
| 115 | 217 | HSTPHPPQPPERRR |
| 116 | 224 | RRKSEPHSLSGGYQTGAD |
| 117 | 234 | HRTGHYTRCRQRCRSRSHNRH |
| 118 | 243 | RRCRSILPLLLLSR |
| 119 | 256 | RTLHGRRVILHEGGHSISDLK |
| 120 | 266 | HHRLSYFIVRRHSTHASR |
| 121 | 293 | RRIRIDPQHD |
| 122 | 299 | ILQPDFLIRPE |
| 123 | 307 | HDPRIIRIR |
| 124 | 52 | SPYPIRT |
| 125 | 53 | ILVIIQRIM |
| 126 | 101 | IRFILIR |
| 127 | 102 | SSVHHRG |
| 128 | 103 | LRRQLQL |
| 129 | 113 | HTTAHTH |
| 130 | 115 | HPHNHTVHNVVY |
| 131 | 117 | DHSKFVPLFVRQ |
| 132 | 120 | SIRTLGRFLIIRV |
| 133 | 123 | GLCRIIL |
| 134 | 127 | SPPIRHH |
| 135 | 201 | HPTHPIRLRDNLTR |
| 136 | 212 | myr-REEETILIIRRR |
| 137 | 225 | HTIHSISDFPEPPDRRRR |
| 138 | 228 | DEDAAHSTGHPHNSQHRRRR |
| 139 | 240 | TEQHHYIPHRRR |
| 140 | 251 | RLRRVILRSYHE |
| 141 | 265 | EEPDRQPSGKRGGRKRRSR |
| 142 | 273 | RDFHTIHPSISRR |
| 143 | 276 | RRVDIHDGQRR |
| 144 | 277 | DQPYPHRRIR |
| 145 | 281 | myr-RDFILFIRRLGRR |
| 146 | 295 | LDLYHPRERR |
| 147 | 298 | RRIRDPLGNEHE |
| 148 | 303 | IVEFRIRR |
| 149 | 312 | RRPRIPDYIL |
| 150 | 314 | RSTPHIHEFIRR |
| 151 | 319 | SHDFYPHWMRERIR |
| 152 | 13 | HFSHHLK |
| 153 | 32 | TSPLQSLK |
| 154 | 51 | AILTLILRRVIWP |
| 155 | 94 | LRFIDYP |
| 156 | 109 | GPIKHHLQHH |
| 157 | 163 | LTLS |
| 158 | 222 | RYEENNGVNPPVQVFESRTR |
| 159 | 239 | REGFYGPWHEQRRR |
| 160 | 285 | RRDIIRHNAHS |
| 161 | 286 | HDFHDYLERR |
| 162 | 305 | IREFDPRRIR |
| 163 | 310 | RLRCLLLLIGRVGRR |
| 164 | 6 | LGIDEDEETETAPE |
| 165 | 22 | SLLIGFGIIRSR |
| 166 | 27 | VHEVTHHWL |
| 167 | 56 | ATPFHQT |
| 168 | 58 | SILPLFLIRRSG |
| 169 | 72 | SCRCRLRRRRRRRRR |
| 170 | 105 | SRIVLGW |
| 171 | 111 | SNIHHQV |
| 172 | 121 | LTLMRLRIIG |
| 173 | 122 | HSYSPYYTFRQH |
| 174 | 167 | FILIR |
| 175 | 205 | RCRNRKKEKTECLQKESEK |
| 176 | 213 | RRIKMIRTSESFIQHIVS |
| 177 | 244 | RRVSELQRNKHGRKHEL |

TABLE 6-continued

| SEQ ID NO: | pCAP NO: | Sequence |
|---|---|---|
| 178 | 246 | RRRLDDEDVQTPTPSEYQN |
| 179 | 261 | RRRQPLPSAPENEE |
| 180 | 7 | SPLQTPAAPGAAAGPALSPV |
| 181 | 18 | SHQVHTHHNN |
| 182 | 37 | KLQVPIK |
| 183 | 74 | IRGRIIRRKKRRQRRRRGDR |
| 184 | 82 | QIPHRSSTALQL |
| 185 | 88 | SYQTMQP |
| 186 | 140 | TDSHSHHRRRRRRRRRR |
| 187 | 143 | IPMNFTSHSLRQRRRRRRRR |
| 188 | 153 | YWSAPQPATRRRRRRRRRR |
| 189 | 220 | STTHPHPGTSAPEPATRRR |
| 190 | 226 | DDSDNRIIRYRR |
| 191 | 238 | TSPHPSLPRHIYPRR |
| 192 | 247 | RRITEIRGRTGKTTLTYIED |
| 193 | 249 | myr-DERTGKTRRYIDTRDIRR |
| 194 | 275 | myr-MTYSDMPRRIITDEDRRR |
| 195 | 278 | RRYDTVIDDIEYRR |
| 196 | 279 | RDTIERPEIRR |
| 197 | 280 | myr-RYRRLILEIWRR |
| 198 | 284 | myr-RHDTHNAHIRR |
| 199 | 288 | THDFDRLLRIRRR |
| 200 | 289 | RHNHIRPDNQ |
| 201 | 290 | RYKEPRITPRE |
| 202 | 302 | LRIEPIRIR |
| 203 | 306 | myr-RLIRIRILM |
| 204 | 318 | RPEFHSFHPIYERR |
| 205 | 91 | STTHIHA |
| 206 | 92 | FPHLVSSLTT |
| 207 | 99 | GLHLFTTDRQGW |
| 208 | 132 | NHPWQFPNRWTRRRRRR |
| 209 | 145 | HSSHHHPVHSWNRRRRRRR |
| 210 | 316 | myr-DIHTIHLPDTHRR |
| 211 | 10 | VAEFAQSIQSRIVEWKERLD |
| 212 | 49 | TRILCIVMM |
| 213 | 55 | FLLPEPDENTRW |
| 214 | 57 | LMSNAQY |
| 215 | 89 | SILTLSCRCRLRLWR |
| 216 | 95 | HQIHRNHTY |
| 217 | 106 | LIRRCSLQR |
| 218 | 137 | GAMHLPWHMGTRRRRRR |
| 219 | 202 | DEDAKFRIRILMRR |
| 220 | 245 | NHITNGGEEDSDCSSRRRRL |
| 221 | 257 | myr-HSSHHHPTVQHRR |
| 222 | 287 | RDFERTIVDI |
| 223 | 313 | myr-RRREILHPEFRILYE |
| 224 | 14 | HHFSHHWKT |
| 225 | 59 | FLIRRSG |
| 226 | 63 | HNHHHSQHTPQH |
| 227 | 80 | HLHKHHYKDSRM |
| 228 | 231 | HRTQSTLILFIRRGRET |
| 229 | 315 | LHFSHIDRR |
| 230 | 62 | YELPHHAYPA |
| 231 | 133 | SLLIGFGIIRSRRRRRRRR |
| 232 | 135 | HTDSHPHHHHPHRRRRRR |
| 233 | 147 | ATQHHYIKRRRRRRRRRR |
| 234 | 129 | FRSFAIPLVVPFRRRRRRR |
| 235 | 138 | YPTQGHLRRRRRRRRRRR |
| 236 | 146 | HANLHHTRRRRRRRRRRR |
| 237 | 152 | YRRLLIGMRRRRRRRRRRR |
| 238 | 233 | SHYHTPQNPPSTRRR |
| 239 | 235 | RSYSKLLCLLERLRISP |
| 240 | 3 | FWTQSIKERKMLNEHDFEVR |
| 241 | 15 | THFSHHLKH |
| 242 | 90 | SCRCRLR |
| 243 | 139 | MHPPDWYHHTPKRRRRRR |
| 244 | 237 | HTIHVHYPGNRQPNPPLILQR |
| 245 | 268 | TPSYGHTPSHHRRR |
| 246 | 301 | myr-IRGRIRIIRRIR |
| 247 | 20 | HHPWTHHQRWS |
| 248 | 48 | IPMNFTSHSLRQ |
| 249 | 118 | SNHHHRHHTNTH |
| 250 | 130 | EVTFRHSVVRRRRRRRRRR |
| 251 | 149 | FPGHTIHRRRRRRRRRRR |
| 252 | 34 | SILTLSRIVLGWW |
| 253 | 47 | TLYLPHWHRH |

TABLE 6-continued

| SEQ ID NO: | pCAP NO: | Sequence |
|---|---|---|
| 254 | 136 | SILTLRLRRLRRRRRRRR |
| 255 | 142 | TLYLPHWHRHRRRRRRRRR |
| 256 | 43 | TDSHSHH |
| 257 | 11 | EWKERLDKEFSLSVYQKMKF |
| 258 | 30 | TIHPSIS |
| 259 | 33 | SILTLRLRRLRR |
| 260 | 44 | VPHIHEFT |
| 261 | 9 | TIIHREDEDEIEW |
| 262 | 61 | KDLPFYSHLSRQ |
| 263 | 65 | THFSHHLKHRRRRRRRRRR |
| 264 | 93 | ATQHHYIK |
| 265 | 108 | IIRGNFLIGGRL |
| 266 | 131 | LPNPPERHHRRRRRRRRRRR |
| 267 | 158 | SFILFIRRGRLGRGDR |
| 268 | 100 | FPGHTIH |
| 269 | 128 | CILRLWW |
| 270 | 206 | RRRSHSQENVDQDTDE |
| 271 | 204 | MSTESNMPRLIQNDDRRR |
| 272 | 104 | LLRLGLI |
| 273 | 23 | IRILMFLIGCGR |
| 274 | 17 | LHSKTLVL |
| 275 | 24 | LRCLLLLIGRVG |
| 276 | 258 | FLIGPDRLIRSR |
| 277 | 16 | LPNPPERHH |
| 278 | 28 | HTDSHPHHHHPH |
| 279 | 160 | Fitc-SFILFIRRGRLGRRRRRRRR |
| 280 | 83 | HSSHHHPVHSWN |
| 281 | 259 | myr-RTLIGIIRSHHLTLIRR |
| 282 | 54 | IRGRIIR |
| 283 | 150 | IIRGNFLIGGRLRRRRRRRRR |
| 284 | 170 | IRILM |
| 285 | 35 | GAMHLPWHMGTL |
| 286 | 267 | KRGGRKRRGGGHRLSYFIRR |
| 287 | 21 | NHPWQFPNRWTV |
| 288 | 42 | MHPPDWYHHTPKH |
| 289 | 141 | SWQALALYAAGWRRRRRR |
| 290 | 161 | HNAH |
| 291 | 210 | DEFERYRRFSTSRRR |
| 292 | 1 | EVTFRHSVV |
| 293 | 75 | TRILCIVRKKRRQRRRRGDR |
| 294 | 70 | SILTLSRGRKKRRQRRRR |
| 295 | 151 | CILRLWWRRRRRRRRRR |
| 296 | 46 | ASWQALALYAAGW |
| 297 | 229 | myr-PRVLPSPHTIHPSQYP |
| 298 | 87 | HANLHHT |
| 299 | 157 | SFILFIRRGRLGRKKRRQRRRP |
| 300 | 36 | YPTQGHLR |
| 301 | 68 | YRRLLIGMMWRRRRRRRRRR |
| 302 | 60 | SFILFIRRGRLG |
| 303 | 134 | IRILMFLIGCGRRRRRRRR |
| 304 | 308 | myr-RRICRFIRICRVR |
| 305 | 155 | IRGRIIRRRRRRRRRR |
| 306 | 203 | RRRHDSCHNQLQNYDHSTE |
| 307 | 148 | WNHHHSTPHPRRRRRRRRRR |
| 308 | 282 | myr-RRPVAPDLRHTIHIPPER |
| 309 | 317 | RRDIHTIHPFYQ |
| 310 | 97 | WNHHHSTPHPAH |
| 311 | 144 | SFILFIRRGRLGRRRRRRRR |
| 312 | 159 | rrrrrrrrglrgrriflifs |
| 313 | 326 | myr-RRHNAHHSTPHPDDR |
| 314 | 174 | HSTPHP |
| 315 | 154 | LRCLLLLIGRVGRKKRRQRR |
| 316 | 221 | myr-RRKHNKHRPEPDSDER |
| 317 | 325 | myr-RRIRDPRILLLHFD |
| 318 | 230 | RKRGKSYAFFVPPSESKERW |
| 319 | 227 | myr-RRKILFIRLMHNKH |
| 320 | 242 | myr-RRLIVRILKLPNPPER |
| 321 | 250 | myr-RRHSTPHPD |

TABLE 7

| SEQ ID NJ: | Name | Peptide Seq | Conform | DNA | Viability | Luc | PCR | AS* |
|---|---|---|---|---|---|---|---|---|
| 292 | pCAP1 | EVTFRHSVV | 2 | 2 | 3 4 3 | 3 2 3 | 5 | 3 | 32 |
| 97 | pCAP2 | VWVHDSCHANLQNYRNYLLP | | | 2 | | | | 2 |
| 240 | pCAP3 | FWTQSIKERKMLNEHDFEVR | 2 | | 3 3 2 | 2 | | | 12 |
| 98 | pCAP4 | EHDFEVRGDVVNGRNHQGPK | | | 2 | | | | 2 |
| 99 | pCAP5 | LEVIYMI | | | 2 | | | | 2 |
| 164 | pCAP6 | LGIDEDEETETAPE | | | 2 3 | | | | 5 |
| 180 | pCAP7 | SPLQTPAAPGAAAGPALSPV | | 3 | 3 | | | | 6 |
| 17 | pCAP8 | LTFEHYWAQLTS | | | | | | | 0 |
| 261 | pCAP9 | TIIHREDEDEIEW | 2 | 3 | 3 2 2 | 3 2 | | | 17 |
| 211 | pCAP10 | VAEFAQSIQSRIVEWKERLD | | 3 | 3 2 | | | | 8 |
| 257 | pCAP11 | EWKERLDKEFSLSVYQKMKF | | | 3 3 5 2 | | | | 16 |
| 18 | pCAP12 | GGGGGGGGGGGG | | | | | | | 0 |
| 152 | pCAP13 | HFSHHLK | | | | 1 3 | | | 4 |
| 224 | pCAP14 | HHFSHHWKT | 2 | | 2 2 3 | | | | 9 |
| 241 | pCAP15 | THFSHHLKH | 2 | | 2 2 3 | 3 | | | 12 |
| 277 | pCAP16 | LPNPPERHH | 2 | 3 | 3 3 4 | 4 2 | | | 24 |
| 274 | pCAP17 | LHSKTLVL | 2 | 2 3 | 3 3 3 | 4 3 | | | 23 |
| 181 | pCAP18 | SHQVHTHHNN | 3 | | | 3 | | | 6 |
| 19 | pCAP19 | NPNTYVPHWMRQ | | | | | | | 0 |
| 247 | pCAP20 | HHPWTHHQRWS | | 2 | 3 | 3 2 | | 3 | 13 |
| 287 | pCAP21 | NHPWQFPNRWTV | 4 2 | 2 | 2 2 3 3 | 4 3 | | 4 | 29 |
| 165 | pCAP22 | SLLIGFGIIRSR | | | 3 | 2 | | | 5 |
| 273 | pCAP23 | IRILMFLIGCGR | 1 | 1 | 3 3 3 3 | 4 3 1 | | | 22 |
| 275 | pCAP24 | LRCLLLLIGRVG | 3 2 | 2 | 3 3 3 3 | 4 | | | 23 |
| 20 | pCAP25 | YRRLLIGMMW | | | | | | | 0 |
| 21 | pCAP26 | DEFHSFYTARQTG | | | | | | | 0 |
| 166 | pCAP27 | VHEVTHHWL | 2 | | 3 | | | | 5 |
| 278 | pCAP28 | HTDSHPHHHHPH | 2 | 2 | 3 3 3 | 4 1 | 3 | 3 | 24 |
| 22 | pCAP29 | KPDSPRV | | | | | | | 0 |
| 258 | pCAP30 | TIHPSIS | 3 | 2 | 3 2 2 2 2 | | | | 16 |
| 23 | pCAP31 | PPYSQFLQWYLS | | | | | | | 0 |
| 153 | pCAP32 | TSPLQSLK | 1 | 3 | | | | | 4 |
| 259 | pCAP33 | SILTLRLRRLRR | 2 2 | | 4 4 | 4 | | | 16 |
| 252 | pCAP34 | SILTLSRIVLGWW | | | 2 4 4 | 4 | | | 14 |
| 285 | pCAP35 | GAMHLPWHMGTL | 2 2 2 | 4 | 3 2 3 3 | 3 4 | | 3 | 28 |
| 300 | pCAP36 | YPTQGHLR | 6 3 | | 2 2 3 3 | 3 5 3 | 3 3 | 3 | 39 |
| 182 | pCAP37 | KLQVPIK | | | 2 2 2 | | | | 6 |
| 100 | pCAP38 | WTLSNYL | | | 2 | | | | 2 |
| 101 | pCAP39 | DSLHSTY | | | 2 | | | | 2 |

TABLE 7-continued

| SEQ ID NJ: | Name | Peptide Seq | Conform | | | DNA | | Viability | | | | | Luc | | PCR | | AS* |
|---|---|---|---|---|---|---|---|---|---|---|---|---|---|---|---|---|---|
| 24 | pCAP40 | SEFPRSWDMETN | | | | | | | | | | | | | | | 0 |
| 102 | pCAP41 | WHHRQQIPRPLE | | | | | | | | 2 | | | | | | | 2 |
| 288 | pCAP42 | MHPPDWYHHTPKH | 3 | 2 | | 4 | | 2 | 2 | 3 | 3 | | 3 | 4 | | | 29 |
| 256 | pCAP43 | TDSHSHH | | | | | | | 2 | 3 | 3 | 3 | | 4 | | | 15 |
| 260 | pCAP44 | VPHIHEFT | 2 | 3 | | | 3 | | 3 | 2 | | | | 3 | | | 16 |
| 25 | pCAP45 | HDTHNAHVG | | | | | | | | | | | | | | | 0 |
| 296 | pCAP46 | ASWQALALYAAGW | 2 | | 2 | | 2 | | 2 | 3 | 3 | 4 | 6 | 2 | 3 | 3 2 | 34 |
| 253 | pCAP47 | TLYLPHWHRH | 2 | | | 3 | | | 3 | | 3 | | | 3 | | | 14 |
| 248 | pCAP48 | IPMNFTSHSLRQ | 2 | | 2 | | | 3 | 3 | 3 | | | | | | | 13 |
| 212 | pCAP49 | TRILCIVMM | | | | | | | | 5 | | 3 | | | | | 8 |
| 26 | pCAP50 | WSEYDIPTPQIPP | | | | | | | | | | | | | | | 0 |
| 154 | pCAP51 | AILTLILRRVIWP | | | | | | 2 | 2 | | | | | | | | 4 |
| 124 | pCAP52 | SPYPIRT | | | | | | | | | | | | 3 | | | 3 |
| 125 | pCAP53 | ILVIIQRIM | | | | | | | | | 3 | | | | | | 3 |
| 282 | pCAP54 | IRGRIIR | 3 | | 2 | 2 | | | | 4 | 4 | 4 | 4 | 3 | | | 26 |
| 213 | pCAP55 | FLLPEPDENTRW | | | | | | | | | | | | 4 | 4 | | 8 |
| 167 | pCAP56 | ATPFHQT | | | | | | | | | | | | 3 | 2 | | 5 |
| 214 | pCAP57 | LMSNAQY | | | | 2 | 2 | | | | | 4 | | | | | 8 |
| 168 | pCAP58 | SILPLFLIRRSG | | | | | | | | 2 | | | | 3 | | | 5 |
| 225 | pCAP59 | FLIRRSG | | | | 2 | | | | 2 | 3 | | | 2 | | | 9 |
| 302 | pCAP60 | SFILFIRRGRLG | | | 2 | 3 | 3 | 3 | 4 | 2 | 3 | 5 | | 4 | 3 | 4 | 4 | 40 |
| 262 | pCAP61 | KDLPFYSHLSRQ | 2 | 3 | | | | | 2 | 2 | 5 | | | 3 | | | 17 |
| 230 | pCAP62 | YELPHHAYPA | | | | | | | | 5 | | 2 | 3 | | | | 10 |
| 226 | pCAP63 | HNHHHSQHTFQH | 2 | | 3 | | | | | 2 | 2 | | | | | | 9 |
| 103 | pCAP64 | APSIFTPHAWRQ | | | | | | | | 2 | | | | | | | 2 |
| 263 | pCAP65 | THFSHHLKHRRRRRRRRRR | | | 2 | | 2 | | 2 | 2 | | 2 | 4 | 3 | | | 17 |
| 104 | pCAP66 | THFSHHLKGGGRRQRRRP | | | | | | | | | | | | 2 | | | 2 |
| 105 | pCAP67 | LHSKTLVLGGGRRRRGDR | | | | | | | | | | | | 2 | | | 2 |
| 301 | pCAP68 | YRRLLIGMMWRRRRRRRRRRR | 4 | | 5 | | 4 | | 3 | 5 | 5 | 4 | 2 | | 2 | 2 | 3 | 39 |
| 27 | pCAP69 | SILTLSRRRRRRRRRR | | | | | | | | | | | | | | | 0 |
| 294 | pCAP70 | SILTLSRGRKKRRQRRRR | 3 | 3 | | 2 | | 2 | 3 | 3 | 3 | 3 | | | 5 | 4 2 | 33 |
| 106 | pCAP71 | WILSNYLGGRKKRRORRRR | 2 | | | | | | | | | | | | | | 2 |
| 169 | pCAP72 | SCRCRLRRRRRRRRRRR | | | | | | | | 2 | | 3 | | | | | 5 |
| 28 | pCAP73 | SCRCRLRGDRGDR | | | | | | | | | | | | | | | 0 |
| 183 | pCAP74 | IRGRIIRRKKRRQRRRRGDR | | | | | | | | 3 | 3 | | | | | | 6 |
| 293 | pCAP75 | TRILCIVRKKRRQRRRRGDR | 3 | 3 | | 2 | | 2 | 5 | 5 | 3 | 4 | 2 | | 3 | | 32 |
| 29 | pCAP76 | GGGGGGGGGRRRRRRR | | | | | | | | | | | | | | | 0 |
| 30 | pCAP77 | SEYLCSSLDAAG | | | | | | | | | | | | | | | 0 |

TABLE 7-continued

| SEQ ID NO: | Name | Peptide Seq | Conform | DNA | Viability | Luc | PCR | AS* |
|---|---|---|---|---|---|---|---|---|
| 31 | pCAP78 | GESFVQHVFRQN | | | | | | 0 |
| 32 | pCAP79 | SVHHHHRMHLVA | | | | | | 0 |
| 227 | pCAP80 | HLHKHHYKDSRM | 3 | 3 | 3 | | | 9 |
| 107 | pCAP81 | VRCIFRGIWVRL | | | 2 | | | 2 |
| 184 | pCAP82 | QIPHRSSTALQL | | | 3 3 | | | 6 |
| 280 | pCAP83 | HSSHHHPVHSWN | 4 1 | 5 | 4 4 3 3 | | 1 | 25 |
| 33 | pCAP84 | GRRRFCM | | | | | | 0 |
| 34 | pCAP85 | KLTIHHH | | | | | | 0 |
| 35 | pCAP86 | FGSHHEL | | | | | | 0 |
| 298 | pCAP87 | HANLHHT | 3 2 | 2 | 3 3 4 4 3 | 5 4 4 | | 37 |
| 185 | pCAP88 | SYQTMQP | | 2 | 4 | | | 6 |
| 215 | pCAP89 | SILTLSCRCRLRLWR | | 2 | 4 2 | | | 8 |
| 242 | pCAP90 | SCRCRLR | | 2 | 4 4 2 | | | 12 |
| 205 | pCAP91 | STTHIHA | | 4 | 3 | | | 7 |
| 206 | pCAP92 | FPHLVSSLTT | | | 4 3 | | | 7 |
| 264 | pCAP93 | ATQHHYIK | 4 4 | | 2 3 | 4 | | 17 |
| 155 | pCAP94 | LRFIDYP | 4 | | | | | 4 |
| 216 | pCAP95 | HQIHRNHTY | | | 4 4 | | | 8 |
| 36 | pCAP96 | GTVDHHA | | | | | | 0 |
| 310 | pCAP97 | WNHHHSTPHPAH | 3 3 | 6 | 4 4 5 4 4 4 | 2 3 5 | | 47 |
| 108 | pCAP98 | HSSGHNFVLVRQ | | | 2 | | | 2 |
| 207 | pCAP99 | GLHLFTTDRQGW | | | 2 3 2 | | | 7 |
| 268 | pCAP100 | FPGHTIH | | 5 | 3 3 2 3 | 3 | | 19 |
| 126 | pCAP101 | IRFILIR | | | 3 | | | 3 |
| 127 | pCAP102 | SSVHHRG | | | 3 | | | 3 |
| 128 | pCAP103 | LRRQLQL | | | 3 | | | 3 |
| 272 | pCAP104 | LLRLGLI | 3 | 3 | 6 3 3 3 | | | 21 |
| 170 | pCAP105 | SRIVLGW | 3 | 2 | | | | 5 |
| 217 | pCAP106 | LIRRCSLQR | 3 | 5 | | | | 8 |
| 37 | pCAP107 | DRLSVFLFIM | | | | | | 0 |
| 265 | pCAP108 | IIRGNFLIGGRL | 3 3 | 2 | 3 3 3 | | | 17 |
| 156 | pCAP109 | GPIKHHLQHH | | | 2 2 | | | 4 |
| 109 | pCAP110 | LFILVFR | | | 2 | | | 2 |
| 171 | pCAP111 | SNIHHQV | | | 3 2 | | | 5 |
| 110 | pCAP112 | TTSHHPK | | | 2 | | | 2 |
| 129 | pCAP113 | HTTAHTH | | | | 3 | | 3 |
| 38 | pCAP114 | AISHHTR | | | | | | 0 |
| 130 | pCAP115 | HPHNHTVHNVVY | | | 3 | | 3 | 3 |
| 39 | pCAP116 | KHHPFDHRLGNQ | | | | | | 0 |

TABLE 7-continued

| SEQ ID NJ: | Name | Peptide Seq | Conform | | | DNA | Viability | | | | | | Luc | | PCR | AS* |
|---|---|---|---|---|---|---|---|---|---|---|---|---|---|---|---|---|
| 131 | pCAP117 | DHSKFVPLFVRQ | 3 | | | | | | | | | | | | | 3 |
| 249 | pCAP118 | SNHHHRHHTNTH | | 2 | | 2 | 3 | 3 | 3 | | | | | | | 13 |
| 40 | pCAP119 | HSAHHTM | | | | | | | | | | | | | | 0 |
| 132 | pCAP120 | SIRTLGRFLIIRV | | | | | 3 | | | | | | | | | 3 |
| 172 | pCAP121 | LTLMRLRIIG | | | | | 2 3 | | | | | | | | | 5 |
| 173 | pCAP122 | HSYSPYYTFRQH | 2 | | | | 3 | | | | | | | | | 5 |
| 133 | pCAP123 | GLCRIIL | | | | | 3 | | | | | | | | | 3 |
| 111 | pCAP124 | VMVLFRILRGSM | | | | | 2 | | | | | | | | | 2 |
| 41 | pCAP125 | ELGLHRH | | | | | | | | | | | | | | 0 |
| 42 | pCAP126 | RRLRICV | | | | | | | | | | | | | | 0 |
| 134 | pCAP127 | SPPIRHH | 3 | | | | | | | | | | | | | 3 |
| 269 | pCAP128 | CILRLWW | 3 | 2 | | 3 | 3 3 | 3 | 2 | | | | | | | 19 |
| 234 | pCAP129 | FRSFAIPVVPFRRRRRRR | | | | | 4 3 2 2 | | | | | | | | | 11 |
| 250 | pCAP130 | EVTFRHSVVRRRRRRRRRR | | | | | 6 3 4 | | | | | | | | | 13 |
| 266 | pCAP131 | LPNPPERHHRRRRRRRRRRR | | 3 | | 3 | 3 3 2 3 1 | | | | | | | | | 18 |
| 208 | pCAP132 | NHPWQFPNRWTRRRRRR | | | | | 3 4 | | | | | | | | | 7 |
| 231 | pCAP133 | SLLIGFGIIRSRRRRRRRR | | | | | 2 2 6 | | | | | | | | | 10 |
| 303 | pCAP134 | IRILMFLIGCGRRRRRRRR | 4 | | | 4 | 3 2 6 6 3 3 | | | | 3 | 3 | 3 | | | 40 |
| 232 | pCAP135 | HTDSHPHHHHPHRRRRR | | | | | 3 3 2 2 | | | | | | | | | 10 |
| 254 | pCAP136 | SILTLRLRRLRRRRRRRR | | | | | 3 3 5 3 | | | | | | | | | 14 |
| 218 | pCAP137 | GAMHLPWHMGTRRRRRR | | | | | 3 3 2 | | | | | | | | | 8 |
| 235 | pCAP138 | YPTQGHLRRRRRRRRRRR | | | | | 3 4 2 2 | | | | | | | | | 11 |
| 243 | pCAP139 | MHPPDWYHHTPKRRRRRR | | | | | 2 3 2 2 | | 3 | | | | | | | 12 |
| 186 | pCAP140 | TDSHSHHRRRRRRRRRR | | | | | 3 3 | | | | | | | | | 6 |
| 289 | pCAP141 | SWQALALYAAGWRRRRRR | | | | | 6 3 5 3 3 3 | | 3 | | | | | | | 29 |
| 255 | pCAP142 | TLYLPHWHRHRRRRRRRRR | | | | | 6 2 3 | | | | 3 | | | | | 14 |
| 187 | pCAP143 | IPMNFTSHSLRQRRRRRRRRR | | | | | 2 4 | | | | | | | | | 6 |
| 311 | pCAP144 | SFILFIRRGRLGRRRRRRRRR | 2 | 2 | 2 | 2 | 3 3 3 3 3 2 6 6 | | | | 4 | | 4 | 4 | | 49 |
| 209 | pCAP145 | HSSHHHPVHSWNRRRRRR | | | | | 3 2 2 | | | | | | | | | 7 |
| 236 | pCAP146 | HANLHHTRRRRRRRRRRR | | | | | 3 2 3 3 | | | | | | | | | 11 |
| 233 | pCAP147 | ATQHHYIKRRRRRRRRRRR | | | | | 4 3 3 | | | | | | | | | 10 |
| 307 | pCAP148 | WNHHHSTPHPRRRRRRRRR | | 4 | 4 | | 4 5 3 4 2 | | 3 | | 3 | 3 | 4 | 4 | | 43 |
| 251 | pCAP149 | FPGHTIHRRRRRRRRRRR | | | | | 3 5 3 2 | | | | | | | | | 13 |
| 283 | pCAP150 | IIRGNFLIGGRLRRRRRRRRR | 4 | 4 | 4 | | 4 3 2 5 | | | | | | | | | 26 |
| 295 | pCAP151 | CILRLWWRRRRRRRRRRR | | | | | 5 4 5 4 3 3 | | 3 | | 3 | 3 | | | | 33 |
| 237 | pCAP152 | YRRLLIGMRRRRRRRRRRR | | | | | 5 3 3 | | | | | | | | | 11 |
| 188 | pCAP153 | YWSAPQPATRRRRRRRRRRR | | | | | 3 3 | | | | | | | | | 6 |
| 315 | pCAP154 | LRCLLLLIGRVGRKKRRORR | | 6 | 4 | 5 | 4 5 5 5 5 3 4 | | | | 5 | 3 | | | | 57 |

TABLE 7-continued

| SEQ ID NJ: | Name | Peptide Seq | Conform | | DNA | | Viability | | | | | | Luc | | PCR | | AS* |
|---|---|---|---|---|---|---|---|---|---|---|---|---|---|---|---|---|---|
| 305 | pCAP155 | IRGRIIRRRRRRRRRR | 3 | | 2 | 2 | 5 5 | 4 | 4 | 4 | 4 | | 3 | | | | 41 |
| 43 | pCAP156 | VPHIHEFTRRRRRRRR | | | | | | | | | | | | | | | 0 |
| 299 | pCAP157 | SFILFIRRGRLGRKKRRQRRRP | 1 | 1 | 1 | 2 | 3 3 | 3 | 3 | 5 | 2 | 2 | 5 | 2 | 4 | | 37 |
| 267 | pCAP158 | SFILFIRRGRLGRGDR | 1 | 1 | | | 4 | 4 | 4 | | 2 | 2 | | | | | 18 |
| 312 | pCAP159 | rrrrrrrrglrgrriflifs | 3 | 1 | 1 | 1 | 3 5 | 4 | 4 | | 5 | 4 | 5 | 4 | 5 | 4 4 | 53 |
| 279 | pCAP160 | Fitc-SFILFIRRGRLGRRRRRRRRR | 1 | | 1 | | 4 | 4 | 4 | | | | 4 | 3 | 3 | | 24 |
| 290 | pCAP161 | HNAH | 3 | 2 | | 2 | 2 3 | 5 | 3 | 5 | | 4 | | | | | 29 |
| 112 | pCAP162 | SILT | | 2 | | | | | | | | | | | | | 2 |
| 157 | pCAP163 | LTLS | | | 4 | | | | | | | | | | | | 4 |
| 44 | pCAP164 | PLTLI | | | | | | | | | | | | | | | 0 |
| 45 | pCAP165 | SLLIG | | | | | | | | | | | | | | | 0 |
| 46 | pCAP166 | KPPER | | | | | | | | | | | | | | | 0 |
| 174 | pCAP167 | FILIR | | | | | | 5 | | | | | | | | | 5 |
| 47 | pCAP168 | CRIIR | | | | | | | | | | | | | | | 0 |
| 48 | pCAP169 | SFILI | | | | | | | | | | | | | | | 0 |
| 284 | pCAP170 | IRILM | | | 5 | 5 | 5 3 | 3 | | 3 | 3 | | | | | | 27 |
| 49 | pCAP171 | PHHHS | | | | | | | | | | | | | | | 0 |
| 50 | pCAP172 | EFHS | | | | | | | | | | | | | | | 0 |
| 51 | pCAP173 | RLRRL | | | | | | | | | | | | | | | 0 |
| 314 | pCAP174 | HSTPHP | 1 | 4 | 4 | 5 | 4 5 | 4 | 5 | 4 | 4 | 5 | 1 | 4 | 4 | | 54 |
| 52 | pCAP175 | DSPR | | | | | | | | | | | | | | | 0 |
| 53 | pCAP176 | HPWTH | | | | | | | | | | | | | | | 0 |
| 54 | pCAP177 | HFSHH | | | | | | | | | | | | | | | 0 |
| 55 | pCAP178 | RRVI | | | | | | | | | | | | | | | 0 |
| 56 | pCAP179 | ILVI | | | | | | | | | | | | | | | 0 |

*AS - Activity Score.

TABLE 8

| SEQ ID NJ: | Name | Sequence | Similarity | Conformation | DNA binding | Viability | | | PCR | AS* |
|---|---|---|---|---|---|---|---|---|---|---|
| 135 | pCAP201 | HPTHPIRLRDNLTR | 14-3-3 | | 3 | | | | | 3 |
| 219 | pCAP202 | DEDAKFRIRILMRR | APAF1 | 3 | 2 | 3 | | | | 8 |
| 306 | pCAP203 | RRRHDSCHNQLQNYDHSTE | ASPP1 | | 3 | | 3 | 2 4 6 4 | 6 6 4 4 | 42 |
| 271 | pCAP204 | MSTESNMPRLIQNDDRRR | ASPP2 | | | | | 2 4 4 | 5 5 | 20 |
| 175 | pCAP205 | RCRNRKKEKTECLQKESEK | ATF3 | | 2 | 3 | | | | 5 |
| 270 | pCAP206 | RRRSHSQ ENVDQDTDE | BAK | | | | 2 | 3 3 2 | 1 2 6 | 19 |
| 57 | pCAP207 | RRSRSNEDVEDKTEDE | BAK | | | | | | | 0 |
| 58 | pCAP208 | RRIRSGGKDHAWTPLHENH | BARD1 | | | | | | | 0 |
| 59 | pCAP209 | HTPHPPVARTSPLQTPRR | BCL2 | | | | | | | 0 |

TABLE 8-continued

| SEQ ID NJ: | Name | Sequence | Similarity | Conformation | DNA binding | Viability | PCR AS* |
|---|---|---|---|---|---|---|---|
| 291 | pCAP210 | DEFERYRRFSTSRRR | BCL-XL | 3 | 2 | 2 2 2 | 6 3 3 6 29 |
| 60 | pCAP211 | PDSEPPRMELRRR | BCR | | | | 0 |
| 136 | pCAP212 | my r-REEETILIIRRR | BRG1 | | 3 | | 3 |
| 176 | pCAP213 | RRIKMIRTSESFIQHIVS | BTF | | 2 | 3 | 5 |
| 113 | pCAP214 | RRRESEQRSISLHHHST | C-ABL | | | 2 | 2 |
| 61 | pCAP215 | RRDTFDIRILMAF | CARM1 | | | | 0 |
| 114 | pCAP216 | my r-HFNHYTFESTCRRRRC | CAS | | 2 | | 2 |
| 115 | pCAP217 | HSTPHPPQPPERRR | CCDC8 | | | 2 | 2 |
| 62 | pCAP218 | RREVTELHHTHEDRR | CEP72 | | | | 0 |
| 96 | pCAP219 | SYRHYSDHWEDRRR | CETD2 | | | 1 | 1 |
| 189 | pCAP220 | STTHPHPGTSAPEPATRRR | CHD6 | | 2 | 2 2 | 6 |
| 316 | pCAP221 | myr-RRKHNKHRPEPDSDER | CTF2 | 3 | 5 3 4 | 4 2 5 6 5 2 5 4 6 6 | 60 |
| 158 | pCAP222 | RYEENNGVNPPVQVFESRTR | CUL7 | | 4 | | 4 |
| 63 | pCAP223 | SPWTHERRCRQR | CYP27B1 | | | | 0 |
| 116 | pCAP224 | RRKSEPHSLSGGYQTGAD | DIABLO | | | 2 | 2 |
| 137 | pCAP225 | HTIHSISDFPEPPDRRRR | DMP1 | | | 3 | 3 |
| 190 | pCAP226 | DDSDNRIIRYRR | G3BP2 | | | 3 3 | 6 |
| 319 | pCAP227 | my r-RRKILFI RLMHNKH | GAS2 | 4 | 6 5 5 | 5 5 6 5 6 3 5 5 3 4 | 67 |
| 138 | pCAP228 | DEDAAHSTGHPHNSQHRRRR | HIPK1 | | | 3 | 3 |
| 297 | pCAP229 | my r-PRVLPSPHTIHPSQYP | HIPK2 | | 2 | 4 4 4 3 3 4 4 4 4 | 36 |
| 318 | pCAP230 | RKRGKSYAFFVPPSESKERW | HMGB1 | 3 | 5 5 3 | 4 3 6 5 5 2 6 4 6 6 | 63 |
| 228 | pCAP231 | HRTQSTLILFIRRGRET | HTRA2 | | 3 | 6 | 9 |
| 64 | pCAP232 | RSRSSHLRDHERTHT | HZF | | | | 0 |
| 238 | pCAP233 | SHYHTPQNPPSTRRR | IFI16 | | 3 | 3 3 2 | 11 |
| 117 | pCAP234 | HRTGHYTRCRQRCRSRSHNRH | KLF4 | | | 2 | 2 |
| 239 | pCAP235 | RSYSKLLCLLERLRISP | MIF | | 2 | 5 2 2 | 11 |
| 65 | pCAP236 | RRRSTNTFLGEDFDQ | MORTALIN | | | | 0 |
| 244 | pCAP237 | HTIHVHYPGN FQPNPPLILQR | MULE | | 3 | 2 5 2 | 12 |
| 191 | pCAP238 | TSPHPSLPRHIYPRR | NFAT | | 2 | 4 | 6 |
| 159 | pCAP239 | REGFYGPWHEQRRR | OGA | | 2 | 2 | 4 |
| 139 | pCAP240 | TEQHHYIPHRRR | OSGIN2 | | | 3 | 3 |
| 66 | pCAP241 | LIGLSTSPRPRIIR | PAR3 | | | | 0 |
| 320 | pCAP242 | my r-RRLIVRILKLPNPPER | PARC | 4 | 3 | 6 6 6 6 3 4 6 6 5 6 | 67 |
| 118 | pCAP243 | RRCRSILPLLLLSR | PERP | | | 2 | 2 |
| 177 | pCAP244 | RRVSELQRNKHGRKHEL | PIAS1 | | 3 | 2 | 5 |
| 220 | pCAP245 | NHITNGGEEDSDCSSRRRRL | PIN1 | | 3 | 3 2 | 8 |
| 178 | pCAP246 | RRRLDDEDVQTPTPSEYQN | PIRH2 | | 3 | 2 | 5 |
| 192 | pCAP247 | RRITEIRGRTGKTTLTYIED | RAD51 | | 3 | 3 | 6 |

TABLE 8-continued

| SEQ ID NJ: | Name | Sequence | Similarity | Conformation | DNA binding | Viability | PCR AS* |
|---|---|---|---|---|---|---|---|
| 67 | pCAP248 | EIYGESGKTDEHALDTEYRR | RAD51 | | | | 0 |
| 193 | pCAP249 | myr-DERTGKTRRYIDTRDIRR | RAD51 | | | 3 3 | 6 |
| 321 | pCAP260 | myr-RRHSTPHPD | RAD9 | 4 | 6 5 4 | 5 5 5 5 6 3 6 6 6 6 | 72 |
| 140 | pCAP251 | RLRRVILRSYHE | RAD9 | | | 3 | 3 |
| 68 | pCAP252 | RRVILRSYDGGHSTPHPD | RAD9 | | | | 0 |
| 69 | pCAP253 | TGKTFVKRHLTEFEKKYR | RAN | | | | 0 |
| 70 | pCAP254 | NHFDYDTIELDTAGEYSRRR | RAS | | | | 0 |
| 71 | pCAP255 | DPEPPRYLPPPPERR | RASSF5 | | | | 0 |
| 119 | pCAP256 | RTLHGRRVILHEGGHSISDLK | RPA70 | | | 2 | 2 |
| 221 | pCAP257 | myr-HSSHHHPTVQHRR | SIN3A | | | 4 4 | 8 |
| 276 | pCAP258 | FLIGPDRLIRSR | SIVA | | | 6 4 5 2 2 4 | 23 |
| 281 | pCAP259 | myr-RTLIGIIRSHHLTLIRR | SMG1 | | 4 | 5 4 5 3 2 2 | 25 |
| 72 | pCAP260 | RRTFIRHRIDSTEVIYQDED | STK11 | | | | 0 |
| 179 | pCAP261 | RRRQPLPSAPENEE | STK15 | | | 2 3 | 5 |
| 73 | pCAP262 | ESKTGHKSEEQRLRRYR | TBP | | | | 0 |
| 74 | pCAP263 | YDDEHNHHPHHSTHRRR | TSC22 | | | | 0 |
| 75 | pCAP264 | RRRREVHTIHQHGIVHSD | TTK | 0 | | | |
| 141 | pCAP265 | EEPDRQPSGKRGGRKRRSR | TWIST | | | 3 | 3 |
| 120 | pCAP266 | HHRLSYFIVRRHSTHASR | TWIST | | | 2 | 2 |
| 286 | pCAP267 | KRGGRKRRGGGHRLSYFIRR | TWIST | 3 | 2 4 | 6 2 3 2 2 2 2 | 28 |
| 245 | pCAP268 | TPSYGHTPSHHRRR | WT1 | 3 | 5 | 4 | 12 |
| 76 | pCAP269 | DEPLPPPERRR | | | | | 0 |
| 77 | pCAP270 | SPHPPY | | | | | 0 |
| 78 | pCAP271 | SPHPPYSPHPPYSPHPPYP | | | | | 0 |
| 79 | pCAP272 | RRPHNLHHD | | | | | 0 |
| 142 | pCAP273 | RDFHTIHPSISRR | | | | 3 | 3 |
| 80 | pCAP274 | LRDPHPPERRIR | | | | | 0 |
| 194 | pCAP275 | myr-MTYSDMPRRIITDEDRRR | ASPP2 | | | 3 3 | 6 |
| 143 | pCAP276 | RRVDIHDGQRR | | | 3 | | 3 |
| 144 | pCAP277 | DQPYPHRRIR | | | 3 | | 3 |
| 195 | pCAP278 | RRYDTVIDDIEYRR | | | 3 | 3 | 6 |
| 196 | pCAP279 | RDTIERPEIRR | | | 3 | 3 | 6 |
| 197 | pCAP280 | myr-RYRRLILEIWRR | | | 3 | 3 | 6 |
| 145 | pCAP281 | myr-RDFI LFIRRLGRR | | | 3 | | 3 |
| 308 | pCAP282 | myr-RRPVAPDLRHTIHIPPER | LTA | 4 | 3 3 4 | 4 6 2 2 4 4 4 3 | 43 |
| 81 | pCAP283 | RRPADQISYLHPPER | | | | | 0 |
| 198 | pCAP284 | myr-RHDTHNAHIRR | | | | 6 | 6 |
| 160 | pCAP285 | RRDIRHNAHS | | | | 4 | 4 |

TABLE 8-continued

| SEQ ID NO: | Name | Sequence | Similarity | Conformation | DNA binding | Viability | PCR AS* |
|---|---|---|---|---|---|---|---|
| 161 | pCAP286 | HDFHDYLERR | | | | 4 | 4 |
| 222 | pCAP287 | RDFERTIVDI | | | 4 | 4 | 8 |
| 199 | pCAP288 | THDFDRLLRIRRR | | | 2 | 4 | 6 |
| 200 | pCAP289 | RHNHIRPDNQ | | | 2 | 4 | 6 |
| 201 | pCAP290 | RYKEPRITPRE | | | 4 | 2 | 6 |
| 82 | pCAP291 | DLQYDFPRIRR | | | | | 0 |
| 83 | pCAP292 | YDELYQKEDPHRRR | | | | | 0 |
| 121 | pCAP293 | RRIRIDPQHD | | | | 2 | 2 |
| 84 | pCAP294 | FKPERFPQNDRRR | | | | | 0 |
| 146 | pCAP295 | LDLYHPRERR | | | | 3 | 3 |
| 85 | pCAP296 | RPADRIRR | | | | | 0 |
| 86 | pCAP297 | HDFDPRYRDRR | | | | | 0 |
| 147 | pCAP298 | RRIRDPLGNEHE | | | | 3 | 3 |
| 122 | pCAP299 | ILQPDFLIRPE | | | | 2 | 2 |
| 87 | pCAP300 | RIRRDPDSPLPHPE | | | | | 0 |
| 246 | pCAP301 | myr-IRGRIRIIRRIR | | | 3 | 3 | 6 | 12 |
| 202 | pCAP302 | LRIEPIRIR | | | 3 | 3 | 6 |
| 148 | pCAP303 | IVEFRIRR | | | 3 | | 3 |
| 88 | pCAP304 | myr-RRIRILMFUGCGRV | | | | | 0 |
| 162 | pCAP305 | IREFDPRRIR | | | | 4 | 4 |
| 203 | pCAP306 | myr-RLIRIRILM | | | 6 | | 6 |
| 123 | pCAP307 | HDPRIIRIR | | | | 2 | 2 |
| 304 | pCAP308 | myr-RRICRFIRICRVR | CDC25B | 6 | 4 4 | 6 4 4 | 2 4 6 40 |
| 89 | pCAP309 | HPHVILPRIRIRIR | | | | | 0 |
| 163 | pCAP310 | RLRCLLLLIGRVGRR | | | 4 | | 4 |
| 90 | pCAP311 | EIHTIHLLPERR | | | | | 0 |
| 149 | pCAP312 | RRPRIPDYIL | | | 3 | | 3 |
| 223 | pCAP313 | myr-RRREILHPEFRILYE | | | 2 | 6 | 8 |
| 150 | pCAP314 | RSTPHIHEFI RR | | | 3 | | 3 |
| 229 | pCAP315 | LHFSHIDRR | | | 3 | 6 | 9 |
| 210 | pCAP316 | myr-DIHTIHLPDTHRR | | | 3 | 4 | 7 |
| 309 | pCAP317 | RRDIHTIHPFYQ | HSD17 | 5 4 | 3 4 2 | 5 1 | 6 5 5 3 43 |
| 204 | pCAP318 | RPEFHSFHPIYERR | | | 3 | 3 | 6 |
| 151 | pCAP319 | SHDFYPHWMRERIR | | | 3 | | 3 |
| 91 | pCAP320 | EPSHPRSRYPRTF | | | | | 0 |
| 92 | pCAP321 | RNIIIRDFIHFSHIDR | | | | | 0 |
| 93 | pCAP322 | RRIRDPQIK-myrLEIHFSHID | | | | | 0 |
| 94 | pCAP323 | myr-DLHTIHI PRDRR | | | | | 0 |

TABLE 8-continued

| SEQ ID NO: | Name | Sequence | Similarity | Conformation | DNA binding | Viability | PCR AS* |
|---|---|---|---|---|---|---|---|
| 95 | pCAP324 | SHDFPHREPRPERR | | | | | 0 |
| 317 | pCAP325 | my r-RRIRDPRILLLHFD | CCT3 | 4 | 6 | 3 | 4    3 6 6 4 3 4 5 4 3 6 61 |
| 313 | pCAP326 | my r-RRHNAHHSTPHPDDR | RAD9A | 3 | 6 | 3 | 3    4   6 4 4    6 4 6 4 53 |

*AS - Activity Score.

TABLE 9

| | Experiment number | | |
|---|---|---|---|
| | 2 | 3 | 4 |
| | Cell line type | | |
| | MDA-MB-231 p53<sup>R280H</sup> | SW-480 p53<sup>R273H,P309S</sup> | SKBR3 p53<sup>R175H</sup> |
| Group | Control pCAPs | Treatment pCAPs | Control pCAPs | Treatment pCAPs | 325 pCAP | Control pCAPs | Treatment pCAPs |
| Number of samples | 12 | 18 | 10 | 10 | 10 | 10 | 10 |
| IVIS average ratio to day 0 | 209% | 1.1% | 275.4% | 3.3% | 4.4% | 1000% | 43.7% |
| Number of total regression | 0 | 10 | 0 | 4 | 2 | 0 | 0 |
| Samples average size | 1.26 | 0.27 | 0.87 | 0.15 | 0.12 | 0.38 | 0.15 |
| Samples average weight | 1.11 | 0.29 | 0.53 | 0.15 | 0.10 | 0.53 | 0.24 |

TABLE 10

| SEQ ID NO: | Plasmid | Sequence | Activity Score |
|---|---|---|---|
| 17 | pCAP8 | LTFEHYWAQLTS | 0 |
| 18 | pCAP12 | GGGGGGGGGGGG | 0 |
| 19 | pCAP19 | NPNTYVPHWMRQ | 0 |
| 20 | pCAP25 | YRRLLIGMMW | 0 |
| 21 | pCAP26 | DEFHSFYTARQTG | 0 |
| 22 | pCAP29 | KPDSPRV | 0 |
| 23 | pCAP31 | PPYSQFLQWYLS | 0 |
| 24 | pCAP40 | SEFPRSWDMETN | 0 |
| 25 | pCAP45 | HDTHNAHVG | 0 |
| 26 | pCAP50 | WSEYDIPTPQIPP | 0 |
| 27 | pCAP69 | SILTLSRRRRRRRR | 0 |
| 28 | pCAP73 | SCRCRLRGDRGDR | 0 |
| 29 | pCAP76 | GGGGGGGGGRRRRRRR | 0 |
| 30 | pCAP77 | SEYLCSSLDAAG | 0 |
| 31 | pCAP78 | GESFVQHVFRQN | 0 |
| 32 | pCAP79 | SVHHHRMHLVA | 0 |
| 33 | pCAP84 | GRRRFCM | 0 |
| 34 | pCAP85 | KLTIHHH | 0 |
| 35 | pCAP86 | FGSHHEL | 0 |
| 36 | pCAP96 | GTVDHHA | 0 |
| 37 | pCAP107 | DRLSVFLFIM | 0 |
| 38 | pCAP114 | AISHHTR | 0 |
| 39 | pCAP116 | KHHPFDHRLGNQ | 0 |
| 40 | pCAP119 | HSAHHTM | 0 |
| 41 | pCAP125 | ELGLHRH | 0 |
| 42 | pCAP126 | RRLRICV | 0 |
| 43 | pCAP156 | VPHIHEFTRRRRRRR | 0 |
| 44 | pCAP164 | PLTLI | 0 |
| 45 | pCAP165 | SLLIG | 0 |
| 46 | pCAP166 | KPPER | 0 |
| 47 | pCAP168 | CRIIR | 0 |
| 48 | pCAP169 | SFILI | 0 |

TABLE 10-continued

| SEQ ID NO: | Plasmid | Sequence | Activity Score |
|---|---|---|---|
| 49 | pCAP171 | PHHHS | 0 |
| 50 | pCAP172 | EFHS | 0 |
| 51 | pCAP173 | RLRRL | 0 |
| 52 | pCAP175 | DSPR | 0 |
| 53 | pCAP176 | HPWTH | 0 |
| 54 | pCAP177 | HFSHH | 0 |
| 55 | pCAP178 | RRVI | 0 |
| 56 | pCAP179 | ILVI | 0 |
| 57 | pCAP207 | RRSRSNEDVEDKTEDE | 0 |
| 58 | pCAP208 | RRIRSGGKDHAWTPLHENH | 0 |
| 59 | pCAP209 | HTPHPPVARTSPLQTPRR | 0 |
| 60 | pCAP211 | PDSEPPRMELRRR | 0 |
| 61 | pCAP215 | RRDTFDIRILMAF | 0 |
| 62 | pCAP218 | RREVTELHHTHEDRR | 0 |
| 63 | pCAP223 | SPWTHERRCRQR | 0 |
| 64 | pCAP232 | RSRSSHLRDHERTHT | 0 |
| 65 | pCAP236 | RRRSTNTFLGEDFDQ | 0 |
| 66 | pCAP241 | LIGLSTSPRPRIIR | 0 |
| 67 | pCAP248 | EIYGESGKTDEHALDTEYRR | 0 |
| 68 | pCAP252 | RRVILRSYDGGHSTPHPD | 0 |
| 69 | pCAP253 | TGKTFVKRHLTEFEKKYR | 0 |
| 70 | pCAP254 | NHFDYDTIELDTAGEYSRRR | 0 |
| 71 | pCAP255 | DPEPPRYLPPPPERR | 0 |
| 72 | pCAP260 | RRTFIRHRIDSTEVIYQDED | 0 |
| 73 | pCAP262 | ESKTGHKSEEQRLRRYR | 0 |
| 74 | pCAP263 | YDDEHNHHPHHSTHRRR | 0 |
| 75 | pCAP264 | RRRREVHTIHQHGIVHSD | 0 |
| 76 | pCAP269 | DEPLPPPERRR | 0 |
| 77 | pCAP270 | SPHPPY | 0 |
| 78 | pCAP271 | SPHPPYSPHPPYSPHPPYP | 0 |
| 79 | pCAP272 | RRPHNLHHD | 0 |
| 80 | pCAP274 | LRDPHPPERRIR | 0 |
| 81 | pCAP283 | RRPADQISYLHPPER | 0 |
| 82 | pCAP291 | DLQYDFPRIRR | 0 |
| 83 | pCAP292 | YDELYQKEDPHRRR | 0 |
| 84 | pCAP294 | FKPERFPQNDRRR | 0 |
| 85 | pCAP296 | RPADRIRR | 0 |
| 86 | pCAP297 | HDFDPRYRDRR | 0 |
| 87 | pCAP300 | RIRRDPDSPLPHPE | 0 |
| 88 | pCAP304 | myr-RRIRILMFLIGCGRV | 0 |
| 89 | pCAP309 | HPHVILPRIRIRIR | 0 |
| 90 | pCAP311 | EIHTIHLLPERR | 0 |
| 91 | pCAP320 | EPSHPRSRYPRTF | 0 |
| 92 | pCAP321 | RNIIIRDFIHFSHIDR | 0 |
| 93 | pCAP322 | RRIRDPQIK-myrLEIHFSHID | 0 |
| 94 | pCAP323 | myr-DLHTIHIPRDRR | 0 |
| 95 | pCAP324 | SHDFPHREPRPERR | 0 |
| 96 | pCAP219 | SYRHYSDHWEDRRR | 1 |
| 97 | pCAP2 | VWVHDSCHANLQNYRNYLLP | 2 |
| 98 | pCAP4 | EHDFEVRGDVVNGRNHQGPK | 2 |
| 99 | pCAP5 | LEVIYMI | 2 |
| 100 | pCAP38 | WTLSNYL | 2 |
| 101 | pCAP39 | DSLHSTY | 2 |
| 102 | pCAP41 | WHHRQQIPRPLE | 2 |
| 103 | pCAP64 | APSIFTPHAWRQ | 2 |
| 104 | pCAP66 | THFSHHLKGGGRRQRRRP | 2 |
| 105 | pCAP67 | LHSKTLVLGGGRRRRGDR | 2 |
| 106 | pCAP71 | WTLSNYLGGRKKRRQRRRR | 2 |
| 107 | pCAP81 | VRCIFRGIWVRL | 2 |
| 108 | pCAP98 | HSSGHNFVLVRQ | 2 |
| 109 | pCAP110 | LFILVFR | 2 |
| 110 | pCAP112 | TTSHHPK | 2 |
| 111 | pCAP124 | VMVLFRILRGSM | 2 |
| 112 | pCAP162 | SILT | 2 |
| 113 | pCAP214 | RRRESEQRSISLHHHST | 2 |
| 114 | pCAP216 | myr-HFNHYTFESTCRRRRC | 2 |
| 115 | pCAP217 | HSTPHPQPPERRR | 2 |
| 116 | pCAP224 | RRKSEPHSLSGGYQTGAD | 2 |
| 117 | pCAP234 | HRTGHYTRCRQRCRSRSHNRH | 2 |
| 118 | pCAP243 | RRCRSILPLLLLSR | 2 |
| 119 | pCAP256 | RTLHGRRVILHEGGHSISDLK | 2 |
| 120 | pCAP266 | HHRLSYFIVRRHSTHASR | 2 |
| 121 | pCAP293 | RRIRIDPQHD | 2 |
| 122 | pCAP299 | ILQPDFLIRPE | 2 |
| 123 | pCAP307 | HDPRIIRIR | 2 |
| 124 | pCAP52 | SPYPIRT | 3 |

TABLE 10-continued

| SEQ ID NO: | Plasmid | Sequence | Activity Score |
|---|---|---|---|
| 125 | pCAP53 | ILVIIQRIM | 3 |
| 126 | pCAP101 | IRFILIR | 3 |
| 127 | pCAP102 | SSVHHRG | 3 |
| 128 | pCAP103 | LRRQLQL | 3 |
| 129 | pCAP113 | HTTAHTH | 3 |
| 130 | pCAP115 | HPHNHTVHNVVY | 3 |
| 131 | pCAP117 | DHSKFVPLFVRQ | 3 |
| 132 | pCAP120 | SIRTLGRFLIIRV | 3 |
| 133 | pCAP123 | GLCRIIL | 3 |
| 134 | pCAP127 | SPPIRHH | 3 |
| 135 | pCAP201 | HPTHPIRLRDNLTR | 3 |
| 136 | pCAP212 | myr-REEETILIIRRR | 3 |
| 137 | pCAP225 | HTIHSISDFPEPPDRRRR | 3 |
| 138 | pCAP228 | DEDAAHSTGHPHNSQHRRRR | 3 |
| 139 | pCAP240 | TEQHHYIPHRRR | 3 |
| 140 | pCAP251 | RLRRVILRSYHE | 3 |
| 141 | pCAP265 | EEPDRQPSGKRGGRKRRSR | 3 |
| 142 | pCAP273 | RDFHTIHPSISRR | 3 |
| 143 | pCAP276 | RRVDIHDGQRR | 3 |
| 144 | pCAP277 | DQPYPHRRIR | 3 |
| 145 | pCAP281 | myr-RDFILFIRRLGRR | 3 |
| 146 | pCAP295 | LDLYHPRERR | 3 |
| 147 | pCAP298 | RRIRDPLGNEHE | 3 |
| 148 | pCAP303 | IVEFRIRR | 3 |
| 149 | pCAP312 | RRPRIPDYIL | 3 |
| 150 | pCAP314 | RSTPHIHEFIRR | 3 |
| 151 | pCAP319 | SHDFYPHWMRERIR | 3 |
| 152 | pCAP13 | HFSHHLK | 4 |
| 153 | pCAP32 | TSPLQSLK | 4 |
| 154 | pCAP51 | AILTLILRRVIWP | 4 |
| 155 | pCAP94 | LRFIDYP | 4 |
| 156 | pCAP109 | GPIKHHLQHH | 4 |
| 157 | pCAP163 | LTLS | 4 |
| 158 | pCAP222 | RYEENNGVNPPVQVFESRTR | 4 |
| 159 | pCAP239 | REGFYGPWHEQRRR | 4 |
| 160 | pCAP285 | RRDIIRHNAHS | 4 |
| 161 | pCAP286 | HDFHDYLERR | 4 |
| 162 | pCAP305 | IREFDPRRIR | 4 |
| 163 | pCAP310 | RLRCLLLLIGRVGRR | 4 |
| 164 | pCAP6 | LGIDEDEETETAPE | 5 |
| 165 | pCAP22 | SLLIGFGIIRSR | 5 |
| 166 | pCAP27 | VHEVTHHWL | 5 |
| 167 | pCAP56 | ATPFHQT | 5 |
| 168 | pCAP58 | SILPLFLIRRSG | 5 |
| 169 | pCAP72 | SCRCRLRRRRRRRRR | 5 |
| 170 | pCAP105 | SRIVLGW | 5 |
| 171 | pCAP111 | SNIHHQV | 5 |
| 172 | pCAP121 | LTLMRLRIIG | 5 |
| 173 | pCAP122 | HSYSPYYTFRQH | 5 |
| 174 | pCAP167 | FILIR | 5 |
| 175 | pCAP205 | RCRNRKKEKTECLQKESEK | 5 |
| 176 | pCAP213 | RRIKMIRTSESFIQHIVS | 5 |
| 177 | pCAP244 | RRVSELQRNKHGRKHEL | 5 |
| 178 | pCAP246 | RRRLDDEDVQTPTPSEYQN | 5 |
| 179 | pCAP261 | RRRQPLPSAPENEE | 5 |
| 180 | pCAP7 | SPLQTPAAPGAAAGPALSPV | 6 |
| 181 | pCAP18 | SHQVHTHHNN | 6 |
| 182 | pCAP37 | KLQVPIK | 6 |
| 183 | pCAP74 | IRGRIIRRKKRRQRRRRGDR | 6 |
| 184 | pCAP82 | QIPHRSSTALQL | 6 |
| 185 | pCAP88 | SYQTMQP | 6 |
| 186 | pCAP140 | TDSHSHHRRRRRRRRRRRR | 6 |
| 187 | pCAP143 | IPMNFTSHSLRQRRRRRRRR | 6 |
| 188 | pCAP153 | YWSAPQPATRRRRRRRRRRR | 6 |
| 189 | pCAP220 | STTHPHPGTSAPEPATRRR | 6 |
| 190 | pCAP226 | DDSDNRIIRYRR | 6 |
| 191 | pCAP238 | TSPHPSLPRHIYPRR | 6 |
| 192 | pCAP247 | RRITEIRGRTGKTTLTYIED | 6 |
| 193 | pCAP249 | myr-DERTGKTRRYIDTRDIRR | 6 |
| 194 | pCAP275 | myr-MTYSDMPRRIITDEDRRR | 6 |
| 195 | pCAP278 | RRYDTVIDDIEYRR | 6 |
| 196 | pCAP279 | RDTIERPEIRR | 6 |
| 197 | pCAP280 | myr-RYRRLILEIWRR | 6 |
| 198 | pCAP284 | myr-RHDTHNAHIRR | 6 |
| 199 | pCAP288 | THDFDRLLRIRRR | 6 |
| 200 | pCAP289 | RHNHIRPDNQ | 6 |

TABLE 10-continued

| SEQ ID NO: | Plasmid | Sequence | Activity Score |
|---|---|---|---|
| 201 | pCAP290 | RYKEPRITPRE | 6 |
| 202 | pCAP302 | LRIEPIRIR | 6 |
| 203 | pCAP306 | myr-RLIRMILM | 6 |
| 204 | pCAP318 | RPEFHSFHPIYERR | 6 |
| 205 | pCAP91 | STTHIHA | 7 |
| 206 | pCAP92 | FPHLVSSLTT | 7 |
| 207 | pCAP99 | GLHLFTTDRQGW | 7 |
| 208 | pCAP132 | NHPWQFPNRWTRRRRRR | 7 |
| 209 | pCAP145 | HSSHHHPVHSWNRRRRRRR | 7 |
| 210 | pCAP316 | myr-DIHTIHLPDTHRR | 7 |
| 211 | pCAP10 | VAEFAQSIQSRIVEWKERLD | 8 |
| 212 | pCAP49 | TRILCIVMM | 8 |
| 213 | pCAP55 | FLLPEPDENTRW | 8 |
| 214 | pCAP57 | LMSNAQY | 8 |
| 215 | pCAP89 | SILTLSCRCRLRLWR | 8 |
| 216 | pCAP95 | HQIHRNHTY | 8 |
| 217 | pCAP106 | LIRRCSLQR | 8 |
| 218 | pCAP137 | GAMHLPWHMGTRRRRRR | 8 |
| 219 | pCAP202 | DEDAKFRIRILMRR | 8 |
| 220 | pCAP245 | NHITNGGEEDSDCSSRRRRL | 8 |
| 221 | pCAP257 | myr-HSSHHHPTVQHRR | 8 |
| 222 | pCAP287 | RDFERTIVDI | 8 |
| 223 | pCAP313 | myr-RRREILHPEFRILYE | 8 |
| 224 | pCAP14 | HHFSHHWKT | 9 |
| 225 | pCAP59 | FLIRRSG | 9 |
| 226 | pCAP63 | HNHHHSQHTPQH | 9 |
| 227 | pCAP80 | HLHKHHYKDSRM | 9 |
| 228 | pCAP231 | HRTQSTLILFIRRGRET | 9 |
| 229 | pCAP315 | LHFSHIDRR | 9 |
| 230 | pCAP62 | YELPHHAYPA | 10 |
| 231 | pCAP133 | SLLIGFGIIRSRRRRRRRR | 10 |
| 232 | pCAP135 | HTDSHPHHHHPHRRRRR | 10 |
| 233 | pCAP147 | ATQHHYIKRRRRRRRRRRR | 10 |
| 234 | pCAP129 | FRSFAIPLVVPFRRRRRR | 11 |
| 235 | pCAP138 | YPTQGHLRRRRRRRRRRR | 11 |
| 236 | pCAP146 | HANLHHTRRRRRRRRRR | 11 |
| 237 | pCAP152 | YRRLLIGMRRRRRRRRRRR | 11 |
| 238 | pCAP233 | SHYHTPQNPPSTRRR | 11 |
| 239 | pCAP235 | RSYSKLLCLLERLRISP | 11 |
| 240 | pCAP3 | FWTQSIKERKMLNEHDFEVR | 12 |
| 241 | pCAP15 | THFSHHLKH | 12 |
| 242 | pCAP90 | SCRCRLR | 12 |
| 243 | pCAP139 | MHPPDWYHHTPKRRRRRR | 12 |
| 244 | pCAP237 | HTIHVHYPGNRQPNPPLILQR | 12 |
| 245 | pCAP268 | TPSYGHTPSHHRRR | 12 |
| 246 | pCAP301 | myr-IRGRIRIIRR1R | 12 |
| 247 | pCAP20 | HHPWTHHQRWS | 13 |
| 248 | pCAP48 | IPMNFTSHSLRQ | 13 |
| 249 | pCAP118 | SNHHRHHTNTH | 13 |
| 250 | pCAP130 | EVTFRHSVVRRRRRRRRRRR | 13 |
| 251 | pCAP149 | FPGHTIHRRRRRRRRRRR | 13 |
| 252 | pCAP34 | SILTLSRIVLGWW | 14 |
| 253 | pCAP47 | TLYLPHWHRH | 14 |
| 254 | pCAP136 | SILTLRLRRLRRRRRRRR | 14 |
| 255 | pCAP142 | TLYLPHWHRHRRRRRRRRRR | 14 |
| 256 | pCAP43 | TDSHSHH | 15 |
| 257 | pCAP11 | EWKERLDKEFSLSVYQKMKF | 16 |
| 258 | pCAP30 | TIHPSIS | 16 |
| 259 | pCAP33 | SILTLRLRRLRR | 16 |
| 260 | pCAP44 | VPHIHEFT | 16 |
| 261 | pCAP9 | TIIHREDEDEIEW | 17 |
| 262 | pCAP61 | KDLPFYSHLRQ | 17 |
| 263 | pCAP65 | THFSHHLKHRRRRRRRRRR | 17 |
| 264 | pCAP93 | ATQHHYIK | 17 |
| 265 | pCAP108 | IIRGNFLIGGRL | 17 |
| 266 | pCAP131 | LPNPPERHHRRRRRRRRRRR | 18 |
| 267 | pCAP158 | SFILFIRRGRLGRGDR | 18 |
| 268 | pCAP100 | FPGHTIH | 19 |
| 269 | pCAP128 | CILRLWW | 19 |
| 270 | pCAP206 | RRRSHSQENVDQDTDE | 19 |
| 271 | pCAP204 | MSTESNMPRLIQNDDRRR | 20 |
| 272 | pCAP104 | LLRLGLI | 21 |
| 273 | pCAP23 | IRILMFLIGCGR | 22 |
| 274 | pCAP17 | LHSKTLVL | 23 |
| 275 | pCAP24 | LRCLLLLIGRVG | 23 |
| 276 | pCAP258 | FLIGPDRLIRSR | 23 |

TABLE 10-continued

| SEQ ID NO: | Plasmid | Sequence | Activity Score |
|---|---|---|---|
| 277 | pCAP16 | LPNPPERHH | 24 |
| 278 | pCAP28 | HTDSHPHHHHPH | 24 |
| 279 | pCAP160 | Fitc-SFILFIRRGRLGRRRRRRRR | 24 |
| 280 | pCAP83 | HSSHHHPVHSWN | 25 |
| 281 | pCAP259 | myr-RTLIGIIRSHHLTLIRR | 25 |
| 282 | pCAP54 | IRGRIIR | 26 |
| 283 | pCAP150 | IIRGNFLIGGRLRRRRRRRR | 26 |
| 284 | pCAP170 | IRILM | 27 |
| 285 | pCAP35 | GAMHLPWHMGTL | 28 |
| 286 | pCAP267 | KRGGRKRRGGGHRLSYFIRR | 28 |
| 287 | pCAP21 | NHPWQFPNRWTV | 29 |
| 288 | pCAP42 | MHPPDWYHHTPKH | 29 |
| 289 | pCAP141 | SWQALALYAAGWRRRRRR | 29 |
| 290 | pCAP161 | HNAH | 29 |
| 291 | pCAP210 | DEFERYRRFSTSRRR | 29 |
| 292 | pCAP1 | EVTFRHSVV | 32 |
| 293 | pCAP75 | TRILCIVRKKRRQRRRRGDR | 32 |
| 294 | pCAP70 | SILTLSRGRKKRRQRRRR | 33 |
| 295 | pCAP151 | CILRLWWRRRRRRRRRRR | 33 |
| 296 | pCAP46 | ASWQALALYAAGW | 34 |
| 297 | pCAP229 | myr-PRVLPSPHTIHPSQYP | 36 |
| 298 | pCAP87 | HANLHHT | 37 |
| 299 | pCAP157 | SFILFIRRGRLGRKKRRQRRRP | 37 |
| 300 | pCAP36 | YPTQGHLR | 39 |
| 301 | pCAP68 | YRRLLIGMMWRRRRRRRRRR | 39 |
| 302 | pCAP60 | SFILFIRRGRLG | 40 |
| 303 | pCAP134 | IRILMFLIGCGRRRRRRR | 40 |
| 304 | pCAP308 | myr-RRICRFIRICRVR | 40 |
| 305 | pCAP155 | IRGRIIRRRRRRRRR | 41 |
| 306 | pCAP203 | RRRHDSCHNQLQNYDHSTE | 42 |
| 307 | pCAP148 | WNHHHSTPHPRRRRRRRRR | 43 |
| 308 | pCAP282 | myr-RRPVAPDLRHTIHIPPER | 43 |
| 309 | pCAP317 | RRDIHTIHPFYQ | 43 |
| 310 | pCAP97 | WNHHHSTPHPAH | 47 |
| 311 | pCAP144 | SFILFIRRGRLGRRRRRRRR | 49 |
| 312 | pCAP159 | rrrrrrrrglrgrriflifs | 53 |
| 313 | pCAP326 | myr-RRHNAHHSTPHPDDR | 53 |
| 314 | pCAP174 | HSTPHP | 54 |
| 315 | pCAP154 | LRCLLLLIGRVGRKKRRQRR | 57 |
| 316 | pCAP221 | myr-RRKHNKHRPEPDSDER | 60 |
| 317 | pCAP325 | myr-RRIRDPRILLLHFD | 61 |
| 318 | pCAP230 | RKRGKSYAFFVPPSESKERW | 63 |
| 319 | pCAP227 | myr-RRKILFIRLMHNKH | 67 |
| 320 | pCAP242 | myr-RRLIVRILKLPNPPER | 67 |
| 321 | pCAP250 | myr-RRHSTPHPD | 72 |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A recombinant or synthetic peptide comprising the amino-acid sequence selected from the group consisting of SEQ ID NO: 139, 140, 203, 216 and 227, wherein said peptide at least partially reactivates a mutant p53 protein; and wherein said peptide is up to 15 amino-acids in length.

2. The peptide of claim 1, conjugated to at least one cell permeation moiety.

3. The peptide of claim 1, wherein said peptide at least partially changes the conformation of said mutant p53 protein to a conformation of a wild-type (WT) p53 protein.

4. The peptide of claim 1, wherein said peptide at least partially changes the conformation of said mutant p53 protein such that said mutant p53 protein is recognized by a monoclonal antibody directed against a WT p53 protein.

5. The peptide of claim 1, wherein said mutant p53 protein is not recognized by a monoclonal antibody directed against a WT p53 protein.

6. The peptide of claim 1, wherein said mutant p53 protein, upon binding to said peptide, is recognized by an antibody directed against a WT p53 protein.

7. The peptide of claim 6, wherein said antibody is Ab1620.

8. The peptide of claim 1, wherein said peptide at least partially restores the activity of said mutant p53 protein to the activity of a WT p53 protein.

9. The peptide of claim 8, wherein said activity is reducing viability of cells expressing said mutant p53 protein.

10. The peptide of claim 8, wherein said activity is promoting apoptosis of cells expressing said mutant p53 protein.

11. The peptide of claim 8, wherein said activity is binding to a p53 consensus DNA binding element in cells expressing said mutant p53 protein.

12. The peptide of claim 11, wherein said binding results in at least partial activation of an endogenous p53 target gene.

13. The peptide of claim 12, wherein said endogenous target gene is selected from the group consisting of p21, MDM2 and PUMA.

14. The peptide of claim 1, wherein said mutant p53 protein is of a different conformation than a WT p53 protein.

15. The peptide of claim 1, wherein said mutant p53 protein is at least partly inactive compared to a WT p53 protein.

16. The peptide of claim 1 attached to a cell penetrating moiety.

17. A recombinant or synthetic peptide comprising the amino-acid sequence set forth in any one of SEQ ID NOs: 139, 140, 203, 216 and 227, wherein said peptide is up to 15 amino-acids in length.

18. A method of treating a disorder associated with mutant p53 protein, lessening a severity of a disease associated with a mutant p53 protein or ameliorating symptoms associated with a disease associated with a mutant p53, comprising the step of administering a therapeutically effective amount of the peptide of claim 1 to a subject in need thereof, thereby treating said disorder associated with mutant p53 protein, lessening the severity of said disease associated with a mutant p53 protein or ameliorating symptoms associated with said disease associated with said mutant p53.

19. The method of claim 18, wherein said disease is cancer.

20. A method of treating a disorder associated with mutant p53 protein, lessening a severity of a disease associated with a mutant p53 protein or ameliorating symptoms associated with a disease associated with a mutant p53, comprising the step of administering a therapeutically effective amount of the peptide of claim 16 to a subject in need thereof, thereby treating said disorder associated with mutant p53 protein, lessening the severity of said disease associated with a mutant p53 protein or ameliorating symptoms associated with said disease associated with said mutant p53.

21. A recombinant or synthetic peptide comprising the amino-acid sequence set forth in any one of SEQ ID NOs: 244 and 263, wherein said peptide is up to 30 amino-acids in length.

22. A method of treating a disorder associated with mutant p53 protein, lessening a severity of a disease associated with a mutant p53 protein or ameliorating symptoms associated with a disease associated with a mutant p53, comprising the step of administering a therapeutically effective amount of the peptide of claim 17 to a subject in need thereof, thereby treating said disorder associated with mutant p53 protein, lessening the severity of said disease associated with a mutant p53 protein or ameliorating symptoms associated with said disease associated with said mutant p53.

23. The method of claim 22, wherein said disease is cancer.

* * * * *

SEQUENCE LISTING

<160> NUMBER OF SEQ ID NOS: 382

<210> SEQ ID NO 1
<211> LENGTH: 21
<212> TYPE: PRT
<213> ORGANISM: Artificial Sequence
<220> FEATURE:
<223> OTHER INFORMATION: Peptide

```
<220> FEATURE:
<221> NAME/KEY: MISC_FEATURE
<222> LOCATION: (12)..(12)
<223> OTHER INFORMATION: can be absent
<220> FEATURE:
<221> NAME/KEY: MISC_FEATURE
<222> LOCATION: (13)..(13)
<223> OTHER INFORMATION: can be absent
<220> FEATURE:
<221> NAME/KEY: MISC_FEATURE
<222> LOCATION: (14)..(14)
<223> OTHER INFORMATION: can be absent
<220> FEATURE:
<221> NAME/KEY: MISC_FEATURE
<222> LOCATION: (15)..(15)
<223> OTHER INFORMATION: can be absent
<220> FEATURE:
<221> NAME/KEY: MISC_FEATURE
<222> LOCATION: (16)..(16)
<223> OTHER INFORMATION: can be absent
<220> FEATURE:
<221> NAME/KEY: MISC_FEATURE
<222> LOCATION: (17)..(17)
<223> OTHER INFORMATION: can be absent
<220> FEATURE:
<221> NAME/KEY: MISC_FEATURE
<222> LOCATION: (18)..(18)
<223> OTHER INFORMATION: can be absent
<220> FEATURE:
<221> NAME/KEY: MISC_FEATURE
<222> LOCATION: (19)..(19)
<223> OTHER INFORMATION: can be absent
<220> FEATURE:
<221> NAME/KEY: MISC_FEATURE
<222> LOCATION: (20)..(20)
<223> OTHER INFORMATION: can be absent
<220> FEATURE:
<221> NAME/KEY: MISC_FEATURE
<222> LOCATION: (21)..(21)
<223> OTHER INFORMATION: can be absent

<400> SEQUENCE: 1

Ile Arg Ile Leu Met Phe Leu Ile Gly Cys Gly Arg Arg Arg Arg
1               5                   10                  15

Arg Arg Arg Arg Arg
                20

<210> SEQ ID NO 2
<211> LENGTH: 28
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: can be absent
<220> FEATURE:
<221> NAME/KEY: MISC_FEATURE
<222> LOCATION: (20)..(20)
<223> OTHER INFORMATION: can be absent
<220> FEATURE:
<221> NAME/KEY: MISC_FEATURE
<222> LOCATION: (21)..(21)
<223> OTHER INFORMATION: can be absent
<220> FEATURE:
<221> NAME/KEY: MISC_FEATURE
<222> LOCATION: (22)..(22)
<223> OTHER INFORMATION: can be absent
<220> FEATURE:
<221> NAME/KEY: MISC_FEATURE
<222> LOCATION: (23)..(23)
<223> OTHER INFORMATION: can be absent
<220> FEATURE:
<221> NAME/KEY: MISC_FEATURE
<222> LOCATION: (24)..(24)
```

```
<223> OTHER INFORMATION: can be absent
<220> FEATURE:
<221> NAME/KEY: MISC_FEATURE
<222> LOCATION: (25)..(25)
<223> OTHER INFORMATION: can be absent
<220> FEATURE:
<221> NAME/KEY: MISC_FEATURE
<222> LOCATION: (26)..(26)
<223> OTHER INFORMATION: can be absent
<220> FEATURE:
<221> NAME/KEY: MISC_FEATURE
<222> LOCATION: (27)..(27)
<223> OTHER INFORMATION: can be absent
<220> FEATURE:
<221> NAME/KEY: MISC_FEATURE
<222> LOCATION: (28)..(28)
<223> OTHER INFORMATION: can be absent

<400> SEQUENCE: 2

Leu Arg Cys Leu Leu Leu Leu Ile Gly Arg Val Gly Arg Lys Lys Arg
1               5                   10                  15

Arg Gln Arg Arg Arg Arg Arg Arg Arg Arg Arg
            20                  25

<210> SEQ ID NO 3
<211> LENGTH: 17
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (8)..(8)
<223> OTHER INFORMATION: can be absent
<220> FEATURE:
<221> NAME/KEY: MISC_FEATURE
<222> LOCATION: (9)..(9)
<223> OTHER INFORMATION: can be absent
<220> FEATURE:
<221> NAME/KEY: MISC_FEATURE
<222> LOCATION: (10)..(10)
<223> OTHER INFORMATION: can be absent
<220> FEATURE:
<221> NAME/KEY: MISC_FEATURE
<222> LOCATION: (11)..(11)
<223> OTHER INFORMATION: can be absent
<220> FEATURE:
<221> NAME/KEY: MISC_FEATURE
<222> LOCATION: (12)..(12)
<223> OTHER INFORMATION: can be absent
<220> FEATURE:
<221> NAME/KEY: MISC_FEATURE
<222> LOCATION: (13)..(13)
<223> OTHER INFORMATION: can be absent
<220> FEATURE:
<221> NAME/KEY: MISC_FEATURE
<222> LOCATION: (14)..(14)
<223> OTHER INFORMATION: can be absent
<220> FEATURE:
<221> NAME/KEY: MISC_FEATURE
<222> LOCATION: (15)..(15)
<223> OTHER INFORMATION: can be absent
<220> FEATURE:
<221> NAME/KEY: MISC_FEATURE
<222> LOCATION: (16)..(16)
<223> OTHER INFORMATION: can be absent
<220> FEATURE:
<221> NAME/KEY: MISC_FEATURE
<222> LOCATION: (17)..(17)
<223> OTHER INFORMATION: can be absent

<400> SEQUENCE: 3

Tyr Pro Thr Gln Gly His Leu Arg Arg Arg Arg Arg Arg Arg Arg
1               5                   10                  15
```

Arg

```
<210> SEQ ID NO 4
<211> LENGTH: 22
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (13)..(13)
<223> OTHER INFORMATION: can be absent
<220> FEATURE:
<221> NAME/KEY: MISC_FEATURE
<222> LOCATION: (14)..(14)
<223> OTHER INFORMATION: can be absent
<220> FEATURE:
<221> NAME/KEY: MISC_FEATURE
<222> LOCATION: (15)..(15)
<223> OTHER INFORMATION: can be absent
<220> FEATURE:
<221> NAME/KEY: MISC_FEATURE
<222> LOCATION: (16)..(16)
<223> OTHER INFORMATION: can be absent
<220> FEATURE:
<221> NAME/KEY: MISC_FEATURE
<222> LOCATION: (17)..(17)
<223> OTHER INFORMATION: can be absent
<220> FEATURE:
<221> NAME/KEY: MISC_FEATURE
<222> LOCATION: (18)..(18)
<223> OTHER INFORMATION: can be absent
<220> FEATURE:
<221> NAME/KEY: MISC_FEATURE
<222> LOCATION: (19)..(19)
<223> OTHER INFORMATION: can be absent
<220> FEATURE:
<221> NAME/KEY: MISC_FEATURE
<222> LOCATION: (20)..(20)
<223> OTHER INFORMATION: can be absent
<220> FEATURE:
<221> NAME/KEY: MISC_FEATURE
<222> LOCATION: (21)..(21)
<223> OTHER INFORMATION: can be absent
<220> FEATURE:
<221> NAME/KEY: MISC_FEATURE
<222> LOCATION: (22)..(22)
<223> OTHER INFORMATION: can be absent

<400> SEQUENCE: 4

Ser Trp Gln Ala Leu Ala Leu Tyr Ala Ala Gly Trp Arg Arg Arg
1               5                   10                  15

Arg Arg Arg Arg Arg Arg Arg
            20

<210> SEQ ID NO 5
<211> LENGTH: 20
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (11)..(11)
<223> OTHER INFORMATION: can be absent
<220> FEATURE:
<221> NAME/KEY: MISC_FEATURE
<222> LOCATION: (12)..(12)
<223> OTHER INFORMATION: can be absent
<220> FEATURE:
<221> NAME/KEY: MISC_FEATURE
<222> LOCATION: (13)..(13)
<223> OTHER INFORMATION: can be absent
<220> FEATURE:
<221> NAME/KEY: MISC_FEATURE
```

```
<222> LOCATION: (14)..(14)
<223> OTHER INFORMATION: can be absent
<220> FEATURE:
<221> NAME/KEY: MISC_FEATURE
<222> LOCATION: (15)..(15)
<223> OTHER INFORMATION: can be absent
<220> FEATURE:
<221> NAME/KEY: MISC_FEATURE
<222> LOCATION: (16)..(16)
<223> OTHER INFORMATION: can be absent
<220> FEATURE:
<221> NAME/KEY: MISC_FEATURE
<222> LOCATION: (17)..(17)
<223> OTHER INFORMATION: can be absent
<220> FEATURE:
<221> NAME/KEY: MISC_FEATURE
<222> LOCATION: (18)..(18)
<223> OTHER INFORMATION: can be absent
<220> FEATURE:
<221> NAME/KEY: MISC_FEATURE
<222> LOCATION: (19)..(19)
<223> OTHER INFORMATION: can be absent
<220> FEATURE:
<221> NAME/KEY: MISC_FEATURE
<222> LOCATION: (20)..(20)
<223> OTHER INFORMATION: can be absent

<400> SEQUENCE: 5

Thr Leu Tyr Leu Pro His Trp His Arg His Arg Arg Arg Arg Arg
1               5                   10                  15

Arg Arg Arg Arg
            20

<210> SEQ ID NO 6
<211> LENGTH: 16
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (7)..(7)
<223> OTHER INFORMATION: can be absent
<220> FEATURE:
<221> NAME/KEY: MISC_FEATURE
<222> LOCATION: (8)..(8)
<223> OTHER INFORMATION: can be absent
<220> FEATURE:
<221> NAME/KEY: MISC_FEATURE
<222> LOCATION: (9)..(9)
<223> OTHER INFORMATION: can be absent
<220> FEATURE:
<221> NAME/KEY: MISC_FEATURE
<222> LOCATION: (10)..(10)
<223> OTHER INFORMATION: can be absent
<220> FEATURE:
<221> NAME/KEY: MISC_FEATURE
<222> LOCATION: (11)..(11)
<223> OTHER INFORMATION: can be absent
<220> FEATURE:
<221> NAME/KEY: MISC_FEATURE
<222> LOCATION: (12)..(12)
<223> OTHER INFORMATION: can be absent
<220> FEATURE:
<221> NAME/KEY: MISC_FEATURE
<222> LOCATION: (13)..(13)
<223> OTHER INFORMATION: can be absent
<220> FEATURE:
<221> NAME/KEY: MISC_FEATURE
<222> LOCATION: (14)..(14)
<223> OTHER INFORMATION: can be absent
<220> FEATURE:
<221> NAME/KEY: MISC_FEATURE
<222> LOCATION: (15)..(15)
<223> OTHER INFORMATION: can be absent
<220> FEATURE:
```

```
<221> NAME/KEY: MISC_FEATURE
<222> LOCATION: (16)..(16)
<223> OTHER INFORMATION: can be absent

<400> SEQUENCE: 6

Ile Arg Gly Arg Ile Arg Arg Arg Arg Arg Arg Arg Arg
1               5                   10                  15

<210> SEQ ID NO 7
<211> LENGTH: 22
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (13)..(13)
<223> OTHER INFORMATION: can be absent
<220> FEATURE:
<221> NAME/KEY: MISC_FEATURE
<222> LOCATION: (14)..(14)
<223> OTHER INFORMATION: can be absent
<220> FEATURE:
<221> NAME/KEY: MISC_FEATURE
<222> LOCATION: (15)..(15)
<223> OTHER INFORMATION: can be absent
<220> FEATURE:
<221> NAME/KEY: MISC_FEATURE
<222> LOCATION: (16)..(16)
<223> OTHER INFORMATION: can be absent
<220> FEATURE:
<221> NAME/KEY: MISC_FEATURE
<222> LOCATION: (17)..(17)
<223> OTHER INFORMATION: can be absent
<220> FEATURE:
<221> NAME/KEY: MISC_FEATURE
<222> LOCATION: (18)..(18)
<223> OTHER INFORMATION: can be absent
<220> FEATURE:
<221> NAME/KEY: MISC_FEATURE
<222> LOCATION: (19)..(19)
<223> OTHER INFORMATION: can be absent
<220> FEATURE:
<221> NAME/KEY: MISC_FEATURE
<222> LOCATION: (20)..(20)
<223> OTHER INFORMATION: can be absent
<220> FEATURE:
<221> NAME/KEY: MISC_FEATURE
<222> LOCATION: (21)..(21)
<223> OTHER INFORMATION: can be absent
<220> FEATURE:
<221> NAME/KEY: MISC_FEATURE
<222> LOCATION: (22)..(22)
<223> OTHER INFORMATION: can be absent

<400> SEQUENCE: 7

Ser Phe Ile Leu Phe Ile Arg Arg Gly Arg Leu Gly Arg Arg Arg
1               5                   10                  15

Arg Arg Arg Arg Arg Arg
            20

<210> SEQ ID NO 8
<211> LENGTH: 22
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (13)..(13)
<223> OTHER INFORMATION: can be absent
<220> FEATURE:
<221> NAME/KEY: MISC_FEATURE
<222> LOCATION: (14)..(14)
```

```
<223> OTHER INFORMATION: can be absent
<220> FEATURE:
<221> NAME/KEY: MISC_FEATURE
<222> LOCATION: (15)..(15)
<223> OTHER INFORMATION: can be absent
<220> FEATURE:
<221> NAME/KEY: MISC_FEATURE
<222> LOCATION: (16)..(16)
<223> OTHER INFORMATION: can be absent
<220> FEATURE:
<221> NAME/KEY: MISC_FEATURE
<222> LOCATION: (17)..(17)
<223> OTHER INFORMATION: can be absent
<220> FEATURE:
<221> NAME/KEY: MISC_FEATURE
<222> LOCATION: (18)..(18)
<223> OTHER INFORMATION: can be absent
<220> FEATURE:
<221> NAME/KEY: MISC_FEATURE
<222> LOCATION: (19)..(19)
<223> OTHER INFORMATION: can be absent
<220> FEATURE:
<221> NAME/KEY: MISC_FEATURE
<222> LOCATION: (20)..(20)
<223> OTHER INFORMATION: can be absent
<220> FEATURE:
<221> NAME/KEY: MISC_FEATURE
<222> LOCATION: (21)..(21)
<223> OTHER INFORMATION: can be absent
<220> FEATURE:
<221> NAME/KEY: MISC_FEATURE
<222> LOCATION: (22)..(22)
<223> OTHER INFORMATION: can be absent

<400> SEQUENCE: 8

His Ser Ser His His His Pro Val His Ser Trp Asn Arg Arg Arg Arg
1               5                   10                  15

Arg Arg Arg Arg Arg Arg
            20

<210> SEQ ID NO 9
<211> LENGTH: 17
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (8)..(8)
<223> OTHER INFORMATION: can be absent
<220> FEATURE:
<221> NAME/KEY: MISC_FEATURE
<222> LOCATION: (9)..(9)
<223> OTHER INFORMATION: can be absent
<220> FEATURE:
<221> NAME/KEY: MISC_FEATURE
<222> LOCATION: (10)..(10)
<223> OTHER INFORMATION: can be absent
<220> FEATURE:
<221> NAME/KEY: MISC_FEATURE
<222> LOCATION: (11)..(11)
<223> OTHER INFORMATION: can be absent
<220> FEATURE:
<221> NAME/KEY: MISC_FEATURE
<222> LOCATION: (12)..(12)
<223> OTHER INFORMATION: can be absent
<220> FEATURE:
<221> NAME/KEY: MISC_FEATURE
<222> LOCATION: (13)..(13)
<223> OTHER INFORMATION: can be absent
<220> FEATURE:
<221> NAME/KEY: MISC_FEATURE
<222> LOCATION: (14)..(14)
<223> OTHER INFORMATION: can be absent
<220> FEATURE:
<221> NAME/KEY: MISC_FEATURE
```

```
<222> LOCATION: (15)..(15)
<223> OTHER INFORMATION: can be absent
<220> FEATURE:
<221> NAME/KEY: MISC_FEATURE
<222> LOCATION: (16)..(16)
<223> OTHER INFORMATION: can be absent
<220> FEATURE:
<221> NAME/KEY: MISC_FEATURE
<222> LOCATION: (17)..(17)
<223> OTHER INFORMATION: can be absent

<400> SEQUENCE: 9

His Ala Asn Leu His His Thr Arg Arg Arg Arg Arg Arg Arg Arg
1               5                   10                  15
Arg

<210> SEQ ID NO 10
<211> LENGTH: 20
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (11)..(11)
<223> OTHER INFORMATION: can be absent
<220> FEATURE:
<221> NAME/KEY: MISC_FEATURE
<222> LOCATION: (12)..(12)
<223> OTHER INFORMATION: can be absent
<220> FEATURE:
<221> NAME/KEY: MISC_FEATURE
<222> LOCATION: (13)..(13)
<223> OTHER INFORMATION: can be absent
<220> FEATURE:
<221> NAME/KEY: MISC_FEATURE
<222> LOCATION: (14)..(14)
<223> OTHER INFORMATION: can be absent
<220> FEATURE:
<221> NAME/KEY: MISC_FEATURE
<222> LOCATION: (15)..(15)
<223> OTHER INFORMATION: can be absent
<220> FEATURE:
<221> NAME/KEY: MISC_FEATURE
<222> LOCATION: (16)..(16)
<223> OTHER INFORMATION: can be absent
<220> FEATURE:
<221> NAME/KEY: MISC_FEATURE
<222> LOCATION: (17)..(17)
<223> OTHER INFORMATION: can be absent
<220> FEATURE:
<221> NAME/KEY: MISC_FEATURE
<222> LOCATION: (18)..(18)
<223> OTHER INFORMATION: can be absent
<220> FEATURE:
<221> NAME/KEY: MISC_FEATURE
<222> LOCATION: (19)..(19)
<223> OTHER INFORMATION: can be absent
<220> FEATURE:
<221> NAME/KEY: MISC_FEATURE
<222> LOCATION: (20)..(20)
<223> OTHER INFORMATION: can be absent

<400> SEQUENCE: 10

Trp Asn His His His Ser Thr Pro His Pro Arg Arg Arg Arg Arg
1               5                   10                  15
Arg Arg Arg Arg
            20

<210> SEQ ID NO 11
<211> LENGTH: 16
<212> TYPE: PRT
<213> ORGANISM: Artificial
```

```
<220> FEATURE:
<223> OTHER INFORMATION: Peptide
<220> FEATURE:
<221> NAME/KEY: MISC_FEATURE
<222> LOCATION: (7)..(7)
<223> OTHER INFORMATION: can be absent
<220> FEATURE:
<221> NAME/KEY: MISC_FEATURE
<222> LOCATION: (8)..(8)
<223> OTHER INFORMATION: can be absent
<220> FEATURE:
<221> NAME/KEY: MISC_FEATURE
<222> LOCATION: (9)..(9)
<223> OTHER INFORMATION: can be absent
<220> FEATURE:
<221> NAME/KEY: MISC_FEATURE
<222> LOCATION: (10)..(10)
<223> OTHER INFORMATION: can be absent
<220> FEATURE:
<221> NAME/KEY: MISC_FEATURE
<222> LOCATION: (11)..(11)
<223> OTHER INFORMATION: can be absent
<220> FEATURE:
<221> NAME/KEY: MISC_FEATURE
<222> LOCATION: (12)..(12)
<223> OTHER INFORMATION: can be absent
<220> FEATURE:
<221> NAME/KEY: MISC_FEATURE
<222> LOCATION: (13)..(13)
<223> OTHER INFORMATION: can be absent
<220> FEATURE:
<221> NAME/KEY: MISC_FEATURE
<222> LOCATION: (14)..(14)
<223> OTHER INFORMATION: can be absent
<220> FEATURE:
<221> NAME/KEY: MISC_FEATURE
<222> LOCATION: (15)..(15)
<223> OTHER INFORMATION: can be absent
<220> FEATURE:
<221> NAME/KEY: MISC_FEATURE
<222> LOCATION: (16)..(16)
<223> OTHER INFORMATION: can be absent

<400> SEQUENCE: 11

His Ser Thr Pro His Pro Arg Arg Arg Arg Arg Arg Arg Arg Arg
1               5                   10                  15

<210> SEQ ID NO 12
<211> LENGTH: 14
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (5)..(5)
<223> OTHER INFORMATION: can be absent
<220> FEATURE:
<221> NAME/KEY: MISC_FEATURE
<222> LOCATION: (6)..(6)
<223> OTHER INFORMATION: can be absent
<220> FEATURE:
<221> NAME/KEY: MISC_FEATURE
<222> LOCATION: (7)..(7)
<223> OTHER INFORMATION: can be absent
<220> FEATURE:
<221> NAME/KEY: MISC_FEATURE
<222> LOCATION: (8)..(8)
<223> OTHER INFORMATION: can be absent
<220> FEATURE:
<221> NAME/KEY: MISC_FEATURE
<222> LOCATION: (9)..(9)
<223> OTHER INFORMATION: can be absent
<220> FEATURE:
<221> NAME/KEY: MISC_FEATURE
<222> LOCATION: (10)..(10)
<223> OTHER INFORMATION: can be absent
```

```
<220> FEATURE:
<221> NAME/KEY: MISC_FEATURE
<222> LOCATION: (11)..(11)
<223> OTHER INFORMATION: can be absent
<220> FEATURE:
<221> NAME/KEY: MISC_FEATURE
<222> LOCATION: (12)..(12)
<223> OTHER INFORMATION: can be absent
<220> FEATURE:
<221> NAME/KEY: MISC_FEATURE
<222> LOCATION: (13)..(13)
<223> OTHER INFORMATION: can be absent
<220> FEATURE:
<221> NAME/KEY: MISC_FEATURE
<222> LOCATION: (14)..(14)
<223> OTHER INFORMATION: can be absent

<400> SEQUENCE: 12

Ser Ile Leu Thr Arg Arg Arg Arg Arg Arg Arg Arg Arg
1               5                   10

<210> SEQ ID NO 13
<211> LENGTH: 20
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (11)..(11)
<223> OTHER INFORMATION: can be absent
<220> FEATURE:
<221> NAME/KEY: MISC_FEATURE
<222> LOCATION: (12)..(12)
<223> OTHER INFORMATION: can be absent
<220> FEATURE:
<221> NAME/KEY: MISC_FEATURE
<222> LOCATION: (13)..(13)
<223> OTHER INFORMATION: can be absent
<220> FEATURE:
<221> NAME/KEY: MISC_FEATURE
<222> LOCATION: (14)..(14)
<223> OTHER INFORMATION: can be absent
<220> FEATURE:
<221> NAME/KEY: MISC_FEATURE
<222> LOCATION: (15)..(15)
<223> OTHER INFORMATION: can be absent
<220> FEATURE:
<221> NAME/KEY: MISC_FEATURE
<222> LOCATION: (16)..(16)
<223> OTHER INFORMATION: can be absent
<220> FEATURE:
<221> NAME/KEY: MISC_FEATURE
<222> LOCATION: (17)..(17)
<223> OTHER INFORMATION: can be absent
<220> FEATURE:
<221> NAME/KEY: MISC_FEATURE
<222> LOCATION: (18)..(18)
<223> OTHER INFORMATION: can be absent
<220> FEATURE:
<221> NAME/KEY: MISC_FEATURE
<222> LOCATION: (19)..(19)
<223> OTHER INFORMATION: can be absent
<220> FEATURE:
<221> NAME/KEY: MISC_FEATURE
<222> LOCATION: (20)..(20)
<223> OTHER INFORMATION: can be absent

<400> SEQUENCE: 13

Tyr Arg Arg Leu Leu Ile Gly Met Met Trp Arg Arg Arg Arg Arg
1               5                   10                  15

Arg Arg Arg Arg
            20
```

-continued

```
<210> SEQ ID NO 14
<211> LENGTH: 20
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (11)..(11)
<223> OTHER INFORMATION: can be absent
<220> FEATURE:
<221> NAME/KEY: MISC_FEATURE
<222> LOCATION: (12)..(12)
<223> OTHER INFORMATION: can be absent
<220> FEATURE:
<221> NAME/KEY: MISC_FEATURE
<222> LOCATION: (13)..(13)
<223> OTHER INFORMATION: can be absent
<220> FEATURE:
<221> NAME/KEY: MISC_FEATURE
<222> LOCATION: (14)..(14)
<223> OTHER INFORMATION: can be absent
<220> FEATURE:
<221> NAME/KEY: MISC_FEATURE
<222> LOCATION: (15)..(15)
<223> OTHER INFORMATION: can be absent
<220> FEATURE:
<221> NAME/KEY: MISC_FEATURE
<222> LOCATION: (16)..(16)
<223> OTHER INFORMATION: can be absent
<220> FEATURE:
<221> NAME/KEY: MISC_FEATURE
<222> LOCATION: (17)..(17)
<223> OTHER INFORMATION: can be absent
<220> FEATURE:
<221> NAME/KEY: MISC_FEATURE
<222> LOCATION: (18)..(18)
<223> OTHER INFORMATION: can be absent
<220> FEATURE:
<221> NAME/KEY: MISC_FEATURE
<222> LOCATION: (19)..(19)
<223> OTHER INFORMATION: can be absent
<220> FEATURE:
<221> NAME/KEY: MISC_FEATURE
<222> LOCATION: (20)..(20)
<223> OTHER INFORMATION: can be absent

<400> SEQUENCE: 14

Tyr Arg Arg Leu Leu Ile Gly Met Met Trp Arg Arg Arg Arg Arg
1               5                   10                  15

Arg Arg Arg Arg
            20

<210> SEQ ID NO 15
<211> LENGTH: 17
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (8)..(8)
<223> OTHER INFORMATION: can be absent
<220> FEATURE:
<221> NAME/KEY: MISC_FEATURE
<222> LOCATION: (9)..(9)
<223> OTHER INFORMATION: can be absent
<220> FEATURE:
<221> NAME/KEY: MISC_FEATURE
<222> LOCATION: (10)..(10)
<223> OTHER INFORMATION: can be absent
<220> FEATURE:
<221> NAME/KEY: MISC_FEATURE
<222> LOCATION: (11)..(11)
<223> OTHER INFORMATION: can be absent
<220> FEATURE:
```

```
<221> NAME/KEY: MISC_FEATURE
<222> LOCATION: (12)..(12)
<223> OTHER INFORMATION: can be absent
<220> FEATURE:
<221> NAME/KEY: MISC_FEATURE
<222> LOCATION: (13)..(13)
<223> OTHER INFORMATION: can be absent
<220> FEATURE:
<221> NAME/KEY: MISC_FEATURE
<222> LOCATION: (14)..(14)
<223> OTHER INFORMATION: can be absent
<220> FEATURE:
<221> NAME/KEY: MISC_FEATURE
<222> LOCATION: (15)..(15)
<223> OTHER INFORMATION: can be absent
<220> FEATURE:
<221> NAME/KEY: MISC_FEATURE
<222> LOCATION: (16)..(16)
<223> OTHER INFORMATION: can be absent
<220> FEATURE:
<221> NAME/KEY: MISC_FEATURE
<222> LOCATION: (17)..(17)
<223> OTHER INFORMATION: can be absent

<400> SEQUENCE: 15

Phe Pro Gly His Thr Ile His Arg Arg Arg Arg Arg Arg Arg Arg
1               5                   10                  15
Arg

<210> SEQ ID NO 16
<211> LENGTH: 22
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: can be absent
<220> FEATURE:
<221> NAME/KEY: MISC_FEATURE
<222> LOCATION: (1)..(22)
<223> OTHER INFORMATION: D-amino_acid_peptide
<220> FEATURE:
<221> NAME/KEY: MISC_FEATURE
<222> LOCATION: (2)..(2)
<223> OTHER INFORMATION: can be absent
<220> FEATURE:
<221> NAME/KEY: MISC_FEATURE
<222> LOCATION: (3)..(3)
<223> OTHER INFORMATION: can be absent
<220> FEATURE:
<221> NAME/KEY: MISC_FEATURE
<222> LOCATION: (4)..(4)
<223> OTHER INFORMATION: can be absent
<220> FEATURE:
<221> NAME/KEY: MISC_FEATURE
<222> LOCATION: (5)..(5)
<223> OTHER INFORMATION: can be absent
<220> FEATURE:
<221> NAME/KEY: MISC_FEATURE
<222> LOCATION: (6)..(6)
<223> OTHER INFORMATION: can be absent
<220> FEATURE:
<221> NAME/KEY: MISC_FEATURE
<222> LOCATION: (7)..(7)
<223> OTHER INFORMATION: can be absent
<220> FEATURE:
<221> NAME/KEY: MISC_FEATURE
<222> LOCATION: (8)..(8)
<223> OTHER INFORMATION: can be absent
<220> FEATURE:
<221> NAME/KEY: MISC_FEATURE
<222> LOCATION: (9)..(9)
<223> OTHER INFORMATION: can be absent
<220> FEATURE:
```

```
<221> NAME/KEY: MISC_FEATURE
<222> LOCATION: (10)..(10)
<223> OTHER INFORMATION: can be absent

<400> SEQUENCE: 16

Arg Arg Arg Arg Arg Arg Arg Arg Arg Gly Leu Arg Gly Arg Arg
1               5                   10                  15

Ile Phe Leu Ile Phe Ser
            20

<210> SEQ ID NO 17
<211> LENGTH: 12
<212> TYPE: PRT
<213> ORGANISM: Artificial
<220> FEATURE:
<223> OTHER INFORMATION: Peptide

<400> SEQUENCE: 17

Leu Thr Phe Glu His Tyr Trp Ala Gln Leu Thr Ser
1               5                   10

<210> SEQ ID NO 18
<211> LENGTH: 12
<212> TYPE: PRT
<213> ORGANISM: Artificial
<220> FEATURE:
<223> OTHER INFORMATION: Peptide

<400> SEQUENCE: 18

Gly Gly Gly Gly Gly Gly Gly Gly Gly Gly Gly Gly
1               5                   10

<210> SEQ ID NO 19
<211> LENGTH: 12
<212> TYPE: PRT
<213> ORGANISM: Artificial
<220> FEATURE:
<223> OTHER INFORMATION: Peptide

<400> SEQUENCE: 19

Asn Pro Asn Thr Tyr Val Pro His Trp Met Arg Gln
1               5                   10

<210> SEQ ID NO 20
<211> LENGTH: 10
<212> TYPE: PRT
<213> ORGANISM: Artificial
<220> FEATURE:
<223> OTHER INFORMATION: peptide

<400> SEQUENCE: 20

Tyr Arg Arg Leu Leu Ile Gly Met Met Trp
1               5                   10

<210> SEQ ID NO 21
<211> LENGTH: 13
<212> TYPE: PRT
<213> ORGANISM: Artificial
<220> FEATURE:
<223> OTHER INFORMATION: peptide

<400> SEQUENCE: 21

Asp Glu Phe His Ser Phe Tyr Thr Ala Arg Gln Thr Gly
1               5                   10

<210> SEQ ID NO 22
```

```
<211> LENGTH: 7
<212> TYPE: PRT
<213> ORGANISM: Artificial
<220> FEATURE:
<223> OTHER INFORMATION: Peptide

<400> SEQUENCE: 22

Lys Pro Asp Ser Pro Arg Val
1               5

<210> SEQ ID NO 23
<211> LENGTH: 12
<212> TYPE: PRT
<213> ORGANISM: Artificial
<220> FEATURE:
<223> OTHER INFORMATION: peptide

<400> SEQUENCE: 23

Pro Pro Tyr Ser Gln Phe Leu Gln Trp Tyr Leu Ser
1               5                   10

<210> SEQ ID NO 24
<211> LENGTH: 12
<212> TYPE: PRT
<213> ORGANISM: Artificial
<220> FEATURE:
<223> OTHER INFORMATION: peptide

<400> SEQUENCE: 24

Ser Glu Phe Pro Arg Ser Trp Asp Met Glu Thr Asn
1               5                   10

<210> SEQ ID NO 25
<211> LENGTH: 9
<212> TYPE: PRT
<213> ORGANISM: Artificial
<220> FEATURE:
<223> OTHER INFORMATION: peptide

<400> SEQUENCE: 25

His Asp Thr His Asn Ala His Val Gly
1               5

<210> SEQ ID NO 26
<211> LENGTH: 13
<212> TYPE: PRT
<213> ORGANISM: Artificial
<220> FEATURE:
<223> OTHER INFORMATION: peptide

<400> SEQUENCE: 26

Trp Ser Glu Tyr Asp Ile Pro Thr Pro Gln Ile Pro Pro
1               5                   10

<210> SEQ ID NO 27
<211> LENGTH: 16
<212> TYPE: PRT
<213> ORGANISM: Artificial
<220> FEATURE:
<223> OTHER INFORMATION: peptide

<400> SEQUENCE: 27

Ser Ile Leu Thr Leu Ser Arg Arg Arg Arg Arg Arg Arg Arg
1               5                   10                  15

<210> SEQ ID NO 28
<211> LENGTH: 13
```

```
<212> TYPE: PRT
<213> ORGANISM: Artificial
<220> FEATURE:
<223> OTHER INFORMATION: peptide

<400> SEQUENCE: 28

Ser Cys Arg Cys Arg Leu Arg Gly Asp Arg Gly Asp Arg
1               5                   10

<210> SEQ ID NO 29
<211> LENGTH: 16
<212> TYPE: PRT
<213> ORGANISM: Artificial
<220> FEATURE:
<223> OTHER INFORMATION: peptide

<400> SEQUENCE: 29

Gly Gly Gly Gly Gly Gly Gly Gly Gly Arg Arg Arg Arg Arg Arg Arg
1               5                   10                  15

<210> SEQ ID NO 30
<211> LENGTH: 12
<212> TYPE: PRT
<213> ORGANISM: Artificial
<220> FEATURE:
<223> OTHER INFORMATION: peptide

<400> SEQUENCE: 30

Ser Glu Tyr Leu Cys Ser Ser Leu Asp Ala Ala Gly
1               5                   10

<210> SEQ ID NO 31
<211> LENGTH: 12
<212> TYPE: PRT
<213> ORGANISM: Artificial
<220> FEATURE:
<223> OTHER INFORMATION: peptide

<400> SEQUENCE: 31

Gly Glu Ser Phe Val Gln His Val Phe Arg Gln Asn
1               5                   10

<210> SEQ ID NO 32
<211> LENGTH: 12
<212> TYPE: PRT
<213> ORGANISM: Artificial
<220> FEATURE:
<223> OTHER INFORMATION: peptide

<400> SEQUENCE: 32

Ser Val His His His His Arg Met His Leu Val Ala
1               5                   10

<210> SEQ ID NO 33
<211> LENGTH: 7
<212> TYPE: PRT
<213> ORGANISM: Artificial
<220> FEATURE:
<223> OTHER INFORMATION: peptide

<400> SEQUENCE: 33

Gly Arg Arg Arg Phe Cys Met
1               5

<210> SEQ ID NO 34
<211> LENGTH: 7
<212> TYPE: PRT
```

<213> ORGANISM: Artificial
<220> FEATURE:
<223> OTHER INFORMATION: peptide

<400> SEQUENCE: 34

Lys Leu Thr Ile His His His
1               5

<210> SEQ ID NO 35
<211> LENGTH: 7
<212> TYPE: PRT
<213> ORGANISM: Artificial
<220> FEATURE:
<223> OTHER INFORMATION: peptide

<400> SEQUENCE: 35

Phe Gly Ser His His Glu Leu
1               5

<210> SEQ ID NO 36
<211> LENGTH: 7
<212> TYPE: PRT
<213> ORGANISM: Artificial
<220> FEATURE:
<223> OTHER INFORMATION: peptide

<400> SEQUENCE: 36

Gly Thr Val Asp His His Ala
1               5

<210> SEQ ID NO 37
<211> LENGTH: 10
<212> TYPE: PRT
<213> ORGANISM: Artificial
<220> FEATURE:
<223> OTHER INFORMATION: peptide

<400> SEQUENCE: 37

Asp Arg Leu Ser Val Phe Leu Phe Ile Met
1               5                   10

<210> SEQ ID NO 38
<211> LENGTH: 7
<212> TYPE: PRT
<213> ORGANISM: Artificial
<220> FEATURE:
<223> OTHER INFORMATION: peptide

<400> SEQUENCE: 38

Ala Ile Ser His His Thr Arg
1               5

<210> SEQ ID NO 39
<211> LENGTH: 12
<212> TYPE: PRT
<213> ORGANISM: Artificial
<220> FEATURE:
<223> OTHER INFORMATION: peptide

<400> SEQUENCE: 39

Lys His His Pro Phe Asp His Arg Leu Gly Asn Gln
1               5                   10

<210> SEQ ID NO 40
<211> LENGTH: 7
<212> TYPE: PRT
<213> ORGANISM: Artificial

```
<220> FEATURE:
<223> OTHER INFORMATION: peptide

<400> SEQUENCE: 40

His Ser Ala His His Thr Met
1               5

<210> SEQ ID NO 41
<211> LENGTH: 7
<212> TYPE: PRT
<213> ORGANISM: Artificial
<220> FEATURE:
<223> OTHER INFORMATION: peptide

<400> SEQUENCE: 41

Glu Leu Gly Leu His Arg His
1               5

<210> SEQ ID NO 42
<211> LENGTH: 7
<212> TYPE: PRT
<213> ORGANISM: Artificial
<220> FEATURE:
<223> OTHER INFORMATION: peptide

<400> SEQUENCE: 42

Arg Arg Leu Arg Ile Cys Val
1               5

<210> SEQ ID NO 43
<211> LENGTH: 16
<212> TYPE: PRT
<213> ORGANISM: Artificial
<220> FEATURE:
<223> OTHER INFORMATION: peptide

<400> SEQUENCE: 43

Val Pro His Ile His Glu Phe Thr Arg Arg Arg Arg Arg Arg Arg Arg
1               5                   10                  15

<210> SEQ ID NO 44
<211> LENGTH: 5
<212> TYPE: PRT
<213> ORGANISM: Artificial
<220> FEATURE:
<223> OTHER INFORMATION: peptide

<400> SEQUENCE: 44

Pro Leu Thr Leu Ile
1               5

<210> SEQ ID NO 45
<211> LENGTH: 5
<212> TYPE: PRT
<213> ORGANISM: Artificial
<220> FEATURE:
<223> OTHER INFORMATION: peptide

<400> SEQUENCE: 45

Ser Leu Leu Ile Gly
1               5

<210> SEQ ID NO 46
<211> LENGTH: 5
<212> TYPE: PRT
<213> ORGANISM: Artificial
<220> FEATURE:
```

```
<223> OTHER INFORMATION: peptide

<400> SEQUENCE: 46

Lys Pro Pro Glu Arg
1               5

<210> SEQ ID NO 47
<211> LENGTH: 5
<212> TYPE: PRT
<213> ORGANISM: Artificial
<220> FEATURE:
<223> OTHER INFORMATION: peptide

<400> SEQUENCE: 47

Cys Arg Ile Ile Arg
1               5

<210> SEQ ID NO 48
<211> LENGTH: 5
<212> TYPE: PRT
<213> ORGANISM: Artificial
<220> FEATURE:
<223> OTHER INFORMATION: peptide

<400> SEQUENCE: 48

Ser Phe Ile Leu Ile
1               5

<210> SEQ ID NO 49
<211> LENGTH: 5
<212> TYPE: PRT
<213> ORGANISM: Artificial
<220> FEATURE:
<223> OTHER INFORMATION: peptide

<400> SEQUENCE: 49

Pro His His His Ser
1               5

<210> SEQ ID NO 50
<211> LENGTH: 4
<212> TYPE: PRT
<213> ORGANISM: Artificial
<220> FEATURE:
<223> OTHER INFORMATION: peptide

<400> SEQUENCE: 50

Glu Phe His Ser
1

<210> SEQ ID NO 51
<211> LENGTH: 5
<212> TYPE: PRT
<213> ORGANISM: Artificial
<220> FEATURE:
<223> OTHER INFORMATION: peptide

<400> SEQUENCE: 51

Arg Leu Arg Arg Leu
1               5

<210> SEQ ID NO 52
<211> LENGTH: 4
<212> TYPE: PRT
<213> ORGANISM: Artificial
<220> FEATURE:
<223> OTHER INFORMATION: peptide
```

```
<400> SEQUENCE: 52

Asp Ser Pro Arg
1

<210> SEQ ID NO 53
<211> LENGTH: 5
<212> TYPE: PRT
<213> ORGANISM: Artificial
<220> FEATURE:
<223> OTHER INFORMATION: peptide

<400> SEQUENCE: 53

His Pro Trp Thr His
1               5

<210> SEQ ID NO 54
<211> LENGTH: 5
<212> TYPE: PRT
<213> ORGANISM: Artificial
<220> FEATURE:
<223> OTHER INFORMATION: peptide

<400> SEQUENCE: 54

His Phe Ser His His
1               5

<210> SEQ ID NO 55
<211> LENGTH: 4
<212> TYPE: PRT
<213> ORGANISM: Artificial
<220> FEATURE:
<223> OTHER INFORMATION: peptide

<400> SEQUENCE: 55

Arg Arg Val Ile
1

<210> SEQ ID NO 56
<211> LENGTH: 4
<212> TYPE: PRT
<213> ORGANISM: Artificial
<220> FEATURE:
<223> OTHER INFORMATION: peptide

<400> SEQUENCE: 56

Ile Leu Val Ile
1

<210> SEQ ID NO 57
<211> LENGTH: 16
<212> TYPE: PRT
<213> ORGANISM: Artificial
<220> FEATURE:
<223> OTHER INFORMATION: peptide

<400> SEQUENCE: 57

Arg Arg Ser Arg Ser Asn Glu Asp Val Glu Asp Lys Thr Glu Asp Glu
1               5                   10                  15

<210> SEQ ID NO 58
<211> LENGTH: 19
<212> TYPE: PRT
<213> ORGANISM: Artificial
<220> FEATURE:
<223> OTHER INFORMATION: peptide
```

```
<400> SEQUENCE: 58

Arg Arg Ile Arg Ser Gly Gly Lys Asp His Ala Trp Thr Pro Leu His
1               5                   10                  15

Glu Asn His

<210> SEQ ID NO 59
<211> LENGTH: 18
<212> TYPE: PRT
<213> ORGANISM: Artificial
<220> FEATURE:
<223> OTHER INFORMATION: peptide

<400> SEQUENCE: 59

His Thr Pro His Pro Pro Val Ala Arg Thr Ser Pro Leu Gln Thr Pro
1               5                   10                  15

Arg Arg

<210> SEQ ID NO 60
<211> LENGTH: 13
<212> TYPE: PRT
<213> ORGANISM: Artificial
<220> FEATURE:
<223> OTHER INFORMATION: peptide

<400> SEQUENCE: 60

Pro Asp Ser Glu Pro Pro Arg Met Glu Leu Arg Arg Arg
1               5                   10

<210> SEQ ID NO 61
<211> LENGTH: 13
<212> TYPE: PRT
<213> ORGANISM: Artificial
<220> FEATURE:
<223> OTHER INFORMATION: peptide

<400> SEQUENCE: 61

Arg Arg Asp Thr Phe Asp Ile Arg Ile Leu Met Ala Phe
1               5                   10

<210> SEQ ID NO 62
<211> LENGTH: 15
<212> TYPE: PRT
<213> ORGANISM: Artificial
<220> FEATURE:
<223> OTHER INFORMATION: peptide

<400> SEQUENCE: 62

Arg Arg Glu Val Thr Glu Leu His His Thr His Glu Asp Arg Arg
1               5                   10                  15

<210> SEQ ID NO 63
<211> LENGTH: 12
<212> TYPE: PRT
<213> ORGANISM: Artificial
<220> FEATURE:
<223> OTHER INFORMATION: peptide

<400> SEQUENCE: 63

Ser Pro Trp Thr His Glu Arg Arg Cys Arg Gln Arg
1               5                   10

<210> SEQ ID NO 64
<211> LENGTH: 15
<212> TYPE: PRT
<213> ORGANISM: Artificial
```

```
<220> FEATURE:
<223> OTHER INFORMATION: peptide

<400> SEQUENCE: 64

Arg Ser Arg Ser Ser His Leu Arg Asp His Glu Arg Thr His Thr
1               5                   10                  15

<210> SEQ ID NO 65
<211> LENGTH: 15
<212> TYPE: PRT
<213> ORGANISM: Artificial
<220> FEATURE:
<223> OTHER INFORMATION: peptide

<400> SEQUENCE: 65

Arg Arg Arg Ser Thr Asn Thr Phe Leu Gly Glu Asp Phe Asp Gln
1               5                   10                  15

<210> SEQ ID NO 66
<211> LENGTH: 14
<212> TYPE: PRT
<213> ORGANISM: Artificial
<220> FEATURE:
<223> OTHER INFORMATION: peptide

<400> SEQUENCE: 66

Leu Ile Gly Leu Ser Thr Ser Pro Arg Pro Arg Ile Ile Arg
1               5                   10

<210> SEQ ID NO 67
<211> LENGTH: 20
<212> TYPE: PRT
<213> ORGANISM: Artificial
<220> FEATURE:
<223> OTHER INFORMATION: peptide

<400> SEQUENCE: 67

Glu Ile Tyr Gly Glu Ser Gly Lys Thr Asp Glu His Ala Leu Asp Thr
1               5                   10                  15

Glu Tyr Arg Arg
            20

<210> SEQ ID NO 68
<211> LENGTH: 18
<212> TYPE: PRT
<213> ORGANISM: Artificial
<220> FEATURE:
<223> OTHER INFORMATION: peptide

<400> SEQUENCE: 68

Arg Arg Val Ile Leu Arg Ser Tyr Asp Gly Gly His Ser Thr Pro His
1               5                   10                  15

Pro Asp

<210> SEQ ID NO 69
<211> LENGTH: 18
<212> TYPE: PRT
<213> ORGANISM: Artificial
<220> FEATURE:
<223> OTHER INFORMATION: peptide

<400> SEQUENCE: 69

Thr Gly Lys Thr Phe Val Lys Arg His Leu Thr Glu Phe Glu Lys Lys
1               5                   10                  15

Tyr Arg
```

<210> SEQ ID NO 70
<211> LENGTH: 20
<212> TYPE: PRT
<213> ORGANISM: Artificial
<220> FEATURE:
<223> OTHER INFORMATION: peptide

<400> SEQUENCE: 70

Asn His Phe Asp Tyr Asp Thr Ile Glu Leu Asp Thr Ala Gly Glu Tyr
1               5                   10                  15

Ser Arg Arg Arg
            20

<210> SEQ ID NO 71
<211> LENGTH: 15
<212> TYPE: PRT
<213> ORGANISM: Artificial
<220> FEATURE:
<223> OTHER INFORMATION: peptide

<400> SEQUENCE: 71

Asp Pro Glu Pro Pro Arg Tyr Leu Pro Pro Pro Glu Arg Arg
1               5                   10                  15

<210> SEQ ID NO 72
<211> LENGTH: 20
<212> TYPE: PRT
<213> ORGANISM: Artificial
<220> FEATURE:
<223> OTHER INFORMATION: peptide

<400> SEQUENCE: 72

Arg Arg Thr Phe Ile Arg His Arg Ile Asp Ser Thr Glu Val Ile Tyr
1               5                   10                  15

Gln Asp Glu Asp
            20

<210> SEQ ID NO 73
<211> LENGTH: 17
<212> TYPE: PRT
<213> ORGANISM: Artificial
<220> FEATURE:
<223> OTHER INFORMATION: peptide

<400> SEQUENCE: 73

Glu Ser Lys Thr Gly His Lys Ser Glu Glu Gln Arg Leu Arg Arg Tyr
1               5                   10                  15

Arg

<210> SEQ ID NO 74
<211> LENGTH: 17
<212> TYPE: PRT
<213> ORGANISM: Artificial
<220> FEATURE:
<223> OTHER INFORMATION: peptide

<400> SEQUENCE: 74

Tyr Asp Asp Glu His Asn His His Pro His His Ser Thr His Arg Arg
1               5                   10                  15

Arg

<210> SEQ ID NO 75
<211> LENGTH: 18

```
<212> TYPE: PRT
<213> ORGANISM: Artificial
<220> FEATURE:
<223> OTHER INFORMATION: peptide

<400> SEQUENCE: 75

Arg Arg Arg Arg Glu Val His Thr Ile His Gln His Gly Ile Val His
1               5                   10                  15

Ser Asp

<210> SEQ ID NO 76
<211> LENGTH: 11
<212> TYPE: PRT
<213> ORGANISM: Artificial
<220> FEATURE:
<223> OTHER INFORMATION: peptide

<400> SEQUENCE: 76

Asp Glu Pro Leu Pro Pro Pro Glu Arg Arg Arg
1               5                   10

<210> SEQ ID NO 77
<211> LENGTH: 6
<212> TYPE: PRT
<213> ORGANISM: Artificial
<220> FEATURE:
<223> OTHER INFORMATION: peptide

<400> SEQUENCE: 77

Ser Pro His Pro Pro Tyr
1               5

<210> SEQ ID NO 78
<211> LENGTH: 19
<212> TYPE: PRT
<213> ORGANISM: Artificial
<220> FEATURE:
<223> OTHER INFORMATION: peptide

<400> SEQUENCE: 78

Ser Pro His Pro Pro Tyr Ser Pro His Pro Pro Tyr Ser Pro His Pro
1               5                   10                  15

Pro Tyr Pro

<210> SEQ ID NO 79
<211> LENGTH: 9
<212> TYPE: PRT
<213> ORGANISM: Artificial
<220> FEATURE:
<223> OTHER INFORMATION: peptide

<400> SEQUENCE: 79

Arg Arg Pro His Asn Leu His His Asp
1               5

<210> SEQ ID NO 80
<211> LENGTH: 12
<212> TYPE: PRT
<213> ORGANISM: Artificial
<220> FEATURE:
<223> OTHER INFORMATION: peptide

<400> SEQUENCE: 80

Leu Arg Asp Pro His Pro Pro Glu Arg Arg Ile Arg
1               5                   10
```

<210> SEQ ID NO 81
<211> LENGTH: 15
<212> TYPE: PRT
<213> ORGANISM: Artificial
<220> FEATURE:
<223> OTHER INFORMATION: peptide

<400> SEQUENCE: 81

Arg Arg Pro Ala Asp Gln Ile Ser Tyr Leu His Pro Pro Glu Arg
1               5                   10                  15

<210> SEQ ID NO 82
<211> LENGTH: 11
<212> TYPE: PRT
<213> ORGANISM: Artificial
<220> FEATURE:
<223> OTHER INFORMATION: peptide

<400> SEQUENCE: 82

Asp Leu Gln Tyr Asp Phe Pro Arg Ile Arg Arg
1               5                   10

<210> SEQ ID NO 83
<211> LENGTH: 14
<212> TYPE: PRT
<213> ORGANISM: Artificial
<220> FEATURE:
<223> OTHER INFORMATION: peptide

<400> SEQUENCE: 83

Tyr Asp Glu Leu Tyr Gln Lys Glu Asp Pro His Arg Arg Arg
1               5                   10

<210> SEQ ID NO 84
<211> LENGTH: 13
<212> TYPE: PRT
<213> ORGANISM: Artificial
<220> FEATURE:
<223> OTHER INFORMATION: peptide

<400> SEQUENCE: 84

Phe Lys Pro Glu Arg Phe Pro Gln Asn Asp Arg Arg Arg
1               5                   10

<210> SEQ ID NO 85
<211> LENGTH: 8
<212> TYPE: PRT
<213> ORGANISM: Artificial
<220> FEATURE:
<223> OTHER INFORMATION: peptide

<400> SEQUENCE: 85

Arg Pro Ala Asp Arg Ile Arg Arg
1               5

<210> SEQ ID NO 86
<211> LENGTH: 11
<212> TYPE: PRT
<213> ORGANISM: Artificial
<220> FEATURE:
<223> OTHER INFORMATION: peptide

<400> SEQUENCE: 86

His Asp Phe Asp Pro Arg Tyr Arg Asp Arg Arg
1               5                   10

```
<210> SEQ ID NO 87
<211> LENGTH: 14
<212> TYPE: PRT
<213> ORGANISM: Artificial
<220> FEATURE:
<223> OTHER INFORMATION: peptide

<400> SEQUENCE: 87

Arg Ile Arg Arg Asp Pro Asp Ser Pro Leu Pro His Pro Glu
1               5                   10

<210> SEQ ID NO 88
<211> LENGTH: 15
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 88

Arg Arg Ile Arg Ile Leu Met Phe Leu Ile Gly Cys Gly Arg Val
1               5                   10                  15

<210> SEQ ID NO 89
<211> LENGTH: 14
<212> TYPE: PRT
<213> ORGANISM: Artificial
<220> FEATURE:
<223> OTHER INFORMATION: peptide

<400> SEQUENCE: 89

His Pro His Val Ile Leu Pro Arg Ile Arg Ile Arg Ile Arg
1               5                   10

<210> SEQ ID NO 90
<211> LENGTH: 12
<212> TYPE: PRT
<213> ORGANISM: Artificial
<220> FEATURE:
<223> OTHER INFORMATION: peptide

<400> SEQUENCE: 90

Glu Ile His Thr Ile His Leu Leu Pro Glu Arg Arg
1               5                   10

<210> SEQ ID NO 91
<211> LENGTH: 13
<212> TYPE: PRT
<213> ORGANISM: Artificial
<220> FEATURE:
<223> OTHER INFORMATION: peptide

<400> SEQUENCE: 91

Glu Pro Ser His Pro Arg Ser Arg Tyr Pro Arg Thr Phe
1               5                   10

<210> SEQ ID NO 92
<211> LENGTH: 16
<212> TYPE: PRT
<213> ORGANISM: Artificial
<220> FEATURE:
<223> OTHER INFORMATION: peptide

<400> SEQUENCE: 92

Arg Asn Ile Ile Ile Arg Asp Phe Ile His Phe Ser His Ile Asp Arg
```

-continued

```
1               5                   10                  15

<210> SEQ ID NO 93
<211> LENGTH: 18
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (09)..(09)
<223> OTHER INFORMATION: MYRISTATE group attached

<400> SEQUENCE: 93

Arg Arg Ile Arg Asp Pro Gln Ile Lys Leu Glu Ile His Phe Ser His
1               5                   10                  15

Ile Asp

<210> SEQ ID NO 94
<211> LENGTH: 12
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 94

Asp Leu His Thr Ile His Ile Pro Arg Asp Arg Arg
1               5                   10

<210> SEQ ID NO 95
<211> LENGTH: 14
<212> TYPE: PRT
<213> ORGANISM: Artificial
<220> FEATURE:
<223> OTHER INFORMATION: peptide

<400> SEQUENCE: 95

Ser His Asp Phe Pro His Arg Glu Pro Arg Pro Glu Arg Arg
1               5                   10

<210> SEQ ID NO 96
<211> LENGTH: 14
<212> TYPE: PRT
<213> ORGANISM: Artificial
<220> FEATURE:
<223> OTHER INFORMATION: peptide

<400> SEQUENCE: 96

Ser Tyr Arg His Tyr Ser Asp His Trp Glu Asp Arg Arg Arg
1               5                   10

<210> SEQ ID NO 97
<211> LENGTH: 20
<212> TYPE: PRT
<213> ORGANISM: Artificial
<220> FEATURE:
<223> OTHER INFORMATION: peptide

<400> SEQUENCE: 97

Val Trp Val His Asp Ser Cys His Ala Asn Leu Gln Asn Tyr Arg Asn
1               5                   10                  15

Tyr Leu Leu Pro
            20
```

<210> SEQ ID NO 98
<211> LENGTH: 20
<212> TYPE: PRT
<213> ORGANISM: Artificial
<220> FEATURE:
<223> OTHER INFORMATION: peptide

<400> SEQUENCE: 98

Glu His Asp Phe Glu Val Arg Gly Asp Val Val Asn Gly Arg Asn His
1               5                   10                  15

Gln Gly Pro Lys
            20

<210> SEQ ID NO 99
<211> LENGTH: 7
<212> TYPE: PRT
<213> ORGANISM: Artificial
<220> FEATURE:
<223> OTHER INFORMATION: peptide

<400> SEQUENCE: 99

Leu Glu Val Ile Tyr Met Ile
1               5

<210> SEQ ID NO 100
<211> LENGTH: 7
<212> TYPE: PRT
<213> ORGANISM: Artificial
<220> FEATURE:
<223> OTHER INFORMATION: peptide

<400> SEQUENCE: 100

Trp Thr Leu Ser Asn Tyr Leu
1               5

<210> SEQ ID NO 101
<211> LENGTH: 7
<212> TYPE: PRT
<213> ORGANISM: Artificial
<220> FEATURE:
<223> OTHER INFORMATION: peptide

<400> SEQUENCE: 101

Asp Ser Leu His Ser Thr Tyr
1               5

<210> SEQ ID NO 102
<211> LENGTH: 12
<212> TYPE: PRT
<213> ORGANISM: Artificial
<220> FEATURE:
<223> OTHER INFORMATION: peptide

<400> SEQUENCE: 102

Trp His His Arg Gln Gln Ile Pro Arg Pro Leu Glu
1               5                   10

<210> SEQ ID NO 103
<211> LENGTH: 12
<212> TYPE: PRT
<213> ORGANISM: Artificial
<220> FEATURE:
<223> OTHER INFORMATION: peptide

<400> SEQUENCE: 103

Ala Pro Ser Ile Phe Thr Pro His Ala Trp Arg Gln
1               5                   10

<210> SEQ ID NO 104
<211> LENGTH: 18
<212> TYPE: PRT
<213> ORGANISM: Artificial
<220> FEATURE:
<223> OTHER INFORMATION: peptide

<400> SEQUENCE: 104

Thr His Phe Ser His His Leu Lys Gly Gly Gly Arg Arg Gln Arg
1               5                   10                  15

Arg Pro

<210> SEQ ID NO 105
<211> LENGTH: 18
<212> TYPE: PRT
<213> ORGANISM: Artificial
<220> FEATURE:
<223> OTHER INFORMATION: peptide

<400> SEQUENCE: 105

Leu His Ser Lys Thr Leu Val Leu Gly Gly Arg Arg Arg Arg Gly
1               5                   10                  15

Asp Arg

<210> SEQ ID NO 106
<211> LENGTH: 19
<212> TYPE: PRT
<213> ORGANISM: Artificial
<220> FEATURE:
<223> OTHER INFORMATION: peptide

<400> SEQUENCE: 106

Trp Thr Leu Ser Asn Tyr Leu Gly Gly Arg Lys Lys Arg Arg Gln Arg
1               5                   10                  15

Arg Arg Arg

<210> SEQ ID NO 107
<211> LENGTH: 12
<212> TYPE: PRT
<213> ORGANISM: Artificial
<220> FEATURE:
<223> OTHER INFORMATION: peptide

<400> SEQUENCE: 107

Val Arg Cys Ile Phe Arg Gly Ile Trp Val Arg Leu
1               5                   10

<210> SEQ ID NO 108
<211> LENGTH: 12
<212> TYPE: PRT
<213> ORGANISM: Artificial
<220> FEATURE:
<223> OTHER INFORMATION: peptide

<400> SEQUENCE: 108

His Ser Ser Gly His Asn Phe Val Leu Val Arg Gln
1               5                   10

<210> SEQ ID NO 109
<211> LENGTH: 7
<212> TYPE: PRT
<213> ORGANISM: Artificial

```
-continued

<220> FEATURE:
<223> OTHER INFORMATION: peptide

<400> SEQUENCE: 109

Leu Phe Ile Leu Val Phe Arg
1               5

<210> SEQ ID NO 110
<211> LENGTH: 7
<212> TYPE: PRT
<213> ORGANISM: Artificial
<220> FEATURE:
<223> OTHER INFORMATION: peptide

<400> SEQUENCE: 110

Thr Thr Ser His His Pro Lys
1               5

<210> SEQ ID NO 111
<211> LENGTH: 12
<212> TYPE: PRT
<213> ORGANISM: Artificial
<220> FEATURE:
<223> OTHER INFORMATION: peptide

<400> SEQUENCE: 111

Val Met Val Leu Phe Arg Ile Leu Arg Gly Ser Met
1               5                   10

<210> SEQ ID NO 112
<211> LENGTH: 4
<212> TYPE: PRT
<213> ORGANISM: Artificial
<220> FEATURE:
<223> OTHER INFORMATION: peptide

<400> SEQUENCE: 112

Ser Ile Leu Thr
1

<210> SEQ ID NO 113
<211> LENGTH: 17
<212> TYPE: PRT
<213> ORGANISM: Artificial
<220> FEATURE:
<223> OTHER INFORMATION: peptide

<400> SEQUENCE: 113

Arg Arg Arg Glu Ser Glu Gln Arg Ser Ile Ser Leu His His His Ser
1               5                   10                  15

Thr

<210> SEQ ID NO 114
<211> LENGTH: 16
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 114

His Phe Asn His Tyr Thr Phe Glu Ser Thr Cys Arg Arg Arg Arg Cys
1               5                   10                  15
```

```
<210> SEQ ID NO 115
<211> LENGTH: 14
<212> TYPE: PRT
<213> ORGANISM: Artificial
<220> FEATURE:
<223> OTHER INFORMATION: peptide

<400> SEQUENCE: 115

His Ser Thr Pro His Pro Pro Gln Pro Pro Glu Arg Arg Arg
1               5                   10

<210> SEQ ID NO 116
<211> LENGTH: 18
<212> TYPE: PRT
<213> ORGANISM: Artificial
<220> FEATURE:
<223> OTHER INFORMATION: peptide

<400> SEQUENCE: 116

Arg Arg Lys Ser Glu Pro His Ser Leu Ser Gly Gly Tyr Gln Thr Gly
1               5                   10                  15

Ala Asp

<210> SEQ ID NO 117
<211> LENGTH: 21
<212> TYPE: PRT
<213> ORGANISM: Artificial
<220> FEATURE:
<223> OTHER INFORMATION: peptide

<400> SEQUENCE: 117

His Arg Thr Gly His Tyr Thr Arg Cys Arg Gln Arg Cys Arg Ser Arg
1               5                   10                  15

Ser His Asn Arg His
            20

<210> SEQ ID NO 118
<211> LENGTH: 14
<212> TYPE: PRT
<213> ORGANISM: Artificial
<220> FEATURE:
<223> OTHER INFORMATION: peptide

<400> SEQUENCE: 118

Arg Arg Cys Arg Ser Ile Leu Pro Leu Leu Leu Leu Ser Arg
1               5                   10

<210> SEQ ID NO 119
<211> LENGTH: 21
<212> TYPE: PRT
<213> ORGANISM: Artificial
<220> FEATURE:
<223> OTHER INFORMATION: peptide

<400> SEQUENCE: 119

Arg Thr Leu His Gly Arg Arg Val Ile Leu His Glu Gly Gly His Ser
1               5                   10                  15

Ile Ser Asp Leu Lys
            20

<210> SEQ ID NO 120
<211> LENGTH: 18
<212> TYPE: PRT
<213> ORGANISM: Artificial
<220> FEATURE:
```

<223> OTHER INFORMATION: peptide

<400> SEQUENCE: 120

His His Arg Leu Ser Tyr Phe Ile Val Arg Arg His Ser Thr His Ala
1               5                   10                  15

Ser Arg

<210> SEQ ID NO 121
<211> LENGTH: 10
<212> TYPE: PRT
<213> ORGANISM: Artificial
<220> FEATURE:
<223> OTHER INFORMATION: peptide

<400> SEQUENCE: 121

Arg Arg Ile Arg Ile Asp Pro Gln His Asp
1               5                   10

<210> SEQ ID NO 122
<211> LENGTH: 11
<212> TYPE: PRT
<213> ORGANISM: Artificial
<220> FEATURE:
<223> OTHER INFORMATION: peptide

<400> SEQUENCE: 122

Ile Leu Gln Pro Asp Phe Leu Ile Arg Pro Glu
1               5                   10

<210> SEQ ID NO 123
<211> LENGTH: 9
<212> TYPE: PRT
<213> ORGANISM: Artificial
<220> FEATURE:
<223> OTHER INFORMATION: peptide

<400> SEQUENCE: 123

His Asp Pro Arg Ile Ile Arg Ile Arg
1               5

<210> SEQ ID NO 124
<211> LENGTH: 7
<212> TYPE: PRT
<213> ORGANISM: Artificial
<220> FEATURE:
<223> OTHER INFORMATION: peptide

<400> SEQUENCE: 124

Ser Pro Tyr Pro Ile Arg Thr
1               5

<210> SEQ ID NO 125
<211> LENGTH: 9
<212> TYPE: PRT
<213> ORGANISM: Artificial
<220> FEATURE:
<223> OTHER INFORMATION: peptide

<400> SEQUENCE: 125

Ile Leu Val Ile Ile Gln Arg Ile Met
1               5

<210> SEQ ID NO 126
<211> LENGTH: 7
<212> TYPE: PRT
<213> ORGANISM: Artificial

```
<220> FEATURE:
<223> OTHER INFORMATION: peptide

<400> SEQUENCE: 126

Ile Arg Phe Ile Leu Ile Arg
1               5

<210> SEQ ID NO 127
<211> LENGTH: 7
<212> TYPE: PRT
<213> ORGANISM: Artificial
<220> FEATURE:
<223> OTHER INFORMATION: peptide

<400> SEQUENCE: 127

Ser Ser Val His His Arg Gly
1               5

<210> SEQ ID NO 128
<211> LENGTH: 7
<212> TYPE: PRT
<213> ORGANISM: Artificial
<220> FEATURE:
<223> OTHER INFORMATION: peptide

<400> SEQUENCE: 128

Leu Arg Arg Gln Leu Gln Leu
1               5

<210> SEQ ID NO 129
<211> LENGTH: 7
<212> TYPE: PRT
<213> ORGANISM: Artificial
<220> FEATURE:
<223> OTHER INFORMATION: peptide

<400> SEQUENCE: 129

His Thr Thr Ala His Thr His
1               5

<210> SEQ ID NO 130
<211> LENGTH: 12
<212> TYPE: PRT
<213> ORGANISM: Artificial
<220> FEATURE:
<223> OTHER INFORMATION: peptide

<400> SEQUENCE: 130

His Pro His Asn His Thr Val His Asn Val Val Tyr
1               5                   10

<210> SEQ ID NO 131
<211> LENGTH: 12
<212> TYPE: PRT
<213> ORGANISM: Artificial
<220> FEATURE:
<223> OTHER INFORMATION: peptide

<400> SEQUENCE: 131

Asp His Ser Lys Phe Val Pro Leu Phe Val Arg Gln
1               5                   10

<210> SEQ ID NO 132
<211> LENGTH: 13
<212> TYPE: PRT
<213> ORGANISM: Artificial
<220> FEATURE:
```

```
<223> OTHER INFORMATION: peptide

<400> SEQUENCE: 132

Ser Ile Arg Thr Leu Gly Arg Phe Leu Ile Ile Arg Val
1               5                   10

<210> SEQ ID NO 133
<211> LENGTH: 7
<212> TYPE: PRT
<213> ORGANISM: Artificial
<220> FEATURE:
<223> OTHER INFORMATION: peptide

<400> SEQUENCE: 133

Gly Leu Cys Arg Ile Ile Leu
1               5

<210> SEQ ID NO 134
<211> LENGTH: 7
<212> TYPE: PRT
<213> ORGANISM: Artificial
<220> FEATURE:
<223> OTHER INFORMATION: peptide

<400> SEQUENCE: 134

Ser Pro Pro Ile Arg His His
1               5

<210> SEQ ID NO 135
<211> LENGTH: 14
<212> TYPE: PRT
<213> ORGANISM: Artificial
<220> FEATURE:
<223> OTHER INFORMATION: peptide

<400> SEQUENCE: 135

His Pro Thr His Pro Ile Arg Leu Arg Asp Asn Leu Thr Arg
1               5                   10

<210> SEQ ID NO 136
<211> LENGTH: 12
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 136

Arg Glu Glu Glu Thr Ile Leu Ile Ile Arg Arg Arg
1               5                   10

<210> SEQ ID NO 137
<211> LENGTH: 18
<212> TYPE: PRT
<213> ORGANISM: Artificial
<220> FEATURE:
<223> OTHER INFORMATION: peptide

<400> SEQUENCE: 137

His Thr Ile His Ser Ile Ser Asp Phe Pro Glu Pro Pro Asp Arg Arg
1               5                   10                  15

Arg Arg
```

```
<210> SEQ ID NO 138
<211> LENGTH: 20
<212> TYPE: PRT
<213> ORGANISM: Artificial
<220> FEATURE:
<223> OTHER INFORMATION: peptide

<400> SEQUENCE: 138

Asp Glu Asp Ala Ala His Ser Thr Gly His Pro His Asn Ser Gln His
1               5                   10                  15

Arg Arg Arg Arg
            20

<210> SEQ ID NO 139
<211> LENGTH: 12
<212> TYPE: PRT
<213> ORGANISM: Artificial
<220> FEATURE:
<223> OTHER INFORMATION: peptide

<400> SEQUENCE: 139

Thr Glu Gln His His Tyr Ile Pro His Arg Arg Arg
1               5                   10

<210> SEQ ID NO 140
<211> LENGTH: 12
<212> TYPE: PRT
<213> ORGANISM: Artificial
<220> FEATURE:
<223> OTHER INFORMATION: peptide

<400> SEQUENCE: 140

Arg Leu Arg Arg Val Ile Leu Arg Ser Tyr His Glu
1               5                   10

<210> SEQ ID NO 141
<211> LENGTH: 19
<212> TYPE: PRT
<213> ORGANISM: Artificial
<220> FEATURE:
<223> OTHER INFORMATION: peptide

<400> SEQUENCE: 141

Glu Glu Pro Asp Arg Gln Pro Ser Gly Lys Arg Gly Gly Arg Lys Arg
1               5                   10                  15

Arg Ser Arg

<210> SEQ ID NO 142
<211> LENGTH: 13
<212> TYPE: PRT
<213> ORGANISM: Artificial
<220> FEATURE:
<223> OTHER INFORMATION: peptide

<400> SEQUENCE: 142

Arg Asp Phe His Thr Ile His Pro Ser Ile Ser Arg Arg
1               5                   10

<210> SEQ ID NO 143
<211> LENGTH: 11
<212> TYPE: PRT
<213> ORGANISM: Artificial
<220> FEATURE:
<223> OTHER INFORMATION: peptide

<400> SEQUENCE: 143
```

```
Arg Arg Val Asp Ile His Asp Gly Gln Arg Arg
1               5                  10
```

<210> SEQ ID NO 144
<211> LENGTH: 10
<212> TYPE: PRT
<213> ORGANISM: Artificial
<220> FEATURE:
<223> OTHER INFORMATION: peptide

<400> SEQUENCE: 144

```
Asp Gln Pro Tyr Pro His Arg Arg Ile Arg
1               5                  10
```

<210> SEQ ID NO 145
<211> LENGTH: 13
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 145

```
Arg Asp Phe Ile Leu Phe Ile Arg Arg Leu Gly Arg Arg
1               5                  10
```

<210> SEQ ID NO 146
<211> LENGTH: 10
<212> TYPE: PRT
<213> ORGANISM: Artificial
<220> FEATURE:
<223> OTHER INFORMATION: peptide

<400> SEQUENCE: 146

```
Leu Asp Leu Tyr His Pro Arg Glu Arg Arg
1               5                  10
```

<210> SEQ ID NO 147
<211> LENGTH: 12
<212> TYPE: PRT
<213> ORGANISM: Artificial
<220> FEATURE:
<223> OTHER INFORMATION: peptide

<400> SEQUENCE: 147

```
Arg Arg Ile Arg Asp Pro Leu Gly Asn Glu His Glu
1               5                  10
```

<210> SEQ ID NO 148
<211> LENGTH: 8
<212> TYPE: PRT
<213> ORGANISM: Artificial
<220> FEATURE:
<223> OTHER INFORMATION: peptide

<400> SEQUENCE: 148

```
Ile Val Glu Phe Arg Ile Arg Arg
1               5
```

<210> SEQ ID NO 149
<211> LENGTH: 10
<212> TYPE: PRT
<213> ORGANISM: Artificial
<220> FEATURE:
<223> OTHER INFORMATION: peptide

<400> SEQUENCE: 149

Arg Arg Pro Arg Ile Pro Asp Tyr Ile Leu
1               5                   10

<210> SEQ ID NO 150
<211> LENGTH: 12
<212> TYPE: PRT
<213> ORGANISM: Artificial
<220> FEATURE:
<223> OTHER INFORMATION: peptide

<400> SEQUENCE: 150

Arg Ser Thr Pro His Ile His Glu Phe Ile Arg Arg
1               5                   10

<210> SEQ ID NO 151
<211> LENGTH: 14
<212> TYPE: PRT
<213> ORGANISM: Artificial
<220> FEATURE:
<223> OTHER INFORMATION: peptide

<400> SEQUENCE: 151

Ser His Asp Phe Tyr Pro His Trp Met Arg Glu Arg Ile Arg
1               5                   10

<210> SEQ ID NO 152
<211> LENGTH: 7
<212> TYPE: PRT
<213> ORGANISM: Artificial
<220> FEATURE:
<223> OTHER INFORMATION: peptide

<400> SEQUENCE: 152

His Phe Ser His His Leu Lys
1               5

<210> SEQ ID NO 153
<211> LENGTH: 8
<212> TYPE: PRT
<213> ORGANISM: Artificial
<220> FEATURE:
<223> OTHER INFORMATION: peptide

<400> SEQUENCE: 153

Thr Ser Pro Leu Gln Ser Leu Lys
1               5

<210> SEQ ID NO 154
<211> LENGTH: 13
<212> TYPE: PRT
<213> ORGANISM: Artificial
<220> FEATURE:
<223> OTHER INFORMATION: peptide

<400> SEQUENCE: 154

Ala Ile Leu Thr Leu Ile Leu Arg Arg Val Ile Trp Pro
1               5                   10

<210> SEQ ID NO 155
<211> LENGTH: 7
<212> TYPE: PRT
<213> ORGANISM: Artificial
<220> FEATURE:
<223> OTHER INFORMATION: peptide

```
<400> SEQUENCE: 155

Leu Arg Phe Ile Asp Tyr Pro
1               5

<210> SEQ ID NO 156
<211> LENGTH: 10
<212> TYPE: PRT
<213> ORGANISM: Artificial
<220> FEATURE:
<223> OTHER INFORMATION: peptide

<400> SEQUENCE: 156

Gly Pro Ile Lys His His Leu Gln His His
1               5                   10

<210> SEQ ID NO 157
<211> LENGTH: 4
<212> TYPE: PRT
<213> ORGANISM: Artificial
<220> FEATURE:
<223> OTHER INFORMATION: peptide

<400> SEQUENCE: 157

Leu Thr Leu Ser
1

<210> SEQ ID NO 158
<211> LENGTH: 20
<212> TYPE: PRT
<213> ORGANISM: Artificial
<220> FEATURE:
<223> OTHER INFORMATION: peptide

<400> SEQUENCE: 158

Arg Tyr Glu Glu Asn Asn Gly Val Asn Pro Pro Val Gln Val Phe Glu
1               5                   10                  15

Ser Arg Thr Arg
            20

<210> SEQ ID NO 159
<211> LENGTH: 14
<212> TYPE: PRT
<213> ORGANISM: Artificial
<220> FEATURE:
<223> OTHER INFORMATION: peptide

<400> SEQUENCE: 159

Arg Glu Gly Phe Tyr Gly Pro Trp His Glu Gln Arg Arg Arg
1               5                   10

<210> SEQ ID NO 160
<211> LENGTH: 11
<212> TYPE: PRT
<213> ORGANISM: Artificial
<220> FEATURE:
<223> OTHER INFORMATION: peptide

<400> SEQUENCE: 160

Arg Arg Asp Ile Ile Arg His Asn Ala His Ser
1               5                   10

<210> SEQ ID NO 161
<211> LENGTH: 10
<212> TYPE: PRT
<213> ORGANISM: Artificial
<220> FEATURE:
```

<223> OTHER INFORMATION: peptide

<400> SEQUENCE: 161

His Asp Phe His Asp Tyr Leu Glu Arg Arg
1               5                   10

<210> SEQ ID NO 162
<211> LENGTH: 10
<212> TYPE: PRT
<213> ORGANISM: Artificial
<220> FEATURE:
<223> OTHER INFORMATION: peptide

<400> SEQUENCE: 162

Ile Arg Glu Phe Asp Pro Arg Arg Ile Arg
1               5                   10

<210> SEQ ID NO 163
<211> LENGTH: 15
<212> TYPE: PRT
<213> ORGANISM: Artificial
<220> FEATURE:
<223> OTHER INFORMATION: peptide

<400> SEQUENCE: 163

Arg Leu Arg Cys Leu Leu Leu Ile Gly Arg Val Gly Arg Arg
1               5                   10                  15

<210> SEQ ID NO 164
<211> LENGTH: 14
<212> TYPE: PRT
<213> ORGANISM: Artificial
<220> FEATURE:
<223> OTHER INFORMATION: peptide

<400> SEQUENCE: 164

Leu Gly Ile Asp Glu Asp Glu Glu Thr Glu Thr Ala Pro Glu
1               5                   10

<210> SEQ ID NO 165
<211> LENGTH: 12
<212> TYPE: PRT
<213> ORGANISM: Artificial
<220> FEATURE:
<223> OTHER INFORMATION: peptide

<400> SEQUENCE: 165

Ser Leu Leu Ile Gly Phe Gly Ile Ile Arg Ser Arg
1               5                   10

<210> SEQ ID NO 166
<211> LENGTH: 9
<212> TYPE: PRT
<213> ORGANISM: Artificial
<220> FEATURE:
<223> OTHER INFORMATION: peptide

<400> SEQUENCE: 166

Val His Glu Val Thr His His Trp Leu
1               5

<210> SEQ ID NO 167
<211> LENGTH: 7
<212> TYPE: PRT
<213> ORGANISM: Artificial
<220> FEATURE:
<223> OTHER INFORMATION: peptide

```
<400> SEQUENCE: 167

Ala Thr Pro Phe His Gln Thr
1               5

<210> SEQ ID NO 168
<211> LENGTH: 12
<212> TYPE: PRT
<213> ORGANISM: Artificial
<220> FEATURE:
<223> OTHER INFORMATION: peptide

<400> SEQUENCE: 168

Ser Ile Leu Pro Leu Phe Leu Ile Arg Arg Ser Gly
1               5                   10

<210> SEQ ID NO 169
<211> LENGTH: 16
<212> TYPE: PRT
<213> ORGANISM: Artificial
<220> FEATURE:
<223> OTHER INFORMATION: peptide

<400> SEQUENCE: 169

Ser Cys Arg Cys Arg Leu Arg Arg Arg Arg Arg Arg Arg Arg Arg Arg
1               5                   10                  15

<210> SEQ ID NO 170
<211> LENGTH: 7
<212> TYPE: PRT
<213> ORGANISM: Artificial
<220> FEATURE:
<223> OTHER INFORMATION: peptide

<400> SEQUENCE: 170

Ser Arg Ile Val Leu Gly Trp
1               5

<210> SEQ ID NO 171
<211> LENGTH: 7
<212> TYPE: PRT
<213> ORGANISM: Artificial
<220> FEATURE:
<223> OTHER INFORMATION: peptide

<400> SEQUENCE: 171

Ser Asn Ile His His Gln Val
1               5

<210> SEQ ID NO 172
<211> LENGTH: 10
<212> TYPE: PRT
<213> ORGANISM: Artificial
<220> FEATURE:
<223> OTHER INFORMATION: peptide

<400> SEQUENCE: 172

Leu Thr Leu Met Arg Leu Arg Ile Ile Gly
1               5                   10

<210> SEQ ID NO 173
<211> LENGTH: 12
<212> TYPE: PRT
<213> ORGANISM: Artificial
<220> FEATURE:
<223> OTHER INFORMATION: peptide
```

```
<400> SEQUENCE: 173

His Ser Tyr Ser Pro Tyr Tyr Thr Phe Arg Gln His
1               5                   10

<210> SEQ ID NO 174
<211> LENGTH: 5
<212> TYPE: PRT
<213> ORGANISM: Artificial
<220> FEATURE:
<223> OTHER INFORMATION: peptide

<400> SEQUENCE: 174

Phe Ile Leu Ile Arg
1               5

<210> SEQ ID NO 175
<211> LENGTH: 19
<212> TYPE: PRT
<213> ORGANISM: Artificial
<220> FEATURE:
<223> OTHER INFORMATION: peptide

<400> SEQUENCE: 175

Arg Cys Arg Asn Arg Lys Lys Glu Lys Thr Glu Cys Leu Gln Lys Glu
1               5                   10                  15

Ser Glu Lys

<210> SEQ ID NO 176
<211> LENGTH: 18
<212> TYPE: PRT
<213> ORGANISM: Artificial
<220> FEATURE:
<223> OTHER INFORMATION: peptide

<400> SEQUENCE: 176

Arg Arg Ile Lys Met Ile Arg Thr Ser Glu Ser Phe Ile Gln His Ile
1               5                   10                  15

Val Ser

<210> SEQ ID NO 177
<211> LENGTH: 17
<212> TYPE: PRT
<213> ORGANISM: Artificial
<220> FEATURE:
<223> OTHER INFORMATION: peptide

<400> SEQUENCE: 177

Arg Arg Val Ser Glu Leu Gln Arg Asn Lys His Gly Arg Lys His Glu
1               5                   10                  15

Leu

<210> SEQ ID NO 178
<211> LENGTH: 19
<212> TYPE: PRT
<213> ORGANISM: Artificial
<220> FEATURE:
<223> OTHER INFORMATION: peptide

<400> SEQUENCE: 178

Arg Arg Arg Leu Asp Asp Glu Asp Val Gln Thr Pro Thr Pro Ser Glu
1               5                   10                  15

Tyr Gln Asn
```

```
<210> SEQ ID NO 179
<211> LENGTH: 14
<212> TYPE: PRT
<213> ORGANISM: Artificial
<220> FEATURE:
<223> OTHER INFORMATION: peptide

<400> SEQUENCE: 179

Arg Arg Arg Gln Pro Leu Pro Ser Ala Pro Glu Asn Glu Glu
1               5                   10

<210> SEQ ID NO 180
<211> LENGTH: 20
<212> TYPE: PRT
<213> ORGANISM: Artificial
<220> FEATURE:
<223> OTHER INFORMATION: peptide

<400> SEQUENCE: 180

Ser Pro Leu Gln Thr Pro Ala Ala Pro Gly Ala Ala Ala Gly Pro Ala
1               5                   10                  15

Leu Ser Pro Val
            20

<210> SEQ ID NO 181
<211> LENGTH: 10
<212> TYPE: PRT
<213> ORGANISM: Artificial
<220> FEATURE:
<223> OTHER INFORMATION: peptide

<400> SEQUENCE: 181

Ser His Gln Val His Thr His His Asn Asn
1               5                   10

<210> SEQ ID NO 182
<211> LENGTH: 7
<212> TYPE: PRT
<213> ORGANISM: Artificial
<220> FEATURE:
<223> OTHER INFORMATION: peptide

<400> SEQUENCE: 182

Lys Leu Gln Val Pro Ile Lys
1               5

<210> SEQ ID NO 183
<211> LENGTH: 20
<212> TYPE: PRT
<213> ORGANISM: Artificial
<220> FEATURE:
<223> OTHER INFORMATION: peptide

<400> SEQUENCE: 183

Ile Arg Gly Arg Ile Ile Arg Arg Lys Lys Arg Arg Gln Arg Arg Arg
1               5                   10                  15

Arg Gly Asp Arg
            20

<210> SEQ ID NO 184
<211> LENGTH: 12
<212> TYPE: PRT
<213> ORGANISM: Artificial
<220> FEATURE:
<223> OTHER INFORMATION: peptide

<400> SEQUENCE: 184
```

Gln Ile Pro His Arg Ser Ser Thr Ala Leu Gln Leu
1               5                   10

<210> SEQ ID NO 185
<211> LENGTH: 7
<212> TYPE: PRT
<213> ORGANISM: Artificial
<220> FEATURE:
<223> OTHER INFORMATION: peptide

<400> SEQUENCE: 185

Ser Tyr Gln Thr Met Gln Pro
1               5

<210> SEQ ID NO 186
<211> LENGTH: 18
<212> TYPE: PRT
<213> ORGANISM: Artificial
<220> FEATURE:
<223> OTHER INFORMATION: peptide

<400> SEQUENCE: 186

Thr Asp Ser His Ser His His Arg Arg Arg Arg Arg Arg Arg Arg
1               5                   10                  15

Arg Arg

<210> SEQ ID NO 187
<211> LENGTH: 21
<212> TYPE: PRT
<213> ORGANISM: Artificial
<220> FEATURE:
<223> OTHER INFORMATION: peptide

<400> SEQUENCE: 187

Ile Pro Met Asn Phe Thr Ser His Ser Leu Arg Gln Arg Arg Arg
1               5                   10                  15

Arg Arg Arg Arg Arg
            20

<210> SEQ ID NO 188
<211> LENGTH: 20
<212> TYPE: PRT
<213> ORGANISM: Artificial
<220> FEATURE:
<223> OTHER INFORMATION: peptide

<400> SEQUENCE: 188

Tyr Trp Ser Ala Pro Gln Pro Ala Thr Arg Arg Arg Arg Arg Arg
1               5                   10                  15

Arg Arg Arg Arg
            20

<210> SEQ ID NO 189
<211> LENGTH: 19
<212> TYPE: PRT
<213> ORGANISM: Artificial
<220> FEATURE:
<223> OTHER INFORMATION: peptide

<400> SEQUENCE: 189

Ser Thr Thr His Pro His Pro Gly Thr Ser Ala Pro Glu Pro Ala Thr
1               5                   10                  15

Arg Arg Arg

```
<210> SEQ ID NO 190
<211> LENGTH: 12
<212> TYPE: PRT
<213> ORGANISM: Artificial
<220> FEATURE:
<223> OTHER INFORMATION: peptide

<400> SEQUENCE: 190

Asp Asp Ser Asp Asn Arg Ile Ile Arg Tyr Arg Arg
1               5                   10

<210> SEQ ID NO 191
<211> LENGTH: 15
<212> TYPE: PRT
<213> ORGANISM: Artificial
<220> FEATURE:
<223> OTHER INFORMATION: peptide

<400> SEQUENCE: 191

Thr Ser Pro His Pro Ser Leu Pro Arg His Ile Tyr Pro Arg Arg
1               5                   10                  15

<210> SEQ ID NO 192
<211> LENGTH: 20
<212> TYPE: PRT
<213> ORGANISM: Artificial
<220> FEATURE:
<223> OTHER INFORMATION: peptide

<400> SEQUENCE: 192

Arg Arg Ile Thr Glu Ile Arg Gly Arg Thr Gly Lys Thr Thr Leu Thr
1               5                   10                  15

Tyr Ile Glu Asp
            20

<210> SEQ ID NO 193
<211> LENGTH: 18
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 193

Asp Glu Arg Thr Gly Lys Thr Arg Arg Tyr Ile Asp Thr Arg Asp Ile
1               5                   10                  15

Arg Arg

<210> SEQ ID NO 194
<211> LENGTH: 18
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 194

Met Thr Tyr Ser Asp Met Pro Arg Arg Ile Ile Thr Asp Glu Asp Arg
1               5                   10                  15

Arg Arg
```

<210> SEQ ID NO 195
<211> LENGTH: 14
<212> TYPE: PRT
<213> ORGANISM: Artificial
<220> FEATURE:
<223> OTHER INFORMATION: peptide

<400> SEQUENCE: 195

Arg Arg Tyr Asp Thr Val Ile Asp Asp Ile Glu Tyr Arg Arg
1               5                   10

<210> SEQ ID NO 196
<211> LENGTH: 11
<212> TYPE: PRT
<213> ORGANISM: Artificial
<220> FEATURE:
<223> OTHER INFORMATION: peptide

<400> SEQUENCE: 196

Arg Asp Thr Ile Glu Arg Pro Glu Ile Arg Arg
1               5                   10

<210> SEQ ID NO 197
<211> LENGTH: 12
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 197

Arg Tyr Arg Arg Leu Ile Leu Glu Ile Trp Arg Arg
1               5                   10

<210> SEQ ID NO 198
<211> LENGTH: 11
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 198

Arg His Asp Thr His Asn Ala His Ile Arg Arg
1               5                   10

<210> SEQ ID NO 199
<211> LENGTH: 13
<212> TYPE: PRT
<213> ORGANISM: Artificial
<220> FEATURE:
<223> OTHER INFORMATION: peptide

<400> SEQUENCE: 199

Thr His Asp Phe Asp Arg Leu Leu Arg Ile Arg Arg Arg
1               5                   10

<210> SEQ ID NO 200
<211> LENGTH: 10
<212> TYPE: PRT
<213> ORGANISM: Artificial

```
<220> FEATURE:
<223> OTHER INFORMATION: peptide

<400> SEQUENCE: 200

Arg His Asn His Ile Arg Pro Asp Asn Gln
1               5                   10

<210> SEQ ID NO 201
<211> LENGTH: 11
<212> TYPE: PRT
<213> ORGANISM: Artificial
<220> FEATURE:
<223> OTHER INFORMATION: peptide

<400> SEQUENCE: 201

Arg Tyr Lys Glu Pro Arg Ile Thr Pro Arg Glu
1               5                   10

<210> SEQ ID NO 202
<211> LENGTH: 9
<212> TYPE: PRT
<213> ORGANISM: Artificial
<220> FEATURE:
<223> OTHER INFORMATION: peptide

<400> SEQUENCE: 202

Leu Arg Ile Glu Pro Ile Arg Ile Arg
1               5

<210> SEQ ID NO 203
<211> LENGTH: 9
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 203

Arg Leu Ile Arg Ile Arg Ile Leu Met
1               5

<210> SEQ ID NO 204
<211> LENGTH: 14
<212> TYPE: PRT
<213> ORGANISM: Artificial
<220> FEATURE:
<223> OTHER INFORMATION: peptide

<400> SEQUENCE: 204

Arg Pro Glu Phe His Ser Phe His Pro Ile Tyr Glu Arg Arg
1               5                   10

<210> SEQ ID NO 205
<211> LENGTH: 7
<212> TYPE: PRT
<213> ORGANISM: Artificial
<220> FEATURE:
<223> OTHER INFORMATION: peptide

<400> SEQUENCE: 205

Ser Thr Thr His Ile His Ala
1               5

<210> SEQ ID NO 206
```

```
<211> LENGTH: 10
<212> TYPE: PRT
<213> ORGANISM: Artificial
<220> FEATURE:
<223> OTHER INFORMATION: peptide

<400> SEQUENCE: 206

Phe Pro His Leu Val Ser Ser Leu Thr Thr
1               5                   10

<210> SEQ ID NO 207
<211> LENGTH: 12
<212> TYPE: PRT
<213> ORGANISM: Artificial
<220> FEATURE:
<223> OTHER INFORMATION: peptide

<400> SEQUENCE: 207

Gly Leu His Leu Phe Thr Thr Asp Arg Gln Gly Trp
1               5                   10

<210> SEQ ID NO 208
<211> LENGTH: 17
<212> TYPE: PRT
<213> ORGANISM: Artificial
<220> FEATURE:
<223> OTHER INFORMATION: peptide

<400> SEQUENCE: 208

Asn His Pro Trp Gln Phe Pro Asn Arg Trp Thr Arg Arg Arg Arg
1               5                   10                  15

Arg

<210> SEQ ID NO 209
<211> LENGTH: 19
<212> TYPE: PRT
<213> ORGANISM: Artificial
<220> FEATURE:
<223> OTHER INFORMATION: peptide

<400> SEQUENCE: 209

His Ser Ser His His His Pro Val His Ser Trp Asn Arg Arg Arg
1               5                   10                  15

Arg Arg Arg

<210> SEQ ID NO 210
<211> LENGTH: 13
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 210

Asp Ile His Thr Ile His Leu Pro Asp Thr His Arg Arg
1               5                   10

<210> SEQ ID NO 211
<211> LENGTH: 20
<212> TYPE: PRT
<213> ORGANISM: Artificial
<220> FEATURE:
<223> OTHER INFORMATION: peptide
```

```
<400> SEQUENCE: 211

Val Ala Glu Phe Ala Gln Ser Ile Gln Ser Arg Ile Val Glu Trp Lys
1               5                   10                  15

Glu Arg Leu Asp
            20

<210> SEQ ID NO 212
<211> LENGTH: 9
<212> TYPE: PRT
<213> ORGANISM: Artificial
<220> FEATURE:
<223> OTHER INFORMATION: peptide

<400> SEQUENCE: 212

Thr Arg Ile Leu Cys Ile Val Met Met
1               5

<210> SEQ ID NO 213
<211> LENGTH: 12
<212> TYPE: PRT
<213> ORGANISM: Artificial
<220> FEATURE:
<223> OTHER INFORMATION: peptide

<400> SEQUENCE: 213

Phe Leu Leu Pro Glu Pro Asp Glu Asn Thr Arg Trp
1               5                   10

<210> SEQ ID NO 214
<211> LENGTH: 7
<212> TYPE: PRT
<213> ORGANISM: Artificial
<220> FEATURE:
<223> OTHER INFORMATION: peptide

<400> SEQUENCE: 214

Leu Met Ser Asn Ala Gln Tyr
1               5

<210> SEQ ID NO 215
<211> LENGTH: 15
<212> TYPE: PRT
<213> ORGANISM: Artificial
<220> FEATURE:
<223> OTHER INFORMATION: peptide

<400> SEQUENCE: 215

Ser Ile Leu Thr Leu Ser Cys Arg Cys Arg Leu Arg Leu Trp Arg
1               5                   10                  15

<210> SEQ ID NO 216
<211> LENGTH: 9
<212> TYPE: PRT
<213> ORGANISM: Artificial
<220> FEATURE:
<223> OTHER INFORMATION: peptide

<400> SEQUENCE: 216

His Gln Ile His Arg Asn His Thr Tyr
1               5

<210> SEQ ID NO 217
<211> LENGTH: 9
<212> TYPE: PRT
<213> ORGANISM: Artificial
<220> FEATURE:
```

```
<223> OTHER INFORMATION: peptide

<400> SEQUENCE: 217

Leu Ile Arg Arg Cys Ser Leu Gln Arg
1               5

<210> SEQ ID NO 218
<211> LENGTH: 17
<212> TYPE: PRT
<213> ORGANISM: Artificial
<220> FEATURE:
<223> OTHER INFORMATION: peptide

<400> SEQUENCE: 218

Gly Ala Met His Leu Pro Trp His Met Gly Thr Arg Arg Arg Arg
1               5                   10                  15

Arg

<210> SEQ ID NO 219
<211> LENGTH: 14
<212> TYPE: PRT
<213> ORGANISM: Artificial
<220> FEATURE:
<223> OTHER INFORMATION: peptide

<400> SEQUENCE: 219

Asp Glu Asp Ala Lys Phe Arg Ile Arg Ile Leu Met Arg Arg
1               5                   10

<210> SEQ ID NO 220
<211> LENGTH: 20
<212> TYPE: PRT
<213> ORGANISM: Artificial
<220> FEATURE:
<223> OTHER INFORMATION: peptide

<400> SEQUENCE: 220

Asn His Ile Thr Asn Gly Gly Glu Glu Asp Ser Asp Cys Ser Ser Arg
1               5                   10                  15

Arg Arg Arg Leu
            20

<210> SEQ ID NO 221
<211> LENGTH: 13
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 221

His Ser Ser His His His Pro Thr Val Gln His Arg Arg
1               5                   10

<210> SEQ ID NO 222
<211> LENGTH: 10
<212> TYPE: PRT
<213> ORGANISM: Artificial
<220> FEATURE:
<223> OTHER INFORMATION: peptide

<400> SEQUENCE: 222

Arg Asp Phe Glu Arg Thr Ile Val Asp Ile
```

<210> SEQ ID NO 223
<211> LENGTH: 15
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 223

Arg Arg Arg Glu Ile Leu His Pro Glu Phe Arg Ile Leu Tyr Glu
1               5                   10                  15

<210> SEQ ID NO 224
<211> LENGTH: 9
<212> TYPE: PRT
<213> ORGANISM: Artificial
<220> FEATURE:
<223> OTHER INFORMATION: peptide

<400> SEQUENCE: 224

His His Phe Ser His His Trp Lys Thr
1               5

<210> SEQ ID NO 225
<211> LENGTH: 7
<212> TYPE: PRT
<213> ORGANISM: Artificial
<220> FEATURE:
<223> OTHER INFORMATION: peptide

<400> SEQUENCE: 225

Phe Leu Ile Arg Arg Ser Gly
1               5

<210> SEQ ID NO 226
<211> LENGTH: 12
<212> TYPE: PRT
<213> ORGANISM: Artificial
<220> FEATURE:
<223> OTHER INFORMATION: peptide

<400> SEQUENCE: 226

His Asn His His His Ser Gln His Thr Pro Gln His
1               5                   10

<210> SEQ ID NO 227
<211> LENGTH: 12
<212> TYPE: PRT
<213> ORGANISM: Artificial
<220> FEATURE:
<223> OTHER INFORMATION: peptide

<400> SEQUENCE: 227

His Leu His Lys His His Tyr Lys Asp Ser Arg Met
1               5                   10

<210> SEQ ID NO 228
<211> LENGTH: 17
<212> TYPE: PRT
<213> ORGANISM: Artificial
<220> FEATURE:
<223> OTHER INFORMATION: peptide

```
<400> SEQUENCE: 228

His Arg Thr Gln Ser Thr Leu Ile Leu Phe Ile Arg Arg Gly Arg Glu
1               5                   10                  15

Thr

<210> SEQ ID NO 229
<211> LENGTH: 9
<212> TYPE: PRT
<213> ORGANISM: Artificial
<220> FEATURE:
<223> OTHER INFORMATION: peptide

<400> SEQUENCE: 229

Leu His Phe Ser His Ile Asp Arg Arg
1               5

<210> SEQ ID NO 230
<211> LENGTH: 10
<212> TYPE: PRT
<213> ORGANISM: Artificial
<220> FEATURE:
<223> OTHER INFORMATION: peptide

<400> SEQUENCE: 230

Tyr Glu Leu Pro His His Ala Tyr Pro Ala
1               5                   10

<210> SEQ ID NO 231
<211> LENGTH: 19
<212> TYPE: PRT
<213> ORGANISM: Artificial
<220> FEATURE:
<223> OTHER INFORMATION: peptide

<400> SEQUENCE: 231

Ser Leu Leu Ile Gly Phe Gly Ile Ile Arg Ser Arg Arg Arg Arg
1               5                   10                  15

Arg Arg Arg

<210> SEQ ID NO 232
<211> LENGTH: 17
<212> TYPE: PRT
<213> ORGANISM: Artificial
<220> FEATURE:
<223> OTHER INFORMATION: peptide

<400> SEQUENCE: 232

His Thr Asp Ser His Pro His His His Pro His Arg Arg Arg Arg
1               5                   10                  15

Arg

<210> SEQ ID NO 233
<211> LENGTH: 19
<212> TYPE: PRT
<213> ORGANISM: Artificial
<220> FEATURE:
<223> OTHER INFORMATION: peptide

<400> SEQUENCE: 233

Ala Thr Gln His His Tyr Ile Lys Arg Arg Arg Arg Arg Arg Arg
1               5                   10                  15

Arg Arg Arg
```

```
<210> SEQ ID NO 234
<211> LENGTH: 19
<212> TYPE: PRT
<213> ORGANISM: Artificial
<220> FEATURE:
<223> OTHER INFORMATION: peptide

<400> SEQUENCE: 234

Phe Arg Ser Phe Ala Ile Pro Leu Val Val Pro Phe Arg Arg Arg
1               5                   10                  15

Arg Arg Arg

<210> SEQ ID NO 235
<211> LENGTH: 19
<212> TYPE: PRT
<213> ORGANISM: Artificial
<220> FEATURE:
<223> OTHER INFORMATION: peptide

<400> SEQUENCE: 235

Tyr Pro Thr Gln Gly His Leu Arg Arg Arg Arg Arg Arg Arg Arg
1               5                   10                  15

Arg Arg Arg

<210> SEQ ID NO 236
<211> LENGTH: 18
<212> TYPE: PRT
<213> ORGANISM: Artificial
<220> FEATURE:
<223> OTHER INFORMATION: peptide

<400> SEQUENCE: 236

His Ala Asn Leu His His Thr Arg Arg Arg Arg Arg Arg Arg Arg
1               5                   10                  15

Arg Arg

<210> SEQ ID NO 237
<211> LENGTH: 20
<212> TYPE: PRT
<213> ORGANISM: Artificial
<220> FEATURE:
<223> OTHER INFORMATION: peptide

<400> SEQUENCE: 237

Tyr Arg Arg Leu Leu Ile Gly Met Arg Arg Arg Arg Arg Arg Arg
1               5                   10                  15

Arg Arg Arg Arg
            20

<210> SEQ ID NO 238
<211> LENGTH: 15
<212> TYPE: PRT
<213> ORGANISM: Artificial
<220> FEATURE:
<223> OTHER INFORMATION: peptide

<400> SEQUENCE: 238

Ser His Tyr His Thr Pro Gln Asn Pro Pro Ser Thr Arg Arg Arg
1               5                   10                  15

<210> SEQ ID NO 239
<211> LENGTH: 17
<212> TYPE: PRT
<213> ORGANISM: Artificial
<220> FEATURE:
```

<223> OTHER INFORMATION: peptide

<400> SEQUENCE: 239

Arg Ser Tyr Ser Lys Leu Leu Cys Leu Leu Glu Arg Leu Arg Ile Ser
1               5                   10                  15
Pro

<210> SEQ ID NO 240
<211> LENGTH: 20
<212> TYPE: PRT
<213> ORGANISM: Artificial
<220> FEATURE:
<223> OTHER INFORMATION: peptide

<400> SEQUENCE: 240

Phe Trp Thr Gln Ser Ile Lys Glu Arg Lys Met Leu Asn Glu His Asp
1               5                   10                  15
Phe Glu Val Arg
            20

<210> SEQ ID NO 241
<211> LENGTH: 9
<212> TYPE: PRT
<213> ORGANISM: Artificial
<220> FEATURE:
<223> OTHER INFORMATION: peptide

<400> SEQUENCE: 241

Thr His Phe Ser His His Leu Lys His
1               5

<210> SEQ ID NO 242
<211> LENGTH: 7
<212> TYPE: PRT
<213> ORGANISM: Artificial
<220> FEATURE:
<223> OTHER INFORMATION: peptide

<400> SEQUENCE: 242

Ser Cys Arg Cys Arg Leu Arg
1               5

<210> SEQ ID NO 243
<211> LENGTH: 18
<212> TYPE: PRT
<213> ORGANISM: Artificial
<220> FEATURE:
<223> OTHER INFORMATION: peptide

<400> SEQUENCE: 243

Met His Pro Pro Asp Trp Tyr His His Thr Pro Lys Arg Arg Arg
1               5                   10                  15
Arg Arg

<210> SEQ ID NO 244
<211> LENGTH: 21
<212> TYPE: PRT
<213> ORGANISM: Artificial
<220> FEATURE:
<223> OTHER INFORMATION: peptide

<400> SEQUENCE: 244

His Thr Ile His Val His Tyr Pro Gly Asn Arg Gln Pro Asn Pro Pro
1               5                   10                  15

Leu Ile Leu Gln Arg
          20

<210> SEQ ID NO 245
<211> LENGTH: 14
<212> TYPE: PRT
<213> ORGANISM: Artificial
<220> FEATURE:
<223> OTHER INFORMATION: peptide

<400> SEQUENCE: 245

Thr Pro Ser Tyr Gly His Thr Pro Ser His His Arg Arg Arg
1               5                   10

<210> SEQ ID NO 246
<211> LENGTH: 12
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 246

Ile Arg Gly Arg Ile Arg Ile Ile Arg Arg Ile Arg
1               5                   10

<210> SEQ ID NO 247
<211> LENGTH: 11
<212> TYPE: PRT
<213> ORGANISM: Artificial
<220> FEATURE:
<223> OTHER INFORMATION: peptide

<400> SEQUENCE: 247

His His Pro Trp Thr His His Gln Arg Trp Ser
1               5                   10

<210> SEQ ID NO 248
<211> LENGTH: 12
<212> TYPE: PRT
<213> ORGANISM: Artificial
<220> FEATURE:
<223> OTHER INFORMATION: peptide

<400> SEQUENCE: 248

Ile Pro Met Asn Phe Thr Ser His Ser Leu Arg Gln
1               5                   10

<210> SEQ ID NO 249
<211> LENGTH: 12
<212> TYPE: PRT
<213> ORGANISM: Artificial
<220> FEATURE:
<223> OTHER INFORMATION: peptide

<400> SEQUENCE: 249

Ser Asn His His His Arg His His Thr Asn Thr His
1               5                   10

<210> SEQ ID NO 250
<211> LENGTH: 20
<212> TYPE: PRT
<213> ORGANISM: Artificial
<220> FEATURE:
<223> OTHER INFORMATION: peptide

<400> SEQUENCE: 250

Glu Val Thr Phe Arg His Ser Val Val Arg Arg Arg Arg Arg
1               5                   10                  15

Arg Arg Arg Arg
            20

<210> SEQ ID NO 251
<211> LENGTH: 18
<212> TYPE: PRT
<213> ORGANISM: Artificial
<220> FEATURE:
<223> OTHER INFORMATION: peptide

<400> SEQUENCE: 251

Phe Pro Gly His Thr Ile His Arg Arg Arg Arg Arg Arg Arg
1               5                   10                  15

Arg Arg

<210> SEQ ID NO 252
<211> LENGTH: 13
<212> TYPE: PRT
<213> ORGANISM: Artificial
<220> FEATURE:
<223> OTHER INFORMATION: peptide

<400> SEQUENCE: 252

Ser Ile Leu Thr Leu Ser Arg Ile Val Leu Gly Trp Trp
1               5                   10

<210> SEQ ID NO 253
<211> LENGTH: 10
<212> TYPE: PRT
<213> ORGANISM: Artificial
<220> FEATURE:
<223> OTHER INFORMATION: peptide

<400> SEQUENCE: 253

Thr Leu Tyr Leu Pro His Trp His Arg His
1               5                   10

<210> SEQ ID NO 254
<211> LENGTH: 18
<212> TYPE: PRT
<213> ORGANISM: Artificial
<220> FEATURE:
<223> OTHER INFORMATION: peptide

<400> SEQUENCE: 254

Ser Ile Leu Thr Leu Arg Leu Arg Arg Leu Arg Arg Arg Arg
1               5                   10                  15

Arg Arg

<210> SEQ ID NO 255
<211> LENGTH: 20
<212> TYPE: PRT
<213> ORGANISM: Artificial
<220> FEATURE:
<223> OTHER INFORMATION: peptide

<400> SEQUENCE: 255

Thr Leu Tyr Leu Pro His Trp His Arg His Arg Arg Arg Arg
1               5                   10                  15

Arg Arg Arg Arg

```
                    20

<210> SEQ ID NO 256
<211> LENGTH: 7
<212> TYPE: PRT
<213> ORGANISM: Artificial
<220> FEATURE:
<223> OTHER INFORMATION: peptide

<400> SEQUENCE: 256

Thr Asp Ser His Ser His His
1               5

<210> SEQ ID NO 257
<211> LENGTH: 20
<212> TYPE: PRT
<213> ORGANISM: Artificial
<220> FEATURE:
<223> OTHER INFORMATION: peptide

<400> SEQUENCE: 257

Glu Trp Lys Glu Arg Leu Asp Lys Glu Phe Ser Leu Ser Val Tyr Gln
1               5                   10                  15

Lys Met Lys Phe
            20

<210> SEQ ID NO 258
<211> LENGTH: 7
<212> TYPE: PRT
<213> ORGANISM: Artificial
<220> FEATURE:
<223> OTHER INFORMATION: peptide

<400> SEQUENCE: 258

Thr Ile His Pro Ser Ile Ser
1               5

<210> SEQ ID NO 259
<211> LENGTH: 12
<212> TYPE: PRT
<213> ORGANISM: Artificial
<220> FEATURE:
<223> OTHER INFORMATION: peptide

<400> SEQUENCE: 259

Ser Ile Leu Thr Leu Arg Leu Arg Arg Leu Arg Arg
1               5                   10

<210> SEQ ID NO 260
<211> LENGTH: 8
<212> TYPE: PRT
<213> ORGANISM: Artificial
<220> FEATURE:
<223> OTHER INFORMATION: peptide

<400> SEQUENCE: 260

Val Pro His Ile His Glu Phe Thr
1               5

<210> SEQ ID NO 261
<211> LENGTH: 13
<212> TYPE: PRT
<213> ORGANISM: Artificial
<220> FEATURE:
<223> OTHER INFORMATION: peptide

<400> SEQUENCE: 261
```

Thr Ile Ile His Arg Glu Asp Glu Asp Glu Ile Glu Trp
1               5                   10

<210> SEQ ID NO 262
<211> LENGTH: 12
<212> TYPE: PRT
<213> ORGANISM: Artificial
<220> FEATURE:
<223> OTHER INFORMATION: peptide

<400> SEQUENCE: 262

Lys Asp Leu Pro Phe Tyr Ser His Leu Ser Arg Gln
1               5                   10

<210> SEQ ID NO 263
<211> LENGTH: 19
<212> TYPE: PRT
<213> ORGANISM: Artificial
<220> FEATURE:
<223> OTHER INFORMATION: peptide

<400> SEQUENCE: 263

Thr His Phe Ser His His Leu Lys His Arg Arg Arg Arg Arg Arg
1               5                   10                  15

Arg Arg Arg

<210> SEQ ID NO 264
<211> LENGTH: 8
<212> TYPE: PRT
<213> ORGANISM: Artificial
<220> FEATURE:
<223> OTHER INFORMATION: peptide

<400> SEQUENCE: 264

Ala Thr Gln His His Tyr Ile Lys
1               5

<210> SEQ ID NO 265
<211> LENGTH: 12
<212> TYPE: PRT
<213> ORGANISM: Artificial
<220> FEATURE:
<223> OTHER INFORMATION: peptide

<400> SEQUENCE: 265

Ile Ile Arg Gly Asn Phe Leu Ile Gly Gly Arg Leu
1               5                   10

<210> SEQ ID NO 266
<211> LENGTH: 20
<212> TYPE: PRT
<213> ORGANISM: Artificial
<220> FEATURE:
<223> OTHER INFORMATION: peptide

<400> SEQUENCE: 266

Leu Pro Asn Pro Pro Glu Arg His His Arg Arg Arg Arg Arg Arg
1               5                   10                  15

Arg Arg Arg Arg
            20

<210> SEQ ID NO 267
<211> LENGTH: 16
<212> TYPE: PRT
<213> ORGANISM: Artificial

<220> FEATURE:
<223> OTHER INFORMATION: peptide

<400> SEQUENCE: 267

Ser Phe Ile Leu Phe Ile Arg Arg Gly Arg Leu Gly Arg Gly Asp Arg
1               5                   10                  15

<210> SEQ ID NO 268
<211> LENGTH: 7
<212> TYPE: PRT
<213> ORGANISM: Artificial
<220> FEATURE:
<223> OTHER INFORMATION: peptide

<400> SEQUENCE: 268

Phe Pro Gly His Thr Ile His
1               5

<210> SEQ ID NO 269
<211> LENGTH: 7
<212> TYPE: PRT
<213> ORGANISM: Artificial
<220> FEATURE:
<223> OTHER INFORMATION: peptide

<400> SEQUENCE: 269

Cys Ile Leu Arg Leu Trp Trp
1               5

<210> SEQ ID NO 270
<211> LENGTH: 16
<212> TYPE: PRT
<213> ORGANISM: Artificial
<220> FEATURE:
<223> OTHER INFORMATION: peptide

<400> SEQUENCE: 270

Arg Arg Arg Ser His Ser Gln Glu Asn Val Asp Gln Asp Thr Asp Glu
1               5                   10                  15

<210> SEQ ID NO 271
<211> LENGTH: 18
<212> TYPE: PRT
<213> ORGANISM: Artificial
<220> FEATURE:
<223> OTHER INFORMATION: peptide

<400> SEQUENCE: 271

Met Ser Thr Glu Ser Asn Met Pro Arg Leu Ile Gln Asn Asp Asp Arg
1               5                   10                  15

Arg Arg

<210> SEQ ID NO 272
<211> LENGTH: 7
<212> TYPE: PRT
<213> ORGANISM: Artificial
<220> FEATURE:
<223> OTHER INFORMATION: peptide

<400> SEQUENCE: 272

Leu Leu Arg Leu Gly Leu Ile
1               5

<210> SEQ ID NO 273
<211> LENGTH: 12
<212> TYPE: PRT

```
<213> ORGANISM: Artificial
<220> FEATURE:
<223> OTHER INFORMATION: peptide

<400> SEQUENCE: 273

Ile Arg Ile Leu Met Phe Leu Ile Gly Cys Gly Arg
1               5                   10

<210> SEQ ID NO 274
<211> LENGTH: 8
<212> TYPE: PRT
<213> ORGANISM: Artificial
<220> FEATURE:
<223> OTHER INFORMATION: peptide

<400> SEQUENCE: 274

Leu His Ser Lys Thr Leu Val Leu
1               5

<210> SEQ ID NO 275
<211> LENGTH: 12
<212> TYPE: PRT
<213> ORGANISM: Artificial
<220> FEATURE:
<223> OTHER INFORMATION: peptide

<400> SEQUENCE: 275

Leu Arg Cys Leu Leu Leu Leu Ile Gly Arg Val Gly
1               5                   10

<210> SEQ ID NO 276
<211> LENGTH: 12
<212> TYPE: PRT
<213> ORGANISM: Artificial
<220> FEATURE:
<223> OTHER INFORMATION: peptide

<400> SEQUENCE: 276

Phe Leu Ile Gly Pro Asp Arg Leu Ile Arg Ser Arg
1               5                   10

<210> SEQ ID NO 277
<211> LENGTH: 9
<212> TYPE: PRT
<213> ORGANISM: Artificial
<220> FEATURE:
<223> OTHER INFORMATION: peptide

<400> SEQUENCE: 277

Leu Pro Asn Pro Pro Glu Arg His His
1               5

<210> SEQ ID NO 278
<211> LENGTH: 12
<212> TYPE: PRT
<213> ORGANISM: Artificial
<220> FEATURE:
<223> OTHER INFORMATION: peptide

<400> SEQUENCE: 278

His Thr Asp Ser His Pro His His His Pro His
1               5                   10

<210> SEQ ID NO 279
<211> LENGTH: 21
<212> TYPE: PRT
<213> ORGANISM: Artificial
```

```
<220> FEATURE:
<223> OTHER INFORMATION: peptide
<220> FEATURE:
<221> NAME/KEY: MOD_RES
<222> LOCATION: (1)..(1)
<223> OTHER INFORMATION: Fluorescein isothiocyanate (FITC) attached

<400> SEQUENCE: 279

Ser Phe Ile Leu Phe Ile Arg Arg Gly Arg Leu Gly Arg Arg Arg
1               5                   10                  15

Arg Arg Arg Arg Arg
            20

<210> SEQ ID NO 280
<211> LENGTH: 12
<212> TYPE: PRT
<213> ORGANISM: Artificial
<220> FEATURE:
<223> OTHER INFORMATION: peptide

<400> SEQUENCE: 280

His Ser Ser His His His Pro Val His Ser Trp Asn
1               5                   10

<210> SEQ ID NO 281
<211> LENGTH: 17
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 281

Arg Thr Leu Ile Gly Ile Ile Arg Ser His His Leu Thr Leu Ile Arg
1               5                   10                  15

Arg

<210> SEQ ID NO 282
<211> LENGTH: 7
<212> TYPE: PRT
<213> ORGANISM: Artificial
<220> FEATURE:
<223> OTHER INFORMATION: peptide

<400> SEQUENCE: 282

Ile Arg Gly Arg Ile Ile Arg
1               5

<210> SEQ ID NO 283
<211> LENGTH: 21
<212> TYPE: PRT
<213> ORGANISM: Artificial
<220> FEATURE:
<223> OTHER INFORMATION: peptide

<400> SEQUENCE: 283

Ile Ile Arg Gly Asn Phe Leu Ile Gly Gly Arg Leu Arg Arg Arg
1               5                   10                  15

Arg Arg Arg Arg Arg
            20

<210> SEQ ID NO 284
<211> LENGTH: 5
```

```
<212> TYPE: PRT
<213> ORGANISM: Artificial
<220> FEATURE:
<223> OTHER INFORMATION: peptide

<400> SEQUENCE: 284

Ile Arg Ile Leu Met
1               5

<210> SEQ ID NO 285
<211> LENGTH: 12
<212> TYPE: PRT
<213> ORGANISM: Artificial
<220> FEATURE:
<223> OTHER INFORMATION: peptide

<400> SEQUENCE: 285

Gly Ala Met His Leu Pro Trp His Met Gly Thr Leu
1               5                   10

<210> SEQ ID NO 286
<211> LENGTH: 20
<212> TYPE: PRT
<213> ORGANISM: Artificial
<220> FEATURE:
<223> OTHER INFORMATION: peptide

<400> SEQUENCE: 286

Lys Arg Gly Gly Arg Lys Arg Arg Gly Gly His Arg Leu Ser Tyr
1               5                   10                  15

Phe Ile Arg Arg
            20

<210> SEQ ID NO 287
<211> LENGTH: 12
<212> TYPE: PRT
<213> ORGANISM: Artificial
<220> FEATURE:
<223> OTHER INFORMATION: peptide

<400> SEQUENCE: 287

Asn His Pro Trp Gln Phe Pro Asn Arg Trp Thr Val
1               5                   10

<210> SEQ ID NO 288
<211> LENGTH: 13
<212> TYPE: PRT
<213> ORGANISM: Artificial
<220> FEATURE:
<223> OTHER INFORMATION: peptide

<400> SEQUENCE: 288

Met His Pro Pro Asp Trp Tyr His His Thr Pro Lys His
1               5                   10

<210> SEQ ID NO 289
<211> LENGTH: 18
<212> TYPE: PRT
<213> ORGANISM: Artificial
<220> FEATURE:
<223> OTHER INFORMATION: peptide

<400> SEQUENCE: 289

Ser Trp Gln Ala Leu Ala Leu Tyr Ala Ala Gly Trp Arg Arg Arg
1               5                   10                  15

Arg Arg
```

<210> SEQ ID NO 290
<211> LENGTH: 4
<212> TYPE: PRT
<213> ORGANISM: Artificial
<220> FEATURE:
<223> OTHER INFORMATION: peptide

<400> SEQUENCE: 290

His Asn Ala His
1

<210> SEQ ID NO 291
<211> LENGTH: 15
<212> TYPE: PRT
<213> ORGANISM: Artificial
<220> FEATURE:
<223> OTHER INFORMATION: peptide

<400> SEQUENCE: 291

Asp Glu Phe Glu Arg Tyr Arg Arg Phe Ser Thr Ser Arg Arg Arg
1               5                   10                  15

<210> SEQ ID NO 292
<211> LENGTH: 9
<212> TYPE: PRT
<213> ORGANISM: Artificial
<220> FEATURE:
<223> OTHER INFORMATION: peptide

<400> SEQUENCE: 292

Glu Val Thr Phe Arg His Ser Val Val
1               5

<210> SEQ ID NO 293
<211> LENGTH: 20
<212> TYPE: PRT
<213> ORGANISM: Artificial
<220> FEATURE:
<223> OTHER INFORMATION: peptide

<400> SEQUENCE: 293

Thr Arg Ile Leu Cys Ile Val Arg Lys Lys Arg Gln Arg Arg Arg
1               5                   10                  15

Arg Gly Asp Arg
            20

<210> SEQ ID NO 294
<211> LENGTH: 18
<212> TYPE: PRT
<213> ORGANISM: Artificial
<220> FEATURE:
<223> OTHER INFORMATION: peptide

<400> SEQUENCE: 294

Ser Ile Leu Thr Leu Ser Arg Gly Arg Lys Lys Arg Arg Gln Arg Arg
1               5                   10                  15

Arg Arg

<210> SEQ ID NO 295
<211> LENGTH: 18
<212> TYPE: PRT
<213> ORGANISM: Artificial
<220> FEATURE:
<223> OTHER INFORMATION: peptide

```
<400> SEQUENCE: 295

Cys Ile Leu Arg Leu Trp Trp Arg Arg Arg Arg Arg Arg Arg Arg
1               5                  10                  15

Arg Arg

<210> SEQ ID NO 296
<211> LENGTH: 13
<212> TYPE: PRT
<213> ORGANISM: Artificial
<220> FEATURE:
<223> OTHER INFORMATION: peptide

<400> SEQUENCE: 296

Ala Ser Trp Gln Ala Leu Ala Leu Tyr Ala Ala Gly Trp
1               5                  10

<210> SEQ ID NO 297
<211> LENGTH: 16
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 297

Pro Arg Val Leu Pro Ser Pro His Thr Ile His Pro Ser Gln Tyr Pro
1               5                  10                  15

<210> SEQ ID NO 298
<211> LENGTH: 7
<212> TYPE: PRT
<213> ORGANISM: Artificial
<220> FEATURE:
<223> OTHER INFORMATION: peptide

<400> SEQUENCE: 298

His Ala Asn Leu His His Thr
1               5

<210> SEQ ID NO 299
<211> LENGTH: 22
<212> TYPE: PRT
<213> ORGANISM: Artificial
<220> FEATURE:
<223> OTHER INFORMATION: peptide

<400> SEQUENCE: 299

Ser Phe Ile Leu Phe Ile Arg Arg Gly Arg Leu Gly Arg Lys Lys Arg
1               5                  10                  15

Arg Gln Arg Arg Arg Pro
            20

<210> SEQ ID NO 300
<211> LENGTH: 8
<212> TYPE: PRT
<213> ORGANISM: Artificial
<220> FEATURE:
<223> OTHER INFORMATION: peptide

<400> SEQUENCE: 300

Tyr Pro Thr Gln Gly His Leu Arg
1               5
```

<210> SEQ ID NO 301
<211> LENGTH: 21
<212> TYPE: PRT
<213> ORGANISM: Artificial
<220> FEATURE:
<223> OTHER INFORMATION: peptide

<400> SEQUENCE: 301

Tyr Arg Arg Leu Leu Ile Gly Met Met Trp Arg Arg Arg Arg Arg
1               5                   10                  15

Arg Arg Arg Arg Arg
            20

<210> SEQ ID NO 302
<211> LENGTH: 12
<212> TYPE: PRT
<213> ORGANISM: Artificial
<220> FEATURE:
<223> OTHER INFORMATION: peptide

<400> SEQUENCE: 302

Ser Phe Ile Leu Phe Ile Arg Arg Gly Arg Leu Gly
1               5                   10

<210> SEQ ID NO 303
<211> LENGTH: 19
<212> TYPE: PRT
<213> ORGANISM: Artificial
<220> FEATURE:
<223> OTHER INFORMATION: peptide

<400> SEQUENCE: 303

Ile Arg Ile Leu Met Phe Leu Ile Gly Cys Gly Arg Arg Arg Arg
1               5                   10                  15

Arg Arg Arg

<210> SEQ ID NO 304
<211> LENGTH: 13
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 304

Arg Arg Ile Cys Arg Phe Ile Arg Ile Cys Arg Val Arg
1               5                   10

<210> SEQ ID NO 305
<211> LENGTH: 16
<212> TYPE: PRT
<213> ORGANISM: Artificial
<220> FEATURE:
<223> OTHER INFORMATION: peptide

<400> SEQUENCE: 305

Ile Arg Gly Arg Ile Ile Arg Arg Arg Arg Arg Arg Arg Arg Arg
1               5                   10                  15

<210> SEQ ID NO 306
<211> LENGTH: 19
<212> TYPE: PRT
<213> ORGANISM: Artificial

<220> FEATURE:
<223> OTHER INFORMATION: peptide

<400> SEQUENCE: 306

Arg Arg Arg His Asp Ser Cys His Asn Gln Leu Gln Asn Tyr Asp His
1               5                   10                  15

Ser Thr Glu

<210> SEQ ID NO 307
<211> LENGTH: 20
<212> TYPE: PRT
<213> ORGANISM: Artificial
<220> FEATURE:
<223> OTHER INFORMATION: peptide

<400> SEQUENCE: 307

Trp Asn His His His Ser Thr Pro His Pro Arg Arg Arg Arg Arg Arg
1               5                   10                  15

Arg Arg Arg Arg
            20

<210> SEQ ID NO 308
<211> LENGTH: 18
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 308

Arg Arg Pro Val Ala Pro Asp Leu Arg His Thr Ile His Ile Pro Pro
1               5                   10                  15

Glu Arg

<210> SEQ ID NO 309
<211> LENGTH: 12
<212> TYPE: PRT
<213> ORGANISM: Artificial
<220> FEATURE:
<223> OTHER INFORMATION: peptide

<400> SEQUENCE: 309

Arg Arg Asp Ile His Thr Ile His Pro Phe Tyr Gln
1               5                   10

<210> SEQ ID NO 310
<211> LENGTH: 12
<212> TYPE: PRT
<213> ORGANISM: Artificial
<220> FEATURE:
<223> OTHER INFORMATION: peptide

<400> SEQUENCE: 310

Trp Asn His His His Ser Thr Pro His Pro Ala His
1               5                   10

<210> SEQ ID NO 311
<211> LENGTH: 21
<212> TYPE: PRT
<213> ORGANISM: Artificial
<220> FEATURE:
<223> OTHER INFORMATION: peptide

```
<400> SEQUENCE: 311

Ser Phe Ile Leu Phe Ile Arg Arg Gly Arg Leu Gly Arg Arg Arg
1               5                   10                  15

Arg Arg Arg Arg Arg
            20

<210> SEQ ID NO 312
<211> LENGTH: 20
<212> TYPE: PRT
<213> ORGANISM: Artificial
<220> FEATURE:
<223> OTHER INFORMATION: peptide
<220> FEATURE:
<221> NAME/KEY: D-amino_acid
<222> LOCATION: (1)..(20)

<400> SEQUENCE: 312

Arg Arg Arg Arg Arg Arg Arg Gly Leu Arg Gly Arg Ile Phe
1               5                   10                  15

Leu Ile Phe Ser
            20

<210> SEQ ID NO 313
<211> LENGTH: 15
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 313

Arg Arg His Asn Ala His His Ser Thr Pro His Pro Asp Asp Arg
1               5                   10                  15

<210> SEQ ID NO 314
<211> LENGTH: 6
<212> TYPE: PRT
<213> ORGANISM: Artificial
<220> FEATURE:
<223> OTHER INFORMATION: peptide

<400> SEQUENCE: 314

His Ser Thr Pro His Pro
1               5

<210> SEQ ID NO 315
<211> LENGTH: 20
<212> TYPE: PRT
<213> ORGANISM: Artificial
<220> FEATURE:
<223> OTHER INFORMATION: peptide

<400> SEQUENCE: 315

Leu Arg Cys Leu Leu Leu Leu Ile Gly Arg Val Gly Arg Lys Lys
1               5                   10                  15

Arg Gln Arg Arg
            20

<210> SEQ ID NO 316
<211> LENGTH: 16
<212> TYPE: PRT
<213> ORGANISM: Artificial
<220> FEATURE:
```

```
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 316

Arg Arg Lys His Asn Lys His Arg Pro Glu Pro Asp Ser Asp Glu Arg
1               5                   10                  15

<210> SEQ ID NO 317
<211> LENGTH: 14
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 317

Arg Arg Ile Arg Asp Pro Arg Ile Leu Leu Leu His Phe Asp
1               5                   10

<210> SEQ ID NO 318
<211> LENGTH: 20
<212> TYPE: PRT
<213> ORGANISM: Artificial
<220> FEATURE:
<223> OTHER INFORMATION: peptide

<400> SEQUENCE: 318

Arg Lys Arg Gly Lys Ser Tyr Ala Phe Phe Val Pro Pro Ser Glu Ser
1               5                   10                  15

Lys Glu Arg Trp
            20

<210> SEQ ID NO 319
<211> LENGTH: 14
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 319

Arg Arg Lys Ile Leu Phe Ile Arg Leu Met His Asn Lys His
1               5                   10

<210> SEQ ID NO 320
<211> LENGTH: 16
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 320

Arg Arg Leu Ile Val Arg Ile Leu Lys Leu Pro Asn Pro Pro Glu Arg
1               5                   10                  15
```

```
<210> SEQ ID NO 321
<211> LENGTH: 9
<212> TYPE: PRT
<213> ORGANISM: Artificial
<220> FEATURE:
<223> OTHER INFORMATION: peptide
<220> FEATURE:
<221> NAME/KEY: LIPID
<222> LOCATION: (1)..(1)
<223> OTHER INFORMATION: MYRISTATE group attached

<400> SEQUENCE: 321

Arg Arg His Ser Thr Pro His Pro Asp
1               5

<210> SEQ ID NO 322
<211> LENGTH: 12
<212> TYPE: PRT
<213> ORGANISM: Artificial
<220> FEATURE:
<223> OTHER INFORMATION: peptide

<400> SEQUENCE: 322

Lys Pro Pro Asp Arg Leu Trp His Tyr Thr Gln Pro
1               5                   10

<210> SEQ ID NO 323
<211> LENGTH: 12
<212> TYPE: PRT
<213> ORGANISM: Artificial
<220> FEATURE:
<223> OTHER INFORMATION: peptide

<400> SEQUENCE: 323

Ala Thr Leu Pro Phe Val Thr Asp Arg Gln Gly Trp
1               5                   10

<210> SEQ ID NO 324
<211> LENGTH: 12
<212> TYPE: PRT
<213> ORGANISM: Artificial
<220> FEATURE:
<223> OTHER INFORMATION: peptide

<400> SEQUENCE: 324

Phe Tyr Ser His Ser Thr Ser Pro Ala Pro Ala Lys
1               5                   10

<210> SEQ ID NO 325
<211> LENGTH: 12
<212> TYPE: PRT
<213> ORGANISM: Artificial
<220> FEATURE:
<223> OTHER INFORMATION: peptide

<400> SEQUENCE: 325

Cys Tyr Ser His Ser Tyr Pro Thr Gln Gly His Leu
1               5                   10

<210> SEQ ID NO 326
<211> LENGTH: 12
<212> TYPE: PRT
<213> ORGANISM: Artificial
<220> FEATURE:
<223> OTHER INFORMATION: peptide

<400> SEQUENCE: 326

Glu Phe His Ser Phe Tyr Thr Ala Arg Gln Thr Gly
```

<210> SEQ ID NO 327
<211> LENGTH: 12
<212> TYPE: PRT
<213> ORGANISM: Artificial
<220> FEATURE:
<223> OTHER INFORMATION: peptide

<400> SEQUENCE: 327

Ser Asp Gly Phe Val Pro His Phe Lys Arg Gln His
1               5                   10

<210> SEQ ID NO 328
<211> LENGTH: 7
<212> TYPE: PRT
<213> ORGANISM: Artificial
<220> FEATURE:
<223> OTHER INFORMATION: peptide

<400> SEQUENCE: 328

Leu Pro Asn Pro Pro Glu Arg
1               5

<210> SEQ ID NO 329
<211> LENGTH: 7
<212> TYPE: PRT
<213> ORGANISM: Artificial
<220> FEATURE:
<223> OTHER INFORMATION: peptide

<400> SEQUENCE: 329

Leu His Ser Lys Thr Leu Val
1               5

<210> SEQ ID NO 330
<211> LENGTH: 6
<212> TYPE: PRT
<213> ORGANISM: Artificial
<220> FEATURE:
<223> OTHER INFORMATION: peptide

<400> SEQUENCE: 330

His Val His Thr His Gln
1               5

<210> SEQ ID NO 331
<211> LENGTH: 7
<212> TYPE: PRT
<213> ORGANISM: Artificial
<220> FEATURE:
<223> OTHER INFORMATION: peptide

<400> SEQUENCE: 331

Ser Ser Ser Leu Gly Thr His
1               5

<210> SEQ ID NO 332
<211> LENGTH: 7
<212> TYPE: PRT
<213> ORGANISM: Artificial
<220> FEATURE:
<223> OTHER INFORMATION: peptide

<400> SEQUENCE: 332

His Glu Val Thr His His Trp
1               5

```
<210> SEQ ID NO 333
<211> LENGTH: 7
<212> TYPE: PRT
<213> ORGANISM: Artificial
<220> FEATURE:
<223> OTHER INFORMATION: peptide

<400> SEQUENCE: 333

Ser Ala Pro Gln Pro Ala Thr
1               5

<210> SEQ ID NO 334
<211> LENGTH: 7
<212> TYPE: PRT
<213> ORGANISM: Artificial
<220> FEATURE:
<223> OTHER INFORMATION: peptide

<400> SEQUENCE: 334

Thr Pro Pro Leu Thr Leu Ile
1               5

<210> SEQ ID NO 335
<211> LENGTH: 6
<212> TYPE: PRT
<213> ORGANISM: Artificial
<220> FEATURE:
<223> OTHER INFORMATION: peptide

<400> SEQUENCE: 335

His Pro Trp Thr His His
1               5

<210> SEQ ID NO 336
<211> LENGTH: 7
<212> TYPE: PRT
<213> ORGANISM: Artificial
<220> FEATURE:
<223> OTHER INFORMATION: peptide

<400> SEQUENCE: 336

Ser Ala Ala Ser Asp Leu Arg
1               5

<210> SEQ ID NO 337
<211> LENGTH: 7
<212> TYPE: PRT
<213> ORGANISM: Artificial
<220> FEATURE:
<223> OTHER INFORMATION: peptide

<400> SEQUENCE: 337

Ser Pro Leu Gln Ser Leu Lys
1               5

<210> SEQ ID NO 338
<211> LENGTH: 7
<212> TYPE: PRT
<213> ORGANISM: Artificial
<220> FEATURE:
<223> OTHER INFORMATION: peptide

<400> SEQUENCE: 338

Arg Pro Thr Gln Val Leu His
1               5
```

<210> SEQ ID NO 339
<211> LENGTH: 20
<212> TYPE: DNA
<213> ORGANISM: Artificial
<220> FEATURE:
<223> OTHER INFORMATION: oligo

<400> SEQUENCE: 339
agacatgccc agacatgtcc                                                 20

<210> SEQ ID NO 340
<211> LENGTH: 20
<212> TYPE: DNA
<213> ORGANISM: Artificial
<220> FEATURE:
<223> OTHER INFORMATION: oligo

<400> SEQUENCE: 340
gaacatgtcc caacatgttg                                                 20

<210> SEQ ID NO 341
<211> LENGTH: 6
<212> TYPE: DNA
<213> ORGANISM: Artificial
<220> FEATURE:
<223> OTHER INFORMATION: oligo

<400> SEQUENCE: 341 aagctt                                                                 6

<210> SEQ ID NO 342
<211> LENGTH: 6
<212> TYPE: DNA
<213> ORGANISM: Artificial
<220> FEATURE:
<223> OTHER INFORMATION: oligo

<400> SEQUENCE: 342 gaattc                                                                 6

<210> SEQ ID NO 343
<211> LENGTH: 21
<212> TYPE: DNA
<213> ORGANISM: Artificial
<220> FEATURE:
<223> OTHER INFORMATION: oligo

<400> SEQUENCE: 343
cccaagcaat ggatgatttg a                                               21

<210> SEQ ID NO 344
<211> LENGTH: 21
<212> TYPE: DNA
<213> ORGANISM: Artificial
<220> FEATURE:
<223> OTHER INFORMATION: oligo

<400> SEQUENCE: 344
ggcattctgg gagcttcatc t                                               21

<210> SEQ ID NO 345
<211> LENGTH: 21
<212> TYPE: DNA
<213> ORGANISM: Artificial
<220> FEATURE:
<223> OTHER INFORMATION: oligo

<400> SEQUENCE: 345
ggcagaccag catgacagat t                                              21

<210> SEQ ID NO 346
<211> LENGTH: 20
<212> TYPE: DNA
<213> ORGANISM: Artificial
<220> FEATURE:
<223> OTHER INFORMATION: oligo

<400> SEQUENCE: 346
gcggattagg gcttcctctt                                                20

<210> SEQ ID NO 347
<211> LENGTH: 21
<212> TYPE: DNA
<213> ORGANISM: Artificial
<220> FEATURE:
<223> OTHER INFORMATION: oligo

<400> SEQUENCE: 347
gacctcaacg cacagtacga g                                              21

<210> SEQ ID NO 348
<211> LENGTH: 22
<212> TYPE: DNA
<213> ORGANISM: Artificial
<220> FEATURE:
<223> OTHER INFORMATION: oligo

<400> SEQUENCE: 348
aggagtccca tgatgagatt gt                                             22

<210> SEQ ID NO 349
<211> LENGTH: 22
<212> TYPE: DNA
<213> ORGANISM: Artificial
<220> FEATURE:
<223> OTHER INFORMATION: oligo

<400> SEQUENCE: 349
aggcaaatgt gcaataccaa ca                                             22

<210> SEQ ID NO 350
<211> LENGTH: 26
<212> TYPE: DNA
<213> ORGANISM: Artificial
<220> FEATURE:
<223> OTHER INFORMATION: oligo

<400> SEQUENCE: 350
ggttacagca ccatcagtag gtacag                                         26

<210> SEQ ID NO 351
<211> LENGTH: 21
<212> TYPE: DNA
<213> ORGANISM: Artificial
<220> FEATURE:
<223> OTHER INFORMATION: oligo

<400> SEQUENCE: 351
cggcagagaa ttccacgtga t                                              21

<210> SEQ ID NO 352

```
<211> LENGTH: 21
<212> TYPE: DNA
<213> ORGANISM: Artificial
<220> FEATURE:
<223> OTHER INFORMATION: oligo

<400> SEQUENCE: 352
atctcttcgc cagctccaac a                                              21

<210> SEQ ID NO 353
<211> LENGTH: 21
<212> TYPE: DNA
<213> ORGANISM: Artificial
<220> FEATURE:
<223> OTHER INFORMATION: oligo

<400> SEQUENCE: 353
gcagagctgg aagtcgagtg t                                              21

<210> SEQ ID NO 354
<211> LENGTH: 21
<212> TYPE: DNA
<213> ORGANISM: Artificial
<220> FEATURE:
<223> OTHER INFORMATION: oligo

<400> SEQUENCE: 354
aagtttctgc cggaagttca g                                              21

<210> SEQ ID NO 355
<211> LENGTH: 21
<212> TYPE: DNA
<213> ORGANISM: Artificial
<220> FEATURE:
<223> OTHER INFORMATION: oligo

<400> SEQUENCE: 355
actgtgaccc ttgcaccaaa t                                              21

<210> SEQ ID NO 356
<211> LENGTH: 21
<212> TYPE: DNA
<213> ORGANISM: Artificial
<220> FEATURE:
<223> OTHER INFORMATION: oligo

<400> SEQUENCE: 356
gccaccccaa gttagatctg g                                              21

<210> SEQ ID NO 357
<211> LENGTH: 24
<212> TYPE: DNA
<213> ORGANISM: Artificial
<220> FEATURE:
<223> OTHER INFORMATION: oligo

<400> SEQUENCE: 357
aggcactcac agagcactac aaac                                           24

<210> SEQ ID NO 358
<211> LENGTH: 18
<212> TYPE: DNA
<213> ORGANISM: Artificial
<220> FEATURE:
<223> OTHER INFORMATION: oligo

<400> SEQUENCE: 358
```
gcccttggac ggcttttc                                                           18

<210> SEQ ID NO 359
<211> LENGTH: 20
<212> TYPE: DNA
<213> ORGANISM: Artificial
<220> FEATURE:
<223> OTHER INFORMATION: oligo

<400> SEQUENCE: 359
acccactcct ccacctttga                                                         20

<210> SEQ ID NO 360
<211> LENGTH: 22
<212> TYPE: DNA
<213> ORGANISM: Artificial
<220> FEATURE:
<223> OTHER INFORMATION: oligo

<400> SEQUENCE: 360
ctgttgctgt agccaaattc gt                                                      22

<210> SEQ ID NO 361
<211> LENGTH: 100
<212> TYPE: DNA
<213> ORGANISM: Artificial
<220> FEATURE:
<223> OTHER INFORMATION: oligo

<400> SEQUENCE: 361
ctgctgaagc ttcgaattcc tagacatgcc cagacatgtc ctactgctgc tgctgctgct             60
gctgcgaaca tgtcccaaca tgttgctgct gctgctgctg                                  100

<210> SEQ ID NO 362
<211> LENGTH: 35
<212> TYPE: DNA
<213> ORGANISM: Artificial
<220> FEATURE:
<223> OTHER INFORMATION: oligo

<400> SEQUENCE: 362
tcgagttgcc tggacttgcc tggccttgcc ttttc                                        35

<210> SEQ ID NO 363
<211> LENGTH: 35
<212> TYPE: DNA
<213> ORGANISM: Artificial
<220> FEATURE:
<223> OTHER INFORMATION: oligo

<400> SEQUENCE: 363
tcgagtttaa tggactttaa tggcctttaa ttttc                                        35

<210> SEQ ID NO 364
<211> LENGTH: 23
<212> TYPE: DNA
<213> ORGANISM: Artificial
<220> FEATURE:
<223> OTHER INFORMATION: oligo
<220> FEATURE:
<221> NAME/KEY: misc_feature
<222> LOCATION: (1)..(8)
<223> OTHER INFORMATION: n is a, c, g, or t

<400> SEQUENCE: 364

```
nnnnnnnnca tggaaagata gtg                                             23
```

<210> SEQ ID NO 365
<211> LENGTH: 24
<212> TYPE: DNA
<213> ORGANISM: Artificial
<220> FEATURE:
<223> OTHER INFORMATION: oligo
<220> FEATURE:
<221> NAME/KEY: misc_feature
<222> LOCATION: (1)..(8)
<223> OTHER INFORMATION: n is a, c, g, or t

<400> SEQUENCE: 365

```
nnnnnnnncc taaaacgatt tgtg                                            24
```

<210> SEQ ID NO 366
<211> LENGTH: 44
<212> TYPE: DNA
<213> ORGANISM: Artificial
<220> FEATURE:
<223> OTHER INFORMATION: oligo

<400> SEQUENCE: 366

```
agacatgccc agacatgtcc ttatagacat gcccagacat gtcc                      44
```

<210> SEQ ID NO 367
<211> LENGTH: 44
<212> TYPE: DNA
<213> ORGANISM: Artificial
<220> FEATURE:
<223> OTHER INFORMATION: oligo

<400> SEQUENCE: 367

```
agaaatgccc agaaatgtcc ttatagaaat gcccagaaat gtcc                      44
```

<210> SEQ ID NO 368
<211> LENGTH: 12
<212> TYPE: PRT
<213> ORGANISM: Artificial
<220> FEATURE:
<223> OTHER INFORMATION: peptide

<400> SEQUENCE: 368

```
Phe Arg Ser Phe Ala Ile Pro Leu Val Val Pro Phe
1               5                   10
```

<210> SEQ ID NO 369
<211> LENGTH: 12
<212> TYPE: PRT
<213> ORGANISM: Artificial
<220> FEATURE:
<223> OTHER INFORMATION: peptide

<400> SEQUENCE: 369

```
Lys Ile Leu Phe Ile Arg Leu Met His Asn Lys His
1               5                   10
```

<210> SEQ ID NO 370
<211> LENGTH: 4
<212> TYPE: PRT
<213> ORGANISM: Artificial
<220> FEATURE:
<223> OTHER INFORMATION: peptide

<400> SEQUENCE: 370

```
His His His Pro
```

<210> SEQ ID NO 371
<211> LENGTH: 4
<212> TYPE: PRT
<213> ORGANISM: Artificial
<220> FEATURE:
<223> OTHER INFORMATION: peptide

<400> SEQUENCE: 371

His Thr Ile His
1

<210> SEQ ID NO 372
<211> LENGTH: 4
<212> TYPE: PRT
<213> ORGANISM: Artificial
<220> FEATURE:
<223> OTHER INFORMATION: peptide

<400> SEQUENCE: 372

His Asn Lys His
1

<210> SEQ ID NO 373
<211> LENGTH: 5
<212> TYPE: PRT
<213> ORGANISM: Artificial
<220> FEATURE:
<223> OTHER INFORMATION: peptide

<400> SEQUENCE: 373

Leu Leu Leu Ile Gly
1               5

<210> SEQ ID NO 374
<211> LENGTH: 5
<212> TYPE: PRT
<213> ORGANISM: Artificial
<220> FEATURE:
<223> OTHER INFORMATION: peptide

<400> SEQUENCE: 374

Ile Leu Phe Ile Arg
1               5

<210> SEQ ID NO 375
<211> LENGTH: 6
<212> TYPE: PRT
<213> ORGANISM: Artificial
<220> FEATURE:
<223> OTHER INFORMATION: peptide

<400> SEQUENCE: 375

Ile Arg Gly Arg Ile Ile
1               5

<210> SEQ ID NO 376
<211> LENGTH: 7
<212> TYPE: PRT
<213> ORGANISM: Artificial
<220> FEATURE:
<223> OTHER INFORMATION: peptide

<400> SEQUENCE: 376

Ser Phe Ile Leu Phe Ile Arg
1               5

```
<210> SEQ ID NO 377
<211> LENGTH: 7
<212> TYPE: PRT
<213> ORGANISM: Artificial
<220> FEATURE:
<223> OTHER INFORMATION: peptide

<400> SEQUENCE: 377

Tyr Pro Thr Gln Gly His Leu
1               5

<210> SEQ ID NO 378
<211> LENGTH: 10
<212> TYPE: PRT
<213> ORGANISM: Artificial
<220> FEATURE:
<223> OTHER INFORMATION: peptide

<400> SEQUENCE: 378

Trp Asn His His His Ser Thr Pro His Pro
1               5                   10

<210> SEQ ID NO 379
<211> LENGTH: 11
<212> TYPE: PRT
<213> ORGANISM: Artificial
<220> FEATURE:
<223> OTHER INFORMATION: peptide

<400> SEQUENCE: 379

Ile Arg Ile Leu Met Phe Leu Ile Gly Cys Gly
1               5                   10

<210> SEQ ID NO 380
<211> LENGTH: 12
<212> TYPE: PRT
<213> ORGANISM: Artificial
<220> FEATURE:
<223> OTHER INFORMATION: peptide

<400> SEQUENCE: 380

Ser Trp Gln Ala Leu Ala Leu Tyr Ala Ala Gly Trp
1               5                   10

<210> SEQ ID NO 381
<211> LENGTH: 12
<212> TYPE: PRT
<213> ORGANISM: Artificial
<220> FEATURE:
<223> OTHER INFORMATION: peptide
<220> FEATURE:
<221> NAME/KEY: D-amino_acids
<222> LOCATION: (1)..(12)

<400> SEQUENCE: 381

Gly Leu Arg Gly Arg Arg Ile Phe Leu Ile Phe Ser
1               5                   10

<210> SEQ ID NO 382
<211> LENGTH: 18
<212> TYPE: PRT
<213> ORGANISM: Artificial
<220> FEATURE:
<223> OTHER INFORMATION: peptide

<400> SEQUENCE: 382
```

-continued

```
Leu Arg Cys Leu Leu Leu Leu Ile Gly Arg Val Gly Arg Lys Lys Arg
1               5                   10                  15
Arg Gln
```